US008680278B2

(12) United States Patent
Kinney et al.

(10) Patent No.: US 8,680,278 B2
(45) Date of Patent: Mar. 25, 2014

(54) ENANTIOSELECTIVE PROCESS FOR PREPARING A SUBSTITUTED ALKANOIC ACID

(75) Inventors: William A. Kinney, Newtown, PA (US); Christopher A. Teleha, Fort Washington, PA (US); Shyamali Ghosh, Norristown, PA (US); Bruce E. Maryanoff, Forest Grove, PA (US); Gabriela Grasa, Dayton, MD (US); Antonio Zanotti-Gerosa, Cambridge (GB); Jonathan Alan Medlock, Rheinfelden (CH)

(73) Assignee: Janssen Pharmaceutica NV (BE)

( * ) Notice: Subject to any disclaimer, the term of this patent is extended or adjusted under 35 U.S.C. 154(b) by 654 days.

(21) Appl. No.: 12/290,438

(22) Filed: Oct. 30, 2008

(65) Prior Publication Data

US 2009/0124804 A1 May 14, 2009

Related U.S. Application Data

(60) Provisional application No. 61/001,004, filed on Oct. 30, 2007, provisional application No. 61/067,842, filed on Feb. 29, 2008.

(51) Int. Cl.
*C07D 215/00* (2006.01)
*C07D 417/02* (2006.01)
*C07D 401/00* (2006.01)

(52) U.S. Cl.
USPC .......................... 546/152; 546/122; 544/333

(58) Field of Classification Search
USPC .................... 546/122, 152; 544/333
See application file for complete search history.

(56) References Cited

U.S. PATENT DOCUMENTS

| 6,465,664 B1 | 10/2002 | Buchwald et al. |
| 6,787,655 B2 | 9/2004 | Buchwald et al. |
| 2004/0077684 A1* | 4/2004 | De Corte et al. ............. 514/317 |
| 2004/0224986 A1 | 11/2004 | De Corte et al. |

FOREIGN PATENT DOCUMENTS

| EP | 0060717 | 9/1982 |
| WO | 2004/020435 | 3/2004 |

OTHER PUBLICATIONS

Tang et al. Chemical Reviews, 2003, 103(8), 3029-3070.*
Wang et al. Journal of American Chemical Society, 2003, 123, 10536-10537.*
Ohta et al, "Asymmetric Hydrogenation with Aprotic Oxygin Functionalities Catalyzed by BINAP-Ru(II) Complexes," J. Org Chem, 1995, p. 357, vol. 60, American Chemical Society, USA.
Dobbs et al, Industrial Synthesis of (+) —cis-Methyl Dibydrojasmonate by Enantioselective Catalytic Hydrogenation; Identification of the Precatalyst [Ru ((-)-Me-DuPHOS) (H)- ($n^6$-1,3,5-cyclooctatriene)] ($BF^4$) **, Angew Chem. Int. Ed., 2000, oo 1992-1995, vol. 39, No. 11.
Ohta et al, "Asymmetric hydrogenation of unsaturated carboxylic acids catalyzed by BINAP-ruthenium (II) complexes," J of Organic Chemistry, 1987, pp. 3174-3176, vol. 52 (14), ACS Publications, USA.
Menges et al, "Threonine-Derived Phosphinite-Oxazoline Ligands for the Ir-Catalyzed Enantioselective Hydrogenation," Adv. Synth. Catal., 2002, pp. 40-44, 3434, No. 1.
Tang et al, "New Chiral Phosphorus Ligands for Enantioselective Hydrogenation," Chemical reviews, 2003, pp. 3029-3070, 103 (8), American Chemical Society, USA.
Qiu, Liqin et al, "Highly Efficient Asymmetric Hydrogenation of αβ-Unsaturated Carboxylic Acids Catalyzed by Ruthenium (II)-Dipyridylphosphine Complexes," Adv. Synth. Catal., 2007, pp. 517-520, vol. 349.
Uemura et al, "Highly Efficient Enantioselective Synthesis of Optically Active Carboxylic Acids by Ru (OCOCH) (S)-H-BINAP]," Journal of Organi c Chemistry, 1996, pp. 5510-5516, vol. 61 (16).
Tellers et al, "On the Mechanism of an Asymmetric αβ-Unsaturated Carboxylic Acid Hydrogenation: Applicaton to the Synthesis of a $PGD_2$ Receptor Antagonist," JACS, 2006, pp. 17063-17073, vol. 128.
Cossy et al, "A Short Synthesis of Argatroban: A Potent Selective Thrombin Inhibitor," Bioorganic and Medicinal Chemistry Letters, 2001, pp. 1989-1992, vol. 11.
Blaser et al, "Selective Hydrogenation for fine Chemicals: Recent Trends and New Developments," Adv. Synth. Catal., 2003, 103-151, 345.
Romero et al, "Asymmetric Synthesis of the C3α Fragment of 5,6-Dihydro-α-pyrone Nonpeptidic HIV-1 Protease Inhibitors," J. Org Chem, 1999, pp. 4980-4984, 64.
Hayashi, T. et al, "Asymmetric hydrogenation of trisubstitutted acrylic acids catalyzed by a chiral (aminoalkyl) ferrocenylphosphine-rhodium complex," J. Am. Chem. Soc., 1987, pp. 7876-7878, vol. 109, (25). American Chemical Society.
De Corte et al, "Piperdine-containing β-arylpropionic acids as potent antagaonist of $α_v β_3/α_v β_5$," Bioorganic & Med. Chem. Lett., 2004, pp. 5227-5232, vol. 14.
EP Search Report, No. 08846194.2-2101, dated Apr. 12, 2012.
Ghosh, et al., "1,2,3,4-Tetrahydroquinoline-containing alphaVbeta3 Integrin Antagonists with Enhanced Oral Bioavailability", bioorganic & Medicanal Chemistry Letters, Pergamon, vol. 14, No. 23, 2004, pp. 5937-5941.
Schrems, et al., "Iridium-Catalyzed Asymmetric Hydrogenation of Unfunctionalized Tetrasubstituted Olefins", Angew. Chem. Int. Ed., vol. 46, 2007, pp. 8274-8276.
Church, et al., Iridium Catalysts for the Asymmetric Hydrogenation of Olefins with Nontraditional Functional Substituents: Coord Chem Rev. vol. 252, 2007, pp. 513-531.
Grasa, Gabriela A. et al., "Efficient, enantioselective synthesis of a β,β-disubstituted carboxylic acid by Ru-XylPhanePhos-catalyzed asymmetric hydrogenation". Tetrahedron Letters 49 (2008) 5328-5331.
Kinney, W.A. et al., "Suzuki-Miyaura Approach to JNJ-26076713, an Orally Active Tetrahydroquinoline-Containing αvβ3/αvβ5 Integrin Antagonist, Enantioselective Synthesis and Stereochemical Studies". J. Org. Chem. (2008), 73, 2302-2310.
Zanotti-Gerosa, A., "Synthesis of an αvβ3 integrin antagonist intermediate via asymmetric hydrogenation of an α,β-unsaturated ester with BoPhoz-iridium and BoPhoz-rhodium catalysts" Tetrahedron: Asymmetry 19 (2008) 938-944.

* cited by examiner

*Primary Examiner* — Nizal Chandrakumar
(74) *Attorney, Agent, or Firm* — Yuriy P. Stercho

(57) ABSTRACT

The present invention is directed to a process for enantioselectively preparing substituted piperidine alkanoic acid integrin antagonist compounds.

9 Claims, No Drawings

ENANTIOSELECTIVE PROCESS FOR PREPARING A SUBSTITUTED ALKANOIC ACID

This U.S. nonprovisional application claims the benefit of U.S. provisional application Ser. No. 61/001,004, filed on Oct. 30, 2007, and of U.S. provisional application Ser. No. 61/067,842, filed on Feb. 29, 2008.

FIELD OF THE INVENTION

The present invention is directed to a process for enantioselectively preparing substituted alkanoic acid integrin antagonist compounds. More particularly, the process is directed to an enantioselective synthesis of a substituted piperidine alkanoic acid dual $\alpha_v\beta_3/\alpha_v\beta_5$ integrin antagonist.

BACKGROUND OF THE INVENTION

The importance of an economically viable synthesis of single-enantiomer chiral molecules is well established and understood. In no sector is this more apparent than in the pharmaceutical industry, where one enantiomer of a chiral drug molecule may exhibit enhanced (or different) therapeutic properties over another enantiomer.

While in many cases chiral resolution often remains the method of choice for large scale production, asymmetric hydrogenation remains the most widespread catalytic alternative because of the economic and environmental benefits over older resolution technologies in which the unwanted enantiomer must be recycled or disposed of.

However, despite the inherent advantages in using asymmetric catalysis to produce single-enantiomer molecules, the process is not readily amenable to use at an industrial scale because of a number of factors: such as the ready availability of the chiral catalyst for public or licensed use in the required quantity at an affordable price, the presence of impurities in the catalyst, which can either inhibit the effectiveness of the catalyst itself or get carried into the final product where they are difficult to remove and that, there is no single ligand family, much less an individual member of a family, which leads to high enantiomer selectivity with all substrates.

Moreover, no general methodology exists, although stereoselective asymmetric hydrogenation reductions of various substrates have been extensively described (Ohta T, Miyake T, Seido N, Kumabayashi H and Takaya H, *J. Org. Chem.* 1995, 60, 357; Dobbs D A, Vanhessche K P M, Brazi E, Rautenstrauch V, Lenoir J-Y, Genet J-P, Wiles J, and Bergens S H, *Angew. Chem., Int. Ed. Engl.* 2000, 39, 1992; Menges F and Pfaltz A, *Adv. Synth. Catal.* 2002, 344, 40; Tang W and Zhang X, *Chem. Rev.* 2003, 103, 3029; Ohta T, Takaya H, Kitamura M, Nagai K and Noyori R, *J. Org. Chem.* 1987, 52, 3174; Liqin Q, Li Y.-M, Kwong F Y, Yu W-Y, Fan Q-H and Chan A S C, *Adv. Synth. Catal.* 2007, 349, 517; Hayashi T, Kawamura N and Ito Y, *J. Am. Chem. Soc.* 1987, 109, 7876; Uemura T, Zhang X, Matsumura K, Sayo N, Kumobayashi H, Ohta T, Nozaki K and Takaya H, *J. Org. Chem.* 1996, 61, 5510; Tellers D M, McWilliams J C, Humphrey G, Journet M, DiMichele L, Hinksmon J, McKeown A E, Rosner T, Sun Y, and Tillyer R D, *J. Am. Chem. Soc.* 2006, 128, 17063; Cossy J and Belotti D, *Biorg. Med. Chem. Lett* 2001, 11, 1989; Blaser H U, Malan C, Pugin B, Steiner H, Spindler F and Studer M, *Adv. Synth. Catal. A* 2003, 345, 103 and references therein; Romero D L, Manninen P R, Han F and Romero A G, *J. Org. Chem.* 1999, 64, 4980-4985; U.S. Pat. No. 6,465,664; and, U.S. Pat. No. 6,787,655.

There remains a need for an efficient enantiomerically and diastereomerically selective hydrogenation process for a chiral integrin antagonist with a maximum conversion to product, having the highest enantiomeric and diastereomeric excess of the desired isomer.

SUMMARY OF THE INVENTION

The present invention is directed to an asymmetric hydrogenation process for preparing a compound of Formula (I) and Formula (II) and intermediates thereof:

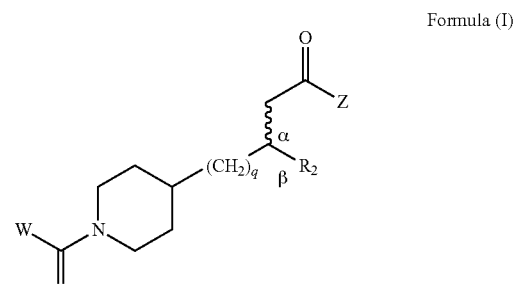

Formula (I)

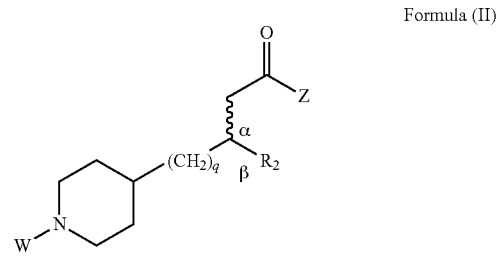

Formula (II)

wherein $R_2$, W, Z and q are as defined herein, wherein $\alpha$ represents a chiral carbon chain atom and, wherein $\beta$ represents a chiral carbon ring member atom.

A series of alkanoic acid dual $\alpha_v\beta_3/\alpha_v\beta_5$ integrin antagonists of Formula (III) and Formula (IV):

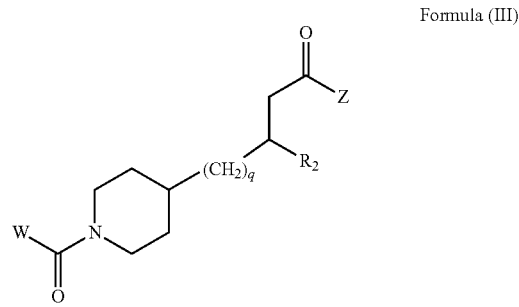

Formula (III)

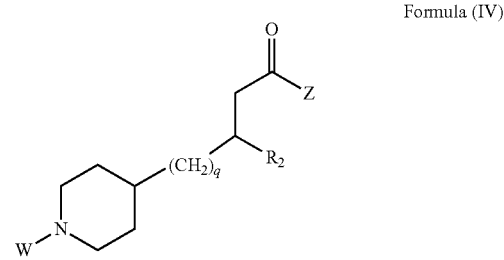

Formula (IV)

were described in De Corte B L, Kinney W A, Liu L, Ghosh S, Brunner L, Hoekstra W J, Santulli R J, Tuman R W, Baker J, Burns C, Proost J C, Tounge B A, Damiano B P, Maryanoff B E, Johnson D L and Galemmo R A Jr., *Bioorg. Med. Chem. Lett.*, 2004, 14, 5227; and, disclosed in United States Patent Publications US2004/0077684 and US2004/0224986, referred to therein as compound of Formula (I) and Formula (II), each of which is incorporated herein by reference in their entirety and for all purposes.

Furthermore, United States Patent Publication US2004/0077684 and U.S. Patent Publication US2004/0224986 describe racemic and stereoisomeric compounds of Formula (III) and Formula (IV). Such compounds may be asymmetrically prepared using the instant process to provide stereoisomeric compounds representative of compounds of Formula (I) and Formula (II) of the present invention.

The present invention is further directed to an asymmetric hydrogenation process for preparing a compound of Formula (Ia) and intermediates thereof:

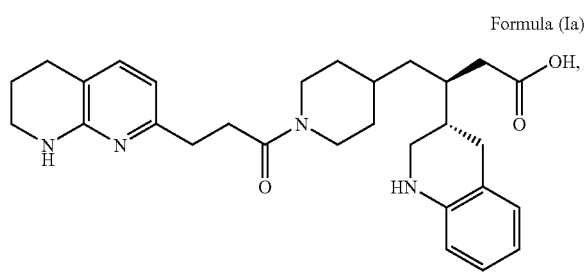

Formula (Ia)

and is referred to herein as (3S,3'S)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid.

The compound of Formula (Ia) has been disclosed in both United States Patent Publication US2004/0077684, in U.S. Patent Publication US2004/0224986 (CIP of US2004/0077684) and in U.S. patent application Ser. No. 11/897,484 (Continuation of US2004/0224986), which are each incorporated herein by reference in their entirety and for all purposes. The compound of Formula (Ia) was referred to therein as an isomer Compound 19-4 of 1,2,3,4-tetrahydro-β-[[1-[1-oxo-3-(5,6,7,8-tetrahydro-1,8-naphthyridin-2-yl)propyl]-4-piperidinyl]methyl]-3-quinolinepropanoic acid. The compound of Formula (Ia) was synthesized as disclosed in Scheme E (alternatively, as in Scheme F) and Example 15 of same.

The process of the present invention is an efficient and stereoselective enantiomeric and diastereomeric hydrogenation which improves conversion and enantiomeric excess of the desired product by optimized reaction conditions for compounds of Formula (I), Formula (II) and Formula (Ia) and intermediates thereof by improving control of geometric isomer formation by stereoselective olefin reduction and substantially avoiding isomer separation using sequential chiral column chromatography.

The process of the present invention provides improved conversion and enantiomeric and diastereomeric excess of a desired enantiomer of a compound of Formula (I), Formula (II), Formula (Ia) and intermediates thereof.

DETAILED DESCRIPTION OF THE INVENTION

The present invention, as shown in Scheme A, is directed to a process for preparing a compound of Formula (I) and Formula (II):

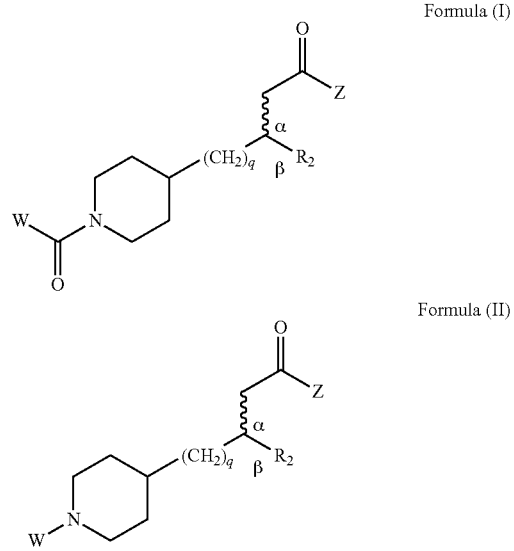

wherein
α represents a chiral carbon chain atom;
W is selected from the group consisting of —$C_{0-6}$alkyl($R_1$), —$C_{1-6}$alkyl($R_{1a}$), —$C_{0-6}$alkyl-aryl($R_1,R_8$), —$C_{0-6}$alkyl-heterocyclyl($R_1,R_8$), —$C_{0-6}$alkoxy($R_1$), —$C_{0-6}$alkoxy-aryl($R_1,R_8$), and —$C_{0-6}$alkoxy-heterocyclyl($R_1,R_8$),
$R_1$ is selected from the group consisting of hydrogen, —$N(R_4)_2$, —$N(R_4)(R_5)$, —$N(R_4)(R_6)$, -heterocyclyl($R_8$) and -heteroaryl($R_8$);
$R_{1a}$ is selected from the group consisting of —C($R_4$)(=N—$R_4$), —C(=N—$R_4$)—N($R_4$)$_2$, —C(=N—$R_4$)—N($R_4$)($R_6$), —C(=N—$R_4$)—N($R_4$)—C(=O)—$R_4$, —C(=N—$R_4$)—N($R_4$)—C(=O)—N($R_4$)$_2$, —C(=N—$R_4$)—N($R_4$)—$CO_2$—$R_4$, —C(=N—$R_4$)—N($R_4$)—$SO_2$—$C_{1-8}$alkyl($R_7$) and —C(=N—$R_4$)—N($R_4$)—$SO_2$—N($R_4$)$_2$;
$R_4$ is selected from the group consisting of hydrogen and —$C_{1-8}$alkyl($R_7$);
$R_5$ is selected from the group consisting of —C(=O)—$R_4$, —C(=O)—N($R_4$)$_2$, —C(=O)-cycloalkyl($R_8$), —C(=O)-heterocyclyl($R_8$), —C(=O)-aryl($R_8$), —C(=O)-heteroaryl($R_8$), —C(=O)—N($R_4$)-cycloalkyl($R_8$), —C(=O)—N($R_4$)-aryl($R_8$), —$CO_2$—$R_4$, —$CO_2$-cycloalkyl($R_8$), —$CO_2$-aryl($R_8$), —C($R_4$)(=N—$R_4$), —C(=N—$R_4$)—N($R_4$)$_2$, —C(=N—$R_4$)—N($R_4$)($R_6$), —C(=N—$R_4$)—N($R_4$)—C(=O)—$R_4$, —C(=N—$R_4$)—N($R_4$)—C(=O)—N($R_4$)$_2$, —C(=N—$R_4$)—N($R_4$)—$CO_2$—$R_4$, —C(=N—$R_4$)—N($R_4$)—$SO_2$—$C_{1-8}$alkyl($R_7$), —C(=N—$R_4$)—N($R_4$)—$SO_2$—N($R_4$)$_2$, —N($R_4$)—C($R_4$)(=N—$R_4$), —N($R_4$)—C(=N—$R_4$)—N($R_4$)$_2$, —N($R_4$)—C(=N—$R_4$)—N($R_4$)($R_6$), —N($R_4$)—C(=N—$R_4$)—N($R_4$)—C(=O)—$R_4$, —N($R_4$)—C(=N—$R_4$)—N($R_4$)—C(=O)—N($R_4$)$_2$, —N($R_4$)—C(=N—$R_4$)—N($R_4$)—$CO_2$—$R_4$, —N($R_4$)—C(=N—$R_4$)—N($R_4$)—$SO_2$—$C_{1-8}$alkyl($R_7$), —N($R_4$)—C(=N—$R_4$)—N($R_4$)—$SO_2$—N($R_4$)$_2$, —$SO_2$—$C_{1-8}$alkyl($R_7$), —$SO_2$—N($R_4$)$_2$, —$SO_2$-cycloalkyl($R_8$) and —$SO_2$-aryl($R_8$);
$R_6$ is selected from the group consisting of -cycloalkyl($R_8$), -heterocyclyl($R_8$), -aryl($R_8$) and -heteroaryl($R_8$);
$R_7$ is one to two substituents independently selected from the group consisting of hydrogen, —$C_{1-8}$alkoxy($R_9$), —$NH_2$, —NH—$C_{1-8}$alkyl($R_9$), —N($C_{1-8}$alkyl($R_9$))$_2$, —C(=O)H, —C(=O)—$C_{1-8}$alkyl($R_9$), —C(=O)—$NH_2$, —C(=O)—NH—$C_{1-8}$alkyl($R_9$), —C(=O)—N($C_{1-8}$alkyl($R_9$))$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —CO$_2$H, —CO$_2$—$C_{1-8}$alkyl($R_9$), —CO$_2$-aryl($R_{10}$), —C(=NH)—NH$_2$, —SH, —S—$C_{1-8}$alkyl($R_9$), —S—$C_{1-8}$alkyl-S—$C_{1-8}$alkyl($R_9$), —S—$C_{1-8}$alkyl-$C_{1-8}$alkoxy($R_9$), —S—$C_{1-8}$alkyl-NH—$C_{1-8}$alkyl($R_9$), —SO$_2$—$C_{1-8}$alkyl($R_9$), —SO$_2$—NH$_2$, —SO$_2$—NH—$C_{1-8}$alkyl($R_9$), —SO$_2$—N($C_{1-8}$alkyl($R_9$))$_2$, —SO$_2$-aryl($R_{10}$), cyano, (halo)$_{1-3}$, hydroxy, nitro, oxo, -cycloalkyl($R_{10}$), -heterocyclyl($R_{10}$), -aryl($R_{10}$) and -heteroaryl($R_{10}$);

$R_8$ is selected from the group consisting of hydrogen, —$C_{1-8}$alkyl($R_9$), —C(=O)H, —C(=O)—$C_{1-8}$alkyl($R_9$), —C(=O)—NH$_2$, —C(=O)—NH—$C_{1-8}$alkyl($R_9$), —C(=O)—N($C_{1-8}$alkyl($R_9$))$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —CO$_2$H, —CO$_2$—$C_{1-8}$alkyl($R_9$), —CO$_2$-aryl($R_{10}$), —C(=NH)—NH$_2$, —SO$_2$—$C_{1-8}$ alkyl ($R_9$), —SO$_2$—NH$_2$, —SO$_2$—NH—$C_{1-8}$alkyl($R_9$), —SO$_2$—N($C_{1-8}$alkyl($R_9$))$_2$, —SO$_2$-aryl($R_{10}$), -cycloalkyl($R_{10}$) and -aryl($R_{10}$) when attached to a nitrogen atom; and, wherein $R_8$ is one to four substituents independently selected from the group consisting of hydrogen, —$C_{1-8}$alkyl($R_9$), —$C_{1-8}$alkoxy($R_9$), —O-cycloalkyl($R_{10}$), —O-aryl($R_{10}$), —C(=O)H, —C(=O)—$C_{1-8}$alkyl($R_9$), —C(=O)—NH$_2$, —C(=O)—NH—$C_{1-8}$alkyl($R_9$), —C(=O)—N($C_{1-8}$alkyl($R_9$))$_2$, —C(=O)—NH-aryl($R_{10}$), —C(=O)-cycloalkyl($R_{10}$), —C(=O)-heterocyclyl($R_{10}$), —C(=O)-aryl($R_{10}$), —C(=O)-heteroaryl($R_{10}$), —CO$_2$H, —CO$_2$—$C_{1-8}$alkyl($R_9$), —CO$_2$-aryl($R_{10}$), —C(=NH)—NH$_2$, —SO$_2$—$C_{1-8}$alkyl($R_9$), —SO$_2$—NH$_2$, —SO$_2$—NH—$C_{1-8}$alkyl($R_9$), —SO$_2$—N($C_{1-8}$alkyl($R_9$))$_2$, —SO$_2$-aryl($R_{10}$), —SH, —S—$C_{1-8}$alkyl($R_9$), —S—$C_{1-8}$alkyl-S—$C_{1-8}$alkyl($R_9$), —S—$C_{1-8}$alkyl-$C_{1-8}$alkoxy($R_9$), —S—$C_{1-8}$alkyl-NH—$C_{1-8}$alkyl($R_9$), —NH$_2$, —NH—$C_{1-8}$alkyl($R_9$), —N($C_{1-8}$alkyl($R_9$))$_2$, cyano, halo, hydroxy, nitro, oxo, -cycloalkyl($R_{10}$), -heterocyclyl($R_{10}$), -aryl($R_{10}$) and -heteroaryl($R_{10}$) when attached to a carbon atom;

$R_9$ is selected from the group consisting of hydrogen, —$C_{1-8}$alkoxy, —NH$_2$, —NH—$C_{1-8}$alkyl, —N($C_{1-8}$alkyl)$_2$, —C(=O)H, —C(=O)—NH$_2$, —C(=O)—NH—$C_{1-8}$alkyl, —C(=O)—N($C_{1-8}$alkyl)$_2$, —CO$_2$H, —CO$_2$—$C_{1-8}$alkyl, —SO$_2$—$C_{1-8}$alkyl, —SO$_2$—NH$_2$, —SO$_2$—NH—$C_{1-8}$alkyl, —SO$_2$—N($C_{1-8}$alkyl)$_2$, cyano, (halo)$_{1-3}$, hydroxy, nitro and oxo;

$R_{10}$ is selected from the group consisting of hydrogen, —$C_{1-8}$alkyl, —C(=O)H, —C(=O)—$C_{1-8}$alkyl, —C(=O)—NH$_2$, —C(=O)—NH—$C_{1-8}$alkyl, —C(=O)—N($C_{1-8}$alkyl)$_2$, —CO$_2$H, —CO$_2$—$C_{1-4}$alkyl, —SO$_2$—$C_{1-8}$alkyl, —SO$_2$—NH$_2$, —SO$_2$—NH—$C_{1-8}$alkyl and —SO$_2$—N($C_{1-8}$alkyl)$_2$ when attached to a nitrogen atom; and, wherein $R_{10}$ is one to four substituents independently selected from the group consisting of hydrogen, —$C_{1-8}$alkyl, —$C_{1-8}$alkoxy, —C(=O)H, —C(=O)—$C_{1-8}$alkyl, —C(=O)—NH$_2$, —C(=O)—NH—$C_{1-8}$alkyl, —C(=O)—N($C_{1-8}$alkyl)$_2$, —CO$_2$H, —CO$_2$—$C_{1-4}$alkyl, —SO$_2$—$C_{1-8}$alkyl, —SO$_2$—NH$_2$, —SO$_2$—NH—$C_{1-8}$alkyl, —SO$_2$—N($C_{1-8}$alkyl)$_2$, —NH$_2$, —NH—$C_{1-8}$alkyl, —N($C_{1-8}$alkyl)$_2$, cyano, halo, hydroxy, nitro and oxo when attached to a carbon atom;

$R_2$ is selected from the group consisting of -cycloalkyl($R_8$), -heterocyclyl($R_8$), -aryl($R_8$) and -heteroaryl($R_8$), wherein β represents a chiral carbon ring member atom of -cycloalkyl($R_8$) and -heterocyclyl($R_8$);

q is 0, 1, 2 or 3; and

Z is selected from the group consisting of hydroxy and —O—$C_{1-8}$alkyl;

comprising the steps of:

Scheme A

Step 1. reacting a Compound A1, wherein PG is a $C_{1-4}$alkoxycarbonyl protecting group such as Boc, with a first hydrogen source, a first ligand-metal complex consisting essentially of a first ligand conjugated with a first metal adduct, in a first solvent in the presence of an optional first additive at an elevated first temperature and an elevated first pressure to provide a substantially pure Compound A2 or a substantially pure Compound A3:

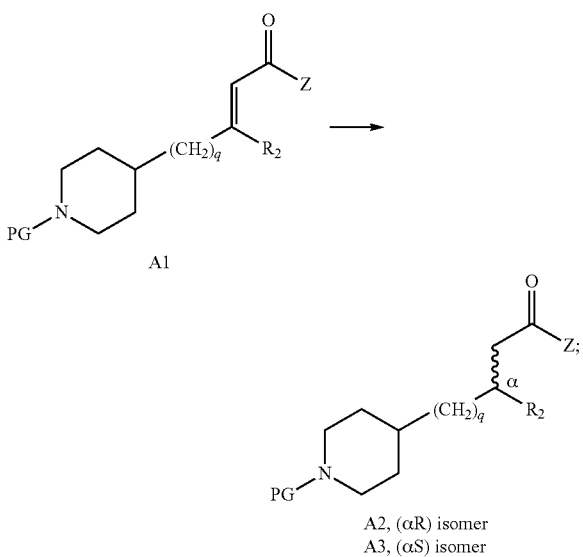

Step 2. optionally converting Compound A2 or Compound A3, each wherein Z is hydroxy, to a Compound A2 or Compound A3, each wherein Z is —O—$C_{1-8}$alkyl;

Step 3. optionally hydrogenating Compound A2 or Compound A3, when $R_2$ is selected from -aryl($R_8$) and -heteroaryl($R_8$), with a second hydrogen source and a hydrogenation agent, in a second solvent at an elevated second temperature and an elevated second pressure to provide an isomeric mixture of a Compound A4, Compound A5, Compound A6 and Compound A7, wherein $R_2$ is selected from -cycloalkyl($R_8$) or -heterocyclyl($R_8$), hydrogenated from the corresponding -aryl($R_8$) and -heteroaryl($R_8$), respectively, of Compound A2 or Compound A3:

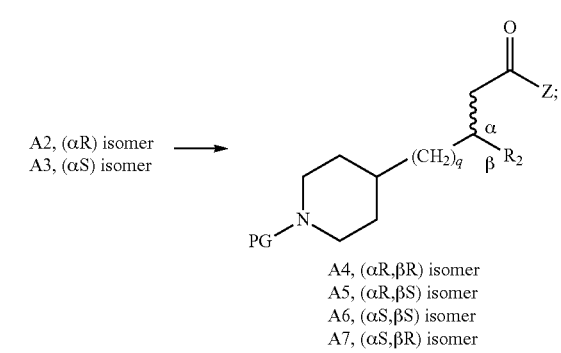

Step 4. when any of Compound A4, Compound A5, Compound A6 or Compound A7, wherein Z is hydroxy, are present, converting each such compound into the corresponding Compound A4, Compound A5, Compound A6 or Compound A7, wherein Z is —O—$C_{1-8}$alkyl;

Step 5. separating each of Compound A2, Compound A3, Compound A4, Compound A5, Compound A6 and Compound A7, each wherein Z is —O—$C_{1-8}$alkyl, from the isomeric mixture;

Step 6. deprotecting the compound selected from Compound A2 to Compound A7, each wherein Z is —O—$C_{1-8}$alkyl, to provide a corresponding compound respectively selected from Compound A8 to a Compound A13:

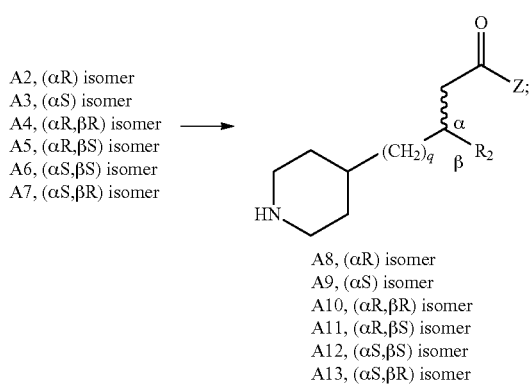

A2, (αR) isomer
A3, (αS) isomer
A4, (αR,βR) isomer
A5, (αR,βS) isomer
A6, (αS,βS) isomer
A7, (αS,βR) isomer A8, (αR) isomer
A9, (αS) isomer
A10, (αR,βR) isomer
A11, (αR,βS) isomer
A12, (αS,βS) isomer
A13, (αS,βR) isomer Step 7. reacting the compound selected from Compound A8 to Compound A13, each wherein Z is —O—$C_{1-8}$alkyl, with a Compound A14 to provide a corresponding compound respectively selected from Compound A15 to a Compound A20 of Formula (I):

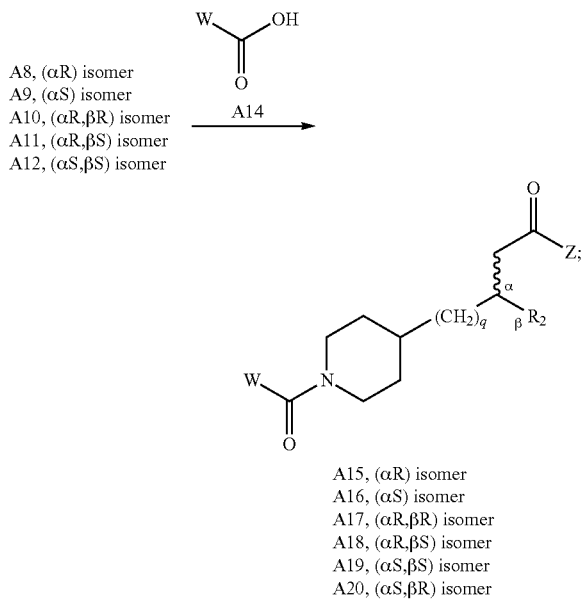

A8, (αR) isomer
A9, (αS) isomer
A10, (αR,βR) isomer
A11, (αR,βS) isomer
A12, (αS,βS) isomer A15, (αR) isomer
A16, (αS) isomer
A17, (αR,βR) isomer
A18, (αR,βS) isomer
A19, (αS,βS) isomer
A20, (αS,βR) isomer and Step 8. converting the compound selected from Compound A15 to Compound A20, each wherein Z is —O—$C_{1-8}$alkyl, to a corresponding Compound A15 to Compound A20, each wherein Z is hydroxy, of Formula (I).

The process described herein above optionally further comprises the step of:

Step 5a dehydrogenating Compound A7, wherein Z is —O—$C_{1-8}$alkyl and $R_2$ is selected from -cycloalkyl($R_8$) or -heterocyclyl($R_8$), to Compound A3, wherein Z is —O—$C_{1-8}$alkyl and $R_2$ is selected from -aryl($R_8$) or -heteroaryl($R_8$), dehydrogenated from the corresponding -cycloalkyl($R_8$) or -heterocyclyl($R_8$), respectively, of Compound A7, and then repeating Step 3 using said Compound A3 as the starting material.

An Example 1 of the invention includes a process wherein the first hydrogen source is selected from gaseous hydrogen or an excess of formic acid.

An Example 2 of the invention includes a process wherein the first ligand-metal complex consists essentially of a first ligand conjugated with a first metal adduct,
wherein the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R)-iPr-PhanePhos, (S)-iPr-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Ph-PHOX, (S)-Ph-PHOX, (R)-iPr-PHOX, (S)-iPr-PHOX, (R)-Me-BoPhoz, (S)-Me-BoPhoz, $CF_3$Ph-(R)-Me-BoPhoz, $CF_3$Ph-(S)-Me-BoPhoz, (R)-Phenethyl-(R)-Me-BoPhoz, (R)-Phenethyl-(S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, PCy-(S)-Me-BoPhoz, (R)-iPr-BoPhoz, (S)-iPr-BoPhoz, (R)-Et-BoPhoz, (S)-Et-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz and (S)-Bn-BoPhoz, and wherein the first metal adduct is selected from the group consisting of [Rh(COD)$_2$]BF$_4$, [Rh(COD)$_2$]OTf, [Rh(ethylene)$_2$Cl]$_2$, [Rh(ethylene)$_2$(acac)], [Rh(CO)$_2$(acac)], [Rh(COD)Cl]$_2$, [Rh(COD)(acac)], [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$, [Ru(mesitylene)Cl$_2$]$_2$, [Ir(COD)Cl]$_2$, [Ir(COD)$_2$]BF$_4$ and [Ir(COD)$_2$]BAr$_F$.

An Example 3 of the invention includes a process wherein the first ligand metal complex is selected from the group consisting of (R)-An-Phanephos/[Rh(COD)]BF$_4$, (R)-Binol-(R)-Me-BoPhoz&[Ir(COD)Cl]$_2$, (R)-Bn-BoPhoz&[Ir(COD)Cl]$_2$, (R)-Et-BoPhoz&[Ir(COD)Cl]$_2$, (R)-iPr-BoPhoz&[Ir(COD)Cl]$_2$, (R)-iPr-BoPhoz&[Rh(COD)$_2$]OTf, (R)-iPr-PHOX/[Ir(COD)]BAr$_F$, (R)-iPr-PHOX/[Ir(COD)]BF$_4$, (R)-Me-BoPhoz&[Ir(COD)Cl]$_2$, (R)-Me-BoPhoz&[Rh(CO)$_2$(acac)], (R)-Me-BoPhoz&[Rh(COD)$_2$]OTf, (R)-Me-BoPhoz&[Rh(ethylene)$_2$(acac)], (R)-Me-BoPhoz&[Rh(ethylene)$_2$Cl]$_2$, (R)-Me-BoPhoz/[RuCl$_2$(DMF)$_2$], (R)-MeOXyl-PhanePhos/[Rh(COD)]BF$_4$, (R)-Phanephos&[Ir(COD)Cl]$_2$, (R)-PhanePhos/[Rh(COD)]BF$_4$, (R)-PhanePhos&[Rh(COD)$_2$]OTf, (R)-Phanephos&[Rh(ethylene)$_2$Cl]$_2$, (R)-PhanePhos/[RuCl$_2$(DMF)$_2$], (R)-Ph-BoPhoz&[Ir(COD)Cl]$_2$, (R)-Phenethyl-(R)-BoPhoz&[Rh(ethylene)$_2$Cl]$_2$, (R)-Phenethyl-(S)-BoPhoz&[Ir(COD)Cl]$_2$, (R)-Phenethyl-(S)-BoPhoz&[Rh(ethylene)$_2$Cl]$_2$, (R)-Phenethyl-(S)-Me-BoPhoz&[Ir(COD)Cl]$_2$, (R)-Ph-PHOX/[Ir(COD)]BAr$_F$, (R)—P-Phos&[Ir(COD)Cl]$_2$, (R)-Tol-Binap/[RuCl(p-cymene)]Cl, (R)-Xyl-Binap&[Ir(COD)Cl]$_2$, (R)-Xyl-PhanePhos&[Ir(COD)Cl]$_2$, (R)-Xyl-Phanephos/[Rh(COD)]BF$_4$, (R)-Xyl-PhanePhos&[Ru(COD)(CF$_3$COO)$_2$]$_2$, (R)-Xyl-PhanePhos&[Ru(COD)(methylallyl)$_2$], (R)-Xyl-PhanePhos/[RuCl$_2$(DMF)$_2$], (R)-Xyl-P-Phos&[Ir(COD)Cl]$_2$, (R)-Xyl-P-Phos&[Rh(CO)$_2$(acac)], (R)-Xyl-P-Phos&[Rh(ethylene)$_2$(acac)], (R)-Xyl-P-Phos&[Rh(ethylene)$_2$Cl]$_2$, (R)-Xyl-P-Phos&[Ru(p-cymene)Cl]Cl, (R)-Xyl-P-Phos/[RuCl$_2$(DMF)$_2$], (R,R)-MeDuPhos/[Rh(COD)]BF$_4$, (S)-Binol-(R)-Me-BoPhoz&[Ir(COD)Cl]$_2$, (S)-Binol-(R)-Me-BoPhoz&[Rh(COD)$_2$]OTf, (S)-Ethyl-Naphthyl-(R)-BoPhoz&[Ir(COD)Cl]$_2$, (S)-iPr-PhanePhos/[Rh(COD)]BF$_4$, (S)-Me-BoPhoz&[Ir(COD)Cl]$_2$, (S)-Me-BoPhoz/[RuCl$_2$(DMF)$_2$], (S)-PhanePhos&[Ir(COD)Cl]$_2$, (S)-Phanephos/[Rh(COD)]BF$_4$, (S)-PhanePhos/[RuCl$_2$(DMF)$_2$], (S)—P-Phos/[Ir(COD)Cl], (S)—P-Phos&[Ir(COD)Cl]$_2$, (S)—P-Phos/[Ru(benzene)Cl]Cl, (S)—P-Phos/[RuCl$_2$(DMF)$_2$], (S)-Tol-Binap/[RuCl(p-cymene)]Cl, (S)-Tol-P-Phos&[Ir(COD)Cl]$_2$, (S)-Xyl-Binap&[Ir(COD)Cl]$_2$, (S)-Xyl-PhanePhos&[Ir(COD)Cl]$_2$, (S)-Xyl-PhanePhos&[Rh(COD)$_2$]OTf, (S)-Xyl-PhanePhos/[RuCl$_2$(DMF)$_2$], (S)-Xyl-P-Phos/[Ir(COD)Cl], (S)-Xyl-P-Phos&[Ir(COD)Cl]$_2$, (S)-Xyl-P-Phos/[RuCl$_2$(DMF)$_2$], 2,4,6-F$_3$Ph-(R)-Me-BoPhoz&[Ir(COD)Cl]$_2$, 3,4-diClPh-(R)-Me-BoPhoz&[Ir(COD)Cl]$_2$, CF$_3$Ph-(R)-Me-BoPhoz&[Rh(COD)$_2$]OTf, DPPF&[Ir(COD)Cl]$_2$, DtBPF&[Ir(COD)Cl]$_2$, PCy-(R)-Me-BoPhoz&[Ir(COD)Cl]$_2$, PCy-(R)-Me-BoPhoz&[Rh(COD)$_2$]OTf, pFPh-(R)-Bn-BoPhoz&[Ir(COD)Cl]$_2$, pFPh-(R)-Et-BoPhoz&[Ir(COD)Cl]$_2$, pFPh-(R)-Me-BoPhoz&[Ir(COD)Cl]$_2$ and Xyl-(R)-Me-BoPhoz&[Ir(COD)Cl]$_2$.

An Example 4 of the invention includes a process wherein the first solvent is selected from the group consisting of MeOH, DCE, EtOH, IPA, THF, toluene, EtOAc, 2-propanol and DMF and mixtures thereof.

An Example 5 of the invention includes a process wherein the optional first additive is selected from the group consisting of AcOH, Et$_3$N, HBF$_4$, HBF$_4$ etherate, HCl, HCl etherate, CF$_3$COOH, CH$_3$COOH and TsOH, and, when present, is in an amount up to about 1.2 Eq.

An Example 6 of the invention includes a process wherein the first temperature is in a range of from about 25° C. to about 90° C., or is in a range of from about 50° C. to about 90° C.

An Example 7 of the invention includes a process wherein the first pressure is in a range of from about 3 bar to about 30 bar, or is in a range of from about 25 bar to about 30 bar.

An Example 8 of the invention includes a process wherein, when Z is hydroxy for Compound A1,
the first ligand is selected from the group consisting of (R)-Xyl-PhanePhos, (S)-Xyl-PhanePhos, (R)-PhanePhos, (S)-PhanePhos, (R)-An-PhanePhos, (S)-An-PhanePhos, (R)-Me-BoPhoz, (S)-Me-BoPhoz, (R)-MeOXyl-PhanePhos, (S)-MeOXyl-PhanePhos, (R)-iPr-PhanePhos, (S)-iPr-PhanePhos, PCy-(R)-Me-BoPhoz and PCy-(S)-Me-BoPhoz,
the first metal adduct is selected from the group consisting of [Rh(COD)$_2$]BF$_4$, [Rh(COD)$_2$]OTf, [Rh(ethylene)$_2$Cl]$_2$, [Rh(ethylene)$_2$(acac)], [Rh(CO)$_2$(acac)], [Rh(COD)Cl]$_2$, [Rh(COD)(acac)], [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$, [Ru(mesitylene)Cl$_2$]$_2$, [Ir(COD)Cl]$_2$, [Ir(COD)$_2$]BF$_4$ and [Ir(COD)$_2$]BAr$_F$,
the first temperature is in a range of from about 25° C. to about 70° C., and
the first pressure is in a range of from about 3 bar to about 30 bar.

An Example 9 of the invention includes a process wherein, when Z is hydroxy for Compound A1, the first ligand-metal complex is selected from the group consisting of (R)-An-PhanePhos/[Rh(COD)]BF$_4$, (R)-Me-BoPhoz&[Ir(COD)Cl]$_2$, (R)-MeOXyl-PhanePhos/[Rh(COD)]BF$_4$, (R)-PhanePhos/[Rh(COD)]BF$_4$, (R)-PhanePhos&[Rh(COD)$_2$]OTf, (R)-PhanePhos/[RuCl$_2$(DMF)$_2$], (R)-Tol-Binap/[RuCl(p-cymene)]Cl, (R)-Xyl-PhanePhos&[Ru(COD)(CF$_3$COO)$_2$]$_2$, (R)-Xyl-PhanePhos&[Ru(COD)(methylallyl)$_2$], (R)-Xyl-PhanePhos/[RuCl$_2$(DMF)$_2$], (R)-Xyl-P-Phos/[RuCl$_2$(DMF)$_2$], (S)-iPr-PhanePhos/[Rh(COD)]BF$_4$, (S)-Me-BoPhoz/[RuCl$_2$(DMF)$_2$], (S)-PhanePhos/[RuCl$_2$(DMF)$_2$], (S)-Tol-Binap/[RuCl(p-cymene)]Cl, (S)-Xyl-PhanePhos&[Rh(COD)$_2$]OTf and (S)-Xyl-PhanePhos/[RuCl$_2$(DMF)$_2$].

An Example 10 of the invention includes a process wherein, when Z is hydroxy for Compound A1,
the first ligand is selected from the group consisting of (R)-Xyl-PhanePhos, (S)-Xyl-PhanePhos, (R)-PhanePhos, (S)-PhanePhos, (R)-An-PhanePhos, (S)-An-PhanePhos, (R)-Me-BoPhoz, (S)-Me-BoPhoz, (R)-MeOXyl-PhanePhos and (S)-MeOXyl-PhanePhos, and
the first metal adduct is selected from the group consisting of [Rh(COD)$_2$]BF$_4$, [Rh(COD)$_2$]OTf, [Ru(COD)(CF$_3$COO)$_2$]$_2$, [Ru(COD)(methylallyl)$_2$], [Ru(benzene)Cl$_2$]$_2$ and [Ir(COD)Cl]$_2$.

An Example 11 of the invention includes a process wherein, when Z is hydroxy for Compound A1,
the first ligand is selected from the group consisting of (R)-Xyl-PhanePhos, (S)-Xyl-PhanePhos, (R)-PhanePhos, (S)-PhanePhos, (R)-An-PhanePhos, (S)-An-PhanePhos, (R)-MeOXyl-PhanePhos and (S)-MeOXyl-PhanePhos, and
the first metal adduct is selected from the group consisting of [Rh(COD)$_2$]BF$_4$, [Rh(COD)$_2$]OTf, [Ru(COD)(CF$_3$COO)$_2$]$_2$, [Ru(COD)(methylallyl)$_2$] and [Ru(benzene)Cl$_2$]$_2$.

An Example 12 of the invention includes a process wherein, when Z is hydroxy for Compound A1,
the first ligand is selected from the group consisting of (R)-Me-BoPhoz and (S)-Me-BoPhoz,
the first metal adduct is [Ir(COD)Cl]$_2$,
the first solvent is selected from the group consisting of THF, DCE and EtOAc,
the first temperature is in a range of from about 65° C. to about 70° C., and
the first pressure is in a range of from about 25 bar to about 30 bar.

An Example 13 of the invention includes a process wherein, when Z is hydroxy for Compound A1,
the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (S)-iPr-PhanePhos and (R)-iPr-PhanePhos,
the first metal adduct is selected from the group consisting of [Rh(COD)$_2$]BF$_4$, [Rh(COD)$_2$]OTf, [Rh(ethylene)$_2$Cl]$_2$, [Rh(ethylene)$_2$(acac)], [Rh(CO)$_2$(acac)], [Rh(COD)Cl]$_2$ and [Rh(COD)(acac)],
the first solvent is MeOH, the first temperature is from about 25° C. to about 60° C., and
the first pressure is from about 3 bar to about 30 bar.

An Example 14 of the invention includes a process wherein, when Z is hydroxy for Compound A1,
the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (S)-iPr-PhanePhos and (R)-iPr-PhanePhos,
the first metal adduct is selected from the group consisting of [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$ and [Ru(mesitylene)Cl$_2$]$_2$,
the first solvent is selected from the group consisting of MeOH, EtOH, IPA, DCE, THF, toluene, EtOAc, DMF and mixtures thereof, and the optional first additive is selected from the group consisting of AcOH, CF$_3$CO$_2$H and Et$_3$N,
the first temperature is in a range of from about 40° C. to about 70° C., and
the first pressure is in a range of from about 3 bar to about 30 bar.

An Example 15 of the invention includes a process wherein, when Z is hydroxy for Compound A1,
the first ligand is (R)-XylPhanePhos,
the first metal adduct is selected from the group consisting of [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$ and [Ru(mesitylene)Cl$_2$]$_2$,
the first solvent is selected from the group consisting of MeOH, DMF and mixtures thereof,
the optional first additive is Et$_3$N,
the first temperature is in a range of from about 40° C. to about 60° C., and
the first pressure is in a range of from about 3 bar to about 30 bar.

An Example 16 of the invention includes a process wherein, when Z is hydroxy for Compound A1,
the first ligand is (R)-XylPhanePhos,
the first metal adduct is selected from the group consisting of [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$ and [Ru(mesitylene)Cl$_2$]$_2$,
the first solvent is selected from the group consisting of MeOH, DMF and mixtures thereof,
the optional first additive is AcOH,
the first temperature is about 40° C., and
the first pressure is about 10 bar.

An Example 17 of the invention includes a process wherein, when Z is hydroxy for Compound A1,
the first ligand is (R)-XylPhanePhos,
the first metal adduct is selected from the group consisting of [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$ and [Ru(mesitylene)Cl$_2$]$_2$,
the first solvent is selected from the group consisting of MeOH, EtOH, IPA, DCE, THF, toluene, EtOAc, DMF and mixtures thereof,
the first temperature is about 40° C., and
the first pressure is about 10 bar.

An Example 18 of the invention includes a process wherein, when Z is hydroxy for Compound A1,
the first ligand is (R)-XylPhanePhos,
the first metal adduct is [Ru(COD)(CF$_3$COO)$_2$]$_2$, [Ru(COD)(CH$_3$COO)$_2$] and [Ru(COD)(methylallyl)$_2$],
the first solvent is MeOH,
the first optional additive is AcOH,
the first temperature is about 40° C., and
the first pressure is about 10 bar.

An Example 19 of the invention includes a process wherein, when Z is —O—C$_{1-8}$alkyl for Compound A1,
the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R)-iPr-PhanePhos, (S)-iPr-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Ph-PHOX, (S)-Ph-PHOX, (R)-iPr-PHOX, (S)-iPr-PHOX, (R)-Me-BoPhoz, (S)-Me-BoPhoz, CF$_3$Ph-(R)-Me-BoPhoz, CF$_3$Ph-(S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, PCy-(S)-Me-BoPhoz, (R)-iPr-BoPhoz, (S)-iPr-BoPhoz, (R)-Et-BoPhoz, (S)-Et-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz and (S)-Bn-BoPhoz,
the first metal adduct is selected from the group consisting of [Ir(COD)$_2$]BAr$_F$, [Ir(COD)$_2$]BF$_4$, [Ir(COD)Cl]$_2$, [Rh(ethylene)$_2$Cl]$_2$, [Rh(ethylene)$_2$(acac)], [Rh(COD)Cl]$_2$, and [Rh(COD)(acac)],
the first solvent is selected from the group consisting of MeOH, DCE, EtOH, IPA, THF, toluene, EtOAc, DMF, and mixtures thereof,
the optional first additive is selected from the group consisting of Et$_3$N, HBF$_4$, CH$_3$COOH and TsOH, and, when present, is in an amount up to about 1.2 Eq.,
the first temperature is in a range of from about 50° C. to about 70° C., and
the first pressure is in a range of from about 10 bar to about 30 bar.

An Example 20 of the invention includes a process wherein, when Z is —O—C$_{1-8}$alkyl for Compound A1, the first ligand-metal complex is selected from the group consisting of (R)-An-Phanephos/[Rh(COD)]BF$_4$, (R)-Binol-(R)-Me-BoPhoz&[Ir(COD)Cl]$_2$, (R)-Bn-BoPhoz&[Ir(COD)Cl]$_2$, (R)-iPr-BoPhoz&[Rh(COD)$_2$]OTf, (R)-iPr-PHOX/[Ir(COD)]BAr$_F$, (R)-iPr-PHOX/[Ir(COD)]BF$_4$, (R)-Me-BoPhoz&[Ir(COD)Cl]$_2$, (R)-Me-BoPhoz&[Rh(CO)$_2$(acac)], (R)-Me-BoPhoz&[Rh(COD)$_2$]OTf, (R)-Me-BoPhoz&[Rh(ethylene)$_2$(acac)], (R)-Me-BoPhoz&[Rh(ethylene)$_2$Cl]$_2$, (R)-Me-BoPhoz/[RuCl$_2$(DMF)$_2$], (R)-Phanephos&[Ir(COD)Cl]$_2$, (R)-Phanephos&[Rh(ethylene)$_2$Cl]$_2$, (R)-Ph-BoPhoz&[Ir(COD)Cl]$_2$, (R)-Phenethyl-(R)-BoPhoz&[Rh(ethylene)$_2$Cl]$_2$, (R)-Phenethyl-(S)-BoPhoz&[Rh(ethylene)$_2$Cl]$_2$, (R)-Phenethyl-(S)-Me-BoPhoz&[Ir(COD)Cl]$_2$, (R)-Ph-PHOX/[Ir(COD)]BAr$_F$, (R)-Xyl-Phanephos/[Rh(COD)]BF$_4$, (R)-Xyl-P-Phos&[Rh(CO)$_2$(acac)], (R)-Xyl-P-Phos&[Rh(ethylene)$_2$(acac)], (R)-Xyl-P-Phos&[Rh(ethylene)$_2$Cl]$_2$, (R)-Xyl-P-Phos/[Ru(p-cymene)Cl]Cl, (R,R)-MeDuPhos/[Rh(COD)]BF$_4$, (S)-Binol-(R)-Me-BoPhoz&[Ir(COD)Cl]$_2$, (S)-Binol-(R)-Me-BoPhoz&[Rh(COD)$_2$]OTf, (S)-Me-BoPhoz&[Ir(COD)Cl]$_2$, (S)-Phanephos/[Rh(COD)]BF$_4$, (S)—P-Phos/[Ir(COD)]Cl, (S)—P-Phos/[Ru(benzene)Cl]Cl, (S)—P-Phos/[RuCl$_2$(DMF)$_2$], (S)-Xyl-P-Phos&[Ir(COD)Cl]$_2$, (S)-Xyl-P-Phos/[Ir(COD)Cl], (S)-Xyl-P-Phos/[RuCl$_2$(DMF)$_2$], 3,4-diClPh-(R)-Me-BoPhoz&[Ir(COD)Cl]$_2$, CF$_3$Ph-(R)-Me-BoPhoz&[Rh(COD)$_2$]OTf, PCy-(R)-Me-BoPhoz&[Ir(COD)Cl]$_2$ and Xyl-(R)-Me-BoPhoz&[Ir(COD)Cl]$_2$.

An Example 21 of the invention includes a process wherein, when Z is —O—C$_{1-8}$alkyl for Compound A1,
the first ligand is selected from the group consisting of (R)-PhanePhos, (S)-PhanePhos, (R)-An-PhanePhos, (R)-Xyl-PhanePhos, (S)—P-Phos, (R)-Xyl-P-Phos, (S)-Xyl-P-Phos, (R)-Ph-PHOX, (R)-iPr-PHOX, (R)-Me-BoPhoz, (S)-Me-BoPhoz, CF$_3$Ph-(R)-Me-BoPhoz, CF$_3$Ph-(S)-Me-BoPhoz, 3,4-diCl-Ph-(R)-Me-BoPhoz, 3,4-diCl-Ph-(S)-Me-BoPhoz, Xyl-(R)-Me-BoPhoz, (R)-Binol-(R)-Me-BoPhoz, (S)-Binol-(R)-Me-BoPhoz, (R)-iPr-BoPhoz, (S)-iPr-BoPhoz, (R)-Phenethyl-(S)-BoPhoz, (R)-Phenethyl-(R)-BoPhoz, (R)-Ph-BoPhoz and (R)-Bn-BoPhoz,
the first metal adduct is selected from the group consisting of [Rh(COD)$_2$]BF$_4$, [Rh(COD)$_2$]OTf, [Rh(ethylene)$_2$Cl]$_2$, [Rh(ethylene)$_2$(acac)], [Rh(CO)$_2$(acac)], [Ru(p-cymene)Cl$_2$]$_2$, [Ir(COD)Cl]$_2$ and [Ir(COD)]BAr$_F$, the first solvent is selected from the group consisting of MeOH, DCE, EtOH, toluene, EtOAc, 2-propanol, THF, and mixtures thereof, the optional first additive is selected from the group consisting of HBF$_4$, AcOH and TsOH, and, when present, is in an amount up to about 1.2 Eq., the first temperature is in a range of from about 50° C. to about 90° C., and the first pressure is in a range of from about 10 bar to about 30 bar.

An Example 22 of the invention includes a process wherein, when Z is —O—C$_{1-8}$alkyl for Compound A1, the first ligand is selected from the group consisting of (R)-PhanePhos, (S)-PhanePhos, (S)—P-Phos, (R)-Xyl-P-Phos, (S)-Xyl-P-Phos, (R)-Ph-PHOX, (R)-iPr-PHOX, (R)-Me-BoPhoz, (S)-Me-BoPhoz, CF$_3$Ph-(R)-Me-BoPhoz, CF$_3$Ph-(S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Binol-(R)-Me-BoPhoz, (S)-Binol-(R)-Me-BoPhoz, (R)-Phenethyl-(S)-BoPhoz, (R)-Phenethyl-(R)-BoPhoz, (R)-Bn-BoPhoz and (S)-Bn-BoPhoz, the first metal adduct is selected from the group consisting of [Rh(COD)$_2$]BF$_4$, [Rh(COD)$_2$]OTf, [Rh(COD)Cl]$_2$, [Rh(ethylene)$_2$Cl]$_2$, [Rh(ethylene)$_2$(acac)], [Rh(CO)$_2$(acac)], [Ru(p-cymene)Cl$_2$]$_2$, [Ir(COD)Cl]$_2$, [Ir(COD)$_2$]BF$_4$ and [Ir(COD)$_2$]BAr$_F$, the first solvent is selected from the group consisting of DCE, THF, toluene, EtOAc, and mixtures thereof, the optional first additive is selected from the group consisting of HBF$_4$ and TsOH, and, when present, is in an amount up to about 1.2 Eq., the first temperature is in a range of from about 50° C. to about 90° C., and the first pressure is about 30 bar.

An Example 23 of the invention includes a process wherein, when Z is —O—C$_{1-8}$alkyl for Compound A1, the first ligand is selected from the group consisting of (R)-Me-BoPhoz, (S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Bn-BoPhoz and (S)-Bn-BoPhoz, the first metal adduct is selected from the group consisting of [Ir(COD)Cl]$_2$ and [Ir(COD)$_2$]BAr$_F$, the first solvent is selected from the group consisting of MeOH, DCE, THF, toluene, EtOAc, IPA, and mixtures thereof, the optional first additive is HBF$_4$, and, when present, is in an amount up to about 1.2 Eq., the first temperature is in a range of from about 50° C. to about 90° C., and the first pressure is from about 25 bar to about 30 bar.

An Example 24 of the invention includes a process wherein, when R$_2$ is selected from -aryl(R$_8$) and -heteroaryl(R$_8$) for Compound A2 or Compound A3, the second hydrogen source is gaseous hydrogen, the hydrogenation agent is selected from either 10% Pd/C or a second ligand-metal complex, wherein the second ligand-metal complex consists essentially of a second ligand and an [Ir(COD)Cl]$_2$ metal adduct combined with iodine in an amount up to about 0.1 Eq., wherein 10% Pd/C is present in a range of weight % of from about 5% weight/weight (w/w) to about 20% (w/w), and wherein the second ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R)-iPr-PhanePhos, (S)-iPr-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Tol-P-Phos, (S)-Tol-P-Phos, (R)-Ph-PHOX, (S)-Ph-PHOX, (R)-iPr-PHOX, (S)-iPr-PHOX, (R)-Me-BoPhoz, (S)-Me-BoPhoz, CF$_3$Ph-(R)-Me-BoPhoz, CF$_3$Ph-(S)-Me-BoPhoz, (R)-Phenethyl-(R)-Me-BoPhoz, (R)-Phenethyl-(S)-Me-BoPhoz, (S)-Ethyl-Napthyl-(R)-Me-BoPhoz, 3,4-diCl-Ph-(R)-Me-BoPhoz, 3,4-diCl-Ph-(S)-Me-BoPhoz, (R)-2,4,6-F$_3$Ph-(R)-Me-BoPhoz, (R)-2,4,6-F$_3$Ph-(S)-Me-BoPhoz, (S)-2,4,6-F$_3$Ph-(S)-Me-BoPhoz, (S)-2,4,6-F$_3$Ph-(R)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, pFPh-(R)-Me-BoPhoz, pFPh-(S)-Me-BoPhoz, (R)-Et-BoPhoz, (S)-Et-BoPhoz, pFPh-(R)-Et-BoPhoz, pFPh-(S)-Et-BoPhoz, (R)-iPr-BoPhoz, (S)-iPr-BoPhoz, (R)-Et-BoPhoz, (S)-Et-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz, (S)-Bn-BoPhoz, pFPh-(R)-Bn-BoPhoz, pFPh-(S)-Bn-BoPhoz, (R)-Xyl-Binap, (S)-Xyl-Binap and DPPF, the second solvent is selected from the group consisting of MeOH, DCE, EtOH, IPA, THF, toluene, EtOAc, 1-BuOH and MTBE and mixtures thereof, the optional second additive is selected from the group consisting of Et$_3$N, iPr$_2$-NH, Cy$_2$NH, (R)-Ph-ethyl-NH$_2$, (S)-Ph-ethyl-NH$_2$, KI, KOH, K$_2$CO$_3$, (R/S)-camphorsulfonic acid and CH$_3$COOH, and, when present, is in an amount up to about 1.2 Eq., the second temperature is in a range of from about 30° C. to about 80° C., or is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 25 of the invention includes a process wherein, when Z is hydroxy and R$_2$ is selected from -aryl(R$_8$) and -heteroaryl(R$_8$) for Compound A2 or Compound A3, the second ligand-metal complex is selected from the group consisting of (R)-Me-BoPhoz&[Ir(COD)Cl]$_2$, (R)-PhanePhos&[Ir(COD)Cl]$_2$, (R)—P-Phos-&[Ir(COD)Cl]$_2$, (R)-Xyl-Binap&[Ir(COD)Cl]$_2$, (R)-Xyl-PhanePhos&[Ir(COD)Cl]$_2$, (R)-Xyl-P-Phos&[Ir(COD)Cl]$_2$, (s)-Me-BoPhoz&[Ir(COD)Cl]$_2$, (S)-PhanePhos&[Ir(COD)Cl]$_2$, (S)—P-Phos&[Ir(COD)Cl]$_2$, (S)-Tol-P-Phos&[Ir(COD)Cl]$_2$, (S)-Xyl-Binap&[Ir(COD)Cl]$_2$, (S)-Xyl-PhanePhos&[Ir(COD)Cl]$_2$ and (S)-Xyl-P-Phos&[Ir(COD)Cl]$_2$.

An Example 26 of the invention includes a process wherein, when Z is —O—C$_{1-8}$alkyl and R$_2$ is selected from -aryl(R$_8$) and -heteroaryl(R$_8$) for Compound A2 or Compound A3, the second ligand-metal complex is selected from the group consisting of (R)-Binol-(R)-Me-BoPhoz&[Ir(COD)Cl]$_2$, (R)-Et-BoPhoz&[Ir(COD)Cl]$_2$, (R)-iPr-BoPhoz&[Ir(COD)Cl]$_2$, (R)-Me-BoPhoz&[Ir(COD)Cl]$_2$, (R)-Ph-BoPhoz&[Ir(COD)Cl]$_2$, (R)-Phenethyl-(S)-BoPhoz&[Ir(COD)Cl]$_2$, (R)-Xyl-PhanePhos&[Ir(COD)Cl]$_2$, (R)-Xyl-P-Phos&[Ir(COD)Cl]$_2$, (S)-Binol-(R)-Me-BoPhoz&[Ir(COD)Cl]$_2$, (S)-Ethyl-Naphthyl-(R)-BoPhoz&[Ir(COD)Cl]$_2$, (S)-Me-BoPhoz&[Ir(COD)Cl]$_2$, (S)-Xyl-PhanePhos&[Ir(COD)Cl]$_2$, (S)-Xyl-P-Phos&[Ir(COD)Cl]$_2$, 2,4,6-F$_3$Ph-(R)-Me-BoPhoz&[Ir(COD)Cl]$_2$, DPPF&[Ir(COD)Cl]$_2$, DtBPF&[Ir(COD)Cl]$_2$, PCy-(R)-Me-BoPhoz&[Ir(COD)Cl]$_2$, pFPh-(R)-Bn-BoPhoz&[Ir(COD)Cl]$_2$, pFPh-(R)-Et-BoPhoz&[Ir(COD)Cl]$_2$, pFPh-(R)-Me-BoPhoz&[Ir(COD)Cl]$_2$ and Xyl-(R)-Me-BoPhoz&[Ir(COD)Cl]$_2$.

An Example 27 of the invention includes a process wherein, when Z is hydroxy and $R_2$ is selected from -aryl($R_8$) and -heteroaryl($R_8$) for Compound A2 or Compound A3, the second ligand is selected from the group consisting of (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Xyl-Binap and (S)-Xyl-Binap, the second solvent is selected from the group consisting of MeOH, DCE, EtOH, IPA, THF, toluene, EtOAc and MTBE and mixtures thereof, the second temperature is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 28 of the invention includes a process wherein, when Z is —O—$C_{1-8}$alkyl and $R_2$ is selected from -aryl($R_8$) and -heteroaryl($R_8$) for Compound A2 or Compound A3, the second ligand is selected from the group consisting of (R)-Xyl-PhanePhos, (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Phenethyl-(S)-Me-BoPhoz, (S)-Ethyl-Napthyl-(R)-Me-BoPhoz, (R)-2,4,6-$F_3$Ph-(R)-Me-BoPhoz, Xyl-(R)-Me-BoPhoz, (R)-Binol-(R)-Me-BoPhoz, (S)-Binol-(R)-Me-BoPhoz, PCy-(R)-Me-BoPhoz, pFPh-(R)-Me-BoPhoz, (R)-Et-BoPhoz, pFPh-(R)-Et-BoPhoz, (R)-iPr-BoPhoz, (R)-Ph-BoPhoz, pFPh-(R)-Bn-BoPhoz, (R)-Xyl-Binap, (S)-Xyl-Binap, DtBPF and DPPF, the second solvent is selected from the group consisting of MeOH, DCE, EtOH, IPA, THF, toluene, EtOAc, 1-BuOH and MTBE and mixtures thereof, the second temperature is in a range of from about 30° C. to about 80° C., and the second pressure is in a range of from about 3 bar to about 25 bar.

An Example 29 of the invention includes a process wherein, when $R_2$ is selected from -aryl($R_8$) and -heteroaryl ($R_8$) for Compound A2 or Compound A3, the second hydrogen source is gaseous hydrogen, 10% Pd/C is present in a range of weight % of from about 5% (w/w) to about 20% (w/w), the second solvent is selected from the group consisting of MeOH, DCE, EtOH, IPA, THF, toluene, EtOAc, I-BuOH and MTBE and mixtures thereof, the optional second additive is selected from the group consisting of $Et_3N$, $iPr_2$-NH, $Cy_2NH$, (R)-Ph-ethyl-$NH_2$, (S)-Ph-ethyl-$NH_2$, KI, KOH, $K_2CO_3$, (R/S)-camphorsulfonic acid and $CH_3COOH$, and, when present, is in an amount up to about 1.2 Eq., the second temperature is in a range of from about 30° C. to about 80° C., or is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 30 of the invention includes a process wherein, when $R_2$ is selected from -aryl($R_8$) and -heteroaryl ($R_8$) for Compound A2 or Compound A3, the second ligand-metal complex consists essentially of a second ligand and an $[Ir(COD)Cl]_2$ second metal adduct combined with iodine in an amount up to about 0.1 Eq., wherein the second ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Tol-P-Phos, (S)-Tol-P-Phos, (R)-Ph-PHOX, (S)-Ph-PHOX, (R)-iPr-PHOX, (S)-iPr-PHOX, (R)-Me-BoPhoz, (S)-Me-BoPhoz, $CF_3$Ph-(R)-Me-BoPhoz, $CF_3$Ph-(S)-Me-BoPhoz, (R)-Phenethyl-(R)-Me-BoPhoz, (R)-Phenethyl-(S)-Me-BoPhoz, (S)-Ethyl-Napthyl -(R)-Me-BoPhoz, 3,4-diCl-Ph-(R)-Me-BoPhoz, 3,4-diCl-Ph-(S)-Me-BoPhoz, (R)-2,4,6-$F_3$Ph-(R)-Me-BoPhoz, (R)-2,4,6-$F_3$Ph-(S)-Me-BoPhoz, (S)-2,4,6-$F_3$Ph-(S)-Me-BoPhoz, (S)-2,4,6-$F_3$Ph-(R)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, pFPh-(R)-Me-BoPhoz, pFPh-(S)-Me-BoPhoz, (R)-Et-BoPhoz, (S)-Et-BoPhoz, pFPh-(R)-Et-BoPhoz, pFPh-(S)-Et-BoPhoz, (R)-iPr-BoPhoz, (S)-iPr-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz, (S)-Bn-BoPhoz, pFPh-(R)-Bn-BoPhoz, pFPh-(S)-Bn-BoPhoz, (R)-Xyl-Binap, (S)-Xyl-Binap and DPPF, the second solvent is selected from the group consisting of MeOH, DCE, EtOH, IPA, THF, toluene, EtOAc, 1-BuOH and MTBE and mixtures thereof, the optional second additive is selected from the group consisting of $Et_3N$, $iPr_2$-NH, $Cy_2NH$, (R)-Ph-ethyl-$NH_2$, (S)-Ph-ethyl-$NH_2$, KI, KOH, $K_2CO_3$, (R/S)-camphorsulfonic acid and $CH_3COOH$, and, when present, is in an amount up to about 1.2 Eq., the second temperature is in a range of from about 30° C. to about 80° C., or is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 31 of the invention includes a process wherein, when Z is hydroxy and $R_2$ is selected from -aryl($R_8$) and -heteroaryl($R_8$) for Compound A2 or Compound A3, the second ligand is selected from the group consisting of (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Xyl-Binap and (S)-Xyl-Binap, the second solvent is selected from the group consisting of MeOH, DCE, EtOH, IPA, THF, toluene, EtOAc and MTBE and mixtures thereof, the second temperature is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 32 of the invention includes a process wherein, when Z is —O—$C_{1-8}$alkyl and $R_2$ is selected from -aryl($R_8$) and -heteroaryl($R_8$) for Compound A2 or Compound A3, the second ligand is selected from the group consisting of (R)-Xyl-PhanePhos, (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Phenethyl-(S)-Me-BoPhoz, (S)-Ethyl-Napthyl-(R)-Me-BoPhoz, (R)-2,4,6-$F_3$Ph-(R)-Me-BoPhoz, Xyl-(R)-Me-BoPhoz, (R)-Binol-(R)-Me-BoPhoz, (S)-Binol-(R)-Me-BoPhoz, PCy-(R)-Me-BoPhoz, pFPh-(R)-Me-BoPhoz, (R)-Et-BoPhoz, pFPh-(R)-Et-BoPhoz, (R)-iPr-BoPhoz, (R)-Ph-BoPhoz, pFPh-(R)-Bn-BoPhoz, (R)-Xyl-Binap, (S)-Xyl-Binap and DPPF, the second solvent is selected from the group consisting of MeOH, DCE, EtOH, IPA, THF, toluene, EtOAc, 1-BuOH and MTBE and mixtures thereof, the second temperature is in a range of from about 30° C. to about 80° C., and the second pressure is in a range of from about 3 bar to about 25 bar.

An Example 33 of the invention includes a process comprising the steps:

Step 1. reacting Compound A1, wherein Z is hydroxy and PG is a $C_{1-4}$alkoxycarbonyl protecting group such as Boc, with a first hydrogen source, a first ligand-metal complex consisting essentially of a first ligand conjugated with a first metal adduct, in a first solvent in the presence of an optional first additive at a first elevated temperature and a first elevated pressure, to provide a substantially pure Compound A2 or a substantially pure Compound A3, wherein the first hydrogen source is selected from gaseous hydrogen or an excess of formic acid, the first ligand is selected from the group consisting of (R)-Xyl-PhanePhos, (S)-Xyl-PhanePhos, (R)-PhanePhos, (S)-PhanePhos, (R)-An-PhanePhos, (S)-An-PhanePhos, (R)-MeOXyl-PhanePhos, (S)-MeOXyl-PhanePhos, PCy-(R)-Me-BoPhoz and PCy-(S)-Me-BoPhoz, the first metal adduct is selected from the group consisting of [Rh(COD)$_2$]BF$_4$, [Rh(COD)$_2$]OTf, [Ru(COD)(CF$_3$COO)$_2$]$_2$, [Ru(COD)(methylallyl)$_2$], [Ru(benzene)Cl$_2$]$_2$ and [Ir(COD)Cl]$_2$, the first solvent is selected from the group consisting of MeOH, EtOH, IPA, DCE, THF, toluene, EtOAc, DMF and mixtures thereof, the optional first additive is selected from the group consisting of AcOH, Et$_3$N, HBF$_4$, HBF$_4$ etherate, HCl, HCl etherate, CF$_3$COOH, CH$_3$COOH and TsOH, and, when present, is in an amount up to about 1.2 Eq., the first temperature is in a range of from about 25° C. to about 70° C., and the first pressure is in a range of from about 3 bar to about 30 bar;

Step 2. optionally converting Compound A2 or Compound A3, each wherein Z is hydroxy, to a Compound A2 or Compound A3, each wherein Z is —O—$C_{1-8}$alkyl;

Step 3. reacting Compound A2 or Compound A3, when R$_2$ is selected from -aryl(R$_8$) and -heteroaryl(R$_8$), with a second hydrogen source and a hydrogenation agent in a second solvent in the presence of an optional second additive at a second elevated temperature and a second elevated pressure to provide an isomeric mixture of a Compound A4, Compound A5, Compound A6 and Compound A7, wherein R$_2$ is selected from -cycloalkyl(R$_8$) or -heterocyclyl(R$_8$), hydrogenated from the corresponding -aryl(R$_8$) and -heteroaryl(R$_8$), respectively, of Compound A2 or Compound A3, wherein the hydrogenation agent is selected from either 10% Pd/C or a second ligand-metal complex, wherein the second ligand-metal complex consists essentially of a second ligand and an [Ir(COD)Cl]$_2$ metal adduct combined with iodine in an amount up to about 0.1 Eq., wherein 10% Pd/C is present in a range of weight % of from about 5% (w/w) to about 20% (w/w), and wherein the second ligand is selected from the group consisting of (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Xyl-Binap and (S)-Xyl-Binap, the second solvent is selected from the group consisting of MeOH, DCE, EtOH, IPA, THF, toluene, EtOAc and MTBE and mixtures thereof, the optional second additive is selected from the group consisting of Et$_3$N, iPr$_2$-NH, Cy$_2$NH, (R)-Ph-ethyl-NH$_2$, (S)-Ph-ethyl-NH$_2$, KI, KOH, K$_2$CO$_3$, (R/S)-camphorsulfonic acid and CH$_3$COOH, and, when present, is in an amount up to about 1.2 Eq., the second temperature is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 34 of the invention includes a process comprising the steps:

Step 1. reacting Compound A1, wherein Z is —O—$C_{1-8}$alkyl and PG is a $C_{1-4}$alkoxycarbonyl protecting group such as Boc, with a first hydrogen source, a first ligand-metal complex consisting essentially of a first ligand conjugated with a first metal adduct, in a first solvent in the presence of an optional first additive at a first elevated temperature and first elevated pressure, to provide a substantially pure Compound A2 or a substantially pure Compound A3, wherein the first hydrogen source is selected from gaseous hydrogen or an excess of formic acid, the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R)-iPr-PhanePhos, (S)-iPr-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Ph-PHOX, (S)-Ph-PHOX, (R)-iPr-PHOX, (S)-iPr-PHOX, (R)-Me-BoPhoz, (S)-Me-BoPhoz, CF$_3$Ph-(R)-Me-BoPhoz, CF$_3$Ph-(S)-Me-BoPhoz, (R)-Phenethyl-(R)-Me-BoPhoz, (R)-Phenethyl-(S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, PCy-(S)-Me-BoPhoz, (R)-iPr-BoPhoz, (S)-iPr-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz and (S)-Bn-BoPhoz, the first metal adduct is selected from the group consisting of [Rh(COD)$_2$]BF$_4$, [Rh(COD)$_2$]OTf, [Rh(ethylene)$_2$Cl]$_2$, [Rh(ethylene)$_2$(acac)], [Rh(CO)$_2$(acac)], [Rh(COD)(acac)], [Ru(COD)(CF$_3$COO)$_2$]$_2$, [Ru(COD)(methylallyl)$_2$], [Ru(benzene)Cl$_2$]$_2$, [Ru(p-cymene)Cl$_2$]$_2$, [Ir(COD)Cl]$_2$, [Ir(COD)$_2$]BF$_4$ and [Ir(COD)$_2$]BAr$_F$, the first solvent is selected from the group consisting of MeOH, EtOH, IPA, DCE, THF, toluene, EtOAc, DMF and mixtures thereof, the optional first additive is selected from the group consisting of AcOH, Et$_3$N, HBF$_4$, HBF$_4$ etherate, HCl, HCl etherate, CF$_3$COOH, CH$_3$COOH and TsOH, and, when present, is in an amount up to about 1.2 Eq., the first temperature is in a range of from about 25° C. to about 70° C., and the first pressure is in a range of from about 3 bar to about 30 bar; and Step 2. reacting Compound A2 or Compound A3, when R$_2$ is selected from -aryl(R$_8$) and -heteroaryl(R$_8$) and Z is —O—$C_{1-8}$alkyl, with a second hydrogen source and a hydrogenation agent in a second solvent in the presence of an optional second additive at a second elevated temperature and a second elevated pressure to provide an isomeric mixture of a Compound A4, Compound A5, Compound A6 and Compound A7, wherein R$_2$ is selected from -cycloalkyl(R$_8$) or -heterocyclyl(R$_8$), hydrogenated from the corresponding -aryl($R_8$) and -heteroaryl($R_8$), respectively, of Compound A2 or Compound A3, wherein the second hydrogen source is gaseous hydrogen, the hydrogenation agent is selected from either 10% Pd/C or a second ligand-metal complex, the second ligand-metal complex consists essentially of a second ligand and an [Ir(COD)Cl]$_2$ metal adduct combined with iodine in an amount up to about 0.1 Eq., 10% Pd/C is present in a range of weight % of from about 5% (w/w) to about 20% (w/w), the second ligand is selected from the group consisting of (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Xyl-Binap and (S)-Xyl-Binap, the second solvent is selected from the group consisting of MeOH, DCE, EtOH, IPA, THF, toluene, EtOAc and MTBE and mixtures thereof, the optional second additive is selected from the group consisting of Et$_3$N, iPr$_2$-NH, Cy$_2$NH, (R)-Ph-ethyl-NH$_2$, (S)-Ph-ethyl-NH$_2$, KI, KOH, K$_2$CO$_3$, (R/S)-camphorsulfonic acid and CH$_3$COOH, and, when present, is in an amount up to about 1.2 Eq., the second temperature is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 35 of the invention includes a process comprising the steps:

Step 1: reacting Compound A1, wherein Z is hydroxy and PG is a $C_{1-4}$alkoxycarbonyl protecting group such as Boc, with a first hydrogen source, a first ligand-metal complex consisting essentially of a first ligand conjugated with a first metal adduct, in a first solvent at a first temperature and a first pressure to provide a substantially pure Compound A2 or a substantially pure Compound A3, wherein the first hydrogen source is selected from gaseous hydrogen or an excess of formic acid, the first ligand is selected from the group consisting of (R)-Me-BoPhoz, (S)-Me-BoPhoz, (R)-Xyl-P-Phos, (S)-Xyl-P-Phos, (R)—P-Phos, (S)—P-Phos, (R)-Et-BoPhoz, (S)-Et-BoPhoz, (R)-iPr-BoPhoz, (S)-iPr-BoPhoz, (R)-Bn-BoPhoz, (S)-Bn-BoPhoz, (R)-Ph-BoPhoz, (S)-Ph-BoPhoz, the first metal adduct is [Ir(COD)Cl]$_2$, [Ir(COD)$_2$]BF$_4$ and [Ir(COD)$_2$]BAr$_F$, the first solvent is selected from the group consisting of THF, EtOAc and toluene, the first temperature is about 70° C., and the first pressure is about 25 bar, and Step 2. reacting Compound A2 or Compound A3, when R$_2$ is selected from -aryl($R_8$) and -heteroaryl($R_8$) and Z is hydroxy, by the direct addition of iodine in an amount up to about 0.1 Eq., and recharging the reaction mixture at an elevated second temperature and an elevated second pressure, wherein the second temperature is in a range of from about 30° C. to about 80° C., and the second pressure is in a range of from about 3 bar to about 25 bar.

An Example 36 of the invention includes a process wherein, when Z is hydroxy for Compound A1, the first ligand is selected from the group consisting of (R)-Me-BoPhoz and (S)-Me-BoPhoz, and the first metal adduct is [Ir(COD)Cl]$_2$.

An Example 37 of the invention includes a process comprising the steps:

Step 1. reacting Compound A1, wherein Z is —O—$C_{1-8}$alkyl and PG is a $C_{1-4}$alkoxycarbonyl protecting group such as Boc, with a first hydrogen source, a first ligand-metal complex consisting essentially of a first ligand conjugated with a first metal adduct, in a first solvent at a first temperature and a first pressure to provide a substantially pure Compound A2 or a substantially pure Compound A3, wherein the first hydrogen source is selected from gaseous hydrogen or an excess of formic acid, the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R)-iPr-PhanePhos, (S)-iPr-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Ph-PHOX, (S)-Ph-PHOX, (R)-iPr-PHOX, (S)-iPr-PHOX, (R)-Me-BoPhoz, (S)-Me-BoPhoz, CF$_3$Ph-(R)-Me-BoPhoz, CF$_3$Ph-(S)-Me-BoPhoz, (R)-Phenethyl-(R)-Me-BoPhoz, (R)-Phenethyl-(S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, PCy-(S)-Me-BoPhoz, (R)-iPr-BoPhoz, (S)-iPr-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz and (S)-Bn-BoPhoz, the first metal adduct is selected from the group consisting of [Ir(COD)Cl]$_2$, [Ir(COD)$_2$]BF$_4$ and [Ir(COD)$_2$]BAr$_F$, the first solvent is selected from the group consisting of THF, toluene, EtOAc and mixtures thereof, the first temperature is in a range of from about 25° C. to about 70° C., and the first pressure is in a range of from about 3 bar to about 30 bar; and Step 2. reacting Compound A2 or Compound A3, when R$_2$ is selected from -aryl($R_8$) and -heteroaryl($R_8$) and Z is —O—$C_{1-8}$alkyl, by the direct addition of iodine in an amount up to about 0.1 Eq., and recharging the reaction mixture at an elevated second temperature and an elevated second pressure, wherein the second temperature is in a range of from about 30° C. to about 80° C., and the second pressure is in a range of from about 3 bar to about 25 bar.

An Example 38 of the invention includes a process wherein, when Z is —O—$C_{1-8}$alkyl for Compound A1, the first ligand is selected from the group consisting of (R)-Me-BoPhoz and (S)-Me-BoPhoz, and the first metal adduct is [Ir(COD)Cl]$_2$.

An Example 39 of the invention includes a Compound A1, wherein the compound is selected from the group consisting of:

| Cpd | Names |
|---|---|
| C1 | (Z)-4-(3-methoxycarbonyl-2-quinolin-3-yl-allyl)-piperidine-1-carboxylic acid tert-butyl ester, and |
| D1 | (Z)-4-(3-carboxy-2-quinolin-3-yl-allyl)-piperidine-1-carboxylic acid tert-butyl ester. |

As used throughout the various schemes presented, the Greek letters "α" and "β" refer to targeted chiral carbon atoms in the compound of Formula (I) for enantioselective hydrogenation according to the process of the present invention. The Greek letter "α" refers to asymmetric hydrogenation of the vinyl ester bond of Compound A1, for example, that is "α" to the chiral carbon atom, wherein the bond is hydrogenated to an R or S enantiomer, depending on the isomer of the ligand-metal complex used. The Greek letter "β" refers to enantioselective hydrogenation of the $R_2$ aromatic ring system of Compound A2 or Compound A3 (wherein $R_2$ is selected from -aryl($R_8$) and -heteroaryl($R_8$)), for example, that is "β" to the chiral carbon atom, wherein the bond is hydrogenated to an isomeric mixture of Compound A4 (an αR,βR isomer), Compound A5 (an αR,βS isomer), Compound A6 (an αS,βS isomer) and Compound A7 (an αS,βR isomer) (each wherein $R_2$ is selected from -cycloalkyl($R_8$) or -heterocyclyl($R_8$)).

Alternatively, Scheme B represents a process for providing a desired isomer of a compound of Formula (I).

Scheme B

Step 1. reacting a Compound B1 with a first hydrogen source, a first ligand-metal complex consisting essentially of a first ligand conjugated with a first metal adduct, in a first solvent in the presence of an optional first additive at an elevated first temperature and an elevated first pressure to provide a substantially pure Compound B2 or a substantially pure Compound B3:

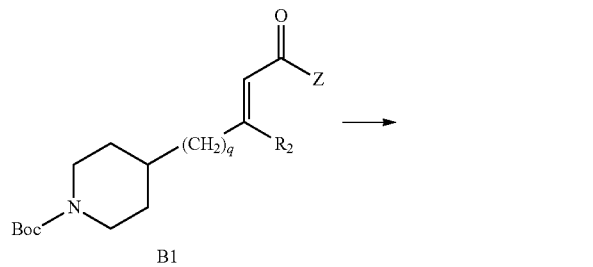

B1

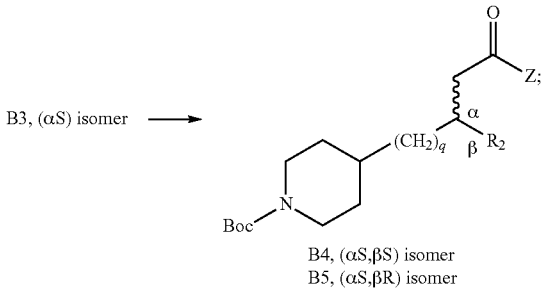

B2, (αR) isomer
B3, (αS) isomer

Step 2. optionally converting Compound B2 or Compound B3, each wherein Z is hydroxy, to a Compound B2 or a Compound B3, each wherein Z is —O—$C_{1-8}$alkyl;

Step 3. optionally reacting Compound B3, when $R_2$ is selected from -aryl($R_8$) and -heteroaryl($R_8$), with a second hydrogen source and a hydrogenation agent in a second solvent at an elevated second temperature and an elevated second pressure to provide an isomeric mixture of a Compound B4 and Compound B5, wherein $R_2$ is selected from -cycloalkyl($R_8$) or -heterocyclyl($R_8$), hydrogenated from the corresponding -aryl($R_8$) and -heteroaryl($R_8$), respectively, of Compound B3:

B3, (αS) isomer ⟶

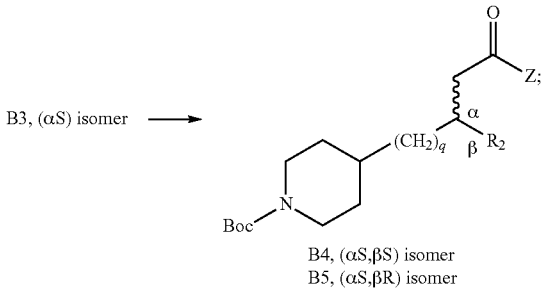

B4, (αS,βS) isomer
B5, (αS,βR) isomer

Step 4. converting the isomeric mixture of Compound B4 and Compound B5, each when Z is hydroxy, to an isomeric mixture of Compound B4 and Compound B5, each wherein Z is —O—$C_{1-8}$alkyl;

Step 5. separating each of Compound B4 and Compound B5, each wherein Z is —O—$C_{1-8}$alkyl, from the isomeric mixture;

Step 6. optionally dehydrogenating Compound B5, wherein Z is —O—$C_{1-8}$alkyl and $R_2$ is selected from -cycloalkyl($R_8$) or -heterocyclyl($R_8$), to Compound B3, wherein Z is —O—$C_{1-8}$alkyl and $R_2$ is selected from -aryl($R_8$) or -heteroaryl($R_8$), dehydrogenated from the corresponding -cycloalkyl($R_8$) or -heterocyclyl($R_8$), respectively, of Compound B5, and then repeating Step 3 using said Compound B3 as the starting material;

Step 7. deprotecting Compound B4, wherein Z is —O—$C_{1-8}$alkyl, to provide a Compound B6:

B4, (αS,βS) isomer ⟶

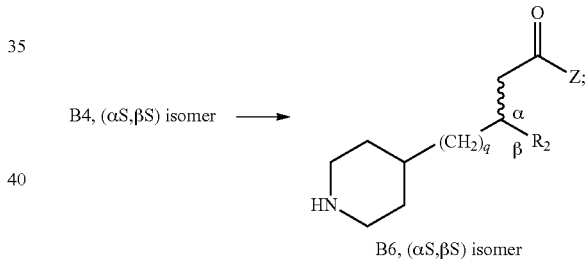

B6, (αS,βS) isomer

Step 8. reacting the Compound B6, wherein Z is —O—$C_{1-8}$alkyl, with a Compound A14 to provide a Compound B7, wherein Z is —O—$C_{1-8}$alkyl of Formula (I):

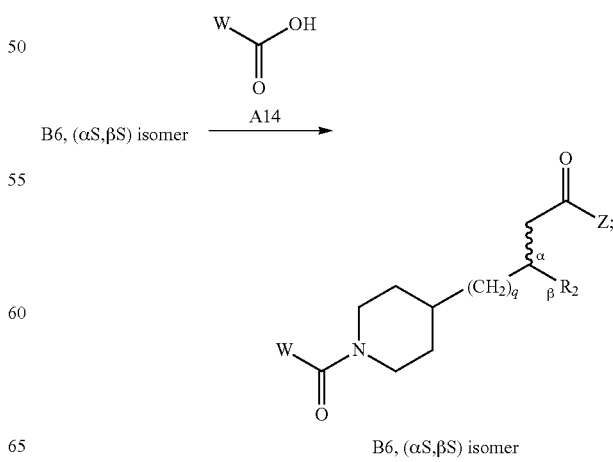

B6, (αS,βS) isomer and

Step 9. converting the Compound B7, wherein Z is —O—C$_{1-8}$alkyl, to a Compound B7, wherein Z is hydroxy, of Formula (I).

An Example 40 of the invention includes a process wherein, Compound B2 is carried forward in place of Compound B3 to provide an (αR,βR) isomer and an (αR,βS) isomer of Formula (I).

An Example 41 of the invention includes a process wherein, when Z is hydroxy for Compound B1,
the first ligand is selected from the group consisting of (R)-Xyl-PhanePhos, (S)-Xyl-PhanePhos, (R)-PhanePhos, (S)-PhanePhos, (R)-An-PhanePhos, (S)-An-PhanePhos, (R)-Me-BoPhoz, (S)-Me-BoPhoz, (R)-MeOXyl-PhanePhos, (S)-MeOXyl-PhanePhos, (R)-iPr-PhanePhos, (S)-iPr-PhanePhos, (S)-An-PhanePhos, (R)-Me-BoPhoz, (S)-Me-BoPhoz, (R)-MeOXyl-PhanePhos,
the first metal adduct is selected from the group consisting of [Rh(COD)$_2$]BF$_4$, [Rh(COD)$_2$]OTf, [Rh(ethylene)$_2$Cl]$_2$, [Rh(ethylene)$_2$(acac)], [Rh(CO)$_2$(acac)], [Rh(COD)$_2$Cl]$_2$, [Rh(COD)(acac)], [Ru(COD)(CF$_3$COO)$_2$]$_2$, [Ru(p-cymene)Cl$_2$]$_2$, [Ru(mesitylene)Cl$_2$]$_2$, [Ir(COD)Cl]$_2$, [Ir(COD)$_2$]BF$_4$ and [Ir(COD)$_2$]BAr$_F$,
the first temperature is in a range of from about 25° C. to about 70° C., and
the first pressure is in a range of from about 3 bar to about 30 bar.

An Example 42 of the invention includes a process wherein, when Z is hydroxy for Compound B1, the first ligand-metal complex is selected from the group consisting of (R)-An-PhanePhos/[Rh(COD)]BF$_4$, (R)-Me-BoPhoz&[Ir(COD)Cl]$_2$, (R)-MeOXyl-PhanePhos/[Rh(COD)]BF$_4$, (R)-PhanePhos/[Rh(COD)]BF$_4$, (R)-PhanePhos &[Rh(COD)$_2$]OTf, (R)-PhanePhos/[RuCl$_2$(DMF)$_2$], (R)-Tol-Binap/[RuCl(p-cymene)]Cl, (R)-Xyl-PhanePhos&[Ru(COD)(CF$_3$COO)$_2$]$_2$, (R)-Xyl-PhanePhos &[Ru(COD)(methylallyl)$_2$], (R)-Xyl-PhanePhos/[RuCl$_2$(DMF)$_2$], (R)-Xyl-PPhos/[RuCl$_2$(DMF)$_2$], (S)-iPr-PhanePhos/[Rh(COD)]BF$_4$, (S)-Me-BoPhoz/[RuCl$_2$(DMF)$_2$], (S)-PhanePhos/[RuCl$_2$(DMF)$_2$], (S)-Tol-Binap/[RuCl(p-cymene)]Cl, (S)-Xyl-PhanePhos &[Rh(COD)$_2$]OTf and (S)-Xyl-PhanePhos/[RuCl$_2$(DMF)$_2$].

An Example 43 of the invention includes a process wherein, when Z is hydroxy for Compound B1,
the first ligand is selected from the group consisting of (R)-Xyl-PhanePhos, (S)-Xyl-PhanePhos, (R)-PhanePhos, (S)-PhanePhos, (R)-An-PhanePhos, (S)-An-PhanePhos, (R)-Me-BoPhoz, (S)-Me-BoPhoz, (R)-MeOXyl-PhanePhos and (S)-MeOXyl-PhanePhos, and
the first metal adduct is selected from the group consisting of [Rh(COD)$_2$]BF$_4$, [Rh(COD)$_2$]OTf, [Ru(COD)(CF$_3$COO)$_2$]$_2$, [Ru(COD)(methylallyl)$_2$], [Ru(benzene)Cl$_2$]$_2$ and [Ir(COD)CL]$_2$.

An Example 44 of the invention includes a process wherein, when Z is hydroxy for Compound B1,
the first ligand is selected from the group consisting of (R)-Xyl-PhanePhos, (S)-Xyl-PhanePhos, (R)-PhanePhos, (S)-PhanePhos, (R)-An-PhanePhos, (S)-An-PhanePhos, (R)-Me-BoPhoz, (S)-Me-BoPhoz, (R)-MeOXyl-PhanePhos and (S)-MeOXyl-PhanePhos, and
the first metal adduct is selected from the group consisting of [Rh(COD)$_2$]BF$_4$, [Rh(COD)$_2$]OTf, [Ru(COD)(CF$_3$COO)$_2$]$_2$, [Ru(COD)(methylallyl)$_2$], [Ru(benzene)Cl$_2$]$_2$ and [Ir(COD)Cl]$_2$.

An Example 45 of the invention includes a process wherein, when Z is hydroxy for Compound B1,
the first ligand is selected from the group consisting of (R)-Me-BoPhoz and (S)-Me-BoPhoz,
the first metal adduct is [Ir(COD)Cl]$_2$,
the first solvent is selected from the group consisting of THF, DCE and EtOAc,
the first temperature is in a range of from about 65° C. to about 70° C., and
the first pressure is in a range of from about 25 bar to about 30 bar.

An Example 46 of the invention includes a process wherein, when Z is hydroxy for Compound B1,
the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (S)-iPr-PhanePhos and (R)-iPr-PhanePhos,
the first metal adduct is selected from the group consisting of [Rh(COD)$_2$]BF$_4$, [Rh(COD)$_2$]OTf, [Rh(ethylene)$_2$Cl]$_2$, [Rh(ethylene)$_2$(acac)], [Rh(CO)$_2$(acac)], [Rh(COD)Cl]$_2$ and [Rh(COD)(acac)],
the first solvent is MeOH, the first temperature is from about 25° C. to about 60° C., and
the first pressure is from about 3 bar to about 30 bar.

An Example 47 of the invention includes a process wherein, when Z is hydroxy for Compound B1,
the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (S)-iPr-PhanePhos and (R)-iPr-PhanePhos,
the first metal adduct is selected from the group consisting of [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$ and [Ru(mesitylene)Cl$_2$]$_2$,
the first solvent is selected from the group consisting of MeOH, EtOH, IPA, DCE, THF, toluene, EtOAc, DMF and mixtures thereof,
the optional first additive is selected from the group consisting of AcOH, CF$_3$CO$_2$H and Et$_3$N,
the first temperature is in a range of from about 40° C. to about 70° C., and
the first pressure is in a range of from about 3 bar to about 30 bar.

An Example 48 of the invention includes a process wherein, when Z is hydroxy for Compound B1,
the first ligand is (R)-XylPhanePhos,
the first metal adduct is selected from the group consisting of [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$ and [Ru(mesitylene)Cl$_2$]$_2$,
the first solvent is selected from the group consisting of MeOH, DMF and mixtures thereof,
the optional first additive is Et$_3$N,
the first temperature is in a range of from about 40° C. to about 60° C., and
the first pressure is in a range of from about 3 bar to about 30 bar.

An Example 49 of the invention includes a process wherein, when Z is hydroxy for Compound B1,
the first ligand is (R)-XylPhanePhos,
the first metal adduct is selected from the group consisting of [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$ and [Ru(mesitylene)Cl$_2$]$_2$, the first solvent is selected from the group consisting of MeOH, DMF and mixtures thereof,
the optional first additive is AcOH,
the first temperature is about 40° C., and
the first pressure is about 10 bar.

An Example 50 of the invention includes a process wherein, when Z is hydroxy for Compound B1,
the first ligand is (R)-XylPhanePhos,
the first metal adduct is selected from the group consisting of [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$ and [Ru(mesitylene)Cl$_2$]$_2$,
the first solvent is selected from the group consisting of MeOH, EtOH, IPA, DCE, THF, toluene, EtOAc, DMF and mixtures thereof,
the first temperature is about 40° C., and
the first pressure is about 10 bar.

An Example 51 of the invention includes a process wherein, when Z is hydroxy for Compound B1,
the first ligand is (R)-XylPhanePhos,
the first metal adduct is [Ru(COD)(CF$_3$COO)$_2$]$_2$, [Ru(COD)(CH$_3$COO)$_2$] and [Ru(COD)(methylallyl)$_2$],
the first solvent is MeOH, and
the first temperature is about 40° C., and
the first pressure is about 10 bar.

An Example 52 of the invention includes a process wherein, when Z is —O—C$_{1-8}$alkyl for Compound B1,
the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R)-iPr-PhanePhos, (S)-iPr-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Ph-PHOX, (S)-Ph-PHOX, (R)-iPr-PHOX, (S)-iPr-PHOX, (R)-Me-BoPhoz, (S)-Me-BoPhoz, CF$_3$Ph-(R)-Me-BoPhoz, CF$_3$Ph-(S)-Me-BoPhoz, (R)-Phenethyl-(S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, PCy-(S)-Me-BoPhoz, (R)-iPr-BoPhoz, (S)-iPr-BoPhoz, (R)-Et-BoPhoz, (S)-Et-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz and (S)-Bn-BoPhoz,
the first metal adduct is selected from the group consisting of [Ir(COD)$_2$]BAr$_F$, [Ir(COD)$_2$]BF$_4$, [Ir(COD)Cl]$_2$, [Rh(ethylene)$_2$Cl]$_2$, [Rh(ethylene)$_2$(acac)], [Rh(COD) Cl]$_2$, and [Rh(COD)(acac)],
the first solvent is selected from the group consisting of MeOH, DCE, EtOH, IPA, THF, toluene, EtOAc, DMF, and mixtures thereof,
the optional first additive is selected from the group consisting of Et$_3$N, HBF$_4$, CH$_3$COOH and TsOH, and, when present, is in an amount up to about 1.2 Eq.,
the first temperature is in a range of from about 50° C. to about 70° C., and
the first pressure is in a range of from about 10 bar to about 30 bar.

An Example 53 of the invention includes a process wherein, when Z is —O—C$_{1-8}$alkyl for Compound B1, the first ligand-metal complex is selected from the group consisting of (R)-An-Phanephos/[Rh(COD)]BF$_4$, (R)-Binol-(R)-Me-BoPhoz &[Ir(COD)Cl]$_2$, (R)-Bn-BoPhoz &[Ir(COD)Cl]$_2$, (R)-iPr-BoPhoz &[Rh(COD)$_2$]OTf, (R)-iPr-PHOX/[Ir(COD)]BAr$_F$, (R)-iPr-PHOX/[Ir(COD)]BF$_4$, (R)-Me-BoPhoz &[Ir(COD)Cl]$_2$, (R)-Me-BoPhoz &[Rh(CO)$_2$(acac)], (R)-Me-BoPhoz &[Rh(COD)$_2$]OTf, (R)-Me-BoPhoz &[Rh(ethylene)$_2$(acac)], (R)-Me-BoPhoz &[Rh(ethylene)$_2$Cl]$_2$, (R)-Me-BoPhoz/[RuCl$_2$(DMF)$_2$], (R)-Phanephos &[Ir(COD)Cl]$_2$, (R)-Phanephos &[Rh(ethylene)$_2$Cl]$_2$, (R)-Ph-BoPhoz &[Ir(COD)Cl]$_2$, (R)-Phenethyl-(R)-BoPhoz &[Rh(ethylene)$_2$Cl]$_2$, (R)-Phenethyl-(S)-BoPhoz &[Rh(ethylene)$_2$Cl]$_2$, (R)-Phenethyl-(S)-Me-BoPhoz &[Ir(COD)Cl]$_2$, (R)-Ph-PHOX/[Ir(COD)]BAr$_F$, (R)-Xyl-Phanephos/[Rh(COD)]BF$_4$, (R)-Xyl-P-Phos &[Rh(CO)$_2$(acac)], (R)-Xyl-P-Phos &[Rh(ethylene)$_2$(acac)], (R)-Xyl-P-Phos &[Rh(ethylene)$_2$Cl]$_2$, (R)-Xyl-P-Phos/[Ru(p-cymene)Cl]Cl, (R,R)-MeDuPhos/[Rh(COD)]BF$_4$, (S)-Binol-(R)-Me-BoPhoz &[Ir(COD)Cl]$_2$, (S)-Binol-(R)-Me-BoPhoz &[Rh(COD)$_2$]OTf, (S)-Me-BoPhoz &[Ir(COD)Cl]$_2$, (S)-PhanePhos/[Rh(COD)]BF$_4$, (S)—P-Phos/[Ir(COD)]Cl, (S)—P-Phos&[Ir(COD)Cl]$_2$, (S)—P-Phos/[Ru(benzene)Cl]Cl, (S)—P-Phos/[RuCl$_2$(DMF)$_2$], (S)-Xyl-P-Phos/[Ir(COD)]Cl, (S)-Xyl-P-Phos &[Ir(COD)Cl]$_2$, (S)-Xyl-P-Phos/[RuCl$_2$(DMF)$_2$], 3,4-diClPh-(R)-Me-BoPhoz &[Ir(COD)Cl]$_2$, CF$_3$Ph-(R)-Me-BoPhoz &[Rh(COD)$_2$]OTf, PCy-(R)-Me-BoPhoz&[Ir(COD)Cl]$_2$ and Xyl-(R)-Me-BoPhoz &[Ir(COD)Cl]$_2$.

An Example 54 of the invention includes a process wherein, when Z is —O—C$_{1-8}$alkyl for Compound B1,
the first ligand is selected from the group consisting of (R)-PhanePhos, (S)-PhanePhos, (R)-An-PhanePhos, (R)-Xyl-PhanePhos, (S)—P-Phos, (R)-Xyl-P-Phos, (S)-Xyl-P-Phos, (R)-Ph-PHOX, (R)-iPr-PHOX, (R)-Me-BoPhoz, (S)-Me-BoPhoz, CF$_3$Ph-(R)-Me-BoPhoz, CF$_3$Ph-(S)-Me-BoPhoz, 3,4-diCl-Ph-(R)-Me-BoPhoz, 3,4-diCl-Ph-(S)-Me-BoPhoz, Xyl-(R)-Me-BoPhoz, (R)-Binol-(R)-Me-BoPhoz, (S)-Binol-(R)-Me-BoPhoz, (R)-iPr-BoPhoz, (S)-iPr-BoPhoz, (R)-Phenethyl-(S)-BoPhoz, (R)-Phenethyl-(R)-BoPhoz, (R)-Ph-BoPhoz and (R)-Bn-BoPhoz,
the first metal adduct is selected from the group consisting of [Rh(COD)$_2$]BF$_4$, [Rh(COD)$_2$]OTf, [Rh(ethylene)$_2$Cl]$_2$, [Rh(ethylene)$_2$(acac)], [Rh(CO)$_2$(acac)], [Ru(p-cymene)Cl$_2$]$_2$, [Ir(COD)Cl]$_2$ and [Ir(COD)$_2$]BAr$_F$,
the first solvent is selected from the group consisting of MeOH, DCE, EtOH, toluene, EtOAc, 2-propanol, THF, and mixtures thereof,
the optional first additive is selected from the group consisting of HBF$_4$, AcOH and TsOH, and, when present, is in an amount up to about 1.2 Eq.,
the first temperature is in a range of from about 50° C. to about 90° C., and
the first pressure is in a range of from about 10 bar to about 30 bar.

An Example 55 of the invention includes a process wherein, when Z is —O—C$_{1-8}$alkyl for Compound B1,
the first ligand is selected from the group consisting of (R)-PhanePhos, (S)-PhanePhos, (S)—P-Phos, (R)-Xyl-P-Phos, (S)-Xyl-P-Phos, (R)-Ph-PHOX, (R)-iPr-PHOX, (R)-Me-BoPhoz, (S)-Me-BoPhoz, CF$_3$Ph-(R)-Me-BoPhoz, CF$_3$Ph-(S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Binol-(R)-Me-BoPhoz, (S)-Binol-(R)-Me-BoPhoz, (R)-Phenethyl-(S)-BoPhoz, (R)-Phenethyl-(R)-BoPhoz, (R)-Bn-BoPhoz and (S)-Bn-BoPhoz,
the first metal adduct is selected from the group consisting of [Rh(COD)$_2$]BF$_4$, [Rh(COD)$_2$]OTf, [Rh(COD)Cl]$_2$, [Rh(ethylene)$_2$Cl]$_2$, [Rh(ethylene)$_2$(acac)], [Rh(CO)$_2$(acac)], [Ru(p-cymene)Cl$_2$]$_2$, [Ir(COD)Cl]$_2$, [Ir(COD)$_2$]BF$_4$ and [Ir(COD)$_2$]BAr$_F$,
the first solvent is selected from the group consisting of DCE, THF, toluene, EtOAc, and mixtures thereof, the optional first additive is selected from the group consisting of $HBF_4$ and TsOH, and, when present, is in an amount up to about 1.2 Eq., the first temperature is in a range of from about 50° C. to about 90° C., and the first pressure is about 30 bar.

An Example 56 of the invention includes a process wherein, when Z is —O—$C_{1-8}$alkyl for Compound B1, the first ligand is selected from the group consisting of (R)-Me-BoPhoz, (S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Bn-BoPhoz and (S)-Bn-BoPhoz, the first metal adduct is selected from the group consisting of $[Ir(COD)Cl]_2$ and $[Ir(COD)_2]BAr_F$, the first solvent is selected from the group consisting of MeOH, DCE, THF, toluene, EtOAc, IPA, and mixtures thereof, the first temperature is in a range of from about 50° C. to about 90° C., and the first pressure is from about 25 bar to about 30 bar.

An Example 57 of the invention includes a process wherein, when $R_2$ is selected from -aryl($R_8$) and -heteroaryl ($R_8$) for Compound B2 or Compound B3, the second hydrogen source is gaseous hydrogen, the hydrogenation agent is selected from either 10% Pd/C or a second ligand-metal complex, wherein the second ligand-metal complex consists essentially of a second ligand and an $[Ir(COD)Cl]_2$ metal adduct combined with iodine in an amount up to about 0.1 Eq., wherein 10% Pd/C is present in a range of weight % of from about 5% weight/weight (w/w) to about 20% (w/w), and wherein the second ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R)-iPr-PhanePhos, (S)-iPr-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Tol-P-Phos, (S)-Tol-P-Phos, (R)-Ph-PHOX, (S)-Ph-PHOX, (R)-iPr-PHOX, (S)-iPr-PHOX, (R)-Me-BoPhoz, (S)-Me-BoPhoz, $CF_3$Ph-(R)-Me-BoPhoz, $CF_3$Ph-(S)-Me-BoPhoz, (R)-Phenethyl-(R)-Me-BoPhoz, (R)-Phenethyl-(S)-Me-BoPhoz, (S)-Ethyl-Naphtyl-(R)-Me-BoPhoz, 3,4-diCl-Ph-(R)-Me-BoPhoz, 3,4-diCl-Ph-(S)-Me-BoPhoz, (R)-2,4,6-$F_3$Ph-(R)-Me-BoPhoz, (R)-2,4,6-$F_3$Ph-(S)-Me-BoPhoz, (S)-2,4,6-$F_3$Ph-(S)-Me-BoPhoz, (S)-2,4,6-$F_3$Ph-(R)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, pFPh-(R)-Me-BoPhoz, pFPh-(S)-Me-BoPhoz, (R)-Et-BoPhoz, (S)-Et-BoPhoz, pFPh-(R)-Et-BoPhoz, pFPh-(S)-Et-BoPhoz, (R)-iPr-BoPhoz, (S)-iPr-BoPhoz, (R)-Et-BoPhoz, (S)-Et-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz, (S)-Bn-BoPhoz, pFPh-(R)-Bn-BoPhoz, pFPh-(S)-Bn-BoPhoz, (R)-Xyl-Binap, (S)-Xyl-Binap and DPPF, the second solvent is selected from the group consisting of MeOH, DCE, EtOH, IPA, THF, toluene, EtOAc, 1-BuOH and MTBE and mixtures thereof, the optional second additive is selected from the group consisting of $Et_3N$, $iPr_2$-NH, $Cy_2NH$, (R)-Ph-ethyl-$NH_2$, (S)-Ph-ethyl-$NH_2$, KI, KOH, $K_2CO_3$, (R/S)-camphorsulfonic acid and $CH_3COOH$, and, when present, is in an amount up to about 1.2 Eq., the second temperature is in a range of from about 30° C. to about 80° C., or is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 58 of the invention includes a process wherein, when Z is hydroxy and $R_2$ is selected from -aryl($R_8$) and -heteroaryl($R_8$) for Compound B2 or Compound B3, the second ligand-metal complex is selected from the group consisting of (R)-Me-BoPhoz &$[Ir(COD)Cl]_2$, (R)-PhanePhos &$[Ir(COD)Cl]_2$, (R)—P-Phos &$[Ir(COD)Cl]_2$, (R)-Xyl-Binap &$[Ir(COD)Cl]_2$, (R)-Xyl-PhanePhos &$[Ir(COD)Cl]_2$, (R)-Xyl-P-Phos &$[Ir(COD)Cl]_2$, (S)-Me-BoPhoz &$[Ir(COD)Cl]_2$, (S)-PhanePhos &$[Ir(COD)Cl]_2$, (S)—P-Phos&$[Ir(COD)Cl]_2$, (S)-Tol-P-Phos&$[Ir(COD)Cl]_2$, (S)-Xyl-Binap &$[Ir(COD)Cl]_2$, (S)-Xyl-PhanePhos &$[Ir(COD)Cl]_2$ and (S)-Xyl-P-Phos &$[Ir(COD)CL]_2$.

An Example 59 of the invention includes a process wherein, when Z is —O—$C_{1-8}$alkyl and $R_2$ is selected from -aryl($R_8$) and -heteroaryl($R_8$) for Compound B2 or Compound B3, the second ligand-metal complex is selected from the group consisting of (R)-Binol-(R)-Me-BoPhoz &$[Ir(COD)Cl]_2$, (R)-Et-BoPhoz &$[Ir(COD)Cl]_2$, (R)-iPr-BoPhoz &$[Ir(COD)Cl]_2$, (R)-Me-BoPhoz &$[Ir(COD)Cl]_2$, (R)-Ph-BoPhoz &$[Ir(COD)Cl]_2$, (R)-Phenethyl-(S)-BoPhoz &$[Ir(COD)Cl]_2$, (R)-Xyl-PhanePhos &$[Ir(COD)Cl]_2$, (R)-Xyl-P-Phos &$[Ir(COD)Cl]_2$, (S)-Binol-(R)-Me-BoPhoz &$[Ir(COD)Cl]_2$, (S)-Ethyl-Naphthyl-(R)-BoPhoz &$[Ir(COD)Cl]_2$, (S)-Me-BoPhoz &$[Ir(COD)Cl]_2$, (S)-Xyl-PhanePhos &$[Ir(COD)Cl]_2$, (S)-Xyl-P-Phos &$[Ir(COD)Cl]_2$, 2,4,6-$F_3$Ph-(R)-Me-BoPhoz &$[Ir(COD)Cl]_2$, DPPF &$[Ir(COD)Cl]_2$, DtBPF &$[Ir(COD)Cl]_2$, PCy-(R)-Me-BoPhoz &$[Ir(COD)Cl]_2$, pFPh-(R)-Bn-BoPhoz &$[Ir(COD)Cl]_2$, pFPh-(R)-Et-BoPhoz &$[Ir(COD)Cl]_2$, pFPh-(R)-Me-BoPhoz &$[Ir(COD)Cl]_2$ and Xyl-(R)-Me-BoPhoz &$[Ir(COD)Cl]_2$.

An Example 60 of the invention includes a process wherein, when Z is hydroxy and $R_2$ is selected from -aryl($R_8$) and -heteroaryl($R_8$) for Compound B2 or Compound B3, the second ligand is selected from the group consisting of (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Xyl-Binap and (S)-Xyl-Binap, the second solvent is selected from the group consisting of MeOH, DCE, EtOH, IPA THF, toluene, EtOAc and MTBE and mixtures thereof, the second temperature is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 61 of the invention includes a process wherein, when Z is —O—$C_{1-8}$alkyl and $R_2$ is selected from -aryl($R_8$) and -heteroaryl($R_8$) for Compound B2 or Compound B3, the second ligand is selected from the group consisting of (R)-Xyl-PhanePhos, (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Phenethyl-(S)-Me-BoPhoz, (S)-Ethyl-Naphtyl-(R)-Me-BoPhoz, (R)-2,4,6-$F_3$Ph-(R)-Me-BoPhoz, Xyl-(R)-Me-BoPhoz, (R)-Binol-(R)-Me-BoPhoz, (S)-Binol-(R)-Me-BoPhoz, PCy-(R)-Me-BoPhoz, pFPh-(R)-Me-BoPhoz, (R)-Et-BoPhoz, pFPh-(R)-Et-BoPhoz, (R)-iPr-BoPhoz, (R)-Ph-BoPhoz, pFPh-(R)-Bn-BoPhoz, (R)-Xyl-Binap, (S)-Xyl-Binap, DtBPF and DPPF, the second solvent is selected from the group consisting of MeOH, DCE, EtOH, IPA, THF, toluene, EtOAc, 1-BuOH and MTBE and mixtures thereof, the second temperature is in a range of from about 30° C. to about 80° C., and the second pressure is in a range of from about 3 bar to about 25 bar.

An Example 62 of the invention includes a process wherein, when $R_2$ is selected from -aryl($R_8$) and -heteroaryl ($R_8$) for Compound B2 or Compound B3, the second hydrogen source is gaseous hydrogen, 10% Pd/C is present in a range of weight % of from about 5% (w/w) to about 20% (w/w), the second solvent is selected from the group consisting of MeOH, DCE, EtOH, IPA, THF, toluene, EtOAc, 1-BuOH and MTBE and mixtures thereof, the optional second additive is selected from the group consisting of Et$_3$N, iPr$_2$-NH, Cy$_2$NH, (R)-Ph-ethyl-NH$_2$, (S)-Ph-ethyl-NH$_2$, KI, KOH, K$_2$CO$_3$, (R/S)-camphorsulfonic acid and CH$_3$COOH, and, when present, is in an amount up to about 1.2 Eq., the second temperature is in a range of from about 30° C. to about 80° C., or is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 63 of the invention includes a process wherein, when $R_2$ is selected from -aryl($R_8$) and -heteroaryl ($R_8$) for Compound B2 or Compound B3, the second ligand-metal complex consists essentially of a second ligand and an [Ir(COD)Cl]$_2$ second metal adduct combined with iodine in an amount up to about 0.1 Eq., wherein the second ligand is selected from the group consisting of (R)-PhanePhos, (S)-PhanePhos, (R)-An-Phane-Phos, (S)-An-PhanePhos, (R)-Xyl-PhanePhos, (S)-Xyl-PhanePhos, (R)-MeOXyl-PhanePhos, (S)-MeOXyl-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Tol-P-Phos, (S)-Tol-P-Phos, (R)-Ph-PHOX, (S)-Ph-PHOX, (R)-iPr-PHOX, (S)-iPr-PHOX, (R)-Me-BoPhoz, (S)-Me-BoPhoz, CF$_3$Ph-(R)-Me-BoPhoz, CF$_3$Ph-(S)-Me-BoPhoz, (R)-Phenethyl-(R)-Me-BoPhoz, (R)-Phenethyl-(S)-Me-BoPhoz, (S)-Ethyl-Napthyl-(R)-Me-BoPhoz, 3,4-diCl-Ph-(R)-Me-BoPhoz, 3,4-diCl-Ph-(S)-Me-BoPhoz, (R)-2,4,6-F$_3$Ph-(R)-Me-BoPhoz, (R)-2,4,6-F$_3$Ph-(S)-Me-BoPhoz, (S)-2,4,6-F$_3$Ph-(S)-Me-BoPhoz, (S)-2,4,6-F$_3$Ph-(R)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, pFPh-(R)-Me-BoPhoz, pFPh-(S)-Me-BoPhoz, (R)-Et-BoPhoz, (S)-Et-BoPhoz, pFPh-(R)-Et-BoPhoz, pFPh-(S)-Et-BoPhoz, (R)-iPr-BoPhoz, (S)-iPr-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz, (S)-Bn-BoPhoz, pFPh-(R)-Bn-BoPhoz, pFPh-(S)-Bn-BoPhoz, (R)-Xyl-Binap, (S)-Xyl-Binap and DPPF, the second solvent is selected from the group consisting of MeOH, DCE, EtOH, IPA, THF, toluene, EtOAc, 1-BuOH and MTBE and mixtures thereof, the optional second additive is selected from the group consisting of Et$_3$N, iPr$_2$-NH, Cy$_2$NH, (R)-Ph-ethyl-NH$_2$, (S)-Ph-ethyl-NH$_2$, KI, KOH, K$_2$CO$_3$, (R/S)-camphorsulfonic acid and CH$_3$COOH, and, when present, is in an amount up to about 1.2 Eq., the second temperature is in a range of from about 30° C. to about 80° C., or is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 64 of the invention includes a process wherein, when Z is hydroxy and $R_2$ is selected from -aryl($R_8$) and -heteroaryl($R_8$) for Compound B2 or Compound B3, the second ligand is selected from the group consisting of (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Xyl-Binap and (S)-Xyl-Binap, the second solvent is selected from the group consisting of MeOH, DCE, EtOH, IPA, THF, toluene, EtOAc and MTBE and mixtures thereof, the second temperature is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 65 of the invention includes a process wherein, when Z is —O—C$_{1-8}$alkyl and $R_2$ is selected from -aryl($R_8$) and -heteroaryl($R_8$) for Compound B2 or Compound B3, the second ligand is selected from the group consisting of (R)-Xyl-PhanePhos, (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Phenethyl-(S)-Me-BoPhoz, (S)-Ethyl-Napthyl-(R)-Me-BoPhoz, (R)-2,4,6-F$_3$Ph-(R)-Me-BoPhoz, Xyl-(R)-Me-BoPhoz, (R)-Binol-(R)-Me-BoPhoz, (S)-Binol-(R)-Me-BoPhoz, PCy-(R)-Me-BoPhoz, pFPh-(R)-Me-BoPhoz, (R)-Et-BoPhoz, pFPh-(R)-Et-BoPhoz, (R)-iPr-BoPhoz, (R)-Ph-BoPhoz, pFPh-(R)-Bn-BoPhoz, (R)-Xyl-Binap, (S)-Xyl-Binap and DPPF, the second solvent is selected from the group consisting of MeOH, DCE, EtOH, IPA, THF, toluene, EtOAc, 1-BuOH and MTBE and mixtures thereof, the second temperature is in a range of from about 30° C. to about 80° C., and the second pressure is in a range of from about 3 bar to about 25 bar.

An Example 66 of the invention includes a process comprising the steps:

Step 1. reacting Compound B1, wherein Z is hydroxy, with a first hydrogen source, a first ligand-metal complex consisting essentially of a first ligand conjugated with a first metal adduct, in a first solvent in the presence of an optional first additive at a first elevated temperature and a first elevated pressure, to provide a substantially pure Compound B2 or a substantially pure Compound B3, wherein the first hydrogen source is selected from gaseous hydrogen or an excess of formic acid, the first ligand is selected from the group consisting of (R)-Xyl-PhanePhos, (S)-Xyl-PhanePhos, (R)-PhanePhos, (S)-PhanePhos, (R)-An-PhanePhos, (S)-An-PhanePhos, (R)-MeOXyl-PhanePhos, (S)-MeOXyl-PhanePhos, PCy-(R)-Me-BoPhoz and PCy-(S)-Me-BoPhoz, the first metal adduct is selected from the group consisting of [Rh(COD)$_2$]BF$_4$, [Rh(COD)$_2$]OTf, [Ru(COD)(CF$_3$COO)$_2$]$_2$, [Ru(COD)(methylallyl)$_2$], [Ru(benzene)Cl$_2$]$_2$ and [Ir(COD)Cl]$_2$, the first solvent is selected from the group consisting of MeOH, EtOH, IPA, DCE, THF, toluene, EtOAc, DMF and mixtures thereof, the optional first additive is selected from the group consisting of AcOH, Et$_3$N, HBF$_4$, HBF$_4$ etherate, HCl, HCl etherate, CF$_3$COOH, CH$_3$COOH and TsOH, and, when present, is in an amount up to about 1.2 Eq., the first temperature is in a range of from about 25° C. to about 70° C., and the first pressure is in a range of from about 3 bar to about 30 bar;

Step 2. optionally converting Compound B2 or Compound B3, each wherein Z is hydroxy, to a Compound B2 or Compound B3, each wherein Z is —O—C$_{1-8}$alkyl;

Step 3. reacting Compound B2 or Compound B3, when R$_2$ is selected from -aryl(R$_8$) and -heteroaryl(R$_8$), with a second hydrogen source and a hydrogenation agent in a second solvent in the presence of an optional second additive at a second elevated temperature and a second elevated pressure to provide an isomeric mixture of a Compound B4 and Compound B5, wherein R$_2$ is selected from -cycloalkyl (R$_8$) or -heterocyclyl(R$_8$), hydrogenated from the corresponding -aryl(R$_8$) and -heteroaryl(R$_8$), respectively, of Compound B2 or Compound B3, wherein the hydrogenation agent is selected from either 10% Pd/C or a second ligand-metal complex, wherein the second ligand-metal complex consists essentially of a second ligand and an [Ir(COD)Cl]$_2$ metal adduct combined with iodine in an amount up to about 0.1 Eq., wherein 10% Pd/C is present in a range of weight % of from about 5% (w/w) to about 20% (w/w), and wherein the second ligand is selected from the group consisting of (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Xyl-Binap and (S)-Xyl-Binap, the second solvent is selected from the group consisting of MeOH, DCE, EtOH, IPA, THF, toluene, EtOAc and MTBE and mixtures thereof, the optional second additive is selected from the group consisting of Et$_3$N, iPr$_2$-NH, Cy$_2$NH, (R)-Ph-ethyl-NH$_2$, (S)-Ph-ethyl-NH$_2$, KI, KOH, K$_2$CO$_3$, (R/S)-camphorsulfonic acid and CH$_3$COOH, and, when present, is in an amount up to about 1.2 Eq., the second temperature is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 67 of the invention includes a process comprising the steps:

Step 1. reacting Compound B1, wherein Z is —O—C$_{1-8}$alkyl, with a first hydrogen source, a first ligand-metal complex consisting essentially of a first ligand conjugated with a first metal adduct, in a first solvent in the presence of an optional first additive at a first elevated temperature and first elevated pressure, to provide a substantially pure Compound B2 or a substantially pure Compound B3, wherein the first hydrogen source is selected from gaseous hydrogen or an excess of formic acid, the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R)-iPr-PhanePhos, (S)-iPr-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Ph-PHOX, (S)-Ph-PHOX, (R)-iPr-PHOX, (S)-iPr-PHOX, (R)-Me-BoPhoz, (S)-Me-BoPhoz, CF$_3$Ph-(R)-Me-BoPhoz, CF$_3$Ph-(S)-Me-BoPhoz, (R)-Phenethyl-(R)-Me-BoPhoz, (R)-Phenethyl-(S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, PCy-(S)-Me-BoPhoz, (R)-iPr-BoPhoz, (S)-iPr-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz and (S)-Bn-BoPhoz, the first metal adduct is selected from the group consisting of [Rh(COD)$_2$]BF$_4$, [Rh(COD)$_2$]OTf, [Rh(ethylene)$_2$Cl]$_2$, [Rh(ethylene)$_2$(acac)], [Rh(CO)$_2$(acac)], [Rh(COD) (acac)], [Ru(COD)(CF$_3$COO)$_2$]$_2$, [Ru(COD)(methylallyl)$_2$], [Ru(benzene)Cl$_2$]$_2$, [Ru(p-cymene)Cl$_2$]$_2$, [Ir (COD)Cl]$_2$, [Ir(COD)$_2$]BF$_4$ and [Ir(COD)$_2$]BAr$_F$, the first solvent is selected from the group consisting of MeOH, EtOH, IPA, DCE, THF, toluene, EtOAc, DMF and mixtures thereof, the optional first additive is selected from the group consisting of AcOH, Et$_3$N, HBF$_4$, HBF$_4$ etherate, HCl, HCl etherate, CF$_3$COOH, CH$_3$COOH and TsOH, and, when present, is in an amount up to about 1.2 Eq., the first temperature is in a range of from about 25° C. to about 70° C., and the first pressure is in a range of from about 3 bar to about 30 bar; and Step 2. reacting Compound B2 or Compound B3, when R$_2$ is selected from -aryl(R$_8$) and -heteroaryl(R$_8$) and Z is —O—C$_{1-8}$alkyl, with a second hydrogen source and a hydrogenation agent in a second solvent in the presence of an optional second additive at a second elevated temperature and a second elevated pressure to provide an isomeric mixture of a Compound B4 and Compound B5, wherein R$_2$ is selected from -cycloalkyl(R$_8$) or -heterocyclyl(R$_8$), hydrogenated from the corresponding -aryl(R$_8$) and -heteroaryl(R$_8$), respectively, of Compound B2 or Compound B3, wherein the second hydrogen source is gaseous hydrogen, the hydrogenation agent is selected from either 10% Pd/C or a second ligand-metal complex, the second ligand-metal complex consists essentially of a second ligand and an [Ir(COD)Cl]$_2$ metal adduct combined with iodine in an amount up to about 0.1 Eq., 10% Pd/C is present in a range of weight % of from about 5% (w/w) to about 20% (w/w), the second ligand is selected from the group consisting of (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Xyl-Binap and (S)-Xyl-Binap, the second solvent is selected from the group consisting of MeOH, DCE, EtOH, IPA, THF, toluene, EtOAc and MTBE and mixtures thereof, the optional second additive is selected from the group consisting of Et$_3$N, iPr$_2$-NH, Cy$_2$NH, (R)-Ph-ethyl-NH$_2$, (S)-Ph-ethyl-NH$_2$, KI, KOH, K$_2$CO$_3$, (R/S)-camphorsulfonic acid and CH$_3$COOH, and, when present, is in an amount up to about 1.2 Eq., the second temperature is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 68 of the invention includes a process comprising the steps:

Step 1. reacting Compound B1, wherein Z is hydroxy, with a first hydrogen source, a first ligand-metal complex consisting essentially of a first ligand conjugated with a first metal adduct, in a first solvent at a first temperature and a first pressure to provide a substantially pure Compound B2 or a substantially pure Compound B3, wherein the first hydrogen source is selected from gaseous hydrogen or an excess of formic acid, the first ligand is selected from the group consisting of (R)-Me-BoPhoz, (S)-Me-BoPhoz, (R)-Xyl-P-Phos, (S)-Xyl-P-Phos, (R)—P-Phos, (S)—P-Phos, (R)-Et-BoPhoz, (S)-Et-BoPhoz, (R)-iPr-BoPhoz, (S)-iPr-BoPhoz, (R)-Bn-BoPhoz, (S)-Bn-BoPhoz, (R)-Ph-BoPhoz, (S)-Ph-BoPhoz, the first metal adduct is $[Ir(COD)Cl]_2$, $[Ir(COD)_2]BF_4$ and $[Ir(COD)_2]BAr_F$, the first solvent is selected from the group consisting of THF, EtOAc and toluene, the first temperature is about 70° C., and the first pressure is about 25 bar, and Step 2. reacting Compound B2 or Compound B3, when $R_2$ is selected from -aryl($R_8$) and -heteroaryl($R_8$) and Z is hydroxy, by the direct addition of iodine in an amount up to about 0.1 Eq., and recharging the reaction mixture at an elevated second temperature and an elevated second pressure, wherein the second temperature is in a range of from about 30° C. to about 80° C., and the second pressure is in a range of from about 3 bar to about 25 bar.

An Example 69 of the invention includes a process wherein, when Z is hydroxy for Compound B1, the first ligand is selected from the group consisting of (R)-Me-BoPhoz and (S)-Me-BoPhoz, and the first metal adduct is $[Ir(COD)Cl]_2$.

An Example 70 of the invention includes a process comprising the steps:

Step 1. reacting Compound B1, wherein Z is —O—$C_{1-8}$alkyl, with a first hydrogen source, a first ligand-metal complex consisting essentially of a first ligand conjugated with a first metal adduct, in a first solvent at a first temperature and a first pressure to provide a substantially pure Compound B2 or a substantially pure Compound B3, wherein the first hydrogen source is selected from gaseous hydrogen or an excess of formic acid, the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R)-iPr-PhanePhos, (S)-iPr-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Ph-PHOX, (S)-Ph-PHOX, (R)-iPr-PHOX, (S)-iPr-PHOX, (R)-Me-BoPhoz, (S)-Me-BoPhoz, $CF_3$Ph-(R)-Me-BoPhoz, $CF_3$Ph-(S)-Me-BoPhoz, (R)-Phenethyl-(R)-Me-BoPhoz, (R)-Phenethyl-(S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, PCy-(S)-Me-BoPhoz, (R)-iPr-BoPhoz, (S)-iPr-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz and (S)-Bn-BoPhoz, the first metal adduct is selected from the group consisting of $[Ir(COD)Cl]_2$, $[Ir(COD)_2]BF_4$ and $[Ir(COD)_2]BAr_F$, the first solvent is selected from the group consisting of THF, toluene, EtOAc and mixtures thereof, the first temperature is in a range of from about 25° C. to about 70° C., and the first pressure is in a range of from about 3 bar to about 30 bar; and Step 2. reacting Compound B2 or Compound B3, when $R_2$ is selected from -aryl($R_8$) and -heteroaryl($R_8$) and Z is —O—$C_{1-8}$alkyl, by the direct addition of iodine in an amount up to about 0.1 Eq., and recharging the reaction mixture at an elevated second temperature and an elevated second pressure, wherein the second temperature is in a range of from about 30° C. to about 80° C., and the second pressure is in a range of from about 3 bar to about 25 bar.

An Example 71 of the invention includes a process wherein, when Z is —O—$C_{1-8}$alkyl for Compound B1, the first ligand is selected from the group consisting of (R)-Me-BoPhoz and (S)-Me-BoPhoz, and the first metal adduct is $[Ir(COD)Cl]_2$.

The present invention further relates to a process, as shown in Scheme C, for preparing a compound of Formula (Ia) and intermediates thereof:

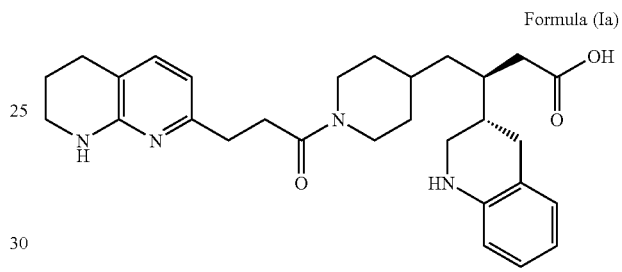

Formula (Ia)

comprising the steps of:

Scheme C

Step 1. reacting a Compound C1 with a first hydrogen source, a first ligand-metal complex consisting essentially of a first ligand conjugated with a first metal adduct, in a first solvent in the presence of an optional first additive at an elevated first temperature and an elevated first pressure to provide a substantially pure Compound C3:

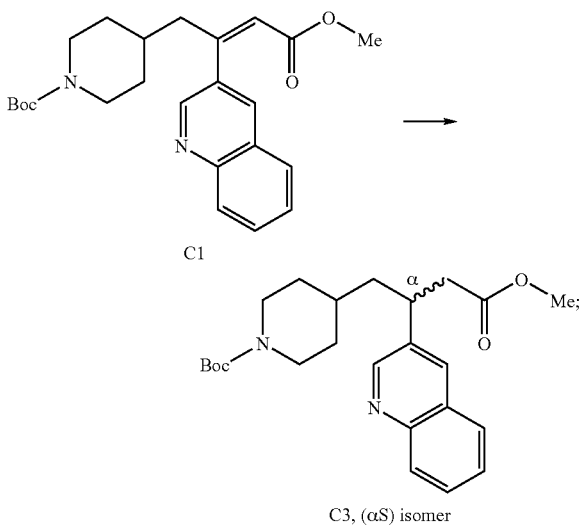

C3, (αS) isomer

Step 2. reacting Compound C3 with a second hydrogen source and a hydrogenation agent in a second solvent in the presence of an optional second additive at an elevated second temperature and an elevated second pressure to provide an isomeric mixture of a Compound C4 and Compound C5:

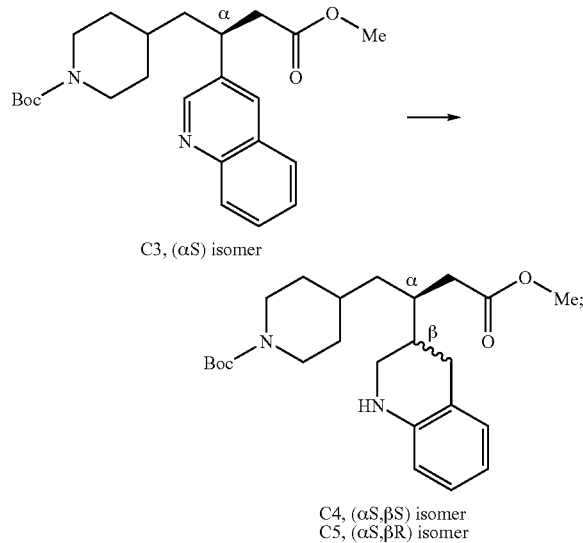

C3, (αS) isomer

C4, (αS,βS) isomer
C5, (αS,βR) isomer

Step 3. separating each of Compound C4 and Compound C5 from the isomeric mixture;

Step 4. optionally dehydrogenating Compound C5 to Compound C3, and then repeating Step 2 using said Compound C3 as the starting material;

Step 5. deprotecting the Compound C4 to provide a Compound C6:

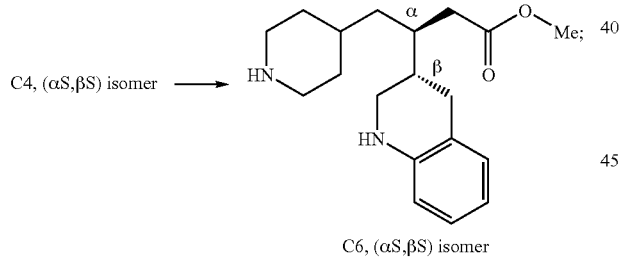

C4, (αS,βS) isomer → C6, (αS,βS) isomer

Step 6. reacting Compound C6 with a Compound C7 to provide a Compound C8:

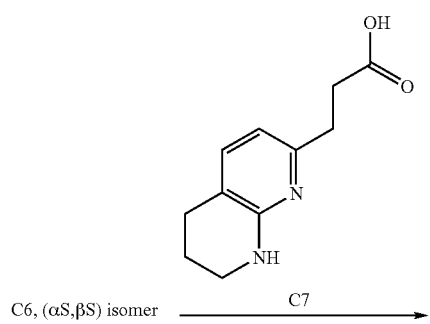

C6, (αS,βS) isomer    C7

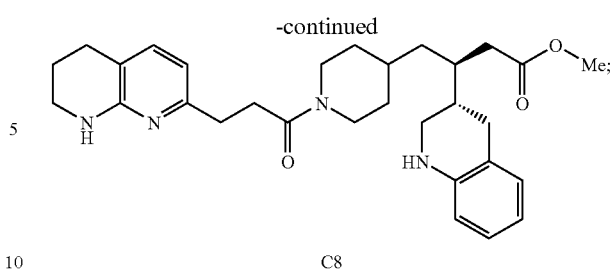

C8 and

Step 7. converting Compound C8 to the compound of Formula (Ia).

The present invention provides a process for making substantially pure Compound C2 comprising the step of:
reacting a Compound C1 with a first hydrogen source, a first ligand-metal complex consisting essentially of a first ligand conjugated with a first metal adduct, in a first solvent in the presence of an optional first additive at an elevated first temperature and an elevated first pressure to provide a substantially pure Compound C2:

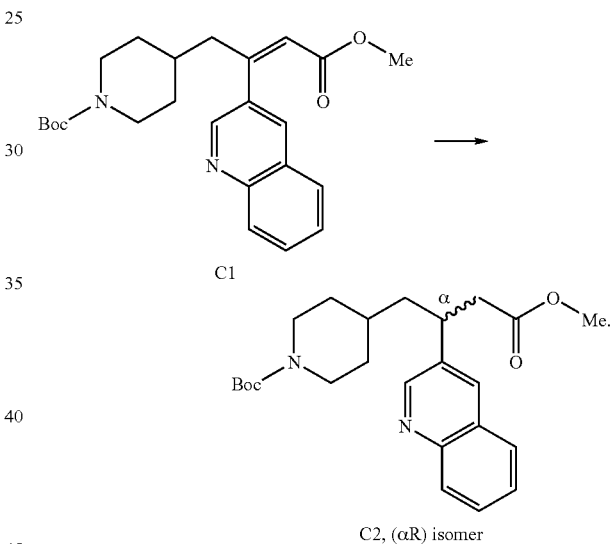

C1

C2, (αR) isomer

An Example 72 of the invention includes a process wherein Compound C2 is carried forward in place of Compound C3 to provide an (αR,βR) isomer and an (αR,βS) isomer of Formula (I).

An Example 73 of the invention includes a process for reacting Compound C1 to provide Compound C2, and a process for reacting Compound C1 to provide Compound C3, both processes as described herein above, wherein the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R)-iPr-PhanePhos, (S)-iPr-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Ph-PHOX, (S)-Ph-PHOX, (R)-iPr-PHOX, (S)-iPr-PHOX, (R)-Me-BoPhoz, (S)-Me-BoPhoz, CF$_3$Ph-(R)-Me-BoPhoz, CF$_3$Ph-(S)-Me-BoPhoz, (R)-Phenethyl-(S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol- (R)-Me-BoPhoz, PCy-(R)-Me-BoPhoz, PCy-(S)-Me-BoPhoz, (R)-iPr-BoPhoz, (S)-iPr-BoPhoz, (R)-Et-BoPhoz, (S)-Et-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz and (S)-Bn-BoPhoz, the first metal adduct is selected from the group consisting of [Ir(COD)$_2$]BAr$_F$, [Ir(COD)$_2$]BF$_4$, [Ir(COD)Cl]$_2$, [Rh(ethylene)$_2$Cl]$_2$, [Rh(ethylene)$_2$(acac)], [Rh(COD)Cl]$_2$, and [Rh(COD)(acac)], the first solvent is selected from the group consisting of MeOH, DCE, EtOH, IPA, THF, toluene, EtOAc, DMF, and mixtures thereof, the optional first additive is selected from the group consisting of Et$_3$N, HBF$_4$, CH$_3$COOH and TsOH, and, when present, is in an amount up to about 1.2 Eq., the first temperature is in a range of from about 50° C. to about 70° C., and the first pressure is in a range of from about 10 bar to about 30 bar.

An Example 74 of the invention includes a process for reacting Compound C1, wherein the first ligand-metal complex is selected from the group consisting of (R)-An-Phanephos/[Rh(COD)]BF$_4$, (R)-Binol-(R)-Me-BoPhoz &[Ir(COD)Cl]$_2$, (R)-Bn-BoPhoz &[Ir(COD)Cl]$_2$, (R)-iPr-BoPhoz &[Rh(COD)$_2$]OTf, (R)-iPr-PHOX/[Ir(COD)]BAr$_F$, (R)-iPr-PHOX/[Ir(COD)]BF$_4$, (R)-Me-BoPhoz &[Ir(COD)Cl]$_2$, (R)-Me-BoPhoz &[Rh(CO)$_2$(acac)], (R)-Me-BoPhoz &[Rh(COD)$_2$]OTf, (R)-Me-BoPhoz &[Rh(ethylene)$_2$(acac)], (R)-Me-BoPhoz &[Rh(ethylene)$_2$Cl]$_2$, (R)-Me-BoPhoz/[RuCl$_2$(DMF)$_2$], (R)-Phanephos &[Ir(COD)Cl]$_2$, (R)-Phanephos &[Rh(ethylene)$_2$Cl]$_2$, (R)-Ph-BoPhoz &[Ir(COD)Cl]$_2$, (R)-Phenethyl-(R)-BoPhoz &[Rh(ethylene)$_2$Cl]$_2$, (R)-Phenethyl-(S)-BoPhoz &[Rh(ethylene)$_2$C]$_2$, (R)-Phenethyl-(S)-Me-BoPhoz &[Ir(COD)Cl]$_2$, (R)-Ph-PHOX/[Ir(COD)]BAr$_F$, (R)-Xyl-Phanephos/[Rh(COD)]BF$_4$, (R)-Xyl-P-Phos &[Rh(CO)$_2$(acac)], (R)-Xyl-P-Phos &[Rh(ethylene)$_2$(acac)], (R)-Xyl-P-Phos &[Rh(ethylene)$_2$Cl]$_2$, (R)-Xyl-P-Phos/[Ru(p-cymene)Cl]Cl, (R,R)-MeDuPhos/[Rh(COD)]BF$_4$, (S)-Binol-(R)-Me-BoPhoz &[Ir(COD)Cl]$_2$, (S)-Binol-(R)-Me-BoPhoz &[Rh(COD)$_2$]OTf, (S)-Me-BoPhoz &[Ir(COD)Cl]$_2$, (S)-PhanePhos/[Rh(COD)]BF$_4$, (S)—P-Phos/[Ir(COD)]Cl, (S)—P-Phos &[Ir(COD)Cl]$_2$, (S)—P-Phos/[Ru(benzene)Cl]Cl, (S)—P-Phos/[RuCl$_2$(DMF)$_2$], (S)-Xyl-P-Phos/[Ir(COD)]Cl, (S)-Xyl-P-Phos &[Ir(COD)Cl]$_2$, (S)-Xyl-P-Phos/[RuCl$_2$(DMF)$_2$], 3,4-diClPh-(R)-Me-BoPhoz &[Ir(COD)Cl]$_2$, CF$_3$Ph-(R)-Me-BoPhoz &[Rh(COD)$_2$]OTf, PCy-(R)-Me-BoPhoz &[Ir(COD)Cl]$_2$ and Xyl-(R)-Me-BoPhoz &[Ir(COD)Cl]$_2$.

An Example 75 of the invention includes a process for reacting Compound C1, wherein the first ligand is selected from the group consisting of (R)-PhanePhos, (S)-PhanePhos, (R)-An-PhanePhos, (R)-Xyl-PhanePhos, (S)—P-Phos, (R)-Xyl-P-Phos, (S)-Xyl-P-Phos, (R)-Ph-PHOX, (R)-iPr-PHOX, (R)-Me-BoPhoz, (S)-Me-BoPhoz, CF$_3$Ph-(R)-Me-BoPhoz, CF$_3$Ph-(S)-Me-BoPhoz, 3,4-diCl-Ph-(R)-Me-BoPhoz, 3,4-diCl-Ph-(S)-Me-BoPhoz, Xyl-(R)-Me-BoPhoz, (R)-Binol-(R)-Me-BoPhoz, (S)-Binol-(R)-Me-BoPhoz, (R)-iPr-BoPhoz, (S)-iPr-BoPhoz, (R)-Phenethyl-(S)-BoPhoz, (R)-Phenethyl-(R)-BoPhoz, (R)-Ph-BoPhoz and (R)-Bn-BoPhoz, the first metal adduct is selected from the group consisting of [Rh(COD)$_2$]BF$_4$, [Rh(COD)$_2$]OTf, [Rh(ethylene)$_2$Cl]$_2$, [Rh(ethylene)$_2$(acac)], [Rh(CO)$_2$(acac)], [Ru(p-cymene)Cl$_2$]$_2$, [Ir(COD)Cl]$_2$ and [Ir(COD)$_2$]BAr$_F$, the first solvent is selected from the group consisting of MeOH, DCE, EtOH, toluene, EtOAc, 2-propanol, THF, and mixtures thereof, the optional first additive is selected from the group consisting of HBF$_4$, AcOH and TsOH, and, when present, is in an amount up to about 1.2 Eq., the first temperature is in a range of from about 50° C. to about 90° C., and the first pressure is in a range of from about 10 bar to about 30 bar.

An Example 76 of the invention includes a process for reacting Compound C1, wherein the first ligand is selected from the group consisting of (R)-PhanePhos, (S)-PhanePhos, (S)—P-Phos, (R)-Xyl-P-Phos, (S)-Xyl-P-Phos, (R)-Ph-PHOX, (R)-iPr-PHOX, (R)-Me-BoPhoz, (S)-Me-BoPhoz, CF$_3$Ph-(R)-Me-BoPhoz, CF$_3$Ph-(S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Binol-(R)-Me-BoPhoz, (S)-Binol-(R)-Me-BoPhoz, (R)-Phenethyl-(S)-BoPhoz, (R)-Phenethyl-(R)-BoPhoz, (R)-Bn-BoPhoz and (S)-Bn-BoPhoz, the first metal adduct is selected from the group consisting of [Rh(COD)$_2$]BF$_4$, [Rh(COD)$_2$]OTf, [Rh(COD) Cl]$_2$, [Rh (ethylene)$_2$Cl]$_2$, [Rh(ethylene)$_2$(acac)], [Rh(CO)$_2$(acac)], [Ru(p-cymene)Cl$_2$]$_2$, [Ir(COD)Cl]$_2$, [Ir(COD)$_2$]BF$_4$ and [Ir(COD)$_2$]BAr$_F$, the first solvent is selected from the group consisting of DCE, THF, toluene, EtOAc, and mixtures thereof, the optional first additive is selected from the group consisting of HBF$_4$ and TsOH, and, when present, is in an amount up to about 1.2 Eq., the first temperature is in a range of from about 50° C. to about 90° C., and the first pressure is about 30 bar.

An Example 77 of the invention includes a process for reacting Compound C1, wherein the first ligand is selected from the group consisting of (R)-Me-BoPhoz, (S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Bn-BoPhoz and (S)-Bn-BoPhoz, the first metal adduct is selected from the group consisting of [Ir(COD)Cl]$_2$ and [Ir(COD)$_2$]BAr$_F$, the first solvent is selected from the group consisting of MeOH, DCE, THF, toluene, EtOAc, IPA, and mixtures thereof, the optional first additive is HBF$_4$, and, when present, is in an amount up to about 1.2 Eq., the first temperature is in a range of from about 50° C. to about 90° C., and the first pressure is from about 25 bar to about 30 bar.

An Example 78 of the invention includes a process for reacting Compound C2 or Compound C3, wherein the second hydrogen source is gaseous hydrogen, the hydrogenation agent is selected from either 10% Pd/C or a second ligand-metal complex, wherein the second ligand-metal complex consists essentially of a second ligand and an [Ir(COD)Cl]$_2$ metal adduct combined with iodine in an amount up to about 0.1 Eq., wherein 10% Pd/C is present in a range of weight % of from about 5% weight/weight (w/w) to about 20% (w/w), and wherein the second ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R)-iPr-PhanePhos, (S)-iPr-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Tol-P-Phos, (S)-Tol-P-Phos, (R)-Ph-PHOX, (S)-Ph-PHOX, (R)-iPr-PHOX, (S)-iPr-PHOX, (R)-Me-BoPhoz, (S)-Me-BoPhoz, $CF_3$Ph-(R)-Me-BoPhoz, $CF_3$Ph-(S)-Me-BoPhoz, (R)-Phenethyl-(R)-Me-BoPhoz, (R)-Phenethyl-(S)-Me-BoPhoz, (S)-Ethyl-Napthyl-(R)-Me-BoPhoz, 3,4-diCl-Ph-(R)-Me-BoPhoz, 3,4-diCl-Ph-(S)-Me-BoPhoz, (R)-2,4,6-$F_3$Ph-(R)-Me-BoPhoz, (R)-2,4,6-$F_3$Ph-(S)-Me-BoPhoz, (S)-2,4,6-$F_3$Ph-(S)-Me-BoPhoz, (S)-2,4,6-$F_3$Ph-(R)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, pFPh-(R)-Me-BoPhoz, pFPh-(S)-Me-BoPhoz, (R)-Et-BoPhoz, (S)-Et-BoPhoz, pFPh-(R)-Et-BoPhoz, pFPh-(S)-Et-BoPhoz, (R)-iPr-BoPhoz, (S)-iPr-BoPhoz, (R)-Et-BoPhoz, (S)-Et-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz, (S)-Bn-BoPhoz, pFPh-(R)-Bn-BoPhoz, pFPh-(S)-Bn-BoPhoz, (R)-Xyl-Binap, (S)-Xyl-Binap and DPPF, the second solvent is selected from the group consisting of MeOH, DCE, EtOH, IPA, THF, toluene, EtOAc, 1-BuOH and MTBE and mixtures thereof, the optional second additive is selected from the group consisting of $Et_3N$, $iPr_2$-NH, $Cy_2NH$, (R)-Ph-ethyl-$NH_2$, (S)-Ph-ethyl-$NH_2$, KI, KOH, $K_2CO_3$, (R/S)-camphorsulfonic acid and $CH_3COOH$, and, when present, is in an amount up to about 1.2 Eq., the second temperature is in a range of from about 30° C. to about 80° C., or is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 79 of the invention includes a process for reacting Compound C2 or Compound C3, wherein the second ligand-metal complex is selected from the group consisting of (R)-Binol-(R)-Me-BoPhoz &[Ir(COD)Cl]$_2$, (R)-Et-BoPhoz &[Ir(COD)Cl]$_2$, (R)-iPr-BoPhoz &[Ir(COD)Cl]$_2$, (R)-Me-BoPhoz &[Ir(COD)Cl]$_2$, (R)-Ph-BoPhoz &[Ir(COD)Cl]$_2$, (R)-Phenethyl-(S)-BoPhoz&[Ir(COD)Cl]$_2$, (R)-Xyl-PhanePhos &[Ir(COD)Cl]$_2$, (R)-Xyl-P-Phos &[Ir(COD)Cl]$_2$, (S)-Binol-(R)-Me-BoPhoz&[Ir(COD)Cl]$_2$, (S)-Ethyl-Naphthyl-(R)-BoPhoz &[Ir(COD)Cl]$_2$, (S)-Me-BoPhoz &[Ir(COD)Cl]$_2$, (S)-Xyl-PhanePhos &[Ir(COD)Cl]$_2$, (S)-Xyl-P-Phos &[Ir(COD)Cl]$_2$, 2,4,6-$F_3$Ph-(R)-Me-BoPhoz &[Ir(COD)Cl]$_2$, DPPF &[Ir(COD)Cl]$_2$, DtBPF &[Ir(COD)Cl]$_2$, PCy-(R)-Me-BoPhoz &[Ir(COD)Cl]$_2$, pFPh-(R)-Bn-BoPhoz &[Ir(COD)Cl]$_2$, pFPh-(R)-Et-BoPhoz &[Ir(COD)Cl]$_2$, pFPh-(R)-Me-BoPhoz &[Ir(COD)Cl]$_2$ and Xyl-(R)-Me-BoPhoz &[Ir(COD)Cl]$_2$.

An Example 80 of the invention includes a process for reacting Compound C2 or Compound C3, wherein the second ligand is selected from the group consisting of (R)-Xyl-PhanePhos, (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Phenethyl-(S)-Me-BoPhoz, (S)-Ethyl-Napthyl-(R)-Me-BoPhoz, (R)-2,4,6-$F_3$Ph-(R)-Me-BoPhoz, Xyl-(R)-Me-BoPhoz, (R)-Binol-(R)-Me-BoPhoz, (S)-Binol-(S)-Me-BoPhoz, PCy-(R)-Me-BoPhoz, pFPh-(R)-Me-BoPhoz, (R)-Et-BoPhoz, pFPh-(R)-Et-BoPhoz, (R)-iPr-BoPhoz, (R)-Ph-BoPhoz, pFPh-(R)-Bn-BoPhoz, (R)-Xyl-Binap, (S)-Xyl-Binap, DtBPF and DPPF, the second solvent is selected from the group consisting of MeOH, DCE, EtOH, IPA, THF, toluene, EtOAc, 1-BuOH and MTBE and mixtures thereof, the second temperature is in a range of from about 30° C. to about 80° C., and the second pressure is in a range of from about 3 bar to about 25 bar.

An Example 81 of the invention includes a process for reacting Compound C2 or Compound C3, wherein the second hydrogen source is gaseous hydrogen, 10% Pd/C is present in a range of weight % of from about 5% (w/w) to about 20% (w/w), the second solvent is selected from the group consisting of MeOH, DCE, EtOH, IPA, THF, toluene, EtOAc, 1-BuOH and MTBE and mixtures thereof, the optional second additive is selected from the group consisting of $Et_3N$, $iPr_2$-NH, $Cy_2NH$, (R)-Ph-ethyl-$NH_2$, (S)-Ph-ethyl-$NH_2$, KI, KOH, $K_2CO_3$, (R/S)-camphorsulfonic acid and $CH_3COOH$, and, when present, is in an amount up to about 1.2 Eq., the second temperature is in a range of from about 30° C. to about 80° C., or is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 82 of the invention includes a process for reacting Compound C2 or Compound C3, wherein the second ligand-metal complex consists essentially of a second ligand and an [Ir(COD)Cl]$_2$ second metal adduct combined with iodine in an amount up to about 0.1 Eq., wherein the second ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Tol-P-Phos, (S)-Tol-P-Phos, (R)-Ph-PHOX, (S)-Ph-PHOX, (R)-iPr-PHOX, (S)-iPr-PHOX, (R)-Me-BoPhoz, (S)-Me-BoPhoz, $CF_3$Ph-(R)-Me-BoPhoz, $CF_3$Ph-(S)-Me-BoPhoz, (R)-Phenethyl-(R)-Me-BoPhoz, (R)-Phenethyl-(S)-Me-BoPhoz, (S)-Ethyl-Napthyl-(R)-Me-BoPhoz, 3,4-diCl-Ph-(R)-Me-BoPhoz, 3,4-diCl-Ph-(S)-Me-BoPhoz, (R)-2,4,6-$F_3$Ph-(R)-Me-BoPhoz, (R)-2,4,6-$F_3$Ph-(S)-Me-BoPhoz, (S)-2,4,6-$F_3$Ph-(S)-Me-BoPhoz, (S)-2,4,6-$F_3$Ph-(R)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, pFPh-(R)-Me-BoPhoz, pFPh-(S)-Me-BoPhoz, (R)-Et-BoPhoz, (S)-Et-BoPhoz, pFPh-(R)-Et-BoPhoz, pFPh-(S)-Et-BoPhoz, (R)-iPr-BoPhoz, (S)-iPr-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz, (S)-Bn-BoPhoz, pFPh-(R)-Bn-BoPhoz, pFPh-(S)-Bn-BoPhoz, (R)-Xyl-Binap, (S)-Xyl-Binap and DPPF, the second solvent is selected from the group consisting of MeOH, DCE, EtOH, IPA, THF, toluene, EtOAc, 1-BuOH and MTBE and mixtures thereof, the optional second additive is selected from the group consisting of $Et_3N$, $iPr_2$-NH, $Cy_2NH$, (R)-Ph-ethyl-$NH_2$, (S)-Ph-ethyl-$NH_2$, KI, KOH, $K_2CO_3$, (R/S)-camphorsulfonic acid and $CH_3COOH$, and, when present, is in an amount up to about 1.2 Eq., the second temperature is in a range of from about 30° C. to about 80° C., or is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 83 of the invention includes a process for reacting Compound C2 or Compound C3, wherein the second ligand is selected from the group consisting of (R)-Xyl-PhanePhos, (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Phenethyl-(S)-Me-BoPhoz, (S)-Ethyl-Napthyl-(R)-Me-BoPhoz, (R)-2,4,6-$F_3$Ph-(R)-Me-BoPhoz, Xyl-(R)-Me-BoPhoz, (R)-Binol-(R)-Me-BoPhoz, (S)-Binol-(R)-Me-BoPhoz, PCy-(R)-Me-BoPhoz, pFPh-(R)-Me-BoPhoz, (R)-Et-BoPhoz, pFPh-(R)-Et-BoPhoz, (R)-iPr-BoPhoz, (R)-Ph-BoPhoz, pFPh-(R)-Bn-BoPhoz, (R)-Xyl-Binap, (S)-Xyl-Binap and DPPF, the second solvent is selected from the group consisting of MeOH, DCE, EtOH, IPA, THF, toluene, EtOAc, 1-BuOH and MTBE and mixtures thereof, the second temperature is in a range of from about 30° C. to about 80° C., and the second pressure is in a range of from about 3 bar to about 25 bar.

An Example 84 of the invention includes a process comprising the steps:

Step 1. reacting Compound C1 with a first hydrogen source, a first ligand-metal complex consisting essentially of a first ligand conjugated with a first metal adduct, in a first solvent in the presence of an optional first additive at a first elevated temperature and first elevated pressure, to provide a substantially pure Compound C2 or a substantially pure Compound C3, wherein the first hydrogen source is selected from gaseous hydrogen or an excess of formic acid, the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R)-iPr-PhanePhos, (S)-iPr-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Ph-PHOX, (S)-Ph-PHOX, (R)-iPr-PHOX, (S)-iPr-PHOX, (R)-Me-BoPhoz, (S)-Me-BoPhoz, $CF_3$Ph-(R)-Me-BoPhoz, $CF_3$Ph-(S)-Me-BoPhoz, (R)-Phenethyl-(R)-Me-BoPhoz, (R)-Phenethyl-(S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, PCy-(S)-Me-BoPhoz, (R)-iPr-BoPhoz, (S)-iPr-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz and (S)-Bn-BoPhoz, the first metal adduct is selected from the group consisting of [Rh(COD)$_2$]BF$_4$, [Rh(COD)$_2$]OTf, [Rh(ethylene)$_2$Cl]$_2$, [Rh(ethylene)$_2$(acac)], [Rh(CO)$_2$(acac)], [Rh(COD)(acac)], [Ru(COD)(C F$_3$COO)$_2$]$_2$, [Ru(COD)(methylallyl)$_2$], [Ru(benzene)Cl$_2$]$_2$, [Ru(p-cymene)Cl$_2$]$_2$, [Ir(COD)Cl]$_2$, [Ir(COD)$_2$]BF$_4$ and [Ir(COD)$_2$]BAr$_F$, the first solvent is selected from the group consisting of MeOH, EtOH, IPA, DCE, THF, toluene, EtOAc, DMF and mixtures thereof, the optional first additive is selected from the group consisting of AcOH, Et$_3$N, HBF$_4$, HBF$_4$ etherate, HCl, HCl etherate, CF$_3$COOH, CH$_3$COOH and TsOH, and, when present, is in an amount up to about 1.2 Eq., the first temperature is in a range of from about 25° C. to about 70° C., and the first pressure is in a range of from about 3 bar to about 30 bar; and Step 2. reacting Compound C3 with a second hydrogen source and a hydrogenation agent in a second solvent in the presence of an optional second additive at a second elevated temperature and a second elevated pressure to provide an isomeric mixture of Compound C4 and Compound C5, wherein the second hydrogen source is gaseous hydrogen, the hydrogenation agent is selected from either 10% Pd/C or a second ligand-metal complex, wherein the second ligand-metal complex consists essentially of a second ligand and an [Ir(COD)Cl]$_2$ metal adduct combined with iodine in an amount up to about 0.1 Eq., wherein 10% Pd/C is present in a range of weight % of from about 5% (w/w) to about 20% (w/w), and wherein the second ligand is selected from the group consisting of (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Xyl-Binap and (S)-Xyl-Binap, the second solvent is selected from the group consisting of MeOH, DCE, EtOH, IPA, THF, toluene, EtOAc and MTBE and mixtures thereof, the optional second additive is selected from the group consisting of Et$_3$N, iPr$_2$-NH, Cy$_2$NH, (R)-Ph-ethyl-NH$_2$, (S)-Ph-ethyl-NH$_2$, KI, KOH, K$_2$CO$_3$, (R/S)-camphorsulfonic acid and CH$_3$COOH, and, when present, is in an amount up to about 1.2 Eq., the second temperature is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 85 of the invention includes a process comprising the steps:

Step 1. reacting Compound C1 with a first hydrogen source, a first ligand-metal complex consisting essentially of a first ligand conjugated with a first metal adduct, in a first solvent at a first temperature and a first pressure to provide a substantially pure Compound C2 or a substantially pure Compound C3, wherein the first hydrogen source is selected from gaseous hydrogen or an excess of formic acid, the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R)-iPr-PhanePhos, (S)-iPr-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Ph-PHOX, (S)-Ph-PHOX, (R)-iPr-PHOX, (S)-iPr-PHOX, (R)-Me-BoPhoz, (S)-Me-BoPhoz, CF$_3$Ph-(R)-Me-BoPhoz, CF$_3$Ph-(S)-Me-BoPhoz, (R)-Phenethyl-(R)-Me-BoPhoz, (R)-Phenethyl-(S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, PCy-(S)-Me-BoPhoz, (R)-iPr-BoPhoz, (S)-iPr-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz and (S)-Bn-BoPhoz, the first metal adduct is selected from the group consisting of [Ir(COD)Cl]$_2$, [Ir(COD)$_2$]BF$_4$ and [Ir(COD)$_2$]BAr$_F$, the first solvent is selected from the group consisting of THF, toluene, EtOAc and mixtures thereof, the first temperature is in a range of from about 25° C. to about 70° C., and the first pressure is in a range of from about 3 bar to about 30 bar; and Step 2. reacting Compound C2 or Compound C3 by the direct addition of iodine in an amount up to about 0.1 Eq. and recharging the reaction mixture at an elevated second temperature and an elevated second pressure, wherein the second temperature is in a range of from about 30° C. to about 80° C., and the second pressure is in a range of from about 3 bar to about 25 bar.

An Example 86 of the invention includes a process for reacting Compound C1, wherein the first ligand is selected from the group consisting of (R)-Me-BoPhoz and (S)-Me-BoPhoz, and the first metal adduct is [Ir(COD)Cl]$_2$.

An Example 87 of the invention includes a process, according to Scheme C, for preparing a compound of Formula (Ia) and intermediates thereof, wherein the first hydrogen source is gaseous hydrogen;

the first ligand-metal complex is (R)-Me-BoPhoz &[Ir(COD)Cl]$_2$;

the first solvent is DCE;

the first temperature is about 70° C.; the first pressure is about 25 bar;

the second hydrogen source is gaseous hydrogen; and the hydrogenation agent is selected from either 10% Pd/C or a second ligand-metal complex, wherein, when the hydrogenation agent is a second ligand-metal complex selected from (R)-Me-BoPhoz &[Ir(COD)Cl]$_2$ combined with iodine in an amount of about 0.1 Eq., then the second solvent is EtOAc; the second temperature is about 50° C.; and the second pressure is about 25 bar; and, wherein, when the hydrogenation agent is selected from 10% Pd/C in an amount of about 10% (w/w); the second solvent is IPA; the optional second additive is Et$_3$N in an amount of about 0.75 Eq.; the second temperature is about 40° C.; and, the second pressure is about 10 bar.

The present invention further relates to an alternative process, as shown in Scheme D, for preparing a compound of Formula (Ia) and intermediates thereof, comprising the steps of:

Scheme D

Step 1. reacting a Compound D1 with a first hydrogen source, a first ligand-metal complex consisting essentially of a first ligand conjugated with a first metal adduct, in a first solvent in the presence of an optional first additive at an elevated first temperature and elevated first pressure to provide a substantially pure Compound D3:

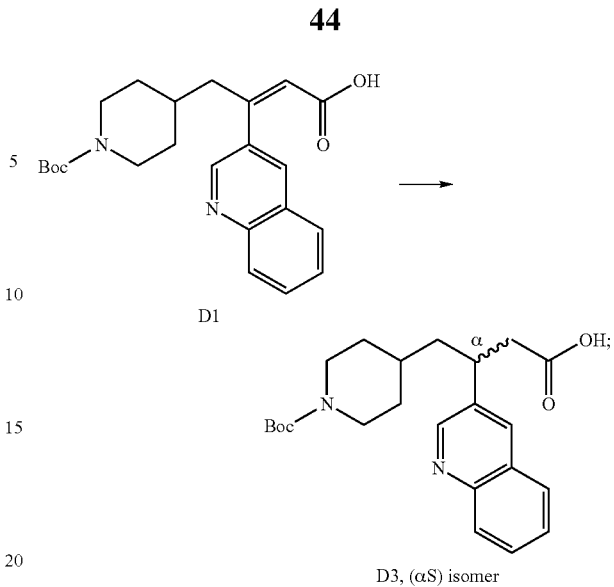

D1

D3, (αS) isomer

Step 2. optionally converting the Compound D3 hydroxy group to the Compound C3 —O—C$_{1-8}$alkyl group, and carrying forward Compound C3 according to Step 2 of Scheme C;

Step 3. reacting Compound D3 with a second hydrogen source and a hydrogenation agent in a second solvent in the presence of an optional second additive at an elevated second temperature and an elevated second pressure to provide an isomeric mixture of a Compound D4 and Compound D5:

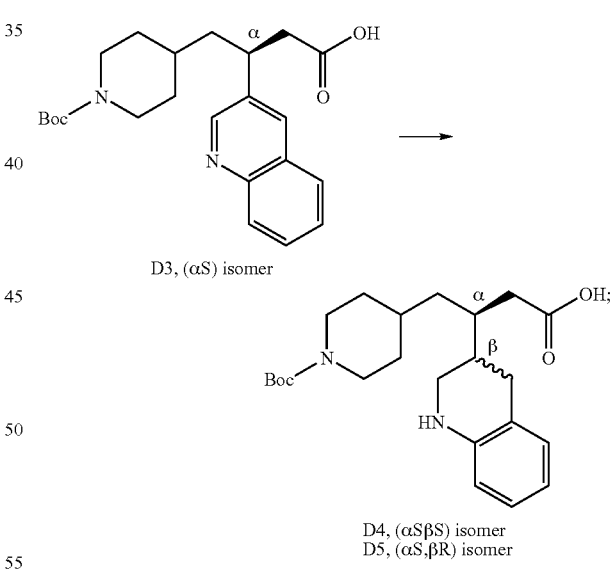

D3, (αS) isomer

D4, (αSβS) isomer
D5, (αS,βR) isomer and

Step 4. converting the hydroxy group in the isomeric mixture of Compound D4 and Compound D5 to an —O—C$_{1-8}$alkyl group to provide an isomeric mixture of Compound C4 and Compound C5; and carrying forward the isomeric mixture of Compound C4 and Compound C5 according to Step 3 of Scheme C.

The present invention provides a process for making substantially pure Compound D2 comprising the step of:

reacting a Compound D1 with a first hydrogen source, a first ligand-metal complex consisting essentially of a first ligand conjugated with a first metal adduct, in a first solvent in the presence of an optional first additive at an elevated first temperature and an elevated first pressure to provide a substantially pure Compound D2:

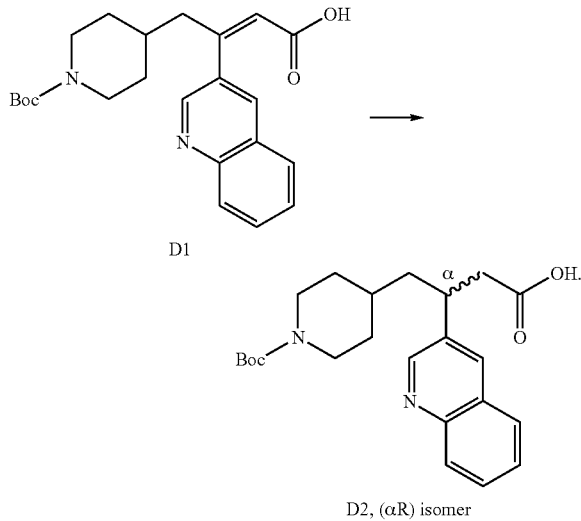

D1

D2, (αR) isomer

An Example 88 of the invention includes a process wherein Compound D2 is carried forward in place of Compound D3 to provide an (αR,βR) isomer and an (αR,βS) isomer of Formula (I).

An Example 89 of the invention includes a process for reacting Compound D1 to provide Compound D2, and a process for reacting Compound D1 to provide Compound D3, both processes as described herein above, wherein
the first ligand is selected from the group consisting of (R)-Xyl-PhanePhos, (S)-Xyl-PhanePhos, (R)-PhanePhos, (S)-PhanePhos, (R)-An-PhanePhos, (S)-An-PhanePhos, (R)-Me-BoPhoz, (S)-Me-BoPhoz, (R)-MeOXyl-PhanePhos, (S)-MeOXyl-PhanePhos, (R)-iPr-PhanePhos, (S)-iPr-PhanePhos, PCy-(R)-Me-BoPhoz and PCy-(S)-Me-BoPhoz,
the first metal adduct is selected from the group consisting of [Rh(COD)$_2$]BF$_4$, [Rh(COD)$_2$]OTf, [Rh(ethylene)$_2$Cl]$_2$, [Rh(ethylene)$_2$(acac)], [Rh(CO)$_2$(acac)], [Rh(COD)Cl]$_2$, [Rh(COD)(acac)], [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$, [Ru(mesitylene)Cl$_2$]$_2$, [Ir(COD)Cl]$_2$, [Ir(COD)$_2$]BF$_4$ and [Ir(COD)$_2$]BAr$_F$,
the first temperature is in a range of from about 25° C. to about 70° C., and
the first pressure is in a range of from about 3 bar to about 30 bar.

An Example 90 of the invention includes a process for reacting Compound D1, wherein the first ligand-metal complex is selected from the group consisting of (R)-An-PhanePhos/[Rh(COD)]BF$_4$, (R)-Me-BoPhoz &[Ir(COD)Cl]$_2$, (R)-MeOXyl-PhanePhos/[Rh(COD)]BF$_4$, (R)-PhanePhos/[Rh(COD)]BF$_4$, (R)-PhanePhos &[Rh(COD)$_2$]OTf, (R)-PhanePhos/[RuCl$_2$(DMF)$_2$], (R)-Tol-Binap/[RuCl(p-cymene)]Cl, (R)-Xyl-PhanePhos &[Ru(COD)(CF$_3$COO)$_2$]$_2$, (R)-Xyl-PhanePhos &[Ru(COD)(methylallyl)$_2$], (R)-Xyl-PhanePhos/[RuCl$_2$(DMF)$_2$], (R)-Xyl-P-Phos/[RuCl$_2$(DMF)$_2$], (S)-iPr-PhanePhos/[Rh(COD)]BF$_4$, (S)-Me-BoPhoz/[RuCl$_2$(DMF)$_2$], (S)-PhanePhos/[RuCl$_2$(DMF)$_2$], (S)-Tol-Binap/[RuCl(p-cymene)]Cl, (S)-Xyl-PhanePhos &[Rh(COD)$_2$]OTf and (S)-Xyl-PhanePhos/[RuCl$_2$(DMF)$_2$].

An Example 91 of the invention includes a process for reacting Compound D1, wherein
the first ligand is selected from the group consisting of (R)-Xyl-PhanePhos, (S)-Xyl-PhanePhos, (R)-PhanePhos, (S)-PhanePhos, (R)-An-PhanePhos, (S)-An-PhanePhos, (R)-Me-BoPhoz, (S)-Me-BoPhoz, (R)-MeOXyl-PhanePhos and (S)-MeOXyl-PhanePhos, and
the first metal adduct is selected from the group consisting of [Rh(COD)$_2$]BF$_4$, [Rh(COD)$_2$]OTf, [Ru(COD)(CF$_3$COO)$_2$]$_2$, [Ru(COD)(methylallyl)$_2$], [Ru(benzene)Cl$_2$]$_2$ and [Ir(COD)Cl]$_2$.

An Example 92 of the invention includes a process for reacting Compound D1, wherein
the first ligand is selected from the group consisting of (R)-Xyl-PhanePhos, (S)-Xyl-PhanePhos, (R)-PhanePhos, (S)-PhanePhos, (R)-An-PhanePhos, (S)-An-PhanePhos, (R)-Me-BoPhoz, (S)-Me-BoPhoz, (R)-MeOXyl-PhanePhos and (S)-MeOXyl-PhanePhos, and
the first metal adduct is selected from the group consisting of [Rh(COD)$_2$]BF$_4$, [Rh(COD)$_2$]OTf, [Ru(COD)(CF$_3$COO)$_2$]$_2$, [Ru(COD)(methylallyl)$_2$], [Ru(benzene)Cl$_2$]$_2$ and [Ir(COD)Cl]$_2$.

An Example 93 of the invention includes a process for reacting Compound D1, wherein
the first ligand is selected from the group consisting of (R)-Me-BoPhoz and (S)-Me-BoPhoz,
the first metal adduct is [Ir(COD)Cl]$_2$,
the first solvent is selected from the group consisting of THF, DCE and EtOAc,
the first temperature is in a range of from about 65° C. to about 70° C., and
the first pressure is in a range of from about 25 bar to about 30 bar.

An Example 94 of the invention includes a process for reacting Compound D1, wherein
the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (S)-iPr-PhanePhos and (R)-iPr-PhanePhos,
the first metal adduct is selected from the group consisting of [Rh(COD)$_2$]BF$_4$, [Rh(COD)$_2$]OTf, [Rh(ethylene)$_2$Cl]$_2$, [Rh(ethylene)$_2$(acac)], [Rh(CO)$_2$(acac)], [Rh(COD)Cl]$_2$ and [Rh(COD)(acac)],
the first solvent is MeOH, the first temperature is from about 25° C. to about 60° C., and
the first pressure is from about 3 bar to about 30 bar.

An Example 95 of the invention includes a process for reacting Compound D1, wherein
the first ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (S)-iPr-PhanePhos and (R)-iPr-PhanePhos,
the first metal adduct is selected from the group consisting of [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$ and [Ru(mesitylene)Cl$_2$]$_2$,
the first solvent is selected from the group consisting of MeOH, EtOH, IPA, DCE, THF, toluene, EtOAc, DMF and mixtures thereof,
the optional first additive is selected from the group consisting of AcOH, CF$_3$CO$_2$H and Et$_3$N,
the first temperature is in a range of from about 40° C. to about 70° C., and
the first pressure is in a range of from about 3 bar to about 30 bar.

An Example 96 of the invention includes a process for reacting Compound D1, wherein
the first ligand is (R)-XylPhanePhos,
the first metal adduct is selected from the group consisting of [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$ and [Ru(mesitylene)Cl$_2$]$_2$,
the first solvent is selected from the group consisting of MeOH, DMF and mixtures thereof,
the optional first additive is Et$_3$N,
the first temperature is in a range of from about 40° C. to about 60° C., and
the first pressure is in a range of from about 3 bar to about 30 bar.

An Example 97 of the invention includes a process for reacting Compound D1, wherein
the first ligand is (R)-XylPhanePhos,
the first metal adduct is selected from the group consisting of [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$ and [Ru(mesitylene)Cl$_2$]$_2$,
the first solvent is selected from the group consisting of MeOH, DMF and mixtures thereof,
the optional first additive is AcOH,
the first temperature is about 40° C., and
the first pressure is about 10 bar.

An Example 98 of the invention includes a process for reacting Compound D1, wherein
the first ligand is (R)-XylPhanePhos,
the first metal adduct is selected from the group consisting of [Ru(COD)(CF$_3$COO)$_2$]$_2$, [Ru(COD)(CH$_3$COO)$_2$], [Ru(COD)(methylallyl)$_2$], [Ru(benzene)Cl$_2$]$_2$, [Ru(p-cymene)Cl$_2$]$_2$ and [Ru(mesitylene)Cl$_2$]$_2$,
the first solvent is selected from the group consisting of MeOH, EtOH, IPA, DCE, THF, toluene, EtOAc, DMF and mixtures thereof,
the first temperature is about 40° C. and
the first pressure is about 10 bar.

An Example 99 of the invention includes a process for reacting Compound D1, wherein
the first ligand is (R)-XylPhanePhos,
the first metal adduct is [Ru(COD)(CF$_3$COO)$_2$]$_2$, [Ru(COD)(CH$_3$COO)$_2$] and [Ru(COD)(methylallyl)$_2$],
the first solvent is MeOH,
the first optional additive is AcOH,
the first temperature is about 40° C., and
the first pressure is about 10 bar.

An Example 100 of the invention includes a process for reacting Compound D2 or Compound D3, wherein
the second hydrogen source is gaseous hydrogen,
the hydrogenation agent is selected from either 10% Pd/C or a second ligand-metal complex,
wherein the second ligand-metal complex consists essentially of a second ligand and an [Ir(COD)Cl]$_2$ metal adduct combined with iodine in an amount up to about 0.1 Eq.,
wherein 10% Pd/C is present in a range of weight % of from about 5% weight/weight (w/w) to about 20% (w/w), and
wherein the second ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R)-iPr-PhanePhos, (S)-iPr-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Tol-P-Phos, (S)-Tol-P-Phos, (R)-Ph-PHOX, (S)-Ph-PHOX, (R)-iPr-PHOX, (S)-iPr-PHOX, (R)-Me-BoPhoz, (S)-Me-BoPhoz, CF$_3$Ph-(R)-Me-BoPhoz, CF$_3$Ph-(S)-Me-BoPhoz, (R)-Phenethyl-(R)-Me-BoPhoz, (R)-Phenethyl-(S)-Me-BoPhoz, (S)-Ethyl-Napthyl-(R)-Me-BoPhoz, 3,4-diCl-Ph-(R)-Me-BoPhoz, 3,4-diCl-Ph-(S)-Me-BoPhoz, (R)-2,4,6-F$_3$Ph-(R)-Me-BoPhoz, (R)-2,4,6-F$_3$Ph-(S)-Me-BoPhoz, (S)-2,4,6-F$_3$Ph-(S)-Me-BoPhoz, (S)-2,4,6-F$_3$Ph-(R)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, pFPh-(R)-Me-BoPhoz, pFPh-(S)-Me-BoPhoz, (R)-Et-BoPhoz, (S)-Et-BoPhoz, pFPh-(R)-Et-BoPhoz, pFPh-(S)-Et-BoPhoz, (R)-iPr-BoPhoz, (S)-iPr-BoPhoz, (R)-Et-BoPhoz, (S)-Et-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz, (S)-Bn-BoPhoz, pFPh-(R)-Bn-BoPhoz, pFPh-(S)-Bn-BoPhoz, (R)-Xyl-Binap, (S)-Xyl-Binap and DPPF,
the second solvent is selected from the group consisting of MeOH, DCE, EtOH, IPA, THF, toluene, EtOAc, 1-BuOH and MTBE and mixtures thereof,
the optional second additive is selected from the group consisting of Et$_3$N, iPr$_2$-NH, Cy$_2$NH, (R)-Ph-ethyl-NH$_2$, (S)-Ph-ethyl-NH$_2$, KI, KOH, K$_2$CO$_3$, (R/S)-camphorsulfonic acid and CH$_3$COOH, and, when present, is in an amount up to about 1.2 Eq.,
the second temperature is in a range of from about 30° C. to about 80° C., or is in a range of from about 40° C. to about 60° C., and
the second pressure is in a range of from about 3 bar to about 25 bar, or is in a range of from about 10 bar to about 25 bar, or is in a range of from about 3 bar to about 10 bar.

An Example 101 of the invention includes a process for reacting Compound D2 or Compound D3, wherein the second ligand-metal complex is selected from the group consisting of (R)-Me-BoPhoz &[Ir(COD)Cl]$_2$, (R)-PhanePhos &[Ir(COD)Cl]$_2$, (R)—P-Phos &[Ir(COD)Cl]$_2$, (R)-Xyl-Binap &[Ir(COD)Cl]$_2$, (R)-Xyl-PhanePhos &[Ir(COD)Cl]$_2$, (R)-Xyl-P-Phos &[Ir(COD)Cl]$_2$, (S)-Me-BoPhoz &[Ir(COD)Cl]$_2$, (S)-PhanePhos &[Ir(COD)Cl]$_2$, (S)—P-Phos &[Ir(COD)Cl]$_2$, (S)-Tol-P-Phos &[Ir(COD)Cl]$_2$, (S)-Xyl-Binap &[Ir(COD)Cl]$_2$, (S)-Xyl-PhanePhos &[Ir(COD)Cl]$_2$ and (S)-Xyl-P-Phos &[Ir(COD)Cl]$_2$.

An Example 102 of the invention includes a process for reacting Compound D2 or Compound D3, wherein
the second ligand is selected from the group consisting of (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Xyl-Binap and (S)-Xyl-Binap,
the second solvent is selected from the group consisting of MeOH, DCE, EtOH, IPA, THF, toluene, EtOAc and MTBE and mixtures thereof,
the second temperature is in a range of from about 40° C. to about 60° C., and
the second pressure is in a range of from about 3 bar to about 25 bar, or is in a range of from about 10 bar to about 25 bar, or is in a range of from about 3 bar to about 10 bar.

An Example 103 of the invention includes a process for reacting Compound D2 or Compound D3, wherein
the second hydrogen source is gaseous hydrogen,
10% Pd/C is present in a range of weight % of from about 5% (w/w) to about 20% (w/w),
the second solvent is selected from the group consisting of MeOH, DCE, EtOH, IPA, THF, toluene, EtOAc, I-BuOH and MTBE and mixtures thereof,
the optional second additive is selected from the group consisting of Et$_3$N, iPr$_2$-NH, Cy$_2$NH, (R)-Ph-ethyl-NH$_2$, (S)-

Ph-ethyl-$NH_2$, KI, KOH, $K_2CO_3$, (R/S)-camphorsulfonic acid and $CH_3COOH$, and, when present, is in an amount up to about 1.2 Eq., the second temperature is in a range of from about 30° C. to about 80° C., or is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 104 of the invention includes a process for reacting Compound D2 or Compound D3, wherein the second ligand-metal complex consists essentially of a second ligand and an $[Ir(COD)Cl]_2$ second metal adduct combined with iodine in an amount up to about 0.1 Eq., wherein the second ligand is selected from the group consisting of (R)-PhanePhos, (S)-PhanePhos, (R)-An-PhanePhos, (S)-An-PhanePhos, (R)-Xyl-PhanePhos, (S)-Xyl-PhanePhos, (R)-MeOXyl-PhanePhos, (S)-MeOXyl-PhanePhos, (R,R)-Me-DuPhos, (S,S)-Me-DuPhos, (R)—P-Phos, (S)—P-Phos, (R)-Xyl-P-Phos, (S)-Xyl-P-Phos, (R)-Tol-P-Phos, (S)-Tol-P-Phos, (R)-Ph-PHOX, (S)-Ph-PHOX, (R)-iPr-PHOX, (S)-iPr-PHOX, (R)-Me-BoPhoz, (S)-Me-BoPhoz, $CF_3$Ph-(R)-Me-BoPhoz, $CF_3$Ph-(S)-Me-BoPhoz, (R)-Phenethyl-(R)-Me-BoPhoz, (R)-Phenethyl-(S)-Me-BoPhoz, (S)-Ethyl-Napthyl-(R)-Me-BoPhoz, 3,4-diCl-Ph-(R)-Me-BoPhoz, 3,4-diCl-Ph-(S)-Me-BoPhoz, (R)-2,4,6-$F_3$Ph-(R)-Me-BoPhoz, (R)-2,4,6-$F_3$Ph-(S)-Me-BoPhoz, (S)-2,4,6-$F_3$Ph-(S)-Me-BoPhoz, (S)-2,4,6-$F_3$Ph-(R)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, pFPh-(R)-Me-BoPhoz, pFPh-(S)-Me-BoPhoz, (R)-Et-BoPhoz, (S)-Et-BoPhoz, pFPh-(R)-Et-BoPhoz, pFPh-(S)-Et-BoPhoz, (R)-iPr-BoPhoz, (S)-iPr-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz, (S)-Bn-BoPhoz, pFPh-(R)-Bn-BoPhoz, pFPh-(S)-Bn-BoPhoz, (R)-Xyl-Binap, (S)-Xyl-Binap and DPPF, the second solvent is selected from the group consisting of MeOH, DCE, EtOH, IPA, THF, toluene, EtOAc, 1-BuOH and MTBE and mixtures thereof, the optional second additive is selected from the group consisting of $Et_3N$, $iPr_2$-NH, $Cy_2NH$, (R)-Ph-ethyl-$NH_2$, (S)-Ph-ethyl-$NH_2$, KI, KOH, $K_2CO_3$, (R/S)-camphorsulfonic acid and CH3COOH, and, when present, is in an amount up to about 1.2 Eq., the second temperature is in a range of from about 30° C. to about 80° C., or is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 105 of the invention includes a process for reacting Compound D2 or Compound D3, wherein the second ligand is selected from the group consisting of (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Xyl-Binap and (S)-Xyl-Binap, the second solvent is selected from the group consisting of MeOH, DCE, EtOH, IPA, THF, toluene, EtOAc and MTBE and mixtures thereof, the second temperature is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 106 of the invention includes a process comprising the steps:

Step 1. reacting Compound D1 with a first hydrogen source, a first ligand-metal complex consisting essentially of a first ligand conjugated with a first metal adduct, in a first solvent in the presence of an optional first additive at a first elevated temperature and a first elevated pressure, to provide a substantially pure Compound D2 or a substantially pure Compound D3, wherein the first hydrogen source is selected from gaseous hydrogen or an excess of formic acid, the first ligand is selected from the group consisting of (R)-Xyl-PhanePhos, (S)-Xyl-PhanePhos, (R)-PhanePhos, (S)-PhanePhos, (R)-An-PhanePhos, (S)-An-PhanePhos, (R)-MeOXyl-PhanePhos, (S)-MeOXyl-PhanePhos, PCy-(R)-Me-BoPhoz and PCy-(S)-Me-BoPhoz, the first metal adduct is selected from the group consisting of $[Rh(COD)_2]BF_4$, $[Rh(COD)_2]OTf$, $[Ru(COD)(CF_3COO)_2]_2$, $[Ru(COD)(methylallyl)_2]$, $[Ru(benzene)Cl_2]_2$ and $[Ir(COD)Cl]_2$, the first solvent is selected from the group consisting of MeOH, EtOH, IPA, DCE, THF, toluene, EtOAc, DMF and mixtures thereof, the optional first additive is selected from the group consisting of AcOH, $Et_3N$, $HBF_4$, $HBF_4$ etherate, HCl, HCl etherate, $CF_3COOH$, $CH_3COOH$ and TsOH, and, when present, is in an amount up to about 1.2 Eq., the first temperature is in a range of from about 25° C. to about 70° C. and the first pressure is in a range of from about 3 bar to about 30 bar;

Step 2. optionally converting the Compound D2 or Compound D3 hydroxy group to the Compound C2 or Compound C3-O—$C_{1-8}$alkyl group, and carrying forward Compound C2 or Compound C3 according to Step 2 of Scheme C; and Step 3. reacting Compound D3 with a second hydrogen source and a hydrogenation agent in a second solvent in the presence of an optional second additive at an elevated second temperature and an elevated second pressure to provide an isomeric mixture of a Compound D4 and Compound D5, wherein the second hydrogen source is gaseous hydrogen, the hydrogenation agent is selected from either 10% Pd/C or a second ligand-metal complex, wherein the second ligand-metal complex consists essentially of a second ligand and an $[Ir(COD)Cl]_2$ metal adduct combined with iodine in an amount up to about 0.1 Eq., wherein 10% Pd/C is present in a range of weight % of from about 5% (w/w) to about 20% (w/w), and wherein the second ligand is selected from the group consisting of (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Xyl-Binap and (S)-Xyl-Binap, the second solvent is selected from the group consisting of MeOH, DCE, EtOH, IPA, THF, toluene, EtOAc and MTBE and mixtures thereof, the optional second additive is selected from the group consisting of $Et_3N$, $iPr_2$-NH, $Cy_2NH$, (R)-Ph-ethyl-$NH_2$, (S)-Ph-ethyl-$NH_2$, KI, KOH, $K_2CO_3$, (R/S)-camphorsulfonic acid and $CH_3COOH$, and, when present, is in an amount up to about 1.2 Eq., the second temperature is in a range of from about 40° C. to about 60° C., and the second pressure is in a range of from about 3 bar to about 25 bar, or is in a range of from about 10 bar to about 25 bar, or is in a range of from about 3 bar to about 10 bar.

An Example 107 of the invention includes a process comprising the steps:

Step 1. reacting Compound D1 with a first hydrogen source, a first ligand-metal complex consisting essentially of a first ligand conjugated with a first metal adduct, in a first solvent in the presence of an optional first additive at a first elevated temperature and a first elevated pressure, to provide a substantially pure Compound D2 or a substantially pure Compound D3, wherein the first hydrogen source is selected from gaseous hydrogen or an excess of formic acid, the first ligand is selected from the group consisting of (R)-Me-BoPhoz, (S)-Me-BoPhoz, (R)-Xyl-P-Phos, (S)-Xyl-P-Phos, (R)—P-Phos, (S)—P-Phos, (R)-Et-BoPhoz, (S)-Et-BoPhoz, (R)-iPr-BoPhoz, (S)-iPr-BoPhoz, (R)-Bn-BoPhoz, (S)-Bn-BoPhoz, (R)-Ph-BoPhoz, (S)-Ph-BoPhoz, the first metal adduct is [Ir(COD)Cl]$_2$, [Ir(COD)$_2$]BF$_4$ and [Ir(COD)$_2$]BAr$_F$, the first solvent is selected from the group consisting of THF, EtOAc and toluene, the first temperature is about 70° C., and the first pressure is about 25 bar, and Step 2. optionally converting the Compound D2 or Compound D3 hydroxy group to the Compound C2 or Compound C3-O—C$_{1-8}$alkyl group, and carrying forward Compound C2 or Compound C3 according to Step 2 of Scheme C;

Step 3. reacting Compound D3 by the direct addition of iodine in an amount up to about 0.1 Eq., and recharging the reaction mixture at an elevated second temperature and an elevated second pressure, wherein the second temperature is in a range of from about 30° C. to about 80° C., and the second pressure is in a range of from about 3 bar to about 25 bar.

An Example 108 of the invention includes a process for reacting Compound D1, wherein the first ligand is selected from the group consisting of (R)-Me-BoPhoz and (S)-Me-BoPhoz, and the first metal adduct is [Ir(COD)Cl]$_2$.

An Example 109 of the invention includes a process, according to Scheme D, for preparing a compound of Formula (Ia) and intermediates thereof, wherein the first hydrogen source is gaseous hydrogen;

the first ligand-metal complex is (R)-Xyl-PhanePhos &[Ru(COD)(CF$_3$COO)$_2$]$_2$;

the first solvent is MeOH;

the first temperature is about 40° C.;

the first pressure is about 10 bar;

the second hydrogen source is gaseous hydrogen; and the hydrogenation agent is selected from either 10% Pd/C or a second ligand-metal complex, wherein, when the hydrogenation agent is a second ligand-metal complex selected from (R)-Me-BoPhoz &[Ir(COD)Cl]$_2$ combined with iodine in an amount of about 0.1 Eq., then the second solvent is EtOAc; the second temperature is about 50° C.; and the second pressure is about 25 bar; and, wherein, when the hydrogenation agent is selected from 10% Pd/C in an amount of about 10% (w/w); the second solvent is MeOH; the optional second additive is Et$_3$N in an amount of about 0.75 Eq.; the second temperature is about 40° C.; and, the second pressure is about 10 bar.

An Example 110 of the invention includes a process which provides an enantiomer or diastereomer of a compound of Formula (I) or a compound of Formula (II) selected from the group consisting of:

| Cpd | Names |
|---|---|
| 1 | β-[1-[[3-[(1,4,5,6-tetrahydro-5-hydroxy-2-pyrimidinyl)amino]phenyl]acetyl]-4-piperidinyl]-3-quinolinepropanoic acid, |
| 2 | 3-(1-{2-[3-(5-hydroxy-1,4,5,6-tetrahydro-pyrimidin-2-ylamino)-phenyl]-acetyl}-piperidin-4-yl)-3-quinolin-3-yl-propionic acid methyl ester, |
| 3 | β-[1-[1-oxo-4-(5,6,7,8-tetrahydro-1,8-naphthyridin-2-yl)butyl]-4-piperidinyl]-3-quinolinepropanoic acid, |
| 4 | 3-quinolin-3-yl-3-[1-(4-5,6,7,8-tetrahydro-[1,8]naphthyridin-2-yl-butyryl)-piperidin-4-yl]-propionic acid methyl ester, |
| 5 | 3-[1-(4-5,6,7,8-tetrahydro-[1,8]naphthyridin-2-yl-butyryl)-piperidin-4-yl]-3-(1,2,3,4-tetrahydro-quinolin-3-yl)-propionic acid, |
| 6 | (3R*,3'S*)-3-[1-(4-5,6,7,8-tetrahydro-[1,8]naphthyridin-2-yl-butyryl)-piperidin-4-yl]-3-(1,2,3,4-tetrahydro-quinolin-3-yl)-propionic acid, |
| 7 | (3R*,3'R*)-3-[1-(4-5,6,7,8-tetrahydro-[1,8]naphthyridin-2-yl-butyryl)-piperidin-4-yl]-3-(1,2,3,4-tetrahydro-quinolin-3-yl)-propionic acid, |
| 8 | (3S*,3'R*)-3-[1-(4-5,6,7,8-tetrahydro-[1,8]naphthyridin-2-yl-butyryl)-piperidin-4-yl]-3-(1,2,3,4-tetrahydro-quinolin-3-yl)-propionic acid, |
| 9 | (3S*,3'S*)-3-[1-(4-5,6,7,8-tetrahydro-[1,8]naphthyridin-2-yl-butyryl)-piperidin-4-yl]-3-(1,2,3,4-tetrahydro-quinolin-3-yl)-propionic acid, |
| 10 | 3-[1-(4-5,6,7,8-tetrahydro-[1,8]naphthyridin-2-yl-butyryl)-piperidin-4-yl]-3-(1,2,3,4-tetrahydro-quinolin-3-yl)-propionic acid methyl ester, |
| 11 | β-[2-[1-[3-[(1,4,5,6-tetrahydro-2-pyrimidinyl)amino]benzoyl]-4-piperidinyl]ethyl]-3-pyridinepropanoic acid, |
| 12 | 3-pyridin-3-yl-5-{1-[3-(1,4,5,6-tetrahydro-pyrimidin-2-ylamino)-benzoyl]-piperidin-4-yl}-pentanoic acid methyl ester, |
| 13 | β-[2-[1-[3-[(1,4,5,6-tetrahydro-5-hydroxy-2-pyrimidinyl)amino]benzoyl]-4-piperidinyl]ethyl]-3-pyridinepropanoic acid, |
| 14 | 5-{1-[3-(5-hydroxy-1,4,5,6-tetrahydro-pyrimidin-2-ylamino)-benzoyl]-piperidin-4-yl}-3-pyridin-3-yl-pentanoic acid methyl ester, |
| 15 | β-[2-[1-[1-oxo-3-(5,6,7,8-tetrahydro-1,8-naphthyridin-2-yl)propyl]-4-piperidinyl]ethyl]-3-pyridinepropanoic acid, |
| 16 | 3-pyridin-3-yl-5-[1-(3-5,6,7,8-tetrahydro-[1,8]naphthyridin-2-yl-propionyl)-piperidin-4-yl]-pentanoic acid methyl ester, |

-continued

| Cpd | Names |
|---|---|
| 17 | β-[2-[1-[1-oxo-4-(2-pyridinylamino)butyl]-4-piperidinyl]ethyl]-3-pyridinepropanoic acid, |
| 18 | 3-pyridin-3-yl-5-{1-[4-(pyridin-2-ylamino)-butyryl]-piperidin-4-yl}-pentanoic acid methyl ester, |
| 19 | 6-methoxy-β-[2-[1-[3-[(1,4,5,6-tetrahydro-5-hydroxy-2-pyrimidinyl)amino]benzoyl]-4-piperidinyl]ethyl]-3-pyridinepropanoic acid, |
| 20 | 5-{1-[3-(5-hydroxy-1,4,5,6-tetrahydro-pyrimidin-2-ylamino)-benzoyl]-piperidin-4-yl}-3-(6-methoxy-pyridin-3-yl)-pentanoic acid methyl ester, |
| 21 | β-(1,3-benzodioxol-5-yl)-1-[1-oxo-3-(5,6,7,8-tetrahydro-1,8-naphthyridin-2-yl)propyl]-4-piperidinebutanoic acid, |
| 22 | 3-benzo[1,3]dioxol-5-yl-4-[1-(3-5,6,7,8-tetrahydro-[1,8]naphthyridin-2-yl-propionyl)-piperidin-4-yl]-butyric acid methyl ester, |
| 23 | β-[2-[1-[3-[(1,4,5,6-tetrahydro-2-pyrimidinyl)amino]benzoyl]-4-piperidinyl]ethyl]-3-quinolinepropanoic acid, |
| 24 | 3-quinolin-3-yl-5-{1-[3-(1,4,5,6-tetrahydro-pyrimidin-2-ylamino)-benzoyl]-piperidin-4-yl}-pentanoic acid methyl ester, |
| 25 | 1-[1-oxo-3-(5,6,7,8-tetrahydro-1,8-naphthyridin-2-yl)propyl]-β-phenyl-4-piperidinebutanoic acid, |
| 26 | 3-phenyl-4-[1-(3-5,6,7,8-tetrahydro-[1,8]naphthyridin-2-yl-propionyl)-piperidin-4-yl]-butyric acid methyl ester, |
| 27 | β-(1,3-benzodioxol-5-yl)-1-[1-oxo-3-(5,6,7,8-tetrahydro-1,8-naphthyridin-2-yl)propyl]-4-piperidinepropanoic acid, |
| 28 | 3-benzo[1,3]dioxol-5-yl-3-[1-(3-5,6,7,8-tetrahydro-[1,8]naphthyridin-2-yl-propionyl)-piperidin-4-yl]-propionic acid methyl ester, |
| 29 | β-(1,3-benzodioxol-5-yl)-1-[1-oxo-4-(5,6,7,8-tetrahydro-1,8-naphthyridin-2-yl)butyl]-4-piperidinepropanoic acid, |
| 30 | 3-benzo[1,3]dioxol-5-yl-3-[1-(4-5,6,7,8-tetrahydro-[1,8]naphthyridin-2-yl-butyryl)-piperidin-4-yl]-propionic acid methyl ester, |
| 31 | β-(1,3-benzodioxol-5-yl)-1-[(5,6,7,8-tetrahydro-1,8-naphthyridin-2-yl)acetyl]-4-piperidinepropanoic acid, |
| 32 | 3-benzo[1,3]dioxol-5-yl-3-[1-(2-5,6,7,8-tetrahydro-[1,8]naphthyridin-2-yl-acetyl)-piperidin-4-yl]-propionic acid methyl ester, |
| 33 | 6-methoxy-β-[1-[1-oxo-4-(5,6,7,8-tetrahydro-1,8-naphthyridin-2-yl)butyl]-4-piperidinyl]-3-pyridinepropanoic acid, |
| 34 | 3-(6-methoxy-pyridin-3-yl)-3-[1-(4-5,6,7,8-tetrahydro-[1,8]naphthyridin-2-yl-butyryl)-piperidin-4-yl]-propionic acid methyl ester, |
| 35 | 3-(2-methyl-1,4,5,6-tetrahydro-pyrimidin-5-yl)-4-[1-(3-5,6,7,8-tetrahydro-[1,8]naphthyridin-2-yl-propionyl)-piperidin-4-yl]-butyric acid, |
| 36 | 3-(2-methyl-1,4,5,6-tetrahydro-pyrimidin-5-yl)-4-[1-(3-5,6,7,8-tetrahydro-[1,8]naphthyridin-2-yl-propionyl)-piperidin-4-yl]-butyric acid methyl ester, |
| 37 | 4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid, |
| 38 | (3R,3'R)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid, |
| 39 | (3R,3'R)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid methyl ester, |
| 40 | (3R,3'S)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid, |
| 41 | (3R,3'S)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid methyl ester, |
| 42 | (3S,3'R)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid, |
| 43 | (3S,3'R)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid methyl ester, |
| (Ia) | (3S,3'S)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid, |
| 44 | (3S,3'S)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid methyl ester, |
| 45 | 4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid methyl ester, |
| 46 | β-(1,3-benzodioxol-5-yl)-1-[1-oxo-3-(5,6,7,8-tetrahydro-1,8-naphthyridin-2-yl)propyl]-4-piperidinepentanoic acid, |
| 47 | 3-benzo[1,3]dioxol-5-yl-5-[1-(3-5,6,7,8-tetrahydro-[1,8]naphthyridin-2-yl-propionyl)-piperidin-4-yl]-pentanoic acid methyl ester, |
| 48 | 6-methoxy-β-[2-[1-[1-oxo-3-(5,6,7,8-tetrahydro-1,8-naphthyridin-2-yl)propyl]-4-piperidinyl]ethyl]-3-pyridinepropanoic acid, |
| 49 | 3-(6-methoxy-pyridin-3-yl)-5-[1-(3-5,6,7,8-tetrahydro-[1,8]naphthyridin-2-yl-propionyl)-piperidin-4-yl]-pentanoic acid methyl ester, |
| 50 | (3S*)-3-(6-methoxy-pyridin-3-yl)-5-[1-(3-5,6,7,8-tetrahydro-[1,8]naphthyridin-2-yl-propionyl)-piperidin-4-yl]-pentanoic acid, |
| 51 | (3R*)-3-(6-methoxy-pyridin-3-yl)-5-[1-(3-5,6,7,8-tetrahydro-[1,8]naphthyridin-2-yl-propionyl)-piperidin-4-yl]-pentanoic acid, |
| 52 | β-[2-[1-[1-oxo-4-(2-pyridinylamino)butyl]-4-piperidinyl]ethyl]-3-quinolinepropanoic acid, |
| 53 | 5-{1-[4-(pyridin-2-ylamino)-butyryl]-piperidin-4-yl}-3-quinolin-3-yl-pentanoic acid methyl ester, |
| 54 | β-(1,3-benzodioxol-5-yl)-1-[1-oxo-4-(2-pyridinylamino)butyl]-4-piperidinepentanoic acid, |

-continued

| Cpd | Names |
|---|---|
| 55 | 3-benzo[1,3]dioxol-5-yl-5-{1-[4-(pyridin-2-ylamino)-butyryl]-piperidin-4-yl}-pentanoic acid methyl ester, |
| 56 | β-(1,3-benzodioxol-5-yl)-1-[1-oxo-4-(2-pyridinylamino)butyl]-4-piperidinepropanoic acid, |
| 57 | 3-benzo[1,3]dioxol-5-yl-3-{1-[4-(pyridin-2-ylamino)-butyryl]-piperidin-4-yl}-propionic acid methyl ester, |
| 58 | 6-methoxy-β-[2-[1-[1-oxo-4-(2-pyridinylamino)butyl]-4-piperidinyl]ethyl]-3-pyridinepropanoic acid, |
| 59 | 3-(6-methoxy-pyridin-3-yl)-5-{1-[4-(pyridin-2-ylamino)-butyryl]-piperidin-4-yl}-pentanoic acid methyl ester, |
| 60 | β-(1,3-benzodioxol-5-yl)-1-[1-oxo-4-(5,6,7,8-tetrahydro-1,8-naphthyridin-2-yl)butyl]-4-piperidinebutanoic acid, |
| 61 | 3-benzo[1,3]dioxol-5-yl-4-[1-(4-5,6,7,8-tetrahydro-[1,8]naphthyridin-2-yl-butyryl)-piperidin-4-yl]-butyric acid methyl ester, |
| 62 | β-(1,3-benzodioxol-5-yl)-1-[3-[(1,4,5,6-tetrahydro-5-hydroxy-2-pyrimidinyl)amino]benzoyl]-4-piperidinebutanoic acid, |
| 63 | 3-benzo[1,3]dioxol-5-yl-4-{1-[3-(5-hydroxy-1,4,5,6-tetrahydro-pyrimidin-2-ylamino)-benzoyl]-piperidin-4-yl}-butyric acid methyl ester, |
| 64 | 6-methoxy-β-[[1-[1-oxo-3-(5,6,7,8-tetrahydro-1,8-naphthyridin-2-yl)propyl]-4-piperidinyl]methyl]-3-pyridinepropanoic acid, |
| 65 | 3-(6-methoxy-pyridin-3-yl)-4-[1-(3-5,6,7,8-tetrahydro-[1,8]naphthyridin-2-yl-propionyl)-piperidin-4-yl]-butyric acid methyl ester, |
| 66 | (3R*)-3-(6-methoxy-pyridin-3-yl)-4-[1-(3-5,6,7,8-tetrahydro-[1,8]naphthyridin-2-yl-propionyl)-piperidin-4-yl]-butyric acid, |
| 67 | (3S*)-3-(6-methoxy-pyridin-3-yl)-4-[1-(3-5,6,7,8-tetrahydro-[1,8]naphthyridin-2-yl-propionyl)-piperidin-4-yl]-butyric acid, |
| 68 | β-[[1-[1-oxo-4-(5,6,7,8-tetrahydro-1,8-naphthyridin-2-yl)butyl]-4-piperidinyl]methyl]-3-quinolinepropanoic acid, |
| 69 | 3-quinolin-3-yl-4-[1-(4-5,6,7,8-tetrahydro-[1,8]naphthyridin-2-yl-butyryl)-piperidin-4-yl]-butyric acid methyl ester, |
| 70 | β-(3-fluorophenyl)-1-[1-oxo-3-(5,6,7,8-tetrahydro-1,8-naphthyridin-2-yl)propyl]-4-piperidinebutanoic acid, |
| 71 | 3-(3-fluoro-phenyl)-4-[1-(3-5,6,7,8-tetrahydro-[1,8]naphthyridin-2-yl-propionyl)-piperidin-4-yl]-butyric acid methyl ester, |
| 72 | (3R*)-3-(3-fluoro-phenyl)-4-[1-(3-5,6,7,8-tetrahydro-[1,8]naphthyridin-2-yl-propionyl)-piperidin-4-yl]-butyric acid, |
| 73 | (3S*)-3-(3-fluoro-phenyl)-4-[1-(3-5,6,7,8-tetrahydro-[1,8]naphthyridin-2-yl-propionyl)-piperidin-4-yl]-butyric acid, |
| 74 | β-(3-fluorophenyl)-1-[1-oxo-4-(5,6,7,8-tetrahydro-1,8-naphthyridin-2-yl)butyl]-4-piperidinebutanoic acid, |
| 75 | 3-(3-fluoro-phenyl)-4-[1-(4-5,6,7,8-tetrahydro-[1,8]naphthyridin-2-yl-butyryl)-piperidin-4-yl]-butyric acid methyl ester, |
| 76 | β-[[1-[1-oxo-3-(5,6,7,8-tetrahydro-1,8-naphthyridin-2-yl)propyl]-4-piperidinyl]methyl]-3-quinolinepropanoic acid, |
| 77 | 3-quinolin-3-yl-4-[1-(3-5,6,7,8-tetrahydro-[1,8]naphthyridin-2-yl-propionyl)-piperidin-4-yl]-butyric acid methyl ester, |
| 78 | β-(4-fluorophenyl)-1-[1-oxo-3-(5,6,7,8-tetrahydro-1,8-naphthyridin-2-yl)propyl]-4-piperidinebutanoic acid, |
| 79 | 3-(4-fluoro-phenyl)-4-[1-(3-5,6,7,8-tetrahydro-[1,8]naphthyridin-2-yl-propionyl)-piperidin-4-yl]-butyric acid methyl ester, |
| 80 | β-(4-fluorophenyl)-1-[1-oxo-4-(5,6,7,8-tetrahydro-1,8-naphthyridin-2-yl)butyl]-4-piperidinebutanoic acid, |
| 81 | 3-(4-fluoro-phenyl)-4-[1-(4-5,6,7,8-tetrahydro-[1,8]naphthyridin-2-yl-butyryl)-piperidin-4-yl]-butyric acid methyl ester, |
| 82 | 2-methyl-β-[[1-[1-oxo-3-(5,6,7,8-tetrahydro-1,8-naphthyridin-2-yl)propyl]-4-piperidinyl]methyl]-5-pyrimidinepropanoic acid, |
| 83 | 3-(2-methyl-pyrimidin-5-yl)-4-[1-(3-5,6,7,8-tetrahydro-[1,8]naphthyridin-2-yl-propionyl)-piperidin-4-yl]-butyric acid methyl ester, |
| 84 | β-(2,3-dihydro-6-benzofuranyl)-1-[1-oxo-3-(5,6,7,8-tetrahydro-1,8-naphthyridin-2-yl)propyl]-4-piperidinebutanoic acid, |
| 85 | 3-(2,3-dihydro-benzofuran-6-yl)-4-[1-(3-5,6,7,8-tetrahydro-[1,8]naphthyridin-2-yl-propionyl)-piperidin-4-yl]-butyric acid methyl ester, |
| 86 | (3S*)-3-(2,3-dihydro-benzofuran-6-yl)-4-[1-(3-5,6,7,8-tetrahydro-[1,8]naphthyridin-2-yl-propionyl)-piperidin-4-yl]-butyric acid, |
| 87 | (3R*)-3-(2,3-dihydro-benzofuran-6-yl)-4-[1-(3-5,6,7,8-tetrahydro-[1,8]naphthyridin-2-yl-propionyl)-piperidin-4-yl]-butyric acid, |
| 88 | β-(3,5-difluorophenyl)-1-[1-oxo-3-(5,6,7,8-tetrahydro-1,8-naphthyridin-2-yl)propyl]-4-piperidinebutanoic acid, |
| 89 | 3-(3,5-difluoro-phenyl)-4-[1-(3-5,6,7,8-tetrahydro-[1,8]naphthyridin-2-yl-propionyl)-piperidin-4-yl]-butyric acid methyl ester, |
| 90 | β-(3,5-difluorophenyl)-1-[1-oxo-4-(5,6,7,8-tetrahydro-1,8-naphthyridin-2-yl)butyl]-4-piperidinebutanoic acid, |
| 91 | 3-(3,5-difluoro-phenyl)-4-[1-(4-5,6,7,8-tetrahydro-[1,8]naphthyridin-2-yl-butyryl)-piperidin-4-yl]-butyric acid methyl ester, |
| 92 | 1-[1-oxo-3-(5,6,7,8-tetrahydro-1,8-naphthyridin-2-yl)propyl]-β-[3-(trifluoromethyl)phenyl]-4-piperidinebutanoic acid, |
| 93 | 4-[1-(3-5,6,7,8-tetrahydro-[1,8]naphthyridin-2-yl-propionyl)-piperidin-4-yl]-3-(3-trifluoromethyl-phenyl)-butyric acid methyl ester, |

-continued

| Cpd | Names |
|---|---|
| 94 | 1-[1-oxo-3-(5,6,7,8-tetrahydro-1,8-naphthyridin-2-yl)propyl]-β-[4-(trifluoromethoxy)phenyl]-4-piperidinebutanoic acid, |
| 95 | 4-[1-(3-5,6,7,8-tetrahydro-[1,8]naphthyridin-2-yl-propionyl)-piperidin-4-yl]-3-(4-trifluoromethoxy-phenyl)-butyric acid methyl ester, |
| 96 | β-(2-fluoro[1,1'-biphenyl]-4-yl)-1-[1-oxo-3-(5,6,7,8-tetrahydro-1,8-naphthyridin-2-yl)propyl]-4-piperidinebutanoic acid, |
| 97 | 3-(2-fluoro-biphenyl-4-yl)-4-[1-(3-5,6,7,8-tetrahydro-[1,8]naphthyridin-2-yl-propionyl)-piperidin-4-yl]-butyric acid methyl ester, |
| 98 | β-(3-fluoro-4-methoxyphenyl)-1-[1-oxo-3-(5,6,7,8-tetrahydro-1,8-naphthyridin-2-yl)propyl]-4-piperidinebutanoic acid, |
| 99 | 3-(3-fluoro-4-methoxy-phenyl)-4-[1-(3-5,6,7,8-tetrahydro-[1,8]naphthyridin-2-yl-propionyl)-piperidin-4-yl]-butyric acid methyl ester, |
| 100 | 1-[1-oxo-3-(5,6,7,8-tetrahydro-1,8-naphthyridin-2-yl)propyl]-β-(4-phenoxyphenyl)-4-piperidinebutanoic acid, |
| 101 | 3-(4-phenoxy-phenyl)-4-[1-(3-5,6,7,8-tetrahydro-[1,8]naphthyridin-2-yl-propionyl)-piperidin-4-yl]-butyric acid methyl ester, |
| 102 | β-[[1-[1-oxo-3-(5,6,7,8-tetrahydro-1,8-naphthyridin-2-yl)propyl]-4-piperidinyl]methyl]-4-isoquinolinepropanoic acid, |
| 103 | 3-isoquinolin-4-yl-4-[1-(3-5,6,7,8-tetrahydro-[1,8]naphthyridin-2-yl-propionyl)-piperidin-4-yl]-butyric acid methyl ester, |
| 104 | β-[[1-[1-oxo-3-(5,6,7,8-tetrahydro-1,8-naphthyridin-2-yl)propyl]-4-piperidinyl]methyl]-3-pyridinepropanoic acid, |
| 105 | 3-pyridin-3-yl-4-[1-(3-5,6,7,8-tetrahydro-[1,8]naphthyridin-2-yl-propionyl)-piperidin-4-yl]-butyric acid methyl ester, |
| 106 | β-(2,3-dihydro-5-benzofuranyl)-1-[1-oxo-3-(5,6,7,8-tetrahydro-1,8-naphthyridin-2-yl)propyl]-4-piperidinebutanoic acid, |
| 107 | 3-(2,3-dihydro-benzofuran-5-yl)-4-[1-(3-5,6,7,8-tetrahydro-[1,8]naphthyridin-2-yl-propionyl)-piperidin-4-yl]-butyric acid methyl ester, |
| 108 | 2,4-dimethoxy-β-[[1-[1-oxo-3-(5,6,7,8-tetrahydro-1,8-naphthyridin-2-yl)propyl]-4-piperidinyl]methyl]-5-pyrimidinepropanoic acid, |
| 109 | 3-(2,4-dimethoxy-pyrimidin-5-yl)-4-[1-(3-5,6,7,8-tetrahydro-[1,8]naphthyridin-2-yl-propionyl)-piperidin-4-yl]-butyric acid methyl ester, |
| 110 | 2-methoxy-β-[[1-[1-oxo-3-(5,6,7,8-tetrahydro-1,8-naphthyridin-2-yl)propyl]-4-piperidinyl]methyl]-5-pyrimidinepropanoic acid, |
| 111 | 3-(2-methoxy-pyrimidin-5-yl)-4-[1-(3-5,6,7,8-tetrahydro-[1,8]naphthyridin-2-yl-propionyl)-piperidin-4-yl]-butyric acid methyl ester, |
| 112 | β-[2-[1-[3-[(1,4,5,6-tetrahydro-5-hydroxy-2-pyrimidinyl)amino]benzoyl]-4-piperidinyl]ethyl]-3-quinolinepropanoic acid, |
| 113 | 5-{1-[3-(5-hydroxy-1,4,5,6-tetrahydro-pyrimidin-2-ylamino)-benzoyl]-piperidin-4-yl}-3-quinolin-3-yl-pentanoic acid methyl ester, |
| 114 | β-[2-[1-[3-[(3,4,5,6-tetrahydro-2-pyridinyl)amino]benzoyl]-4-piperidinyl]ethyl]-3-quinolinepropanoic acid, |
| 115 | 3-quinolin-3-yl-5-{1-[3-(3,4,5,6-tetrahydro-pyridin-2-ylamino)-benzoyl]-piperidin-4-yl}-pentanoic acid methyl ester, |
| 116 | β-[2-[1-[1-oxo-3-(5,6,7,8-tetrahydro-1,8-naphthyridin-2-yl)propyl]-4-piperidinyl]ethyl]-3-quinolinepropanoic acid, |
| 117 | 3-quinolin-3-yl-5-[1-(3-5,6,7,8-tetrahydro-[1,8]naphthyridin-2-yl-propionyl)-piperidin-4-yl]-pentanoic acid methyl ester, |
| 118 | β-[2-[1-[1-oxo-3-(5,6,7,8-tetrahydro-1,8-naphthyridin-2-yl)propyl]-4-piperidinyl]ethyl]-3-quinolinepropanoic acid, |
| 119 | 3-quinolin-3-yl-5-[1-(3-5,6,7,8-tetrahydro-[1,8]naphthyridin-2-yl-propionyl)-piperidin-4-yl]-pentanoic acid methyl ester, |
| 120 | β-(1,3-benzodioxol-5-yl)-1-[3-[(3,4,5,6-tetrahydro-2-pyridinyl)amino]benzoyl]-4-piperidinepentanoic acid, |
| 121 | 3-benzo[1,3]dioxol-5-yl-5-{1-[3-(3,4,5,6-tetrahydro-pyridin-2-ylamino)-benzoyl]-piperidin-4-yl}-pentanoic acid methyl ester, |
| 122 | β-(1,3-benzodioxol-5-yl)-1-[3-[(1,4,5,6-tetrahydro-5-hydroxy-2-pyrimidinyl)amino]benzoyl]-4-piperidinepentanoic acid, |
| 123 | 3-benzo[1,3]dioxol-5-yl-5-{1-[3-(5-hydroxy-1,4,5,6-tetrahydro-pyrimidin-2-ylamino)-benzoyl]-piperidin-4-yl}-pentanoic acid methyl ester, |
| 124 | β-(1,3-benzodioxol-5-yl)-1-[(5,6,7,8-tetrahydro-1,8-naphthyridin-2-yl)acetyl]-4-piperidinepentanoic acid, |
| 125 | 3-benzo[1,3]dioxol-5-yl-5-[1-(2-5,6,7,8-tetrahydro-[1,8]naphthyridin-2-yl-acetyl)-piperidin-4-yl]-pentanoic acid methyl ester, |
| 126 | β-(2-naphthalenyl)-1-[1-oxo-3-(5,6,7,8-tetrahydro-1,8-naphthyridin-2-yl)propyl]-4-piperidinebutanoic acid, |
| 127 | 3-naphthalen-2-yl-4-[1-(3-5,6,7,8-tetrahydro-[1,8]naphthyridin-2-yl-propionyl)-piperidin-4-yl]-butyric acid methyl ester, |
| 128 | (3S*)-3-naphthalen-2-yl-4-[1-(3-5,6,7,8-tetrahydro-[1,8]naphthyridin-2-yl-propionyl)-piperidin-4-yl]-butyric acid, |
| 129 | (3R*)-3-naphthalen-2-yl-4-[1-(3-5,6,7,8-tetrahydro-[1,8]naphthyridin-2-yl-propionyl)-piperidin-4-yl]-butyric acid, |

| Cpd | Names |
|---|---|
| 130 | 3-[1-(3-5,6,7,8-tetrahydro-[1,8]naphthyridin-2-yl-propionyl)-piperidin-4-yl]-4-(5,6,7,8-tetrahydro-quinolin-3-yl)-butyric acid, |
| 131 | 3-[1-(3-5,6,7,8-tetrahydro-[1,8]naphthyridin-2-yl-propionyl)-piperidin-4-yl]-4-(5,6,7,8-tetrahydro-quinolin-3-yl)-butyric acid methyl ester, |
| 132 | 5,6,7,8-tetrahydro-β-[1-[1-oxo-4-(5,6,7,8-tetrahydro-1,8-naphthyridin-2-yl)butyl]-4-piperidinyl]-3-quinolinepropanoic acid, |
| 133 | 5,6,7,8-tetrahydro-β-[1-[1-oxo-4-(5,6,7,8-tetrahydro-1,8-naphthyridin-2-yl)butyl]-4-piperidinyl]-3-quinolinepropanoic acid, |
| 134 | 5,6,7,8-tetrahydro-β-[1-[1-oxo-4-(5,6,7,8-tetrahydro-1,8-naphthyridin-2-yl)butyl]-4-piperidinyl]-3-quinolinepropanoic acid, |
| 135 | 3-[1-(4-5,6,7,8-tetrahydro-[1,8]naphthyridin-2-yl-butyryl)-piperidin-4-yl]-3-(5,6,7,8-tetrahydro-quinolin-3-yl)-propionic acid methyl ester, |
| 136 | 3-(3-methoxy-phenyl)-4-[1-(3-5,6,7,8-tetrahydro-[1,8]naphthyridin-2-yl-propionyl)-piperidin-4-yl]-butyric acid, |
| 137 | 3-(3-methoxy-phenyl)-4-[1-(3-5,6,7,8-tetrahydro-[1,8]naphthyridin-2-yl-propionyl)-piperidin-4-yl]-butyric acid methyl ester, |
| 138 | 3-(4-methoxy-phenyl)-4-[1-(3-5,6,7,8-tetrahydro-[1,8]naphthyridin-2-yl-propionyl)-piperidin-4-yl]-butyric acid, |
| 139 | 3-(4-methoxy-phenyl)-4-[1-(3-5,6,7,8-tetrahydro-[1,8]naphthyridin-2-yl-propionyl)-piperidin-4-yl]-butyric acid methyl ester, |
| 140 | 3-(tetrahydro-furan-3-yl)-4-[1-(3-5,6,7,8-tetrahydro-[1,8]naphthyridin-2-yl-propionyl)-piperidin-4-yl]-butyric acid, |
| 141 | 3-(tetrahydro-furan-3-yl)-4-[1-(3-5,6,7,8-tetrahydro-[1,8]naphthyridin-2-yl-propionyl)-piperidin-4-yl]-butyric acid methyl ester, |
| 142 | 4-[1-(3-5,6,7,8-tetrahydro-[1,8]naphthyridin-2-yl-propionyl)-piperidin-4-yl]-3-thiophen-2-yl-butyric acid, |
| 143 | 4-[1-(3-5,6,7,8-tetrahydro-[1,8]naphthyridin-2-yl-propionyl)-piperidin-4-yl]-3-thiophen-2-yl-butyric acid methyl ester, |
| 144 | 3-(2,3-dihydro-benzo[1,4]dioxin-6-yl)-4-[1-(3-5,6,7,8-tetrahydro-[1,8]naphthyridin-2-yl-propionyl)-piperidin-4-yl]-butyric acid, |
| 145 | 3-(2,3-dihydro-benzo[1,4]dioxin-6-yl)-4-[1-(3-5,6,7,8-tetrahydro-[1,8]naphthyridin-2-yl-propionyl)-piperidin-4-yl]-butyric acid methyl ester, |
| 146 | 3-(3-methylsulfanyl-phenyl)-4-[1-(3-5,6,7,8-tetrahydro-[1,8]naphthyridin-2-yl-propionyl)-piperidin-4-yl]-butyric acid, |
| 147 | 3-(3-methylsulfanyl-phenyl)-4-[1-(3-5,6,7,8-tetrahydro-[1,8]naphthyridin-2-yl-propionyl)-piperidin-4-yl]-butyric acid methyl ester, |
| 148 | N-methyl-1,2,3,4-tetrahydro-β-[[1-[1-oxo-3-(5,6,7,8-tetrahydro-1,8-naphthyridin-2-yl)propyl]-4-piperidinyl]methyl]-3-quinolinepropanoic acid, |
| 149 | 3-(1-methyl-1,2,3,4-tetrahydro-quinolin-3-yl)-4-[1-(3-5,6,7,8-tetrahydro-[1,8]naphthyridin-2-yl-propionyl)-piperidin-4-yl]-butyric acid methyl ester, |
| 150 | 3-(3-dimethylamino-phenyl)-4-[1-(3-5,6,7,8-tetrahydro-[1,8]naphthyridin-2-yl-propionyl)-piperidin-4-yl]-butyric acid, |
| 151 | 3-(3-dimethylamino-phenyl)-4-[1-(3-5,6,7,8-tetrahydro-[1,8]naphthyridin-2-yl-propionyl)-piperidin-4-yl]-butyric acid methyl ester, |
| 152 | 3-(4-hydroxy-3-methoxy-phenyl)-4-[1-(3-5,6,7,8-tetrahydro-[1,8]naphthyridin-2-yl-propionyl)-piperidin-4-yl]-butyric acid, |
| 153 | 3-(4-hydroxy-3-methoxy-phenyl)-4-[1-(3-5,6,7,8-tetrahydro-[1,8]naphthyridin-2-yl-propionyl)-piperidin-4-yl]-butyric acid methyl ester, |
| 154 | (3S*)-3-(4-hydroxy-3-methoxy-phenyl)-4-[1-(3-5,6,7,8-tetrahydro-[1,8]naphthyridin-2-yl-propionyl)-piperidin-4-yl]-butyric acid, |
| 155 | 4-{1-[3-(4,5-dihydro-1H-imidazol-2-ylamino)-benzoyl]-piperidin-4-yl}-3-(3-fluoro-phenyl)-butyric acid, |
| 156 | 4-{1-[3-(4,5-dihydro-1H-imidazol-2-ylamino)-benzoyl]-piperidin-4-yl}-3-(3-fluoro-phenyl)-butyric acid methyl ester, |
| 157 | 3-(3-ethylamino-phenyl)-4-[1-(3-5,6,7,8-tetrahydro-[1,8]naphthyridin-2-yl-propionyl)-piperidin-4-yl]-butyric acid, |
| 158 | 3-(3-ethylamino-phenyl)-4-[1-(3-5,6,7,8-tetrahydro-[1,8]naphthyridin-2-yl-propionyl)-piperidin-4-yl]-butyric acid methyl ester, |
| 159 | 3-(3-methylamino-phenyl)-4-[1-(3-5,6,7,8-tetrahydro-[1,8]naphthyridin-2-yl-propionyl)-piperidin-4-yl]-butyric acid, |
| 160 | 3-(3-methylamino-phenyl)-4-[1-(3-5,6,7,8-tetrahydro-[1,8]naphthyridin-2-yl-propionyl)-piperidin-4-yl]-butyric acid methyl ester, |
| 161 | 3-(2,3-dihydro-benzofuran-6-yl)-3-[1-(4-5,6,7,8-tetrahydro-[1,8]naphthyridin-2-yl-butyryl)-piperidin-4-yl]-propionic acid, |
| 162 | 3-(2,3-dihydro-benzofuran-6-yl)-3-[1-(4-5,6,7,8-tetrahydro-[1,8]naphthyridin-2-yl-butyryl)-piperidin-4-yl]-propionic acid methyl ester, |
| 163 | 3-(3-fluoro-phenyl)-4-{1-[3-(5,6,7,8-tetrahydro-[1,8]naphthyridin-2-yl)-propyl]-piperidin-4-yl}-butyric acid, |
| 164 | 3-(3-fluoro-phenyl)-4-{1-[3-(5,6,7,8-tetrahydro-[1,8]naphthyridin-2-yl)-propyl]-piperidin-4-yl}-butyric acid methyl ester, |
| 165 | 3-(2,3-dihydro-benzofuran-6-yl)-3-[1-4-(5,6,7,8-tetrahydro-1,8-naphthyridin-2-yl)butyl]-4-piperidinyl]-propanoic acid, |
| 166 | 3-(2,3-dihydro-benzofuran-6-yl)-3-[1-4-(5,6,7,8-tetrahydro-1,8-naphthyridin-2-yl)butyl]-4-piperidinyl]-propanoic acid methyl ester, |
| 167 | 3-{4-[2-(2-bromo-ethoxy)-ethoxy]-3-methoxy-phenyl}-4-[1-(3-5,6,7,8-tetrahydro-[1,8]naphthyridin-2-yl-propionyl)-piperidin-4-yl]-butyric acid, |

-continued

| Cpd | Names |
|-----|-------|
| 168 | 3-{4-[2-(2-bromo-ethoxy)-ethoxy]-3-methoxy-phenyl}-4-[1-(3-5,6,7,8-tetrahydro-[1,8]naphthyridin-2-yl-propionyl)-piperidin-4-yl]-butyric acid methyl ester, |
| 169 | 3-{4-[2-(2-acetylsulfanyl-ethoxy)-ethoxy]-3-methoxy-phenyl}-4-[1-(3-5,6,7,8-tetrahydro-[1,8]naphthyridin-2-yl-propionyl)-piperidin-4-yl]-butyric acid, |
| 170 | 3-{4-[2-(2-acetylsulfanyl-ethoxy)-ethoxy]-3-methoxy-phenyl}-4-[1-(3-5,6,7,8-tetrahydro-[1,8]naphthyridin-2-yl-propionyl)-piperidin-4-yl]-butyric acid methyl ester, |
| 171 | 3-{4-[2-(2-mercapto-ethoxy)-ethoxy]-3-methoxy-phenyl}-4-[1-(3-5,6,7,8-tetrahydro-[1,8]naphthyridin-2-yl-propionyl)-piperidin-4-yl]-butyric acid, |
| 172 | 3-{4-[2-(2-mercapto-ethoxy)-ethoxy]-3-methoxy-phenyl}-4-[1-(3-5,6,7,8-tetrahydro-[1,8]naphthyridin-2-yl-propionyl)-piperidin-4-yl]-butyric acid methyl ester, |
| 173 | 3-(4-{2-[2-(2-chloro-ethoxy)-ethoxy]-ethoxy}-3-methoxy-phenyl)-4-[1-(3-5,6,7,8-tetrahydro-[1,8]naphthyridin-2-yl-propionyl)-piperidin-4-yl]-butyric acid, |
| 174 | 3-(4-{2-[2-(2-chloro-ethoxy)-ethoxy]-ethoxy}-3-methoxy-phenyl)-4-[1-(3-5,6,7,8-tetrahydro-[1,8]naphthyridin-2-yl-propionyl)-piperidin-4-yl]-butyric acid methyl ester, |
| 175 | 3-(4-{2-[2-(2-mercapto-ethoxy)-ethoxy]-ethoxy}-3-methoxy-phenyl)-4-[1-(3-5,6,7,8-tetrahydro-[1,8]naphthyridin-2-yl-propionyl)-piperidin-4-yl]-butyric acid, |
| 176 | 3-(4-{2-[2-(2-mercapto-ethoxy)-ethoxy]-ethoxy}-3-methoxy-phenyl)-4-[1-(3-5,6,7,8-tetrahydro-[1,8]naphthyridin-2-yl-propionyl)-piperidin-4-yl]-butyric acid methyl ester, |
| 177 | 3-(4-{2-[2-(2-acetylsulfanyl-ethoxy)-ethoxy]-ethoxy}-3-methoxy-phenyl)-4-[1-(3-5,6,7,8-tetrahydro-[1,8]naphthyridin-2-yl-propionyl)-piperidin-4-yl]-butyric acid methyl ester, and |
| 178 | 3-(4-{2-[2-(2-acetylsulfanyl-ethoxy)-ethoxy]-ethoxy}-3-methoxy-phenyl)-4-[1-(3-5,6,7,8-tetrahydro-[1,8]naphthyridin-2-yl-propionyl)-piperidin-4-yl]-butyric acid. |

The foregoing Schemes are offered by way of illustration; the invention should not be construed as being limited by the chemical reactions and conditions expressed. The methods for preparing the various starting materials used in the Schemes are within the skill of persons versed in the art.

Discussion of the Problem

In the asymmetric homogeneous reaction of the present invention, the amount of conversion of the starting material and the enantiomeric purity of the product was found to depend on a number of factors. Such factors include, but are not limited to, various ligands conjugated with various metal adducts, the resulting ligand-metal complexes thus formed, the solvents used and other additives, the reaction temperature and pressure conditions and the reaction length. Alone and in combination, the influence of each of these factors was explored.

Scheme E illustrates a synthesis of the compound of Formula (Ia) (as described in Ghosh S, Santulli R J, Kinney W A, DeCorte B L, Liu L, Lewis J M, Proost J C, Leo G C, Masucci J, Hageman W E, Thompson A S, Chen I, Kawahama R, Tuman R W, Galemmo R A Jr., Johnson D L, Damiano B P and Maryanoff B E, *Bioorg. Med. Chem. Lett.,* 2004, 14, 5937).

Scheme E

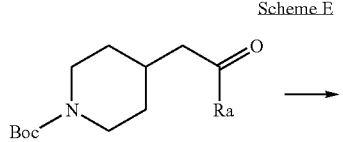

E1, Ra = OH
E2, Ra = NMe(OMe)
E3, Ra = 3-quinolinyl

-continued

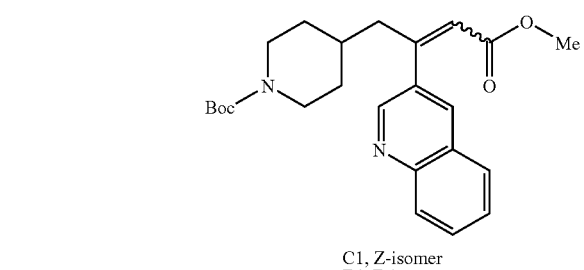

C1, Z-isomer
E4, E-isomer

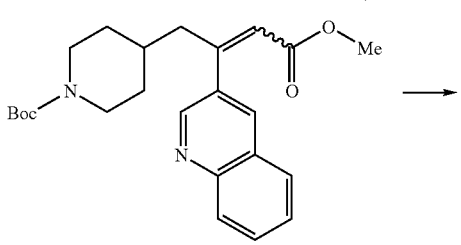

C1, Z-isomer
E4, E-isomer

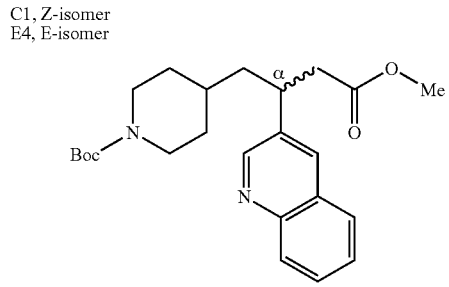

C2, (aR) Z-isomer
C3, (aS) Z-isomer
E4, (aR) E-isomer
E5, (aS) E-isomer

C3 ⟶ ⟶

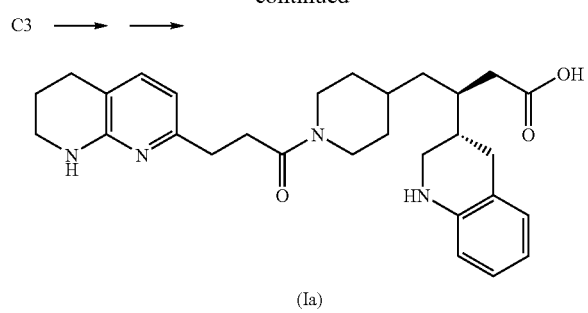

(Ia)

The reaction step for preparing 4-(2-oxo-2-quinolin-3-yl-ethyl)-piperidine-1-carboxylic acid tert-butyl ester Compound E3 uses a 3-lithioquinoline adduct as the reagent and an excess of n-BuLi and 3-bromoquinoline with a low reaction temperature over a period of time.

Additionally, the generation of the product as a mixture of geometric isomers Compound C1 (Z-isomer) and Compound E4 (E-isomer) by the Horner-Emmons reaction results in a mixed isomer ratio.

The hydrogenation of the mixture of Compound C1 and Compound E4 yields a product as an equal mixture of four diastereomers, Compound C2, Compound C3, Compound E4 and Compound E5 and requires two subsequent separations by sequential chiral column chromatography.

Scheme F provides a process for the stereocontrolled synthesis of (Z)-4-(3-methoxycarbonyl-2-quinolin-3-yl-allyl)-piperidine-1-carboxylic acid tert-butyl ester Compound C1 starting from acid Compound F1 via Compound F2 and vinyl triflate Compound F3 (see, Romero D L, Manninen P R, Han F and Romero A G, *J. Org. Chem.* 1999, 64, 4980-4985, for an alternative method for controlling stereoisomeric orientation using a triflate anhydride).

Scheme F

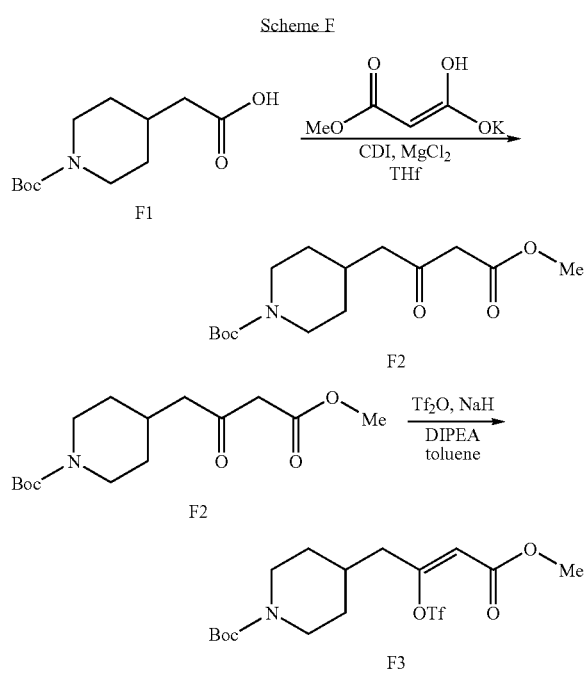

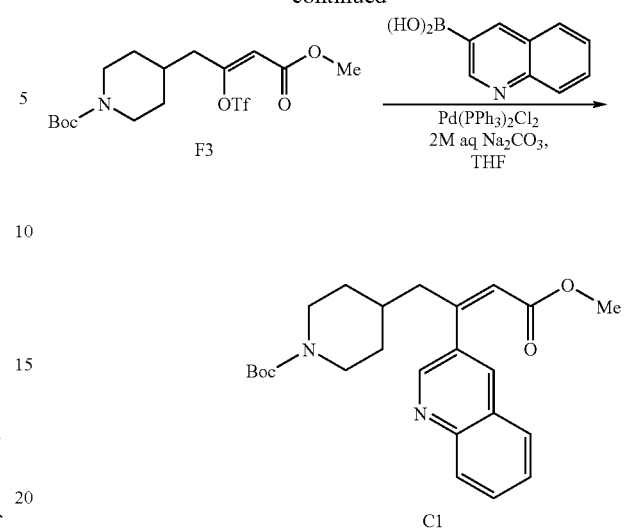

An Example 111 of the invention includes a process for preparing (Z)-4-(3-methoxycarbonyl-2-quinolin-3-yl-allyl)-piperidine-1-carboxylic acid tert-butyl ester Compound C1, comprising the steps:

Step 1. reacting a mixture of a Compound F1 and carbonyl diimidazole (CDI) in tetrahydrofuran (THF);

Step 2. reacting the mixture with the potassium salt of methyl malonate and $MgCl_2$ in THF to provide a Compound F2;

Step 3. reacting Compound F2 with trifluoromethanesulfonic anhydride ($Tf_2O$) in a mixture with sodium hydride (NaH) and DIPEA in toluene to provide a (Z)-isomer Compound F3; and, Step 4. reacting Compound F3 with quinoline-3-boronic acid and $Pd(PPh_3)_2Cl_2$ (bistriphenylphosphine palladium dichloride) in a mixture with 2 M $Na_2CO_3$ in THF to provide Compound C1.

Scheme G illustrates the preparation of a (1S)-(−)-camphanic acid derivative Compound G1 crystalline form. Compound G1 was used in a single-crystal X-ray diffraction study to confirm the absolute configuration of compounds of the present invention.

Scheme G

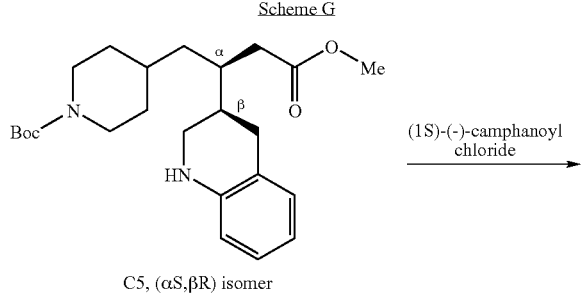

C5, (αS,βR) isomer

-continued

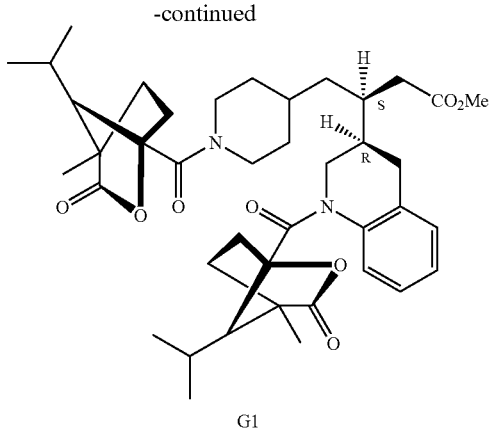

G1

Enantioselective reductions of stereo-defined unsaturated esters have been described where an unsaturated ester was reacted with copper hydride [(PPh$_3$)CuH]$_6$ (Stryker's reagent) in the presence of a catalytic amount of a chiral ligand of the (R,S)-JosiPhos series in a solvent to provide a stereoselective product (Lipshutz B H, Servesko J M and Taft B R, *J. Am. Chem. Soc.* 2004, 126, 8352). Hydrogenation reactions of an unsaturated ester using a (R)-Tol-Binap ligand provided a chiral compound (Hughes G, Kimura M and Buchwald S L, *J. Am. Chem. Soc.* 2003, 125, 11253; U.S. Pat. Nos. 6,465,664 and 6,787,655)

Although the literature describes such enantioselective reductions of unsaturated esters and acids, a more efficient synthetic route is needed.

Compound Definitions

As used herein, with reference to substituents, the term "independently" means that when more than one of such substituent is possible, such substituents may be the same or different from each other.

The term "$C_{1-8}$alkyl" means a straight or branched chain hydrocarbon radical comprising from 1 to 8 carbon atoms, wherein the radical is derived by the removal of one hydrogen atom from a single carbon atom. Examples include methyl, ethyl, 1-propyl, 2-propyl, 1-butyl, 2-butyl, tertiary butyl (also referred to as t-butyl or tert-butyl), 1-pentyl, 2-pentyl, 3-pentyl, 1-hexyl, 2-hexyl, 3-hexyl and the like. Other examples include $C_{1-4}$alkyl groups. $C_{1-8}$alkyl is substituted on one or more available carbon chain atoms with one or more substituents where allowed by available valences.

The term "$C_{1-8}$alkoxy" means a straight or branched chain hydrocarbon alkyl radical of the formula —O—$C_{1-8}$alkyl, comprising from 1 to 8 carbon atoms. Examples include methoxy, ethoxy, propoxy and the like. Other examples include $C_{1-4}$alkoxy. $C_{1-8}$alkoxy is substituted on one or more available carbon chain atoms with one or more substituents where allowed by available valences.

The term "aryl" means monocyclic or bicyclic aromatic ring systems containing from 6 to 12 carbons in the ring. Examples include phenyl, biphenyl, naphthalene (also referred to as naphthalenyl and naphthyl), azulenyl, anthracenyl and the like. Aryl radicals may be attached to a core molecule and further substituted on any atom where allowed by available valences.

The term "hetero," when used as a prefix for a ring system, refers to the replacement of at least one carbon atom member in the ring system with a heteroatom selected from N, O, S, S(O), or SO$_2$. A hetero ring may have 1, 2, 3, or 4 carbon atom members replaced by a nitrogen atom. Alternatively, a ring may have 0, 1, 2, or 3 nitrogen atom members and I oxygen or sulfur atom member. Alternatively, up to two adjacent ring members may be heteroatoms, wherein one heteroatom is nitrogen and the other heteroatom is selected from N, S, or O.

The term "heterocyclyl" means a saturated or partially unsaturated monocyclic or polycyclic "hetero" ring system radical having a cycloalkyl ring as the core molecule. Heterocyclyl ring systems include azetidinyl, 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, 1,4,5,6-tetrahydropyrimidin-2-yl, azepanyl, hexahydro-1,4-diazepinyl, hexahydro-1,4-oxazepanyl, tetrahydro-furanyl, tetrahydro-thienyl, tetrahydro-pyranyl, tetrahydro-pyridazinyl and the like. Heterocyclyl radicals may be attached to a core molecule and further substituted on any atom where allowed by available valences.

The term "heterocyclyl" also includes a benzofused-heterocyclyl ring system radical and the like, such as indolinyl (also referred to as 2,3-dihydro-indolyl), benzo[1,3]dioxolyl (also referred to as 1,3-benzodioxolyl), 5,6,7,8-tetrahydro-[1,8]naphthyridin-2-yl, 1,2,3,4-tetrahydro-quinolin-3-yl, 2,3-dihydro-1,4-benzodioxinyl, 2,3-dihydro-benzofuranyl, 1,2-dihydro-phthalazinyl and the like. Benzofused-heterocyclyl radicals may be attached to a core molecule and further substituted on any atom where allowed by available valences.

The term "heteroaryl" means an aromatic monocyclic or polycyclic heterocyclyl radical. Heteroaryl ring systems include furanyl, thienyl, pyrrolyl, oxazolyl, thiazolyl, 1H-imidazolyl, pyrazolyl, isoxazolyl, isothiazolyl, oxadiazolyl, triazolyl, thiadiazolyl, 1H-tetrazolyl, 2H-tetrazolyl, 1H-[1,2,3]triazolyl, 2H-[1,2,3]triazolyl, 4H-[1,2,4]triazolyl, pyridinyl, pyridazinyl, pyrimidinyl, pyrazinyl and the like. Heteroaryl radicals may be attached to a core molecule and further substituted on any atom where allowed by available valences.

The term "heteroaryl" also includes a benzofused-heteroaryl ring system radical and the like, such as indolizinyl, indolyl, indolinyl, azaindolyl, isoindolyl, benzo[b]furanyl, benzo[b]thienyl, indazolyl, azaindazolyl, benzoimidazolyl, benzothiazolyl, benzooxazolyl, benzoisoxazolyl, benzothiadiazolyl, benzotriazolyl, purinyl, 4H-quinolizinyl, quinolinyl, isoquinolinyl, cinnolinyl, phthalazinyl, quinazolinyl, quinoxalinyl, 1,8-naphthyridinyl, pteridinyl and the like. Benzofused-heteroaryl radicals may be attached to a core molecule and further substituted on any atom where allowed by available valences.

The term "benzofused," when used as a prefix for a ring system, refers to a radical formed by any monocyclic radical fused with a benzene ring; the benzofused radical may be attached to a core molecule via either ring of the bicyclic system.

The term "$C_{1-4}$alkoxycarbonyl protecting group" means a radical of the formula: —C(O)—O—$C_{1-4}$alkyl.

The term "—$C_{0-6}$alkyl($R_1$)" means a radical of the formula: —($R_1$) or —$C_{1-6}$alkyl-($R_1$).

The term "—$C_{0-6}$alkyl-aryl($R_1,R_8$)" means a radical of the formula: -aryl($R_1,R_8$) or —$C_{1-6}$alkyl-aryl($R_1,R_8$).

In general, under standard nomenclature rules used throughout this disclosure, the terminal portion of the designated side chain is described first followed by the adjacent functionality toward the point of attachment.

Thus, for example, a "phenyl-$C_{1-6}$alkyl-amino-carbonyl-$C_{1-6}$alkyl" substituent refers to a group of the formula:

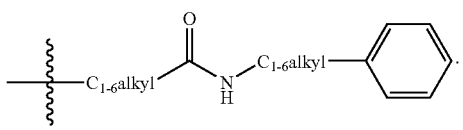

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

Certain compounds of Formula (I), Formula (II) or Formula (Ia) may exist in various stereoisomeric or tautomeric forms and mixtures thereof. The invention encompasses all such compounds, including active compounds in the form of essentially pure enantiomers, racemic mixtures and tautomers.

The compounds of the present invention may be present in the form of pharmaceutically acceptable salts. For use in medicines, the "pharmaceutically acceptable salts" of the compounds of this invention refer to non-toxic acidic/anionic or basic/cationic salt forms.

Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, citric acid, tartaric acid, carbonic acid or phosphoric acid.

Furthermore, when the compounds of the present invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts. Thus, representative pharmaceutically acceptable salts include the following: acetate, benzenesulfonate, benzoate, bicarbonate, bisulfate, bitartrate, borate, bromide, calcium, camsylate (or camphosulphonate), carbonate, chloride, clavulanate, citrate, dihydrochloride, edetate, fumarate, gluconate, glutamate, hydrabamine, hydrobromine, hydrochloride, iodide, isothionate, lactate, malate, maleate, mandelate, mesylate, nitrate, oleate, pamoate, palmitate, phosphate/diphosphate, salicylate, stearate, sulfate, succinate, tartrate, tosylate.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (stereoisomers).

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means an isomer having a nonsuperimposable mirror image. The term "diastereomer" means stereoisomers that are not enantiomers.

The term "chiral" means a molecule that, in a given configuration, cannot be superimposed on its mirror image. This is in contrast to achiral molecules that can be superimposed on their mirror images.

The invention is considered to include the tautomeric forms of all compounds of Formula (I), Formula (II) or Formula (Ia). In addition, some of the compounds represented by Formula (I), Formula (II) or Formula (Ia) may be prodrugs, i.e., derivatives of a drug that possess superior delivery capabilities and therapeutic value as compared to the active drug. Prodrugs are transformed into active drugs by in vivo enzymatic or chemical processes.

The symbols "R" and "S" represent the configuration of groups around a stereogenic carbon atom(s) as determined by the Cahn-Ingold-Prelog priority rules.

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a carbon-carbon double bond may be in an E or Z configuration according to their priority. In the "E" configuration, the substituents having the highest priorities are on opposite sides in relationship to the carbon-carbon double bond. In the "Z" configuration, the substituents having the highest priorities are oriented on the same side in relationship to the carbon-carbon double bond.

The term "conversion" refers to the efficiency of the reduction or hydrogenation of the vinyl bond of the starting material, without consideration to the orientation or for the enantiomeric excess of the stereoisomer produced.

The term "converting" or "converted" refers, when Z is hydroxy, to the alkylation of Z to provide Z is —O—$C_{1-8}$alkyl; and, conversely, when Z is —O—$C_{1-8}$alkyl, to the dealkylation of Z to provide Z is hydroxy.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations relative to a core molecule and are intended to be used as defined in the literature.

Where the processes for the preparation of the compounds according to the invention give rise to mixture of stereoisomers, it may be desirable to separate these isomers by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-d-tartaric acid and/or (+)-di-p-toluoyl-1-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved and percent enantiomeric excess (e.e.) determined using a chiral HPLC column.

The term "catalytic amount" is recognized in the art and means a substoichiometric amount or a reagent relative to a reactant. As used herein, a catalytic amount means an amount of from about 0.0001 to about 90 mole percent reagent relative to reactant, an amount of from about 0.001 to about 50 percent, an amount of from about 0.01 to about 10 percent, or an amount of from about 0.1 to about 5 percent. Additionally, the amount of the ligand-metal complex used can also be represented as a molar ratio of the substrate or reactant to the ligand-metal complex, and can represented by the term "S/C" or "substrate/complex."

The term "preformed" ligand-metal complex is recognized in the art as any form of a conjugated or coordinated metal adduct and ligand that has been isolated in a stable form, wherein a stoichiometric ratio exists between the metal adduct and ligand. The ratio of metal adduct to ligand is typically a fixed stoichiometric ratio, wherein the ligand-metal complex may be accompanied by counterions or may be present as a solvate, thus stabilizing and enabling the isolability of said complex. A preformed ligand-metal complex may or may not be isolable under open atmosphere, but often is handled under an inert atmosphere using methods known in the art. The preformed ligand-metal complex is typically stored for use, and then added to a solvent along with a substrate or reactant and optional additives for reaction with said substrate or reactant. One skilled in the art using methods known in the literature can prepare and isolate the preformed catalysts described herein. Moreover, a preformed ligand-metal complex includes those ligand-metal complexes that may be obtained as an in situ byproduct precipitated from a reaction mixture, isolated and stored in a stable form, then subsequently used as a "preformed" ligand-metal complex in a later reaction. For example, DMF may be incorporated into the stable preformed catalyst, as in [(S)—P-Phos RuCl$_2$(DMF)$_2$], resulting from the coordination of DMF with the metal adduct during the formation of the complex. A convention utilized herein to denote a preformed catalyst is the "/" denotation, used to indicate the ligand/[metal adduct].

Preformed catalysts not otherwise formed may also be purchased from commercial vendors.

Preformed catalysts disclosed and used herein include, and are not limited to, (S)—P-Phos/[RuCl$_2$(DMF)$_2$], (S)-Xyl-P-Phos/[RuCl$_2$(DMF)$_2$], (R)-MeBoPhoz/[RuCl$_2$(DMF)$_2$], (S)—P-Phos/[Ru(benzene)Cl]Cl, (R)-Xyl-P-Phos/[Ru(p-cymene)Cl]Cl, (S)-PhanePhos/[Rh(COD)]BF$_4$, (R)-PhanePhos/[Rh(COD)]BF$_4$, (S)—P-Phos/[Ir(COD)Cl], (S)-Xyl-P-Phos/[Ir(COD)Cl], (R)-iPr-PHOX/[Ir(COD)]BAr$_F$, (R)-Ph-PHOX/[Ir(COD)]BAr$_F$, (R)-MeOXyl-PhanePhos/[Rh(COD)]BF$_4$, (R)-An-PhanePhos/[Rh(COD)]BF$_4$, (R)-iPr-PhanePhos/[Rh(COD)]BF$_4$, (R)-Xyl-P-Xyl-[RuCl$_2$(DMF)$_2$], (S)-PhanePhos/[RuCl$_2$(DMF)$_2$], (R)-Xyl-PhanePhos/[RuCl$_2$(DMF)$_2$], (S)-MeBoPhoz/[RuCl$_2$(DMF)$_2$], (R)-Tol-Binap/[RuCl(p-cymene)]Cl, (S)-Binap/[RuCl(p-cymene)]Cl and (R,R)-MeDuPhos/[Rh(COD)]BF$_4$ and, where not specifically stated, enantiomers of these preformed catalysts therein. Synonymous with these designations is the interchangability of the descriptions, ie: [(S)—P-Phos RuCl$_2$(DMF)$_2$] can also be expressed as (S)—P-Phos/[RuCl$_2$(DMF)$_2$] without loss of meaning or effect.

Although examples of synthetic methods for preparing preformed ligand-metal complexes include various formation conditions, one skilled in the art would generally expect that a set of formation conditions are specific to each of said complexes. For example, a synthetic method for preparing a preformed (S)-PhanePhos/[Rh(COD)]BF$_4$ ligand-metal complex includes the coordination of an (S)-PhanePhos ligand and metal adduct [Rh(COD)$_2$]BF$_4$, with loss of one (COD) group. When dimeric metal adducts are used, as in the case of [Ir(COD)Cl]$_2$ for preparation of the preformed catalyst, [(S)—P-Phos Ir(COD)]Cl, the general preparation is expected to take place using an (S)—P-Phos ligand and a set of formation conditions specific for [(S)—P-Phos Ir(COD)]Cl.

The term "in situ" ligand-metal complex is recognized in the art as a means to prepare a ligand-metal complex by the addition of a metal adduct and a ligand to a solvent, either as a separate step, or in combination with the substrate, whereby the ligand-metal complex is formed in the reaction mixture. The metal adduct and ligand are typically mixed according to a stoichiometric ratio such that the combination will lead to the desired ligand-metal complex. In some cases, various analytical techniques are used to prove that the ligand-metal complex has indeed been formed. In other cases, the formation of the ligand-metal complex cannot be definitively proven. The ligand-metal complex formed in situ may also typically have accompanying, stabilizing counterions or may be present as a solvate, thus stabilizing said ligand-metal complex during the reaction. The ligand-metal complex formed in situ will perform in the same manner as a preformed ligand-metal complex, and have the same characteristics of a preformed ligand-metal complex, as stated above. A ligand-metal complex made in situ may also be prepared in a stable solvent and stored in solution until needed. A convention utilized herein to denote an "in situ" catalyst is the "&" notation, used to indicate a ligand&[metal adduct] group. For example, use of the in situ ligand-metal complex (R)-Me-BoPhoz&[Ir(COD)Cl]$_2$, would involve pre-mixing (in an appropriate solvent) the ligand (R)-Me-BoPhoz with the metal adduct [Ir(COD)Cl]$_2$ for a period of time to allow the active catalyst to form, then performing the reduction reaction with a suitable starting material and a hydrogen source. In some cases herein, for "in situ" ligand-metal complexes involving dimeric metal adducts, the complexes may also be denoted as "ligand&metal precursor" (see description below)

The term "metal adduct" is meant to denote the convenient, weighable, stable form of a metal with its stabilizing ligands and counterions as is understood by one of ordinary skill in the art. In some cases, metal adducts are most stable in a dimeric form, which upon disproportionation under a prescribed set of reaction conditions, leads to a monomeric form, which is referred to herein as a "metal precursor." An example of a dimeric metal adduct is [Ru(COD)(CF$_3$COO)$_2$]$_2$, which upon disproportionation leads to the metal precursor [Ru(COD)(CF$_3$COO)$_2$]. It is understood by one of ordinary skill in the art that the stoichiometry of the disproportionation is such that 1 equivalent dimeric metal adduct provides 2 equivalents of metal precursor.

As discussed more fully below, the reactions contemplated in the present invention include reactions that are enantioselective, diastereoselective, and/or regioselective. In addition, for chiral embodiments of the invention, the invention is considered to include pure enantiomers, racemic mixtures, as well as mixtures of enantiomers having 0.001% to 99.99% enantiomeric excess. Furthermore, an enantioselective reaction is a reaction that hydrogenates an achiral reactant to a chiral product enriched in one enantiomer. Enantioselectivity is generally quantified as "enantiomeric excess" (e.e.) defined as follows:

% enantiomeric exess $A(ee)$=(% enantiomer $A$)–(% enantiomer $B$), where A and B are the enantiomers formed.

An enantioselective reaction yields a product with an e.e. in a range of from about 5% e.e. to about 99% e.e., or in a range of from about 30% e.e. to about 99% e.e., or in a range of from about 60% e.e. to about 99% e.e., or in a range of from about 70% e.e. to about 99% e.e., or in a range of from about 80% e.e. to about 99% e.e.

The term "substantially pure" means, within the scope of the present invention, an isomeric mixture which includes an enantiomerically enriched form of the enantiomer, wherein the mixture is substantially free of the opposite enantiomer. In this context, substantially pure means the opposite enantiomer may be an amount in a range of about less than 25% of the mixture, about less than 10%, about less than 5%, about less than 2% or about less than 1% of the mixture.

An enantiomerically enriched form of the S-enantiomer isolated by HPLC from a racemic mixture may be determined according to the formula:

$$\% \text{ e.e. of } S \text{ enantiomer} = 100 \times \frac{(\% \text{ area } S \text{ enantiomer})}{(\% \text{ area } S \text{ enantiomer}) + (\% \text{ area } R \text{ enantiomer})}.$$

An enantiomerically enriched form of the R-enantiomer isolated by HPLC from a racemic mixture may be determined according to the formula:

$$\% \text{ e.e. of } R \text{ enantiomer} = 100 \times \frac{(\% \text{ area } R \text{ enantiomer})}{(\% \text{ area } S \text{ enantiomer}) + (\% \text{ area } R \text{ enantiomer})}.$$

Furthermore, compounds of the present invention may have at least one crystalline, polymorph or amorphous form. The plurality of such forms is included in the scope of the invention. In addition, some of the compounds may form solvates with water (i.e., hydrates) or common organic solvents (e.g., organic esters such as ethanolate and the like). The plurality of such solvates are also intended to be encompassed within the scope of this invention.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

Discussion of the Invention

In the asymmetric, homogeneous hydrogenation reactions of Scheme C and Scheme D, in accordance with the following examples, the substrate Compound C1 and Compound D1 were reacted with a ligand-metal complex, wherein the ligand-metal complex consists essentially of a ligand and a metal adduct. The following examples illustrate various embodiments of the ligands, metal adducts, the ligand-metal complexes thus formed, other additives and reaction temperature and pressure conditions used in accordance with said embodiments of the present invention.

SCREENING EXAMPLES

Screening of various complexes of ligands conjugated with various metal adducts was performed to identify a suitable ligand-metal complex for the asymmetric hydrogenation of substrate Compound C1 and Compound D1. The screening consisted of reacting substrate Compound C1 and Compound D1 with a series of preformed and in situ formed ligand-metal complexes. In addition, certain reaction conditions were optimized (such as solvent, additive, temperature and pressure and the like) in the hydrogenation of substrate Compounds C1 and D1.

Ligands referred to throughout the specification and used in the following examples include those shown below:

| Ligand | Elements |
|---|---|
| BoPhoz Ligand Family structure (ferrocene with PPh₂ and N(R^b)P(R^a)₂ substituent) | BoPhoz Ligand Family |
| (R/S)-MeBoPhoz | $R^b$ is Me, $R^a$ is Ph |
| (R/S)-Et-BoPhoz | $R^b$ is Et, $R^a$ is Ph |
| (R/S)-iPr-BoPhoz | $R^b$ is i-Pr, $R^a$ is Ph |
| (R/S)-Bn-BoPhoz | $R^b$ is Bn, $R^a$ is Ph |
| (R/S)-Ph-BoPhoz | $R^b$ is Ph, $R^a$ is Ph |
| (R/S)-Phenethyl-(R/S)-BoPhoz | $R^b$ is (R/S)-1-phenyl-ethyl, $R^a$ is Ph |
| (S)-Ethyl-Naphthyl-(R/S)-BoPhoz | $R^b$ is (1S)-1-naphth-1-yl-ethyl, $R^a$ is Ph |
| Xyl-(R/S)-Me-BoPhoz | $R^b$ is Me, $R^a$ is 3,5-Me₂-C₆H₃ |
| pFPh-(R/S)-Me-BoPhoz | $R^b$ is Me, $R^a$ is 4-F-Ph |
| pFPh-(R/S-Et-BoPhoz | $R^b$ is Et, $R^a$ is 4-F-Ph |
| pFPh-(R/S)-Bn-BoPhoz | $R^b$ is Bn, $R^a$ is 4-F-Ph |
| PCy-(R/S)-BoPhoz | $R^b$ is Me, $R^a$ is Cyclohexyl |
| CF₃Ph-(R/S)-Me-BoPhoz | $R^b$ is Me, $R^a$ is 4-CF₃-C₆H₄ |
| 2,4,6-F₃Ph-(R/S)-Me-BoPhoz | $R^b$ is Me, $R^a$ is 2,4,5-F₃-Ph |

-continued

| | |
|---|---|
| Binol-(R/S)-Me-BoPhoz | $R^b$ is Me, $R^a$ is Binol |
| P(R/S,R/S)-Binol-(R/S,S/R)-Me-BoPhoz | $R^a$ and $R^b$ are taken together to form (R/S,R/S)-Binol |

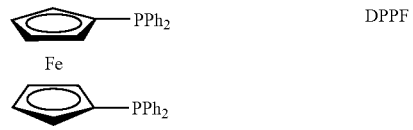

DPPF

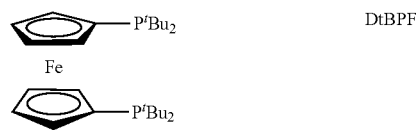

DtBPF

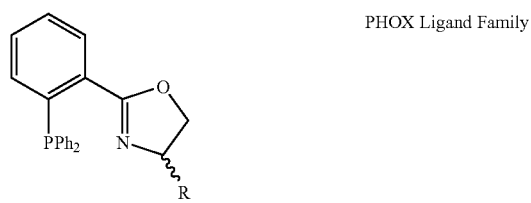

PHOX Ligand Family

| | |
|---|---|
| (R/S)-iPr-PHOX | R is iPr |
| (R/S)-Ph-PHOX | R is Ph |

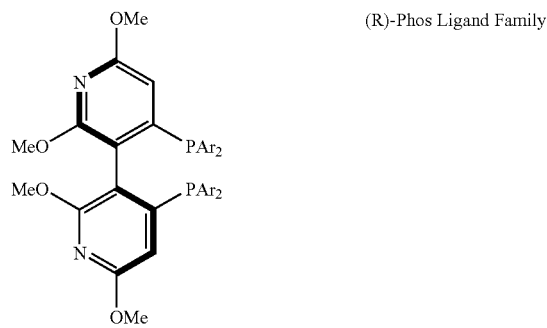

(R)-Phos Ligand Family

| | |
|---|---|
| (R)-P-Phos | Ar is Ph |
| (R)-Xyl-P-Phos | Ar is 3,5-Me$_2$-C$_6$H$_3$ |
| (R)-Tol-P-Phos | Ar is x-Me-C$_6$H$_4$ |

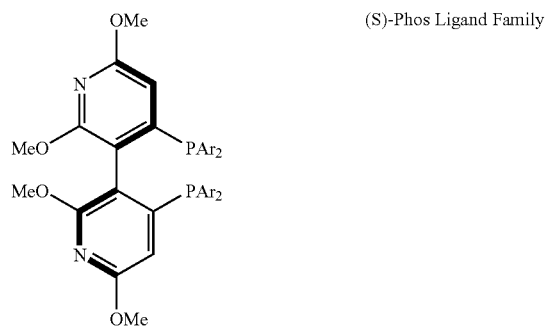

(S)-Phos Ligand Family

| | |
|---|---|
| (S)-P-Phos | Ar is Ph |
| (S)-Xyl-P-Phos | Ar is 3,5-Me$_2$-C$_6$H$_3$ |
| (S)-Tol-P-Phos | Ar is x-Me-C$_6$H$_4$ |

| | |
|---|---|
| 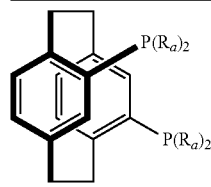 | (R)-Phanephos Ligand Family |
| (R)-Phanephos | $R^a$ is Ph |
| (R)-Xyl-Phanephos | $R^a$ is Xyl: 3,5-Me$_2$-C$_6$H$_3$ |
| (R)-An-Phanephos | $R^a$ is 4-OMe-Ph |
| (R)-iPr-PhanePhos | $R^a$ is iPr |
| (R)-MeOXyl-Phanephos | $R^a$ is MeOXyl: 3,5-Me$_2$-4-OMe-C$_6$H$_2$ |
| 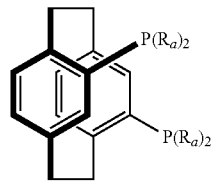 | (S)-Phanephos Ligand Family |
| (S)-Xyl-Phanephos | $R^a$ is Xyl: 3,5-Me$_2$-C$_6$H$_3$ |
| (S)-An-Phanephos | $R^a$ is 4-OMe-Ph |
| (S)-iPr-PhanePhos | $R^a$ is iPr |
| (S)-MeOXyl-Phanephos | $R^a$ is MeOXyl: 3,5-Me$_2$-4-OMe-C$_6$H$_2$ |
| 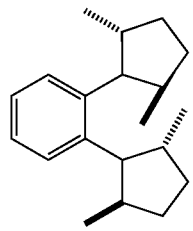 [SMILES: C[C@@H]1CC[C@@H](C)C1c1ccccc1C1[C@H](C)CC[C@H]1C] | (R,R)-Me-Duphos |
| 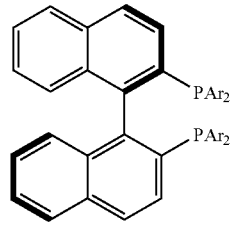 | (R)-Binap Ligand Family |
| (R)-Binap | Ar is Ph |
| (R)-Tol-Binap | Ar is 4-Me-C$_6$H$_4$ |
| (R)-Xyl-Binap | Ar is 3,5-Me$_2$-C$_6$H$_3$ |
| 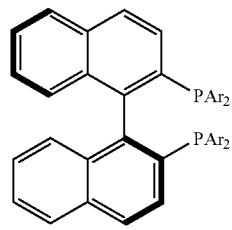 | (S)-Binap Ligand Family |
| (S)-Binap | Ar is Ph |
| (S)-Tol-Binap | Ar is 4-Me-C$_6$H$_4$ |
| (S)-Xyl-Binap | Ar is 3,5-Me$_2$-C$_6$H$_3$ |

General Information. $^1$H NMR spectra were acquired at 300 MHz on a Bruker Avance-300 spectrometer in CDCl$_3$ unless indicated otherwise, using Me$_4$Si as an internal standard. NMR abbreviations used: s, singlet; d, doublet; dd, doublet of doublets; t, triplet; m, multiplet; br, broad. Normal-phase preparative chromatography was performed on an Isco Combiflash Separation System Sg 100c equipped with a Biotage FLASH Si 40M silica gel cartridge (KP-Sil Silica, 32-63μ, 60 Å; 4×15 cm) eluting at 35 mL/min with detection at 254 nm. Optical rotations were measured on a Perkin-Elmer 241 polarimeter. Electrospray (ES) mass spectra were obtained on a Micromass Platform LC single quadrupole mass spectrometer in the positive mode. Elemental analysis and Karl Fischer water analysis were determined by Quantitative Technologies Inc., Whitehouse, N.J.

When the percent e.e. is determined by HPLC (using Diacel ChiralPak AD-H column at 35° C., 1 mL/min, 80:20 eluent ratio of Hexane:IPA after derivatization to the methyl ester), the resulting standard error for percent e.e. is about 2-3% of the HPLC peak area. For derivatization to the methyl ester 0.1 M reactions: a 50 µL reaction sample (2 mg substrate/product, 0.005 mmol,) was treated in an HPLC vial with 50 µL of 2 M TMSCHN$_2$ in Et$_2$O (0.1 mmol) and MeOH (1.5 mL).

SYNTHETIC EXAMPLES

The terms used in describing the invention are commonly used and known to those skilled in the art. When used herein, the following abbreviations have the indicated meanings:

General Synthetic Methods

Representative compounds of the present invention can be synthesized in accordance with the general synthetic methods described below and are illustrated more particularly in the schemes that follow. Since the schemes are illustrations whereby intermediate and target compounds of the present invention may be prepared, the invention should not be construed as being limited by the chemical reactions and conditions expressed. Additional representative compounds and stereoisomers, racemic mixtures, diastereomers and enantiomers thereof can be synthesized using the intermediates prepared in accordance with these schemes and other materials, compounds and reagents known to those skilled in the art. All such compounds, stereoisomers, racemic mixtures, diastereomers and enantiomers thereof are intended to be encompassed within the scope of the present invention. The preparation of the various starting materials used in the schemes is well within the skill of persons versed in the art.

Abbreviations used in the instant specification, particularly the Schemes and Examples, are as follows:

| Abbreviation | Meaning |
|---|---|
| Acac | acetyl-acetone |
| AcOH | acetic acid |
| Bn | Benzyl |
| Boc | tert-butoxycarbonyl |
| COD | Cyclooctadiene |
| Conv | Conversion |
| Cpd | Compound |
| PCy | cyclohexyl substituted on phosphorous |
| DCE | 1,2-dichloroethane |
| DCM | Dichloromethane |
| DIPEA | N,N-diisopropylethylamine |
| DMF | N,N-dimethylformamide |
| d.r. | diastereomeric ratio |
| EDC | N-ethyl-N'-dimethylaminopropylcarbodiimide hydrochloride |
| e.e | enantiomeric excess |
| Et | Ethyl |
| Et$_2$O | diethyl ether |
| Et$_3$N | Triethylamine |
| EtOAc | ethyl acetate |
| EtOH | Ethanol |
| d/hr/min | day(s)/hour(s)/minute(s) |
| HCl | hydrochloric acid |
| Hex | Hexane |
| ICP | inductively coupled plasma |
| i-Pr | Isopropyl |
| Ir | Iridium |
| $^1$HNMR | proton nuclear magnetic resonance |
| HOBt | 1-hydroxybenzotriazole |
| HPLC | high performance liquid chromatography |
| IPA | 2-propanol |
| M | molarity (mmole/mL) |
| Me | Methyl |
| MeOH | Methanol |
| MeCN | Acetonitrile |
| NaHMDS | sodium hexamethyldisilylamide |
| NaOH | sodium hydroxide |
| NH$_4$OH | ammonium hydroxide |
| ND | not determined |
| OTf | Triflate |
| P | pressure (in either PSIG or bar) |
| Pd/C | palladium on carbon |
| Ph | Phenyl |
| PH | acidity/basicity on litmus paper |
| PSIG | pound per square inch - gauge |
| Rh | Rhodium |
| RP-HPLC | reverse phase high performance liquid chromatography |
| RT/rt/r.t. | room temperature |
| Ru | Ruthenium |
| SDS | sodium dodecasulfate |
| T | temperature (in ° C.) |
| TEA | Triethylamine |
| TFA | trifluoroacetic acid |
| THF | Tetrahydrofuran |
| TMS | Tetramethylsilane |
| Tol | Toluene |
| Xyl | xylene (1,4-Me$_2$-Ph) |

Synthetic Example 1

Ru Adduct Complex Hydrogenation of Compound C1

Various basic-screening, preformed Ru adduct complexes were reacted with Compound C1 (82 mg, 0.2 mmol) in a 50:1 substrate:complex ratio in various solvents (3 mL) at a temperature of about 50° C., under H$_2$ pressure of about 360 psig (25 bar) for a period of about 16 to about 18 hours. The percent conversion and e.e. were determined by HPLC (210 nm).

TABLE 1

| Entry | Complex | Solvent | Conv | e.e. |
|---|---|---|---|---|
| 1 | (S)-P-Phos/[RuCl$_2$(DMF)$_2$] | MeOH | 6 | <5 |
| 2 | (S)-P-Phos/[RuCl$_2$(DMF)$_2$] | DCE | <5 | ND |
| 3 | (S)-Xyl-P-Phos/[RuCl$_2$(DMF)$_2$] | MeOH | 6 | 8 (S) |
| 4 | (R)-Me-BoPhoz/[RuCl$_2$(DMF)$_2$] | MeOH | 8 | 23 (S) |
| 5 | (S)-P-Phos/[Ru(benzene)Cl]Cl | MeOH | 8 | 15 (S) |
| 6 | (S)-P-Phos/[Ru(benzene)Cl]Cl | DCE | <5 | ND |
| 7 | (R)-Xyl-P-Phos/[Ru(p-cymene)Cl]Cl | MeOH | <5 | ND |
| 8 | (R)-Xyl-P-Phos/[Ru(p-cymene)Cl]Cl | DCE | 10 | 59 (R) |

The results of Synthetic Example 1 show that the conversion and e.e. are dependent on both the solvent and ligand chosen. The reaction also may need to be run at a higher temperature in order to obtain improved percent conversion and e.e.

Synthetic Example 2

Rh—BoPhoz Hydrogenation of Compound C1

Various Rh—BoPhoz complexes formed in situ from ligand and [Rh(COD)$_2$]OTf were reacted with Compound C1 (82 mg, 0.2 mmol) in a 50:1 substrate:complex ratio in various solvents (3 mL) at a temperature of about 50° C., under H$_2$ pressure of about 360 psig (25 bar) for a period of about 16 to about 18 hours. The percent conversion and e.e. were determined by HPLC (210 nm).

TABLE 2

| Entry | Ligand | Solvent | Conv | e.e. |
|---|---|---|---|---|
| 1 | (R)-Me-BoPhoz | MeOH | 15 | 41 (S) |
| 2 | $CF_3Ph$-(R)-Me-BoPhoz | MeOH | 14 | 37 (S) |
| 3 | (R)-iPr-BoPhoz | MeOH | 13 | 45 (S) |
| 4 | (S)-Binol-(R)-Me-BoPhoz | MeOH | 6 | 7 (S) |
| 5 | (R)-Me-BoPhoz | DCE | 8 | >90 (S) |
| 6 | $CF_3Ph$-(R)-Me-BoPhoz | DCE | 7 | 77 (S) |
| 7 | (R)-Me-BoPhoz | THF | 10 | 80 (S) |
| 8 | $CF_3Ph$-(R)-Me-BoPhoz | THF | 10 | 85 (S) |

Generally, the enantioselectivity obtained in aprotic solvents (such as THF and DCE) was improved over MeOH, even though MeOH provided improved conversion for a given complex. However, the low reactivity for conversion of the substrate may be attributable to coordination of the quinoline ring nitrogen atom to the complex.

Synthetic Example 3

Phanephos-Rh Hydrogenation of Compound C1

A preformed (S)-PhanePhos/[Rh(COD)]$BF_4$ complex was reacted with Compound C1 (82 mg, 0.2 mmol) in a 50:1 substrate:complex ratio with various acid additives in MeOH (3 mL) at a temperature of about 50° C., under $H_2$ pressure of about 360 psig (25 bar) for a period of about 16 to about 18 hrs. The percent conversion and e.e. were determined by HPLC (210 nm).

TABLE 3

| Entry | Additive (Eq) | Conv | e.e. |
|---|---|---|---|
| 1 | TsOH (1 Eq.) | 27 | 67 (R) |
| 2 | TsOH (0.2 Eq.) | 16 | 77 (R) |
| 3 | AcOH (1 Eq.) | 13 | 67 (R) |
| 4 | AcOH (0.2 Eq.) | 14 | 64 (R) |
| 5 | $HBF_4$ (1 Eq.) | 37 | 75 (R) |
| 6 | $HBF_4$ (1 Eq.) | 25 | 85 (R) |
| 7 | No Additive | 14 | <5 |

Generally, percent conversion obtained (compared to a reference Entry 7) was improved (see Entries 1, 5, and 6) by the use of an additive (in a range of from about 0 Eq to about 1.2 Eq) to reduce the coordinative effect of the quinoline ring nitrogen atom on the complex.

The improvement to conversion and enantioselectivity was achieved by the optional use of an additive to reduce the coordinative effect of the quinoline ring nitrogen atom.

Synthetic Example 4

Ir-ligand Complex Hydrogenation of Compound C1

For Entries 1-10, as shown in Table 4 below, various preformed P-Phos-Iridium and Phox-Iridium complexes were reacted with Compound C1 (82 mg, 0.2 mmol) in a 50:1 substrate:complex ratio with various acid additives in either MeOH or DCE (3 mL) at a temperature of about 50° C., under $H_2$ pressure of about 360 psig (25 bar) for a period of about 16 to about 18 hours. The percent conversion and e.e. were determined by HPLC (210 nm).

TABLE 4

| Entry | Ligand | Solvent | Conv | e.e. |
|---|---|---|---|---|
| 1 | (S)-P-Phos/[Ir(COD)]Cl | MeOH | 5 | ND |
| 2 | (S)-P-Phos/[Ir(COD)]Cl | DCE | 7 | >90 (S) |
| 3 | (S)-Xyl-P-Phos/[Ir(COD)]Cl | MeOH | 26 | 45 (S) |
| 4 | (S)-Xyl-P-Phos/[Ir(COD)]Cl | DCE | 27 | 90 (S) |
| 5 | (R)-iPr-PHOX/[Ir(COD)]$BAr_F$ | MeOH | 66 | 70 (S) |
| 6 | (R)-iPr-PHOX/[Ir(COD)]$BAr_F$ | DCE | 0 | ND |
| 7 | (R)-Ph-PHOX/[Ir(COD)]$BAr_F$ | MeOH | 19 | 68 (S) |
| 8 | (R)-Ph-PHOX/[Ir(COD)]$BAr_F$ | DCE | 0 | ND |
| 9 | (R)-Me-BoPhoz/[Ir(COD)Cl]$_2$ | MeOH | 24 | 19 (S) |
| 10 | (R)-Me-BoPhoz/[Ir(COD)Cl]$_2$ | DCE | 88 | 95 (S) |

Generally, the use of iridium complexes compared to rhodium complexes (see Entry 3, Table 4 compared to Entry 3, Table 1) provided an improved conversion and e.e. However, the conversion and e.e. results were solvent-sensitive.

Synthetic Example 5

Ir-ligand Complex Hydrogenation of Compound C1

A preformed (R)-iPr-PHOX/[Ir(COD)]$BAr_F$ complex was reacted with Compound C1 (82 mg, 0.2 mmol) in a 50:1 substrate:complex ratio in various solvents (3 mL) at various temperatures (° C.) and under various $H_2$ pressures (psig) for a period of about 16 to about 18 hours. The percent conversion and e.e. were determined by HPLC (210 nm).

TABLE 5

| Entry | Solvent | Temp | Pressure | Conv | e.e. |
|---|---|---|---|---|---|
| 1 | MeOH | 50 | 360 | 66 | 70 (S) |
| 2 | EtOH | 50 | 360 | 30 | 65 (S) |
| 3 | iPrOH | 50 | 360 | 23 | 34 (S) |
| 4 | MeOH | 70 | 360 | 37 | 55 (S) |
| 5 | EtOH | 70 | 360 | 44 | 61 (S) |
| 6 | MeOH | 50 | 70 | <5 | — |
| 7 | MeOH | 50 | 145 | 29 | 75 (S) |

For use with a (R)-iPr-PHOX/[Ir(COD)]$BAr_F$ complex, lower alcohol solvents gave appreciable conversions and e.e. at a reaction temperature of greater than 50° C. and reaction pressures of greater than 145 psig.

Synthetic Example 6

Hydrogenation of Compound D1

Various preformed Ru-ligand complexes were reacted with Compound D1 (82 mg, 0.2 mmol) in a 1100:1 substrate:complex ratio with various additives in MeOH (2 mL) at a temperature of about 60° C., under $H_2$ pressure of about 430 psig (30 bar) for a period of about 20 hours.

The percent conversion e.e. were determined by HPLC (using Diacel ChiralPak AD-H column at 35° C., 1 mL/min, 80:20 eluent ratio of Hexane:IPA after derivatization to the methyl ester).

TABLE 6

| Entry | Complex | Additive | Conv | e.e. |
|---|---|---|---|---|
| 1 | (R)-Xyl-P-Phos/[RuCl$_2$(DMF)$_2$] | 0.5 Eq. Et$_3$N | >99 | 15 (R) |
| 2 | (R)-PhanePhos/[RuCl$_2$(DMF)$_2$] | 0.5 Eq. Et$_3$N | ND | 58 (S) |
| 3 | (S)-PhanePhos/[RuCl$_2$(DMF)$_2$] | 0.5 Eq. Et$_3$N | 99 | 64 (R) |
| 4 | (R)-Xyl-PhanePhos[RuCl$_2$(DMF)$_2$] | 0.5 Eq. Et$_3$N | >99 | 82 (S) |
| 5 | (S)-Xyl-PhanePhos/[RuCl$_2$(DMF)$_2$] | 0.5 Eq. Et$_3$N | 99 | 82 (R) |

TABLE 6-continued

| Entry | Complex | Additive | Conv | e.e. |
|---|---|---|---|---|
| 6 | (S)-Me-BoPhoz/[RuCl$_2$(DMF)$_2$] | 0.5 Eq. Et$_3$N | >99 | 5 (S) |
| 7 | (R)-Tol-Binap/[RuCl(p-cymene)]Cl | 0.5 Eq. Et$_3$N | 94 | 5 (S) |
| 8 | (S)-Tol-Binap/[RuCl(p-cymene)]Cl | 0.5 Eq. Et$_3$N | ND | 5 (R) |

Entries 5 & 6 refer to use of a ligand in combination with a metal adduct as described in Ohta T, Takaya H, Kitamura M, Nagai K and Noyori R, *J. Org. Chem.* 1987, 52, 3176, under reaction conditions representative of the present invention.

Generally, Ru metal adducts and (R,S)-Xyl-P-Phos complexes in the presence of the additive Et$_3$N led to high conversion but with a low e.e.

Synthetic Example 7

Iridium and Rhodium Complex Hydrogenation of Compound C1

Various preformed iridium and rhodium complexes were reacted with Compound C1 (82 mg, 0.2 mmol) in a 50:1 substrate:complex ratio in MeOH (3 mL) at a temperature of about 50° C., under H$_2$ pressure of about 360 psig (25 bar) for a period of about 16-18 hours. The percent conversion and e.e. were determined by HPLC (210 nm).

TABLE 7

| Entry | Complex | Additive | Conv | e.e. |
|---|---|---|---|---|
| 1 | (R)-An-Phanephos/[Rh(COD)]BF$_4$ | 1 Eq HBF$_4$ | 13 | 47 (S) |
| 2 | (R)-Xyl-Phanephos/[Rh(COD)]BF$_4$ | 1 Eq HBF$_4$ | 15 | 47 (S) |
| 3 | (R,R)-MeDuPhos/[Rh(COD)]BF$_4$ | 1 Eq HBF$_4$ | 12 | 10 (S) |
| 4 | (S)-P-Phos/[Ir(COD)Cl] | 1 Eq HBF$_4$ | 14 | ~80 (S) |
| 5 | (S)-Xyl-P-Phos/[Ir(COD)Cl] | 1 Eq HBF$_4$ | 22 | ~83% (S) |
| 6 | (S)-Phanephos/[Rh(COD)]BF$_4$ | 1 Eq HBF$_4$ | 16 | 46 (R) |
| 7 | (S)-Phanephos/[Rh(COD)]BF$_4$ | No additive | 21 | 11 (R) |
| 8 | (R)-iPr-PHOX/[Ir(COD)]BF$_4$ | No additive | 18 | 78 (S) |

The use of HBF$_4$ in the presence of iridium and rhodium complexes enhanced enantioselectivity when the reaction was run in MeOH.

Synthetic Example 8

Rhodium Hydrogenation of Compound C1

Various rhodium complexes, formed in situ from various ligands (0.005 mmol) and the metal adduct [Rh(ethylene)$_2$Cl]$_2$ (0.002 mmol) by stirring in solvent (2 mL) at room temperature, were reacted with a solution of Compound C1 (82 mg, 0.2 mmol in 1 mL solvent) in a 50:1 substrate:complex ratio in solvent (1 mL), with an optional HBF$_4$ (1 equivalent) additive at a temperature of about 50° C., under H$_2$ pressure of about 360 psig (25 bar) for a period of about 16-18 hours. The percent conversion and e.e. were determined by HPLC (210 nm).

TABLE 8

| Entry | Ligand | Solvent | Conv | e.e. |
|---|---|---|---|---|
| 1 | (R)-Me-BoPhoz | MeOH | 7 | ND |
| 2 | (R)-Me-BoPhoz | DCE | 87 | 95.5 (S) |
| 3 | (R)-Me-BoPhoz | MeOH + HBF$_4$ | 3 | ND |
| 4 | (R)-Me-BoPhoz | DCE + HBF$_4$ | 14 | 80 (S) |
| 5 | (R)-Phenethyl-(S)-BoPhoz | DCE | 40 | 79 (R) |
| 6 | (R)-Phenethyl-(R)-BoPhoz | DCE | 68 | 90 (R) |

TABLE 8-continued

| Entry | Ligand | Solvent | Conv | e.e. |
|---|---|---|---|---|
| 7 | (R)-Phanephos | DCE | 58 | 79 (S) |
| 8 | (R)-Xyl-P-Phos | DCE | <5 | ND |
| 9 | (R)-Me-BoPhoz | DCE (70° C.) | 78 | 90 (S) |

The results of Synthetic Example 8, show that conversion and enantioselectivity provided by certain and ligand metal complexes are sensitive to the solvent. For example, Table 8, Entry 1 shows that MeOH provides a low conversion and e.e. for a rhodium adduct and Me-BoPhoz ligand complex compared to the aforementioned iridium and rhodium PhanePhos complexes. Also, Table 8, Entry 2 shows that DCE provides a desirable conversion and e.e. for a rhodium adduct and Me-BoPhoz ligand complex compared to iridium and rhodium PhanePhos complexes.

Further, unlike the iridium and rhodium PhanePhos complexes, the use of an additive such as HBF$_4$ for a rhodium adduct and (R)-Me-BoPhoz ligand complex results in low conversion and e.e.

Synthetic Example 9

Rhodium Hydrogenation of Compound C1

Various rhodium complexes, formed in situ from various ligands (0.005 mmol) listed in Table 9 and [Rh(ethylene)$_2$(acac)] (0.004 mmol) by stirring in solvent (2 mL) at room temperature for a period of about 30 minutes, were reacted with a solution of Compound C1 (82 mg, 0.2 mmol in 1 mL solvent) in a 50:1 substrate:complex ratio in solvent (1 mL) at a temperature of about 50° C., under H$_2$ pressure of about 360 psig (25 bar) for a period of about 16-18 hours. The percent conversion and e.e. were determined by HPLC (210 nm). Note: acac is a counter ion used to stabilize the metal by supporting a negative charge.

TABLE 9

| Entry | Ligand | Solvent | Conv | e.e. |
|---|---|---|---|---|
| 1 | (R)-Me-BoPhoz | i-PrOH | 55 | 68 (S) |
| 2 | (R)-Me-BoPhoz | DCE | 33 | 93 (S) |
| 3 | (R)-Xyl-P-Phos | i-PrOH | <2 | ND |
| 4 | (R)-Xyl-P-Phos | DCE | 13 | 16 (R) |

The results of Synthetic Example 9, show that the conversion and enantioselectivity provided by certain ligand-solvent combinations are sensitive to the metal adduct (relative to Synthetic Example 8) used.

Synthetic Example 10

[Rh(CO)$_2$(acac)] Hydrogenation of Compound C1

Various rhodium complexes, formed in situ from various ligands (0.005 mmol) and [Rh(CO)$_2$(acac)] (0.004 mmol) by stirring in solvent (2 mL) at room temperature for a period of about 30 minutes, were reacted with a solution of Compound C1 (82 mg, 0.2 mmol in 1 mL solvent) in a 50:1 substrate:complex ratio in solvent (1 mL) at a temperature of about 50° C., under H$_2$ pressure of about 360 psig (25 bar) for a period of about 16-18 hours. The percent conversion and e.e. were determined by HPLC (210 nm).

TABLE 10

| Entry | Ligand | Solvent | Conv | e.e. |
|---|---|---|---|---|
| 1 | (R)-Me-BoPhoz | i-PrOH | 12 | 20 (S) |
| 2 | (R)-Me-BoPhoz | DCE | 10 | 80 (S) |
| 3 | (R)-Xyl-P-Phos | i-PrOH | <2 | ND |
| 4 | (R)-Xyl-P-Phos | DCE | <2 | ND |

The results of Synthetic Example 10, also show that the conversion and enantioselectivity provided by certain ligand-solvent combinations are sensitive to the metal adduct used (relative to Examples 8 and 9).

Synthetic Example 11

[Ir(COD)Cl]$_2$ Hydrogenation of Compound C1

Various iridium complexes, formed in situ from various ligands (0.005 mmol) and [Ir(COD)Cl]$_2$ (0.002 mmol) by stirring in solvent (2 mL) at room temperature for a period of about 30 minutes, were reacted with a solution of Compound C1 (82 mg, 0.2 mmol in 1 mL solvent) in a 50:1 substrate:complex ratio in solvent (1 mL) with an optional HBF$_4$ (1 Equivalent) additive at various temperatures (° C.), under H$_2$ pressure of about 360 psig (25 bar) for a period of about 16-18 hours.

For Entries 1-15, the percent conversion and e.e. were determined by HPLC (210 nm). For Entries 16-20, the percent conversion and e.e. were determined by NMR as discussed in Synthetic Example 13 and shown in Table 13.

TABLE 11

| Entry | Ligand | Solvent | Temp. | Conv. | e.e. |
|---|---|---|---|---|---|
| 1 | (R)-Me-BoPhoz | MeOH | 50 | 24 | 19 (S) |
| 2 | (R)-Me-BoPhoz | MeOH + HBF$_4$ | 50 | 19 | 73 (S) |
| 3 | (R)-Me-BoPhoz | DCE | 50 | 88 | 95 (S) |
| 4 | (R)-Me-BoPhoz | DCE + HBF$_4$ | 50 | 40 | 80 (S) |
| 5 | (S)-Me-BoPhoz | DCE | 50 | 85 | 93 (R) |
| 6 | (R)-Bn-BoPhoz | DCE | 50 | 87 | 95.5 (S) |
| 7 | 3,4-diClPh-(R)-Me-BoPhoz | DCE | 50 | 86 | 93 (S) |
| 8 | PCy-(R)-Me-BoPhoz | DCE | 50 | <5 | ND |
| 9 | Xyl-(R)-Me-BoPhoz | DCE | 50 | 94 | 94 (S) |
| 10 | (R)-Phenethyl-(S)-Me-BoPhoz | DCE | 50 | 69 | 35 (R) |
| 11 | (R)-Phenethyl-(S)-Me-BoPhoz | DCE | 50 | 10 | 82 (S) |
| 12 | (S)-Binol-(R)-Me-BoPhoz | DCE | 50 | 32 | 80 (S) |
| 13 | (R)-Binol-(R)-Me-BoPhoz | DCE | 50 | 25 | 90 (S) |
| 14 | (R)-Ph-BoPhoz | DCE | 50 | 92 | 57 (S) |
| 15 | (R)-Phanephos | DCE | 50 | <5 | ND |
| 16 | (R)-Me-BoPhoz | THF | 50 | 60 | >95 (S) |
| 17 | (R)-Me-BoPhoz | toluene | 50 | 90 | 91 (S) |
| 18 | (R)-Me-BoPhoz | EtOAc | 50 | 75 | 94 (S) |
| 19 | (R)-Me-BoPhoz | DCE | 70 | 100 | 93 (S) |
| 20 | (R)-Me-BoPhoz | DCE | 90 | 100 | 92 (S) |

The iridium complexes generated in situ by reacting [Ir(COD)Cl]$_2$ (0.5 Eq.) and Me-BoPhoz (1.25 Eq.) were highly selective in aprotic solvents giving consistently >90% ee. In MeOH, the addition of HBF$_4$ caused an increase in enantioselectivity (from 19% to 73% ee, Table 11, Entries 1 and 2). In DCE, the addition of HBF$_4$ caused a decrease in both activity and enantioselectivity (Table 11, Entries 3 and 4).

Comparatively, the iridium (R)-Me-BoPhoz complex was tested in non-chlorinated aprotic solvents (Table 11, Entries 16-18) to provide various conversion and enantioselectivity results.

Synthetic Example 12

(R)-Me-BoPhoz &[Ir(COD)Cl]$_2$ Hydrogenation of Compound C1

An (R)-Me-BoPhoz &[Ir(COD)Cl]$_2$ complex, formed in situ from the ligand (0.005 mmol) and [Ir(COD)Cl]$_2$ adduct (0.002 mmol) by stirring in solvent (2 mL) at room temperature for a period of about 30 minutes, was reacted with a solution of Compound C1 (82 mg, 0.2 mmol in 1 mL solvent) in a 50:1 substrate:complex ratio in various solvents (1 mL) at various temperatures for a period of about 18 hours. The percent conversion and e.e. were determined by HPLC$^a$ (210 nm) and NMR$^b$.

The percent conversion were determined by HPLC$^a$ (210 nm) and NMR$^b$ and e.e. was determined by HPLC.

TABLE 12

| Entry | Solvent | Temp | Cpd C1$^b$ (%) | Cpd C2$^b$ (%) | Cpd C2$^a$ (%) | e.e. (%) |
|---|---|---|---|---|---|---|
| 1 | THF | 50 | 40 | 40 | 46 | >95 (S) |
| 2 | toluene | 50 | 10 | 62 | 80 | 91 (S) |
| 3 | EtOAc | 50 | 25 | 50 | 62 | 94 (S) |
| 4 | DCE | 70 | — | 75 | 90 | 93 (S) |
| 5 | DCE | 90 | — | 75 | 90 | 92 (S) |

The results of the Synthetic Example 12 show that NMR can be used to supplement the HPLC analysis for conversion to the desired enantiomer.

Synthetic Example 13

(R)-Me-BoPhoz &[Ir(COD)Cl]$_2$ Hydrogenation of Compound C1

Various concentrations of the (R)-Me-BoPhoz &[Ir(COD)Cl]$_2$ complex, formed in situ from the (R)-Me-BoPhoz ligand (0.0105 mmol) and [Ir(COD)Cl]$_2$ adduct (0.04 mmol) by stirring in DCE (8 mL) at room temperature for a period of about 30 minutes: and then taken to 0.001 M volume with DCE, were reacted with a solution of Compound C1 (1 mmol in 1 mL DCE) in various substrate:complex ratios at a temperature of about 90° C., under H$_2$ pressure of about 360 psig (25 bar) for a period of about 18 hours. The percent conversion was determined by HPLC$^a$ and $^1$H NMR$^b$.

TABLE 13

| Entry | Conc. (M) | S/C | Cpd C1$^b$ (%) | Cpd C2$^b$ (%) | Cpd C2$^a$ (%) | e.e. (%) |
|---|---|---|---|---|---|---|
| 5a | 0.25 | 50/1 | — | 70 | 82 | 91 (S) |
| 5b | 0.25 | 100/1 | 9 | 62 | 75 | 90 (S) |
| 5c | 0.5 | 100/1 | 6 | 64 | 79 | 90 (S) |
| 5d | 0.5 | 200/1 | 35 | 36 | 43 | 88 (S) |

The results of the Synthetic Example 13 show that varying the substrate to complex ratio for Entry 5, Table 12 resulted in a reduced conversion without a substantial loss of e.e.

Synthetic Example 14

Rh-Ligand Complex Hydrogenation of Compound D1

Various preformed Rh-ligand complexes were reacted with Compound D1 (82 mg, 0.2 mmol) in a 100:1 substrate:complex ratio in MeOH (2 mL) at a temperature of about 60° C., under H$_2$ pressure of about 430 psig (30 bar) for a period of about 20 hours.

The percent conversion and e.e. were determined by HPLC (using Diacel ChiralPak AD-H column at 35° C., 1 mL/min, 80:20 eluent ratio of Hexane:IPA after derivatization to the methyl ester).

TABLE 14

| Entry | Complex | Conv | e.e. |
|---|---|---|---|
| 1 | (R)-PhanePhos/[Rh(COD)]BF$_4$ | >99 | 63 (S) |
| 2 | (R)-MeOXyl-PhanePhos/[Rh(COD)]BF$_4$ | 30 | 63 (S) |
| 3 | (R)-An-PhanePhos/[Rh(COD)]BF$_4$ | >99 | 60 (S) |
| 4 | (S)-iPr-PhanePhos/[Rh(COD)]BF$_4$ | >99 | 14 (R) |

The results of Synthetic Example 14 show a high conversion rate with an average e.e. of at least 50% provided by a rhodium metal adduct for the acid Compound D1. Entry 4, Table 14 shows that each enantiomer of the complex provides the opposite enantiomer of Compound D2.

Synthetic Example 15

Rh—BoPhoz Hydrogenation of Compound D1

The Rh—BoPhoz complex formed in situ by the coordination of a PCy-(R)-Me-BoPhoz ligand&[Rh(COD)$_2$]OTf was reacted with Compound D1 (82 mg, 0.2 mmol) in a 100:1 substrate:complex ratio in various solvents (2 mL) at a temperature of about 60° C., under H$_2$ pressure of about 430 psig (30 bar) for a period of about 20 hours. The percent conversion (>99%) and e.e. (30% (S) enantiomer) were determined by HPLC (210 nm).

Synthetic Example 16

Rh-PhanePhos Hydrogenation of Compound D1

Various Rh-PhanePhos complexes that were preformed (Entry 1) or prepared in situ (Entries 2-4) from the PhanePhos ligand and [Rh(COD)$_2$]BF$_4$ or [Rh(COD)$_2$]OTf metal adducts by stirring in MeOH (1 mL) at room temperature were reacted with Compound D1 (82 mg, 0.2 mmol) in a 100:1 substrate:complex ratio and the optionally present additive HBF$_4$ (in molar equivalents) in MeOH (2 mL) at a temperature of about 60° C., under H$_2$ pressure of about 430 psig (30 bar) for a period of about 20 hours.

The percent conversion and e.e. were determined by HPLC (using Diacel ChiralPak AD-H column at 35° C., 1 mL/min, 80:20 eluent ratio of Hexane:IPA after derivatization to the methyl ester).

TABLE 15

| Entry | Complex | HBF$_4$ | Conv | e.e |
|---|---|---|---|---|
| 1 | (R)-PhanePhos/[Rh(COD)]BF$_4$ | None | >99 | 63 (S) |
| 2 | (R)-PhanePhos&[Rh(COD)$_2$]OTf | 1 Eq | >94 | 40 (S) |
| 3 | (S)-Xyl-PhanePhos &[Rh(COD)$_2$]OTf | None | 96 | 67 (R) |
| 4 | (S)-Xyl-PhanePhos&[Rh(COD)$_2$]OTf | 1 Eq | 81 | 40 (R) |

In Table 15, Entries 2-4 further demonstrate that in situ formation is an effective means to prepare the ligand-metal complex and that addition of HBF$_4$ reduces the conversion and e.e.

Synthetic Example 17

Ru-PhanePhos Hydrogenation of Compound D1

Various Ru-PhanePhos complexes (preformed) with a solvate with DMF (0.002 mmol) were reacted with Compound D1 (82 mg, 0.2 mmol) in a 100:1 substrate:complex ratio in the solvent MeOH (2 mL) and the additive Et$_3$N (0.1 mmol) at a temperature of about 60° C., under H$_2$ pressure of about 430 psig (30 bar) for a period of about 20 hours.

The percent conversion was determined by $^1$HNMR on the dried crude reaction mixture and the percent e.e. was determined by HPLC (using Diacel ChiralPak AD-H column at 35° C., 1 mL/min, 80:20 eluent ratio of Hexane:IPA after derivatization to the methyl ester Compound C3).

TABLE 16

| Entry | Complex | Conv | e.e. |
|---|---|---|---|
| 1 | (S)-PhanePhos/[RuCl$_2$(DMF)$_2$] | >99 | 58 (R) |
| 2 | (R)-PhanePhos/[RuCl$_2$(DMF)$_2$] | >99 | 58 (S) |
| 3 | (R)-Xyl-PhanePhos/[RuCl$_2$(DMF)$_2$] | >99 | 83 (S) |
| 4 | (R)-Xyl-PhanePhos/[RuCl$_2$(DMF)$_2$] | >99 | 82-85 (S) |
| 5 | (S)-Xyl-PhanePhos/[RuCl$_2$(DMF)$_2$] | >99 | 82 (R) |

Comparing Entries 1 and 2 and Entries 4 and 5 in Table 16 show that each stereospecific complex provides the opposite enantiomer of Compound D2.

Synthetic Example 18

(R)-Xyl-PhanePhos/[RuCl$_2$(DMF)$_2$] Hydrogenation of Compound D1

A (R)-Xyl-PhanePhos/[RuCl$_2$(DMF)$_2$] complex (0.002 mmol) was reacted with Compound D1 (0.25 M) in various substrate:complex ratios in MeOH and Et$_3$N (0.5 Eq compared to Compound D1) at various temperatures and H$_2$ pressures for a period of about 20 hours.

The percent conversion was determined by $^1$HNMR on the dried crude reaction mixture and the percent e.e. was determined by HPLC (using Diacel ChiralPak AD-H column at 35° C., 1 mL/min, 80:20 eluent ratio of Hexane:IPA after derivatization to the methyl ester).

TABLE 17

| ENTRY | S/C | P (bar) | T (° C.) | Conv (%) | e.e. (%) |
|---|---|---|---|---|---|
| 1 | 250 | 30 | 60 | >99 | 81 (S) |
| 2 | 500 | 30 | 60 | >99 | 84 (S) |
| 3 | 250 | 30 | 40 | >99 | 83 (S) |
| 4 | 500 | 30 | 40 | >99 | 84 (S) |
| 5 | 250 | 10 | 40 | >99 | 85 (S) |
| 6 | 500 | 10 | 40 | >99 | 85 (S) |

The set of reaction conditions shown in Table 17 (using various substrate:complex ratios, pressures and temperatures) optimized the conversion and e.e. percentages using the (R)-Xyl-PhanePhos/[RuCl$_2$(DMF)$_2$] complex.

Synthetic Example 19

Xyl-PhanePhos/[RuCl$_2$(DMF)$_2$] Transfer Hydrogenation of Compound D1

Stereoisomeric Xyl-PhanePhos/[RuCl$_2$(DMF)$_2$] complexes were reacted with Compound D2 (82 mg, 0.2 mmol) in a 100:1 substrate:complex ratio in DCE (3 mL) with formic acid HCO$_2$H (30 Eq excess to Compound D1) and Et$_3$N (in a molar equivalence ratio with HCO$_2$H) at a temperature of about 60° C. for a period of about 24 hours.

The percent conversion and e.e. were determined by HPLC (using Diacel ChiralPak AD-H column at 35° C., 1 mL/min, 80:20 eluent ratio of Hexane:IPA after derivatization to the methyl ester).

TABLE 18

| Entry | Complex | HCOOH/Et₃N | Conv (%) | e.e. (%) |
|---|---|---|---|---|
| 1 | (R)-Xyl-PhanePhos/[RuCl₂(DMF)₂] | 1:1 | 40 | 58 (S) |
| 2 | (S)-Xyl-PhanePhos/[RuCl₂(DMF)₂] | 5:2 | 27 | 42 (R) |

The results of Synthetic Example 19 for substrate Compound D1 show moderate activity and selectivity when HCOOH/Et₃N was used as the hydrogen source.

Synthetic Example 20

Enrichment of Compound D1 and Salt Forms Thereof

Reaction mixtures from Synthetic Example 18 were combined, neutralised and extracted in DCM (1.5 g). The average e.e obtained was 84.5%. Recrystallization from DCM/MTBE at −20° C. precipitated the undersired enantiomer to afford an enriched e.e for the desired enantiomer in the mother liquor. The desired enantiomer was isolated after evaporation of the mother liquor in 97% e.e. and 70% yield.

The ratio of DCM:MTBE is important; DCM dissolves the enantiomeric mixture and addition of MTBE precipitates the undesired enantiomer. The ratio of the mixture may be from 1:1 to 1:3.

The free base form solid obtained from the mother liquiour was redissolved in an excess of DCM/MTBE and treated with cyclohexylamine to obtain a salt of Compound D3. Other salts (from Et₃N, iPr₂—NH) of Compound D3 were tested and found to be also very soluble in DCM/Hexane and DCM/MTBE solvent mixtures.

Synthetic Example 21

(R)-Xyl-PhanePhos/[RuCl₂(DMF)₂] Asymmetric Hydrogenation of Compound D1

The (R)-Xyl-PhanePhos/[RuCl₂(DMF)₂] complex (0.25 M) was reacted with Compound D1 (0.25 M) in various substrate:complex ratios in MeOH (3 mL) with Et₃N (0.5 Eq to Compound D1) at various temperatures and H₂ pressure for time periods of about 20 hours.

The percent conversion was determined by ¹HNMR on the dried crude reaction mixture and the percent e.e. was determined by HPLC (using Diacel ChiralPak AD-H column at 35° C., 1 mL/min, 80:20 eluent ratio of Hexane:IPA after derivatization to the methyl ester).

TABLE 19

| Entry | S/C | P (bar) | T (° C.) | Conv (%) | e.e. (%) |
|---|---|---|---|---|---|
| 1 | 500 | 10 | 40 | 99 | 85 (S) |
| 2 | 1000 | 10 | 60 | 66 | 73 (S) |
| 3 | 2000 | 10 | 60 | 19 | 64 (S) |
| 4 | 500 | 3 | 60 | 94 | 82 (S) |
| 5 | 1000 | 3 | 60 | 93 | 78 (S) |
| 6 | 2000 | 3 | 60 | 11 | 56 (S) |

The results of Synthetic Example 21 show that reaction conditions include a lower H₂ gas pressure and a higher temperature. Entry 1 in Table 19 above corresponds to Entry 6 in Table 17 at a reaction time of about 4 hours. Entries 3 and 6 show the upper limit of the substrate:complex ratio using reaction conditions shown for the (R)-Xyl-PhanePhos/[RuCl₂(DMF)₂] complex. Entries 4 to 6 show the lower limit of the H₂ gas pressure using the reaction conditions shown.

Synthetic Example 22

(R)-Xyl-PhanePhos Hydrogenation of Compound D1

Various Ru-PhanePhos complexes were reacted with Compound D1 in a 100:1 substrate:complex ratio. The Ru-precursor (0.002 mmol), (R)-Xyl-PhanePhos (0.002 mmol) and Compound D1 (82 mg, 0.2 mmol) were loaded in a glass lined reaction chamber. The chamber was sealed and purged with nitrogen, then MeOH (1 mL) was injected. The resulting mixture was stirred at r.t. for 20-30 min, then MeOH (1 mL) was injected with an optional Et₃N additive (0.5 Eq to Compound D1), followed by hydrogen purge. The reaction was run at a temperature of about 40° C., under H₂ pressure of about 145 psig (10 bar) for a period of about 20 hours.

The percent conversion was determined by ¹HNMR on the dried crude reaction mixture and the percent e.e. was determined by HPLC (using Diacel ChiralPak AD-H column at 35° C., 1 mL/min, 80:20 eluent ratio of Hexane:IPA after derivatization to the methyl ester).

TABLE 20

| Entry | Complex | Additive | Conv (%) | e.e. (%) |
|---|---|---|---|---|
| 1 | (R)-Xyl-PhanePhos/[RuCl₂(DMF)₂] | 0.5 Eq Et₃N | >99 | 82-85 (S) |
| 2 | (R)-Xyl-PhanePhos&[Ru(COD)(CF₃COO)₂]₂ | — | 99 | 87 (S) |
| 3 | (R)-Xyl-PhanePhos&[Ru(COD)(methylallyl)₂] | — | 99 | 87 (S) |

The (R)-Xyl-PhanePhos ligand was tested in combination with other ruthenium metal adducts paired with various counterions by generating the complex in situ and were found to provide satisfactory conversion and e.e.

Synthetic Example 23

(R)-Xyl-PhanePhos Hydrogenation of Compound D1

The preformed (R)-Xyl-PhanePhos/[RuCl₂(DMF)₂] complex in Table 21a was paired with various additives and reacted with Compound D1 (196 mg, 0.5 mmol, 0.25 M) in a 500:1 substrate:complex ratio at varying temperatures in MeOH (1 mL), under H₂ pressure of about 145 psig (10 bar) for a period of about 4 hours to about 20 hours.

The in situ formed (R)-Xyl-PhanePhos&[Ru(COD)(CF₃COO)₂]₂ in Table 21b and (R)-Xyl-PhanePhos&[Ru(COD)(methylallyl)₂] complex in Table 21c were prepared by loading the Ru metal adduct, the (R)-XylPhanePhos ligand and Compound D1 in a glass liner. The liner was placed in the reactor. The reactor was sealed and purged with nitrogen, then MeOH (1 mL) was injected and the resulting mixture was stirred at r.t. for 20-30 min, followed by injection of MeOH (1 mL) (with or without additive).

The percent conversion was determined by ¹HNMR on the dried crude reaction mixture; the percent e.e. was determined using Diacel ChiralPak AD-H column (35° C.), 1 mL/min, 80:20 eluent ratio of Hexane:IPA after derivatization to the methyl ester.

TABLE 21a

| Entry | Additive | T (° C.) | Conv (%) | e.e. (%) |
|---|---|---|---|---|
| Table 20, Entry 1 | No additive | 40 | 99 | 85 (S) |
| 1 | 0.5 Eq Et₃N | 40 | 99 | 85 (S) |

TABLE 21a-continued

| Entry | Additive | T (° C.) | Conv (%) | e.e. (%) |
|---|---|---|---|---|
| 2 | 0.5 Eq Et₃N | 25 | 99 | 89-90 (S) |
| 3 | 1 Eq Et₃N | 25 | 88 | 87 (S) |
| 4 | 1 Eq. CH₃COOH | 25 | 2 | ND |

TABLE 21b

| Entry | Additive | T (° C.) | Conv (%) | e.e. (%) |
|---|---|---|---|---|
| 5 | 1 Eq. HBF₄•Et₂O | 40 | 16 | 71 (S) |
| 6 | 1M HCl Et₂O | 40 | 3 | ND |
| 7 | 1 Eq. CF₃COOH | 25 | 73 | 90.5 (S) |
| 8 | 1 Eq. CH₃COOH | 40 | 99 | 88 (S) |
| 9 | No additive | 25 | 99 | 89 (S) |
| 10 | 1 Eq. CH₃COOH | 25 | 98 | 89-90 (S) |
| 11 | 0.2 Eq. CH₃COOH | 25 | 93 | 90 (S) |
| 12 | 0.5 Eq. Et₃N | 25 | 22 | 90 (S) |

TABLE 21c

| Entry | Additive | T (° C.) | Conv (%) | e.e. (%) |
|---|---|---|---|---|
| 13 | 1 Eq. HBF₄•Et₂O | 40 | 24 | 84 (S) |
| 14 | 1M HCl Et₂O | 40 | 13 | 87 (S) |
| 15 | 1 Eq. CF₃COOH | 40 | 99 | 85 (S) |
| 16 | 1 Eq. CF₃COOH | 25 | 52 | 90.5 (S) |
| 17 | 1 Eq. CH₃COOH | 40 | 99 | 86 (S) |
| 18 | 1 Eq. CH₃COOH | 25 | 70 | 90 (S) |
| 19 | 0.5 Eq. Et₃N | 25 | 11 | ND |

The various combinations shown in Table 21a and Table 21b indicate that a variety of additives provide satisfactory conversion and e.e.

While HCl (1M Et₂O) and HBF₄.Et₂O led to low conversion and partial deprotection of the Boc group (3-15%) (Table 21b, Entries 5, 6, 13 and 14), the CH₃COOH and CF₃COOH additives led to full conversion and an e.e. of at least 85% (Table 21b, Entries 8, 15 and 17).

Reaction conditions in Table 21b considered combinations of Ru-precursor, the amount and nature of the additive and the temperature. Each of these factors in combination have an influence on both the amount of conversion and enantioselectivity. The (R)-Xyl-PhanePhos/[RuCl₂(DMF)₂] complex led to full conversion and higher e.e. at 25° C. when using 0.5 Eq. Et₃N. The use of more Et₃N or CH₃COOH led to lower conversion. When no additive was used, the reaction was slightly slower, reaching full conversion in approximately 8 hrs.

When the in situ formed (R)-Xyl-PhanePhos&[Ru(COD) (CF₃COO)₂]₂ and (R)-Xyl-PhanePhos&[Ru(COD)(methylallyl)₂] complexes were employed, the enantioselectivity obtained was 90% (Table 21b, Entry 8, compare with Entry 10). At S/C 500, the amount of CH₃COOH as an additive shows that there might be an influence on the activity of the complex (Table 21b, Entries 9-11). The nature of the additive had an effect on the complex activity (Table 21b, Entries 7, 9-12). Ru-systems that led to full conversion and approximately 90% e.e at S/C 500/1, 25° C. and 10 bar are shown in Table 21b, Entries 2, 9 and 10 and Table 21c, Entry 17).

Synthetic Example 24

(R)-Xyl-PhanePhos Hydrogenation of Compound D1

Compound D1 (0.5 mmol) and a preformed (R)-Xyl-PhanePhos/[RuCl₂(DMF)₂] complex (0.001 mmol) in a S/C ratio of 500:1 in various solvents (2 mL) with no additive was reacted at 40° C., 10 bar (145 psig) H₂, over a period of about 20 hrs.

The percent conversion was determined by ¹HNMR on the dried crude reaction mixture; the percent e.e. was determined using Diacel ChiralPak AD-H column (35° C.), 1 mL/min, 80:20 ratio of Hexane:IPA after derivatization to the methyl ester.

TABLE 22

| Entry | Solvent | Conv (%) | e.e. (%) |
|---|---|---|---|
| 1 | MeOH | >99 | 85 (S) |
| 2 | EtOH | 44 | 84 (S) |
| 3 | IPA | 35 | 75 (S) |
| 4 | MeOH/DCE 1/1 | 63 | 83 (S) |
| 5 | DCE | 26 | 83 (S) |
| 6 | THF | 10 | 72 (S) |
| 7 | Tol | 5 | 83 (S) |
| 8 | EtOAc | 19 | 83 (S) |

As shown in Table 22, unsaturated acid Compound D1 was fully hydrogenated to the corresponding D3 (S-acid, in approximately 90% e.e), via asymmetric hydrogenation in the presence of a (R)-Xyl-PhanePhos/[RuCl₂(DMF)₂] or a (R)-Xyl-PhanePhos&[Ru(COD)(CF₃COO)₂]₂ complex, at S/C 500/1 using in methanol, at 10 bar hydrogen pressure and room temperature.

Synthetic Example 25

(R)-Xyl-PhanePhos Hydrogenation of Compound D1

Compound D1 (0.2 mmol, 79 mg, 0.1 M) and the preformed (R)-Xyl-PhanePhos/[RuCl₂(DMF)₂] complex in Table 25a (0.0002 mmol) in a S/C ratio of 1000:1 in MeOH (2 mL) with various additives was reacted at 40° C., 10 bar (145 psig) H₂, over a period of about 20 hrs.

The percent conversion was determined by ¹HNMR on the dried crude reaction mixture and the percent e.e. was determined using Diacel ChiralPak AD-H column (35° C.), 1 mL/min, 80:20 ratio of Hexane:IPA after derivatization to the methyl ester.

Ligand-metal complex stock solutions (in situ) of a (R)-Xyl-PhanePhos&[Ru(COD)(CF₃COO)₂]₂ complex in Table 25b and a (R)-Xyl-PhanePhos&[Ru(COD)(methylallyl)₂] complex in Table 25c were generated by stirring the ruthenium adduct with the chiral phosphine ligand (0.0002 mmol/mL) in MeOH under N₂ for 30-40 min at r.t. A solution of the complex (1 mL) was injected into the reactor, followed by CH₃COOH (0.5 mL), the stock solution in MeOH, then MeOH (0.5 mL). The preparation of Entry 14 is detailed in Synthetic Example 27.

TABLE 23a

| Entry | Additive | Conv (%) | e.e. (%) |
|---|---|---|---|
| 1 | No additive | 4 | ND |
| 2 | 0.1 Eq. Et₃N | 66 | 82 (S) |
| 3 | 0.25 Eq. Et₃N | 5 | ND |
| 4 | 0.5 Eq. Et₃N | 47 | 86 (S) |
| 5 | 0.75 Eq. Et₃N | 3 | ND |
| 6 | 1 Eq. Et₃N | 2 | ND |
| 7 | 1.2 Eq. Et₃N | 17 | 77 (S) |

TABLE 23b

| Entry | Additive | Conv (%) | e.e. (%) |
|---|---|---|---|
| 8 | No additive | 5 | ND |
| 9 | 0.1 Eq. CH₃COOH | 93 | 86 |
| 10 | 0.25 Eq. CH₃COOH | 50 | 87 |
| 11 | 0.5 Eq. CH₃COOH | 98 | 87 |
| 12 | 0.75 Eq. CH₃COOH | 79 | 87 |
| 13 | 1 Eq. CH₃COOH | 4 | ND |
| 14 | 1.2 Eq. CH₃COOH | 99 | 88 |

TABLE 23c

| Entry | Additive | Conv (%) | e.e. (%) |
|---|---|---|---|
| 15 | No additive | 30 | 87 |
| 16 | 0.1 Eq. CH₃COOH | 33 | 68 |
| 17 | 0.25 Eq. CH₃COOH | 4 | ND |
| 18 | 0.5 Eq. CH₃COOH | 86 | 86 |
| 19 | 0.75 Eq. CH₃COOH | 23 | 85 |
| 20 | 1 Eq. CH₃COOH | 3 | ND |
| 21 | 1.2 Eq. CH₃COOH | 79 | 82 |

Synthetic Example 26

(R)-Xyl-PhanePhos Hydrogenation of Compound D1

Compound D1 (2 mmol, 1M) and preformed (R)-Xyl-PhanePhos[[Ru(COD)(CF$_3$COO)$_2$] (0.0002 mmol) in a S/C ratio of 1000:1 in MeOH (2 mL) with additive CH$_3$COOH (1.2 Eq., 0.5 mL stock solution in MeOH), was reacted at 40° C., 10 bar (145 psig) H$_2$, over a period of about 20 hrs.

The percent conversion was determined by $^1$HNMR on the dried crude reaction mixture and the percent e.e. were determined using Diacel ChiralPak AD-H column (35° C.), 1 mL/min, 80:20 ratio of Hexane:IPA after derivatization to the methyl ester.

Ligand-metal complex stock solutions (for use in situ) were generated by stirring the ruthenium precursor with the chiral phosphine ligand (0.002 mmol/mL) in MeOH under N$_2$ for 2 hrs at 55° C., then stirred with 1.2 eq. of CH$_3$COOH (with respect to the starting material). The corresponding volume of complex stock solution was injected into the reactor, followed by CH$_3$COOH (0.5 mL) stock solution in MeOH, then MeOH (0.5 mL).

TABLE 24

| Entry | T (° C.) | P (bar) | Conv. (%) | e.e. (%) |
|---|---|---|---|---|
| 1 | 40 | 10 | 99.5 | 92 (S) |
| 2 | 50 | 10 | 99.7 | 89 (S) |
| 3 | 50 | 3 | 99 | 82 (S) |

Synthetic Example 27

(R)-Xyl-PhanePhos Hydrogenation of Compound D1

Compound D1 (1 M) and preformed (R)-Xyl-PhanePhos/[Ru(COD)(CF$_3$COO)$_2$] (0.0002 mmol) in a S/C ratio of 1000:1 in MeOH (2 mL) with additive CH$_3$COOH (1.2 Eq., 0.5 mL stock solution in MeOH), was reacted in a stand alone Parr vessel at 40° C., 10 bar (145 psig) H$_2$, over a period of about 20 hrs.

The percent conversion and the percent e.e. were determined using Diacel ChiralPak AD-H column (35° C.), 1 mL/min, 80:20 ratio of Hexane:IPA after derivatization to the methyl ester.

A ligand-metal complex stock solution was generated by stirring the ruthenium precursor with the chiral phosphine ligand in half of the total volume of MeOH under N$_2$ for 2 hrs at 55° C., then stirred while cooling with 1.2 eq. of CH$_3$COOH (with respect to the starting material). This solution was injected to the starting material and the Schlenk flask was rinsed with the remaining solvent.

TABLE 25

| Entry | Cpd D1 (g) | Time (h) | P (bar) | Conv. (%) | e.e. (%) |
|---|---|---|---|---|---|
| 1 | 1.58 | 17 | 10 | 99.5 | 86 (S) |
| 2 | 1.58 | 16 | 3 | 90 | 82 (S) |
| 3 | 1.58 | 24 |  | 98 | 81 (S) |
| 4 | 1.58 | 40 |  | 98.5 | 79 (S) |
| 5 | 3.17 | 17 | 10 | 99.5 | 89 (S) |

Synthetic Example 28

Recrystallization/Extraction of the Crude Acetic Acid Salt of Compound D3

The reaction products from Table 24, Entries 1-3 were combined and crude product Compound D3 (2.6 g) in the acetate salt form was obtained with the following composition: 0.8% starting material, 91% (83% e.e.) of Compound D3 and 8% of the (αR) isomer Compound D2. Since both forms of the product (the free acid and the acetate salt) presented similar solubility, the crude acetate quinolinium salts (Table 24) were examined. The MTBE/Hexane and DCM/MTBE/Hexane solvent combinations led to the isolation of the product in 80% yield and >98% e.e. (Table 26, Entries 6 and 8).

TABLE 26

| Entry | Solvent | T (° C.) | Precipitate | e.e. (%) | Yield (%) |
|---|---|---|---|---|---|
| 1 | IPA | RT | No | 83 | NA |
| 2 | IPA | −20 | No | 83 | NA |
| 3 | IPA/MTBE | −20 | No | 83 | NA |
| 4 | DCM/Hexane | 60 | Yes | 99 | 10 |
| 5 | MTBE | 60 | Yes | 84 | NA |
| 6 | MTBE/Hexane (1:2) | 60 | Yes | 98.3 | 80 |
| 7 | MTBE/Hexane (1:1) | 60 | Yes | 98 | 70 |
| 8 | DCM:MTBE:Hex (1:5:5) | r.t. | Yes | 98.7 | 80 |
| 9 | toluene | r.t. | Yes | 91 | NA |

When the results from Table 26 were applied to the combined reaction products from Table 25, the product Compound D3 generated (5 g, >98% e.e.) was used as the starting material for diastereoselective hydrogenation of the quinoline ring.

Synthetic Example 29

Pd/C Catalyzed Hydrogenation of Compound D3 Et$_3$N Salt

Initial solvent screening in the Pd/C catalyzed diastereoselective hydrogenation of the Compound D3 Et$_3$N salt was performed using 10% Pd/C (w/w, dry basis) at 60° C., 3 bar H$_2$.

The percent conversion and the percent e.e. were determined using Diacel ChiralPak AD-H column (35° C.), 1 mL/min, 80:20 ratio of Hexane:IPA after derivatization to the methyl ester.

TABLE 27

| Entry | Solvent | Conv. (%) | D4/D5 (ratio) |
|---|---|---|---|
| 1 | MeOH | 64 | 28/21 |
| 2 | EtOH | 73 | 33/30 |
| 3 | i-PrOH | 87 | 41/38 |
| 4 | Toluene | 99 | 49/40 |
| 5 | THF | 96 | 44/44 |
| 6 | DCE | 79 | 35/30 |
| 7 | EtOAc | 85 | 37/34 |
| 8 | MTBE | 51 | 19/18 |

Synthetic Example 30

[Ir(COD)Cl]$_2$ Homogeneous Diastereoselective Hydrogenation of Compound D3

[Ir(COD)Cl]$_2$ (0.004 mmol), various ligand stereoisomers (0.0044 mmol) and Compound D3 (0.2 mmol, 80 mg) in a S/C ratio of 50:1 were reacted in toluene (3 mL) with 0.1 Eq. 12 (0.02 mmol, 5 mg), 50° C., 25 bar hydrogen over a period of about 20 hrs.

The percent conversion and the percent e.e. were determined using Diacel ChiralPak AD-H column (35° C.), 1 mL/min, 80:20 eluent ratio of Hexane:IPA after derivatization to the methyl ester or by 1H NMR estimations on the crude dried product.

The [Ir(COD)Cl]$_2$ adduct and various ligands were stirred in 1 mL solvent under N$_2$, r.t. for a period of 30 min, followed by addition of stock solutions of I$_2$ and substrate in toluene.

TABLE 28

| Entry | Ligand | D3 (%) | D4/D5 (d.r.) | D4 + D5 (%) |
|---|---|---|---|---|
| 1 | (R)-Me-BoPhoz | 47 | 28/72 | 82 |
| 2 | (S)-Me-BoPhoz | 40 | 33/67 | 83 |
| 3 | (R)-Xyl-P-Phos | 53 | 45/55 | 81 |
| 4 | (S)-Xyl-P-Phos | 50 | 50/50 | 77 |
| 5 | (R)-Xyl-PhanePhos | 95 | ND | ND |
| 6 | (S)-Xyl-PhanePhos | 95 | ND | ND |

Synthetic Example 31

Me-BoPHoz/[Ir(COD)Cl]$_2$ Homogeneous Diastereoselective Hydrogenation of Compound D3

[Ir(COD)Cl]$_2$ (0.004 mmol), various ligand stereoisomers (0.0044 mmol) and Compound D3 (0.2 mmol, 80 mg) in a S/C ratio of 50:1 were reacted in various solvents (3 mL) with 0.1 Eq. 12 (0.02 mmol, 5 mg) at 50° C. and 25 bar hydrogen over a period of about 20 hrs.

The percent conversion and the percent e.e. were determined using either Diacel ChiralPak AD-H column (35° C.), 1 mL/min, 80:20 eluent ratio of Hexane:IPA after derivatization to the methyl ester or by $^1$HNMR estimations on the crude dried product.

The [Ir(COD)Cl]$_2$ adduct and the ligand were stirred in 1 mL solvent under N$_2$, r.t. for a period of 30 min, followed by addition of stock solutions of I$_2$ and substrate in the indicated solvent.

TABLE 29

| Entry | Ligand | Solvent | Additive | D3 (%) | D4/D5 (d.r.) | D4 + D5 (%) |
|---|---|---|---|---|---|---|
| 1 | (R)-Me-BoPhoz | toluene | None | 47 | 28/72 | 82 |
| 2 | (S)-Me-BoPhoz | toluene | None | 40 | 33/67 | 83 |
| 3 | (R)-Me-BoPhoz | THF | None | — | 41/59 | >99 |
| 4 | (S)-Me-BoPhoz | THF | None | — | 46/54 | >99 |
| 5 | (R)-Me-BoPhoz | EtOAc | None | 3 | 28/72 | >99 |
| 6 | (S)-Me-BoPhoz | EtOAc | None | — | 29/71 | >99 |
| 7 | (R)-Me-BoPhoz | DCE | None | 92 | ND | ND |
| 8 | (S)-Me-BoPhoz | DCE | None | 92 | ND | ND |
| 9 | (R)-Me-BoPhoz | EtOAc | 0.2 Eq. KI | 5 | 25/75 | >99 |
| 10 | (S)-Me-BoPhoz | EtOAc | 0.2 Eq. KI | 5 | 26/74 | >99 |
| 11 | (R)-Me-BoPhoz | EtOAc | 1.2 Eq. Et$_3$N | 98 | ND | ND |
| 12 | (S)-Me-BoPhoz | EtOAc | 1.2 Eq. Et$_3$N | 98 | ND | ND |

Synthetic Example 32

[Ir(COD)Cl]$_2$ Homogeneous Diastereoselective Hydrogenation of Compound D3

[Ir(COD)Cl]$_2$ (0.004 mmol), various ligand stereoisomers (0.0044 mmol) and Compound D3 (0.2 mmol, 80 mg) in a S/C ratio of 50:1 were reacted in EtOAc (3 mL) with 0.1 Eq. 12 (0.02 mmol, 5 mg) at 50° C. and 25 bar hydrogen over a period of about 20 hrs.

The percent conversion and the percent e.e. were determined using either Diacel ChiralPak AD-H column (35° C.), 1 mL/min, 80:20 eluent ratio of Hexane:IPA after derivatization to the methyl ester or by 1H NMR estimations on the crude dried product.

The [Ir(COD)Cl]$_2$ adduct and the ligand were stirred in 1 mL solvent under N$_2$, r.t. for a period of 30 min, followed by addition of stock solutions of I$_2$ and substrate in EtOAc.

TABLE 30

| Entry | Ligand | D3 (%) | D4/D5 (d.r.) | D4 + D5 (%) |
|---|---|---|---|---|
| 1 | (R)-Me-BoPhoz | 3 | 28/72 | >99 |
| 2 | (S)-Me-BoPhoz | ND | 29/71 | >99 |
| 3 | (R)-Xyl-P-Phos | 4 | 38/62 | >99 |
| 4 | (S)-Xyl-P-Phos | 4 | 38/62 | >99 |
| 5 | (R)-P-Phos | 22 | 38/62 | 95 |
| 6 | (S)-P-Phos | 7 | 30/70 | >99 |
| 7 | (S)-Tol-P-Phos | 13 | 31/69 | 95 |
| 8 | (R)-Xyl-Binap | 74 | 50/50 | 47 |
| 9 | (S)-Xyl-Binap | 73 | 50/50 | 45 |
| 10 | (R)-Xyl-PhanePhos | 83 | 31/69 | ND |
| 11 | (S)-Xyl-PhanePhos | 90 | ND | ND |
| 12 | (R)-PhanePhos | 90 | ND | ND |
| 13 | (S)-PhanePhos | 86 | 27/73 | ND |

Synthetic Example 33

[Ir(COD)Cl]$_2$ Homogeneous Diastereoselective Hydrogenation of Compound C3

Metal precursor [Ir(COD)Cl] (0.004 mmol), various ligand stereoisomers (0.0044 mmol) and Compound C3 (0.2 mmol, 83 mg) in a S/C ratio of 50:1 were each reacted in EtOAc (3 mL) with 0.1 Eq. 12 (0.02 mmol, 5 mg) at 50° C. and 25 bar hydrogen over a period of about 18 hrs.

The percent conversion and the percent e.e. were determined using Diacel ChiralPak AD-H column (35° C.), 1 mL/min, 80:20 eluent ratio of Hexane:IPA after derivatization to the methyl ester.

The [Ir(COD)Cl]$_2$ adduct and the ligand were stirred in 1 mL solvent under N$_2$, r.t. for a period of 30 min, followed by addition of stock solutions of I$_2$ and substrate in EtOAc.

TABLE 31

| Entry | Ligand | C3 (%) | C4/C5 (d.r.) |
|---|---|---|---|
| 1 | (R)-Me-BoPhoz | <1 | 50/48 |
| 2 | (S)-Me-BoPhoz | <1 | 50/48 |
| 3 | (R)-Xyl-P-Phos | 3 | 50/50 |
| 4 | (S)-Xyl-P-Phos | 12 | 52/48 |
| 5 | (R)-Xyl-PhanePhos | 76 | 50/50 |
| 6 | (S)-Xyl-PhanePhos | 82 | 47/53 |

Synthetic Example 34

[Ir(COD)Cl]$_2$ Homogeneous Diastereoselective Hydrogenation of Compound C3

Metal precursor [Ir(COD)Cl] (0.004 mmol), various ligand stereoisomers (0.0044 mmol) and Compound C3 (0.2 mmol, 83 mg) in a S/C ratio of 50:1 were reacted in various solvents (3 mL) with 0.1 Eq. 12 (0.02 mmol, 5 mg) at 50° C. and 25 bar hydrogen over a period of about 18 to 20 hrs.

The percent conversion and the percent e.e. were determined using Diacel ChiralPak AD-H column (35° C.), 1 mL/min, 80:20 eluent ratio of Hexane:IPA after derivatization to the methyl ester.

The [Ir(COD)Cl]$_2$ adduct and the ligand were stirred in 1 mL solvent under N$_2$, r.t. for a period of 30 min, followed by addition of stock solutions of I$_2$ and substrate in the indicated solvent.

TABLE 32

| Entry | Ligand | Solvent | C3 (%) | C4/C5 (d.r.) |
|---|---|---|---|---|
| 1 | (R)-Me-BoPhoz | EtOAc | <1 | 50/48 |
| 2 | (S)-Me-BoPhoz | EtOAc | <1 | 50/48 |
| 3 | (R)-Me-BoPhoz | THF | 17 | 51/49 |
| 4 | (S)-Me-BoPhoz | THF | 2 | 52/48 |
| 5 | (R)-Me-BoPhoz | toluene | 58 | 50/50 |
| 6 | (S)-Me-BoPhoz | toluene | 58 | 50/50 |
| 7 | (R)-Me-BoPhoz | DCE | 88 | 50/50 |
| 8 | (S)-Me-BoPhoz | DCE | 88 | 50/50 |
| 9 | (R)-Me-BoPhoz | MeOH | 92 | 50/50 |
| 10 | (S)-Me-BoPhoz | MeOH | 92 | 50/50 |

Synthetic Example 35

[Ir(COD)Cl]$_2$ Homogeneous Diastereoselective Hydrogenation of Compound C3

Metal precursor [Ir(COD)Cl] (0.004 mmol), various ligand stereoisomers (0.0044 mmol) and Compound C3 (0.2 mmol, 83 mg) in a S/C ratio of 50:1 were reacted in EtOAc (3 mL) with 0.1 Eq. 12 (0.02 mmol, 5 mg) at 50° C. and 25 bar hydrogen over a period of about 18 to 20 hrs.

The percent conversion and the percent e.e. were determined using Diacel ChiralPak AD-H column (35° C.), 1 mL/min, 80:20 eluent ratio of Hexane:IPA after derivatization to the methyl ester.

The [Ir(COD)Cl]$_2$ adduct and the ligand were stirred in 1 mL solvent under N$_2$, r.t. for a period of 30 min, followed by addition of stock solutions of I$_2$ and substrate in EtOAc.

TABLE 33

| Entry | Ligand | C3 (%) | C4/C5 (d.r.) |
|---|---|---|---|
| 1 | None | 98 | ND |
| 2 | (R)-Me-BoPhoz | <1 | 50/48 |
| 3 | (S)-Me-BoPhoz | <1 | 50/48 |
| 4 | (R)-Phenethyl-(S)-BoPhoz | 23 | 48/52 |
| 5 | (S)-Ethyl-Naphthyl-(R)-BoPhoz | 6 | 49/51 |
| 6 | (R)-Et-BoPhoz | 1 | 48/51 |
| 7 | (R)-iPr-BoPhoz | 1 | 49/50 |
| 8 | (R)-Ph-BoPhoz | 16 | 49/51 |
| 9 | PCy-(R)-Me-BoPhoz | 75 | 48/52 |
| 10 | 2,4,6-F$_3$Ph-(R)-Me-BoPhoz | 31 | 49/51 |
| 11 | Xyl-(R)-Me-BoPhoz | 2 | 48/51 |
| 12 | pFPh-(R)-Me-BoPhoz | 1 | 49/50 |
| 13 | pFPh-(R)-Et-BoPhoz | 78 | 50/50 |
| 14 | pFPh-(R)-Bn-BoPhoz | 2 | 49/51 |
| 15 | (S)-Binol-(R)-Me-BoPhoz | 10 | 50/50 |
| 16 | (R)-Binol-(R)-Me-BoPhoz | 1 | 48/52 |
| 17 | DtBPF | 94 | ND |
| 18 | DPPF | 29 | 49/51 |

Synthetic Example 36

One Pot (R)-Me-BoPhoz&[Ir(COD)Cl]$_2$ Catalyzed Hydrogenation of Compound C1

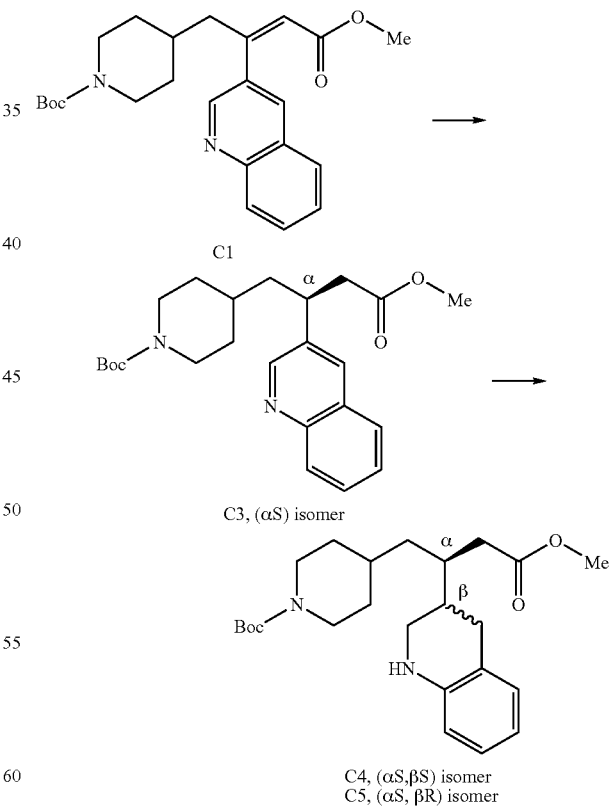

C4, (αS,βS) isomer
C5, (αS, βR) isomer

A one-pot reaction was developed wherein Compound C1 was reacted with an in situ formed (R)-Me-BoPhoz&[Ir(COD)Cl]$_2$ ligand-metal complex at a S/C ratio of 50/1 in the solvent DCE, under 25 bar H$_2$ at a temperature of 70° C. over a period of 24 hrs to provide Compound C3 (75% conversion, 96% e.e.) followed by the direct addition of 10% iodine. The foregoing reaction mixture was recharged under 25 bar $H_2$ at a temperature of 70° C. over a period of 48 hrs to provide an isomeric mixture of Compound C4 (43%) and Compound C5 (45%).

Synthetic Example 37

One Pot (R)-Me-BoPhoz&[Ir(COD)Cl]$_2$ Catalyzed Hydrogenation of Compound D1

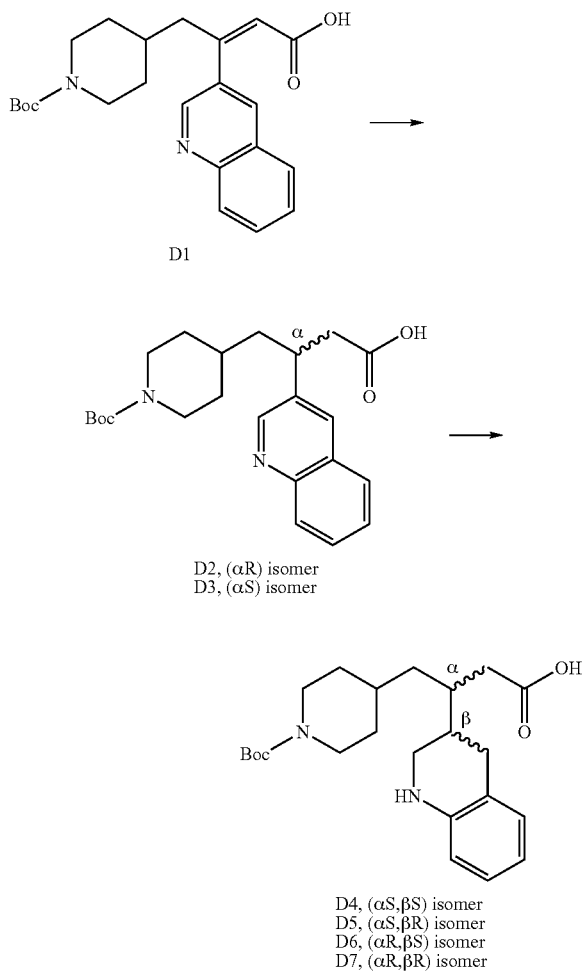

A one-pot reaction was developed wherein Compound D1 was reacted with an in situ formed (R)-Me-BoPhoz&[Ir(COD)Cl]$_2$ ligand-metal complex at a S/C ratio of 50/1 in the solvent THF, under 25 bar $H_2$ at a temperature of 70° C. over a period of 24 hrs to provide Compound D3 (51% conversion, 65% e.e.) followed by the direct addition of 10% iodine. The foregoing reaction mixture was recharged under 25 bar $H_2$ at a temperature of 70° C. over a period of 60 hrs to provide an isomeric mixture of Compound D4 (35%) and Compound D5 (50%) and the (αR)-isomers Compound D6 and Compound D7 (14% combined).

Synthetic Example 38

(R)-Xyl-PhanePhos Hydrogenation of Compound D1

The [Ru(COD)(CF$_3$COO)$_2$] metal precursor (0.004 mmol, 1.74 mg) and the (R)-Xyl-PhanePhos ligand (0.0044 mmol, 3.1 mg) (S/C 1000/1) were loaded in a 5 mL Schlenk tube. The tube was evacuated by performing three vacuum/nitrogen refill cycles and 2 mL anhydrous, degassed MeOH was injected. The resulting mixture was stirred at 55° C. for 2 hrs. After 2 hrs, the tube was taken out of the heating bath and glacial CH$_3$COOH (undegassed)(1.2 eq. to substrate, 4.8 mmol, 0.275 mL) was injected. The resulting solution was stirred while cooling down (approximately 10 min).

The solid substrate Compound D1 (4 mmol, 1.58 g) was loaded in a 25 mL Parr container, the Parr vessel sealed, and purged ten times with hydrogen. The pressure was released and a solution of the ligand-metal complex was injected via the injection port of the Parr vessel. The Schlenk tube was rinsed with 2 mL MeOH (degassed, anhydrous, 4×0.5 mL portions) and injected quickly via the injection port. The resulting mixture was purged five times without stirring and 10 times with stirring. The reaction mixture was stirred at 10 bar $H_2$ and 40° C. The reaction was sampled after 17 hrs and analyzed by HPLC, after in situ conversion to the methyl ester Compound C2: >99.5% conversion and 86% e.e.

Compound D2 was converted to the corresponding methyl ester Compound C2 (for 0.1 M reactions) by in situ derivatization: a 50 μL reaction sample (2 mg substrate/product, 0.005 mmol,) was treated in an HPLC vial with 50 μL of 2 M TMSCHN$_2$ in Et$_2$O (0.1 mmol) and MeOH (1.5 mL), then analyzed directly by the aforementioned chiral HPLC method; LC/MS (ES+) m/z 399.3 (M+1);

The crude reaction mixture was treated with Et$_3$N (4.8 mmol, 0.5 mL), the solvent was evaporated and the product extracted with DCM/sat'd NH$_4$Cl (aq). The DCM extracts were dried over Na$_2$SO$_4$, filtered and solvent evaporated to provide an off-white solid (1.52 g, 96%): $^1$HNMR (CDCl$_3$): free acid form.

The solid was taken up in toluene (30 mL) and stirred, wherein a fine solid formed immediately after addition of toluene. The mother liquor was sampled and analyzed by HPLC after conversion to methyl ester: 91% e.e. The mixture was left stirring at r.t. for greater than 48 hours. Sampling of the mother liquor after conversion to methyl ester showed 99% e.e. The reaction mixture was filtered and the filtrate was evaporated to provide Compound D3 (1.13 g, 75% isolated yield with respect to the crude, 1.52 g) as a brown solid.

HPLC: >99% e.e.; $^1$H NMR (CDCl$_3$): free acid form+ residual toluene; mp 60-70° C.; $^1$H NMR (400 MHz, CDCl$_3$) δ 10.9 (br m, 1H), 8.86 (s, 1H), 8.07 (m, 2H), 7.82 (m, 1H), 7.66 (m, 1H), 7.55 (m, 1H), 4.04 (m, 2H), 3.55 (m, 1H), 2.9-2.4 (m, 4H), 1.9-1.5 (m, 3H), 1.45 (s, 9H), 1.3-1.0 (m, 4H); $^{13}$C NMR (100 MHz, CDCl$_3$) δ 174.47, 154.84, 150.05, 145.79, 137.20, 135.01, 129.54, 128.12, 127.66, 127.07, 79.42, 43.70 (br), 42.55, 42.29, 36.72, 33.27, 32.59, 31.42, 28.43; Anal. Calcd for $C_{23}H_{30}N_2O_4$: C, 69.32; H, 7.59, N, 7.03. Found: C, 69.58; H, 7.92; N, 6.68.

Synthetic Example 39

(R)-Xyl-PhanePhos Hydrogenation of Compound D1 and Enantiomeric Enrichment

The [Ru(COD)(CF$_3$COO)$_2$] metal precursor (0.004 mmol, 1.74 mg) and the (R)-Xyl-PhanePhos ligand (0.0044 mmol, 3.1 mg) (S/C 1000/1) were loaded in a 5 mL Schlenk tube. The tube was evacuated by performing three vacuum/nitrogen refill cycles and 2 mL anhydrous, degassed MeOH was injected. The resulting mixture was stirred at 55° C. for 2 hrs. After 2 hrs, the tube was taken out of the heating bath and glacial CH$_3$COOH (undegassed)(1.2 eq. to substrate, 4.8 mmol, 0.275 mL) was injected. The resulting solution was stirred while cooling down (approximately 10 min). The solid substrate D1 (4 mmol, 1.58 g) was loaded in a 25 mL Parr container, the Parr vessel sealed, then purged ten times with hydrogen. The pressure was released and the complex solution was injected via the injection port of the Parr vessel. The Schlenk tube was rinsed with 2 mL MeOH (degassed, anhydrous, 4×0.5 mL portions) and injected quickly via the injection port. The resulting mixture was purged five times without stirring and 10 times with stirring. The reaction mixture was stirred at 3 bar $H_2$ and 40° C. The reaction was sampled after 16, 24 and 48 and analyzed by HPLC, after in situ conversion to the methyl ester: 16 hrs: 90% conversion, 82% e.e.; 24 hrs: 98% conversion 81% e.e.; 40 hrs: 98.5% conversion and 79% e.e.

The solvent was evaporated and 1.43 g of a brown sticky solid was obtained. To this solid, a mixture of DCM:Hexane:MTBE in a ratio of 10 mL:50 mL:50 mL was added and the mixture stirred at r.t. Upon stirring, the sticky solid went into the solvent as a fine solid. The mother liquor was sampled and analyzed by HPLC after conversion to methyl ester: 1.5% Compound D1, 98.5% product D3, 97.8% e.e. The reaction mixture was filtered, solid washed with 2×5 mL hexane and the filtrate was evaporated. 1.14 g (80% isolated yield with respect to the crude solid, 1.43 g) off-white solid D3 was obtained: HPLC: 1.6% Compound D1, 98.4% conversion, 97.8% e.e.; $^1$H NMR (CDCl$_3$): free acid form, 94% product Compound D3, 6% Compound D1.

Synthetic Example 40

(R)-Xyl-PhanePhos Hydrogenation of Compound D1 and Enantiomeric Enrichment

The [Ru(COD)(CF$_3$COO)$_2$] metal precursor (0.008 mmol, 3.5 mg) and the (R)-Xyl-PhanePhos ligand (0.0088 mmol, 6.1 mg) (S/C=1000/1) were loaded in a 5 mL Schlenk tube. The tube was evacuated by performing three vacuum/nitrogen refill cycles and 4 mL anhydrous, degassed was MeOH injected. The resulting mixture was stirred at 55° C. for 2 hrs. After 2 hrs, the tube was taken out of the heating bath and glacial CH$_3$COOH (undegassed)(1.2 eq. to substrate, 9.6 mmol, 0.550 mL) was injected. The resulting solution was stirred while cooling down (approximately 10 min). The solid Compound D1 (8 mmol, 3.17 g) was loaded in a 50 mL Parr container, the Parr vessel sealed, then purged ten times with hydrogen. The pressure was released and the complex solution was injected via the injection port of the Parr vessel. The Schlenk tube was rinsed with 4 mL MeOH (degassed, anhydrous, 4×1 mL portions) and injected quickly via the injection port. The resulting mixture was purged five times without stirring and 10 times with stirring. The reaction mixture was stirred at 10 bar $H_2$ and 40° C. The reaction was sampled after 17 hrs and analyzed by HPLC, after in situ conversion to the methyl ester: >99.5% conversion and 87% e.e.

The crude reaction mixture was transferred to a 500 mL round bottom flask and solvent evaporated, with the formation of a brown sticky solid. The flask was fitted with an air reflux condenser and lowered in an oil bath at 60° C. and the solid dissolved in 20 mL MTBE (solvents added from the top of the reflux condenser). To this solution, 60 mL hexane was added and a sticky solid formed at the bottom of the flask. Small portions of MTBE and Hexane were added alternately until a fine solid started forming, with concomitant analysis of mother liquor aliquots. The final amounts of solvents were: 100 mL MTBE: 100 mL hexane (analysis of this mother liquor by HPLC after conversion to methyl ester: 98% e.e). The reaction mixture was filtered hot and the solid washed with hot hexane (20 mL). After solvent evaporation, Compound D3 (2.5 g, 80% yield) was obtained as an off-white solid.

Synthetic Example 41

Pd/C Catalyzed Diastereoselective Hydrogenation of Compound C3

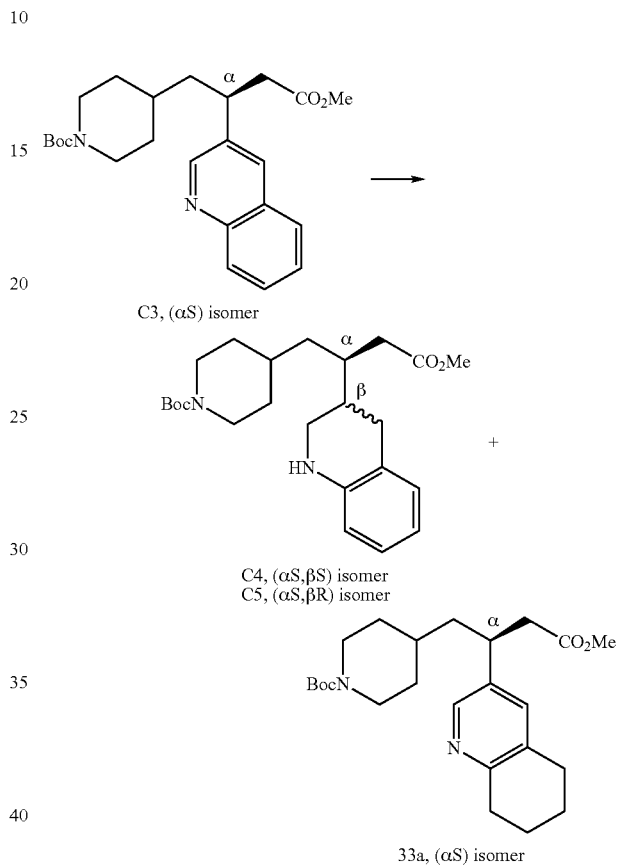

C3, (αS) isomer

C4, (αS,βS) isomer
C5, (αS,βR) isomer 33a, (αS) isomer

Solvent screening in the heterogeneous Pd/C catalyzed diastereoselective hydrogenation of Compound C3 (0.2 mmol, 0.1M) in various solvents was performed using 10% Pd/C (w/w, dry basis) at 60° C., 3 bar $H_2$, over a period of about 18-20 hrs.

The percent conversion and the percent diastereomeric ratio (d.r.) were determined using Diacel ChiralPak AD-H column (35° C.), 1 mL/min, 80:20 ratio of Hexane:IPA after derivatization to the methyl ester and by $^1$HNMR. The by-product Compound 33a overlapped with Compound C4 by HPLC.

TABLE 34

| Entry | Solvent | C3 (%) | (C4 + 33a)/C5 (ratio % by HPLC) | C3/(C4 + C5)/33a (ratio % by NMR) |
|---|---|---|---|---|
| 1 | MeOH | 90 | 6/4 | 88/12/0 |
| 2 | EtOH | 21 | 44/35 | 6/77/17 |
| 3 | i-PrOH | <1 | 55/45 | 0/90/10 |
| 4 | 1-BuOH | <1 | 55/45 | 0/89/11 |
| 5 | Tolene | <1 | 55/45 | 0/87/13 |
| 6 | THF | <1 | 56/44 | 0/80/20 |
| 7 | EtOAc | <1 | 56/44 | 0/88/12 |
| 8 | DCE | <1 | 89/10 | 8/92/0 |

Synthetic Example 42

Pd/C Catalyzed Diastereoselective Hydrogenation of Compound D3

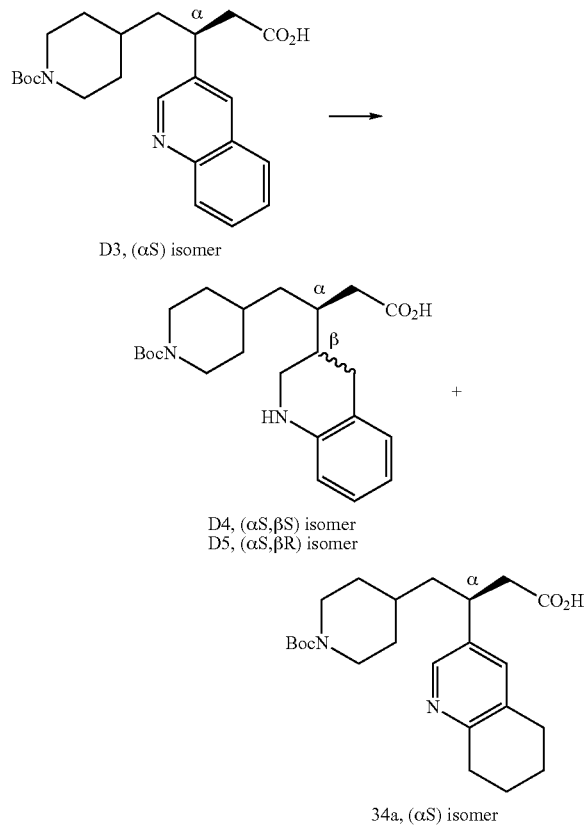

D3, (αS) isomer

D4, (αS,βS) isomer
D5, (αS,βR) isomer 34a, (αS) isomer

Solvent screening in the heterogeneous Pd/C catalyzed diastereoselective hydrogenation of Compound D3 (0.2 mmol, 0.1M) in various solvents was performed using 10% Pd/C (w/w, dry basis) at 60° C., 3 bar $H_2$, over a period of about 18-20 hrs.

The percent conversion and the percent diastereomeric ratio (d.r.) were determined using Diacel ChiralPak AD-H column (35° C.), 1 mL/min, 80:20 ratio of Hexane:IPA after derivatization to the methyl ester and by $^1$HNMR. The by-product Compound 34a overlapped with Compound D4 by HPLC.

TABLE 35

| Entry | Solvent | D3 (%) | (D4 + 34a)/D5 (ratio % by HPLC) | D3/(D4 + D5)/34a (ratio % by NMR) |
|---|---|---|---|---|
| 1 | MeOH | 14 | 46/40 | 0/89/10 |
| 2 | EtOH | 14 | 46/40 | 0/90/10 |
| 3 | i-PrOH | 50 | 27/23 | 23/61/16 |
| 4 | 1-BuOH | <1 | 53/47 | 0/78/32 |
| 5 | toluene | <1 | 49/51 | 0/79/31 |
| 6 | THF | 17 | 38/45 | 2/90/8 |
| 7 | EtOAc | 61 | 20/19 | 30/51/19 |
| 8 | DCE | 35 | 47/18 | 10/35/55 |

Synthetic Example 44

Pd/C Catalyzed Diastereoselective Hydrogenation of Compound D3

Compound D2 (0.2 mmol, 0.1M) in MeOH was reacted with 10% Pd/C (w/w, dry basis) at 60° C., 3 bar $H_2$, over a period of about 18-20 hrs.

The percent conversion and the percent diastereomeric ratio (d.r.) were determined using Diacel ChiralPak AD-H column (35° C.), 1 mL/min, 80:20 ratio of Hexane:IPA after derivatization to the methyl ester and by $^1$HNMR. The by-product Compound 33a overlapped with Compound D4 by HPLC.

TABLE 36

| Entry | Catalyst | Cat. Loading (%, w/w) | D3 (%) | (D4 + 34a)/D5 (ratio % by HPLC) | D3/(D4 + D5)/34a (ratio % by NMR) |
|---|---|---|---|---|---|
| 1 | 10% Pd/C | 10 | 14 | 46/40 | 0/89/10 |
| 2 | 10% Pd/C | 10 | 6 | 52/42 | 0/81/19 |
| 3 | 10% Pd/C | 10 | <1 | 56/44 | 0/75/25 |
| 4 | 5% Pd/C | 20 | <1 | 87/13 | 0/27/73 |
| 5 | 4% Pd-1% Pt/C | 20 | <1 | 56/44 | 0/72/28 |
| 6 | 5% Pt/C | 20 | <1 | 59/40 | 0/84/16 |
| 7 | 5% Ir/CaCO$_3$ | 20 | 77 | 14/9 | 51/33/16 |
|   | 5% Rh/C | 20 | <1 | 90/10 | 0/15/85 |
| 8 | 5% Rh/C | 20 | <1 | 96/4 | 0/9/91 |

Synthetic Example 45

Pd/C Catalyzed Diastereoselective Hydrogenation of Compound D3 and Compound C3

Temperature and pressure optimization screening in the Pd/C catalyzed diastereoselective hydrogenation of Compound D2 (0.2 mmol, 0.1M) in MeOH was performed using 10% Pd/C (w/w, dry basis) at 60° C., 3 bar $H_2$, over a period of about 16 hrs.

The percent conversion and the percent diastereomeric ratio (d.r.) were determined using Diacel ChiralPak AD-H column (35° C.), 1 mL/min, 80:20 ratio of Hexane:IPA after derivatization to the methyl ester and by $^1$HNMR. The byproduct Compound 34a overlapped with Compound D4 by HPLC.

Entries 9 and 10 were performed using Compound C3 in IPA, wherein the analysis by HPLC and NMR were based on the corresponding Me ester product Compounds C3, C4, C5 and 33a.

TABLE 37

| Entry | T (° C.) | P (bar) | D3 (%) | (D4 + 34a)/D5 (ratio % by HPLC) | D3/(D4 + D5)/34a (ratio % by NMR) |
|---|---|---|---|---|---|
| 1 | 30 | 3 | 77 | 13/10 | 53/44/3 |
| 2 | 40 | 3 | 40 | 32/28 | 13/80/7 |
| 3 | 60 | 3 | 14 | 46/40 | 0/89/10 |
| 4 | 80 | 3 | 0 | 68/32 | 0/52/48 |
| 5 | 30 | 10 | 0 | 52/48 | 0/89/10 |
| 6 | 40 | 10 | 0 | 54/46 | 0/95/5 |
| 7 | 30 | 25 | 0 | 53/47 | 0/93/7 |
| 8 | 40 | 25 | 0 | 53/47 | 0/97/3 |
| 9 | 60 | 3 | C3 <1 | 55/45 | 0/90/10 |
| 10 | 30 | 25 | C3: 72 | 16/12 | 55/39/6 |

Synthetic Example 45

Pd/C Catalyzed Diastereoselective Hydrogenation of Compound D3

Additive/pH optimization in the Pd/C catalyzed diastereoselective hydrogenation of Compound D2 (0.2 mmol, 0.1M) in MeOH, using various additives was performed using 10% Pd/C (w/w, dry basis) at 40° C., 10 bar $H_2$, over a period of about 18 hrs.

The percent conversion and the percent diastereomeric ratio (d.r.) were determined using Diacel ChiralPak AD-H column (35° C.), 1 mL/min, 80:20 ratio of Hexane:IPA after derivatization to the methyl ester and by $^1$HNMR. The by-product Compound 34a overlapped with Compound D4 by HPLC.

TABLE 38

| Entry | Additive | Eq. (to D3) | D3 (%) | (D4 + 34a)/D5 (ratio % by HPLC) | D3/(D4 + D5)/34a (ratio % by NMR) |
|---|---|---|---|---|---|
| 1 | None | NA | 0 | 54/46 | 0/95/5 |
| 2 | Et$_3$N | 0.2 | 0 | 51/49 | 0/90/10 |
| 3 | Et$_3$N | 0.5 | 0 | 50/50 | 0/95/5 |
| 4 | Et$_3$N | 0.75 | 0 | 49/51 | 0/99.5/0.5 |
| 5 | Et$_3$N | 1.2 | 0 | 49/51 | 0/97/3 |
| 6 | CH$_3$COOH | 0.2 | 0 | 54/46 | 0/88/12 |
| 7 | CH$_3$COOH | 0.5 | 0 | 55/45 | 0/83/17 |
| 8 | CH$_3$COOH | 0.75 | 0 | 55/45 | 0/84/16 |
| 9 | CH$_3$COOH | 1.2 | 0 | 55/45 | 0/79/21 |

Synthetic Example 46

Pd/C Catalyzed Diastereoselective Hydrogenation of Compound D3

Additive optimization in the Pd/C catalyzed diastereoselective hydrogenation of Compound D3 (0.2 mmol, 0.1M) in MeOH, using various additives was performed using 10% Pd/C (w/w, dry basis) at 40° C., 10 bar $H_2$, over a period of about 20 hrs. The additive is present in a stoichiometric ratio (Eq.) with Compound D3 as shown in Table 39/

The percent conversion and the percent diastereomeric ratio (d.r.) were determined using Diacel ChiralPak AD-H column (35° C.), 1 mL/min, 80:20 ratio of Hexane:IPA after derivatization to the methyl ester and by $^1$HNMR.

TABLE 39

| Entry | Additive | Eq. | D3 (%) | (D4 + 34a)/D5 (ratio % by HPLC) | D3/(D4 + D5)/34a (ratio % by NMR) |
|---|---|---|---|---|---|
| 1 | Et$_3$N | 0.75 | 0 | 49/51 | 0/99.5/0.5 |
| 2 | IPr$_2$NH | 0.75 | 0 | 50/50 | 0/99.3/0.7 |
| 3 | Cy$_2$NH | 0.75 | 0 | 50/50 | 0/95.5/4.5 |
| 4 | (R)-Ph-EtNH$_2$ | 0.75 | 0 | 47/53 | 0/95/5 |
| 5 | (S)-Ph-EtNH$_2$ | 0.75 | 0 | 48/52 | 0/94/6 |
| 6 | KOH | 0.75 | 0 | 50/50 | 0/98/2 |
| 7 | K$_2$CO$_3$ | 0.75 | 0 | 53/47 | 0/98/2 |
| 8 | CH$_3$COOH | 0.2 | 0 | 54/46 | 0/88/12 |
| 9 | (R)-Camph-SO$_3$H | 0.2 | 0 | 55/45 | 0/83/17 |
| 10 | (S)-Camph-SO$_3$H | 0.2 | 0 | 54/46 | 0/87/13 |

Synthetic Example 47

Pd/C Catalyzed Diastereoselective Hydrogenation of Compound D3

Concentration optimization in the Pd/C catalyzed diastereoselective hydrogenation of Compound D3 (0.2 mmol, 0.1M) in MeOH (2 mL), using Et$_3$N as an additive (0.75 Eq. Et$_3$N:Compound D3) was performed using 10% Pd/C (w/w, dry basis) at 40° C., 10 bar $H_2$, over a period of about 20 hrs.

The percent conversion and the percent diastereomeric ratio (d.r.) were determined using Diacel ChiralPak AD-H column (35° C.), 1 mL/min, 80:20 ratio of Hexane:IPA after derivatization to the methyl ester and by $^1$HNMR.

TABLE 40

| Entry | D3 (mmol/$^a$g) | D3 (%) | (D4 + 34a)/D5 (ratio % by HPLC) | D3/(D4 + D5)/34a (ratio % by NMR) |
|---|---|---|---|---|
| 1 | 0.1 | 0 | 49/51 | 0/99.5/0.5 |
| 2 | 0.25 | 0 | 49/51 | ND |
| 3 | 0.5 | 0 | 49/51 | 0/98/2 |
| 4 | 0.75 | 0 | 49/51 | 0/99.5/0.5 |
| 5 | 1 | 0 | 49/51 | 0/99.5/0.5 |
| 6 | 1/$^a$1.6 | 0 | 49/51 | 0/96/4 |

Synthetic Example 48

Pd/C Catalyzed Diastereoselective Hydrogenation of Compound D3

Solid substrate Compound D3 (4 mmol, 1.6 g), 10% Pd/C (10% w/w to substrate on dry basis, 64.78% $H_2O$, 460 mg), MeOH (4 mL) and Et$_3$N (3 mmol, 0.42 mL) were loaded in a 25 mL Parr container, which was sealed and purged ten times with hydrogen without stirring and 10 times with stirring. The reaction mixture was stirred at 10 bar $H_2$ and 40° C. The reaction was sampled after 4 hrs and analyzed by HPLC, after in situ conversion to the methyl ester: >99.5% conversion and a ratio of Compound D4:Compound D5, 1/1 d.r. The reaction was stopped, the reaction mixture filtered and the Pd catalyst washed with 20 mL methanol. This crude solution was acidified with CH$_3$COOH (8.8. mmol, 0.5 mL), the solvent was evaporated and the product extracted with DCM from DCM/sat'd NH$_4$Cl. The DCM extracts were dried over Na$_2$SO$_4$, filtered and the solvent evaporated to dryness to afford 1.55 g white solid as a mixture of Compounds D4 and D5 (96% isolated yield): $^1$H NMR showed some residual CH$_3$COOH, DCM and 4% byproduct Compound 34a.

Synthetic Example 49

Pd/C Catalyzed Diastereoselective Hydrogenation of Compound C3

Compound C3 (1.4 mmol, 0.6 g), 10% Pd/C (10% w/w to substrate on dry basis, 64.78% $H_2O$, 130 mg), i-PrOH (1.5 mL) and Et$_3$N (1.05 mmol, 0.145 mL) were loaded in a glass liner, which was placed in the hydrogenation reactor. The reactor was sealed, purged five times with nitrogen, five times with hydrogen without stirring and five times with hydrogen while stirring. The reaction mixture was stirred at 40° C., 10 bar $H_2$. After the reaction was complete, the reaction mixture was filtered and the Pd catalyst washed with 20 mL methanol. The solvent and Et$_3$N were removed under high vacuum and the crude reaction mixture (0.6 g) was analyzed by HPLC and $^1$H NMR. HPLC: full conversion, 1/1 Compound C4:Compound C5, 1% byproduct Compound 33a. $^1$HNMR (CDCl$_3$): 2% byproduct Compound 33a.

Synthetic Example 50

(R)-Me-BoPhoz&[Ir(COD)Cl]$_2$ Hydrogenation of Compound C1

An [Ir(COD)Cl]$_2$ adduct (0.002 mmol, 1.3 mg) and (R)-Me-BoPhoz ligand (0.005 mmol, 3.1 mg) were loaded in a glass liner. The liner was placed in a hydrogenation reactor which was sealed and purged with nitrogen. DCE (2 mL, anhydrous, degassed) was injected via the injection port and the mixture stirred under nitrogen for 30 min at room temperature. After 30 min, 1 mL stock solution of Compound C1 in DCE was injected via the injection port (0.2 mmol/mL, 82 mg substrate stock solution was prepared under nitrogen, using anhydrous, degassed DCE), followed by the injection of 1 mL DCE (anhydrous, degassed). The resulting mixture was purged five times with hydrogen without stirring and five times with hydrogen while stirring. The reaction mixture was stirred at 70° C., 25 bar $H_2$ for 18 hrs. The crude reaction mixture was analyzed for conversion and e.e. by HPLC and showed 93% conversion and 93% e.e. in Compound C3.

Synthetic Example 51

Esterification of Compound D2 to Compound C2

Compound D2 (0.06 mmol, 0.025 g) was loaded in a 10 mL Schlenk tube. The tube was evacuated via three vacuum/nitrogen cycles, and 3 mL anhydrous MeOH and 0.5 mL anhydrous DCM were injected. The resulting solution was cooled in an ice-water bath and $TMSCHN_2$ (0.18 mol, 0.09 mL 2 M solution in $Et_2O$) was injected slowly. The solution was stirred while warming to room temperature (approximately 2 hrs). The solvent was removed under high vacuum and the resulting crude analyzed by $^1$HNMR and chiral HPLC, which showed full conversion to the methyl ester Compound C3.

Synthetic Example 52

Esterification of Compound D3 to Compound C3

Compound D3 (0.10 g, 0.25 mmol) was dissolved in acetonitrile (9 mL) and treated with 1-hydroxybenzotriazole (0.034 g, 0.25 mmol), dicyclohexylcarbodiimide (0.11 g, 0.53 mmol), and methanol (200 μL, 4.9 mmol) at rt. The reaction mixture was stirred for 4 hrs, filtered thru 0.45 μm filter, washed with acetonitrile (3×3 mL), concentrated in vacuo, and dissolved in dichloromethane. This solution was washed with saturated sodium bicarbonate solution (2×25 mL), water (2×25 mL), and brine (2×25 mL); dried over anhydrous sodium sulfate; filtered; and concentrated in vacuo. The resulting solid was dissolved in boiling heptane. The resulting suspension was reduced in volume (≈1 mL), filtered and allowed to crystallize, yielding Compound C3 as a white solid (0.080 g, 77%), pure by LC/MS and $^1$H-NMR.

Synthetic Example 53

Preparation of 4-(3-methoxycarbonyl-2-quinolin-3-yl-allyl)-piperidine-1-carboxylic acid tert-butyl ester Compound C1

To a 4 neck, 5 L flask, equipped with a Teflon-coated thermocouple, reflux condenser, mechanical stirrer, and a nitrogen inlet was charged the potassium salt of methyl malonate (320.9 g, 2.056 mol), $MgCl_2$ (92.9 g, 0.976 mol), and THF (1.25 L). The suspension was heated at 50° C. for 5 hrs, and cooled to rt.

To a separate three-neck 1 L flask, equipped with a mechanical stirrer, nitrogen inlet, teflon covered thermocouple, and septum, was added carbonyl diimidazole, (CDI, 333.4 g, 2.056 mol) portionwise over 10 min to a cooled solution of 4-carboxymethyl-piperidine-1-carboxylic acid tert-butyl ester Compound F1 (250.0 g, 1.028 mol) in THF (1.25 L) at 0° C. The mixture was allowed to warm to rt and stirred for 1.5 h to provide an acylimidazole intermediate.

The solution of the acylimidazole was transferred into the ambient temperature suspension of methyl malonate and $MgCl_2$ and the resulting mixture was stirred for 12 h at rt. The resulting thick white suspension was diluted with EtOAc (1 L), transferred to a separatory funnel and washed twice with saturated $NaHSO_4$ (2 L). The aqueous phases were combined and extracted with EtOAc (1 L). The combined organic extracts were washed twice with saturated $NaHCO_3$ (500 mL). The combined bicarbonate extracts were back extracted with EtOAc (2 L) and the combined organic extracts were dried over $Na_2SO_4$, filtered, and concentrated under reduced pressure affording 290 g of crude product as a yellow oil which crystallized upon standing over 5 hrs. Purification by chromatography on silica gel (200-400 mesh, 1.25 kg, gradient elution with 4 L of hexanes, 4 L of 20% EtOAc/hexanes, and 8 L of 40% EtOAc/hexanes) afforded the 4-(3-methoxycarbonyl-2-oxo-propyl)-piperidine-1-carboxylic acid tert-butyl ester Compound F2 (272.1 g, 88%) as a pale-yellow oil which crystallized on standing.

$^1$H NMR (300 MHz, $CDCl_3$) δ 4.05 (br s, 2H), 3.74 (s, 3H), 3.43 (s, 2H), 2.79-2.65 (t, J=12.4 Hz, 2H), 2.47 (d, J=6.7 Hz, 2H), 2.10-1.95 (m, 1H), 1.7-1.6 (d, J=12.7 Hz, 2H), 1.44 (s, 9H), 1.18-1.02 (m, 2H); $^{13}$C NMR (75 MHz, $CDCl_3$) (ppm) 201.7, 167.7, 154.9, 90.4, 79.6, 52.6, 49.8, 49.6, 43.8, 42.3, 31.9, 31.7, 28.7; LC/MS (ES+) m/z 300.2 (M+1); Anal. Calcd for $C_{15}H_{25}NO_5$: C, 60.18; H, 8.42; N, 4.68. Found: C, 60.32; H, 8.15; N, 4.59.

To a four-neck, 5 L flask equipped with a mechanical stirrer, Teflon-coated thermocouple, an addition funnel, and a nitrogen inlet, was charged sodium hydride (60% in mineral oil, 30.0 g, 0.752 mol) and toluene (450 mL). The suspension was cooled to an internal temperature of −5° C. and a solution of Compound F2 (150.0 g, 0.501 mol) in toluene (1200 mL) was added dropwise at such a rate as to maintain the internal temperature below −3° C. during the addition. Once addition was complete the mixture was aged for 40 min at 0° C., followed by sequential dropwise addition of diisopropylethylamine (436.3 mL, 2.505 mol), followed by trifluoromethanesulfonic anhydride (118.7 mL, 0.706 mol), maintaining the internal temperature below 5° C. during the addition. After the addition was complete, the mixture was allowed to warm to rt and stirred for 1 h. The mixture was cooled to 0° C., quenched with saturated brine (1.5 L), diluted with EtOAc (1 L), and the two phases were separated. The organic extract was washed with water (1 L) followed by re-extraction of the combined aqueous phases with EtOAc (1 L). The combined organic extracts were dried over $Na_2SO_4$, filtered, and concentrated affording a (Z)-4-(3-methoxycarbonyl-2-trifluoromethanesulfonyloxy-allyl)-piperidine-1-carboxylic acid tert-butyl ester Compound F3 (287 g) as a red-brown oily solid. The material was judged satisfactory for use in the next reaction step by $^1$H NMR analysis. The signal for the vinyl proton appears at ~6.0 ppm in the E-isomer and at 5.88 ppm in the Z-isomer.

$^1$H NMR (300 MHz, $CDCl_3$) δ 5.88 (s, 1H) 4.1 (br s, 2H), 3.78 (s, 3H), 2.61-2.78 (t, J=12.6 Hz, 2H), 2.31 (m, 2H), 1.78 (m, 1H), 1.65-1.77 (d, J=12.8 Hz, 2H), 1.45 (s, 9H), 1.20 (m, 2H), 0.80-1.30 (residual diisopropylethylamine); $^{13}$C NMR ($CDCl_3$, 75 MHz) (ppm) 162.8, 157.0, 154.8, 113.2, 79.8, 54.9, 52.3, 41.9, 33.7, 31.7, 29.9, 28.7; HPLC Method A: (Phenomenex Jupiter: 5 um, C-18, 300 Å, 4.6×250 mm, 29° C.) $H_2O$:$CH_3CN$ 90:10 to 10:90 in 15 min, hold at 90:10 for 2 min. Flow rate: 1.5 mL min$^{-1}$, UV detection: 220 nm, $H_2O$ buffered with 0.025% TFA. Retention time: 15.39 min.

To a suspension of quinoline-3-boronic acid (130.0 g, 0.752 mol), Compound F3 (216.1 g, 0.501 mol) and bistriphenylphosphine palladium dichloride (17.5 g, 0.025 mol) in THF (1.2 L) was added 2 M $Na_2CO_3$ (160 mL, 0.32 mol). The mixture was heated to 40° C. and monitored for completion by HPLC analysis. After 7 hrs the reaction was judged complete (>97% conversion by HPLC) and the mixture was filtered and diluted with EtOAc (1 L). The mixture was washed with NaHCO$_3$ (2×2 L) and 0.5 M NaOH (2×2 L). The combined aqueous phases were extracted with EtOAc (1 L) and the combined organic extracts were dried over Na$_2$SO$_4$, filtered and concentrated under reduced pressure and afforded a crude brown oil (200 g). Purification by chromatography on silica gel (1 kg, 70-230 mesh, gradient elution with 4 L of hexanes, 4 L of 10% EtOAc/hexanes, 2 L of 40% EtOAc/hexanes, and 100% EtOAc afforded a dark brown oily solid. The oily solid was triturated with hexanes (150 mL) and collected by filtration affording the title Compound C1, which was 96% pure by HPLC analysis (139.1 g, 67%, mp 119-124° C.). NMR analysis indicated lower purity in the aromatic region (15% impurity). The olefin was the Z-isomer as determined by nuclear Overhauser effect (nOe) studies (Z-isomer vinyl proton resonance at 6.05 ppm, E-isomer at 6.28 ppm).

$^1$H NMR (300 MHz, CDCl$_3$) δ 8.71 (d, J=2.2 Hz, 1H), 8.10 (d, J=8.4 Hz, 1H), 7.96 (d, J=2.2 Hz, 1H), 7.81 (d, J=8.4 Hz, 1H), 7.72 (d, J=7.0, 1.3 Hz, 1H), 7.56 J=7.0, 1.3 Hz, 1H), 6.05 (s, 1H), 4.01 (br s, 2H), 3.47 (s, 3H), 2.59 (br s, 2H), 2.51 (d, J=7.0 Hz, 2H), 1.70-1.60 (m, 2H), 1.42 (s, 10H), 1.20-1.03 (m, 2H); $^{13}$C NMR (CDCl$_3$, 75 MHz) (ppm) 165.89, 154.91, 154.19, 149.97, 147.72, 133.81, 132.68, 129.95, 129.56, 128.23, 127.14, 120.33, 51.53, 47.74, 44.0 (br), 34.00, 32.10, 28.64; HPLC Method A: retention time: 11.21 min; LC/MS (ES+) m/z 411.2 (M+1); Anal. Calcd for C$_{24}$H$_{30}$N$_2$O$_4$: C, 70.22; H, 7.37; N, 6.82. Found: C, 69.87; H, 7.56; N, 6.58.

Synthetic Example 54

HPLC Identification of Compounds C4, C5, 54a and 54b

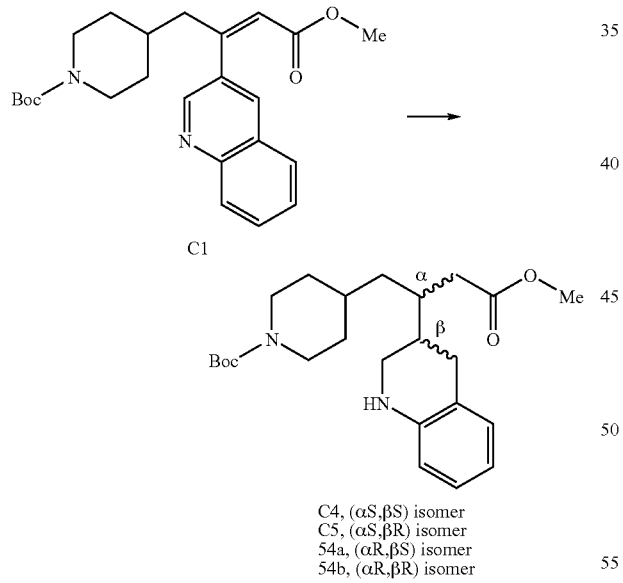

C4, (αS,βS) isomer
C5, (αS,βR) isomer
54a, (αR,βS) isomer
54b, (αR,βR) isomer

A racemic mixture of Compounds C4, C5, 54a and 54b (323 g, 0.775 mol) was purified by sequential chiral chromatography. The elution order using a Chiralpak AD® column is reversed when using a Chiralcel OD® column. The racemic mixture eluted as a 1/1/1/1 ratio of Compounds 54b, 54a, C5 and C4.

Compound 54b and Compound C5 were separated from Compound 54a and Compound C4, using a Chiralcel OD® column (110 mm I.D. dynamic axial compression (DAC) column filled with 2000 g of 20 μm Chiralcel OD® (Daicel); temperature of eluent: 28° C.; column wall temperature: 30° C.; eluent: methanol; flow rate: 750 mL/min). The sample was prepared by dissolving the racemic mixture (5.8 g) in 200 mL of the eluent (29 mg/mL) and injected at a rate of 3.6 runs per hour (20.9 g of the mixture per hour). The purification was complete after 15 h of continuous chromatography (56 injections).

Compound 54a was separated from Compound C4 using a Chiralpak® AD column (110 mm I.D. DAC filled with 2000 g of Chiralpak AD®; temperature of eluent: 38° C.; temperature of column wall: 40° C.; eluent: acetonitrile (750 mL/min), ethanol (rinsing plug); injection amount: 4 g/250 mL of eluent; capacity: 3.5 runs/h at 14 g/h).

From this procedure there was isolated Compound C4 (65 g; 20% yield; 96.1% pure by chiral HPLC; 0.68, 1.87, 1.35% of Compounds C5, 54a and 54b, respectively) was isolated. Samples of the other fractions were also obtained in similar purity, but no attempt was made to maximize the quantity of them in this purification. Chiral HPLC Method A: Chiralpak AD®: (5 μm, 150 mm×4.6 mm), isocratic ethanol, ambient, flow rate: 1.0 mL min$^{-1}$, UV detection: 254 nm, retention times: Compounds 54b, 54a, C5 and C4, 5.5 min, 6.0 min, 7.5 min and 8.5 min, respectively.

Synthetic Example 55

Preparation of Dihydrochloride Salt Compound C6 by HCl Deprotection of Compound C4

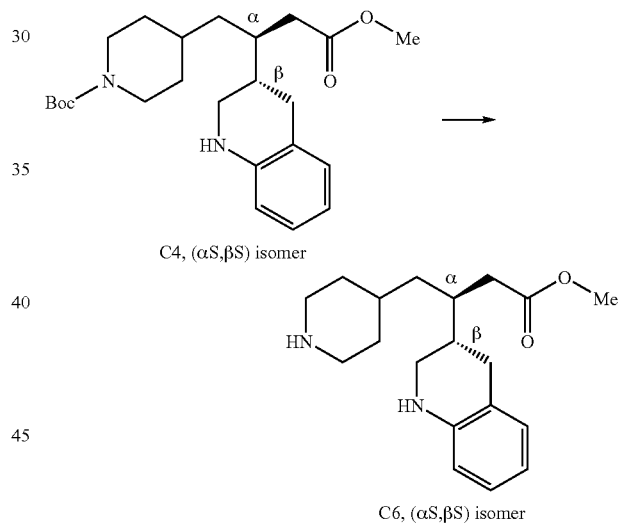

A 3-L three-neck round bottom flask, equipped with magnetic stirrer and argon inlet, was charged with Compound C4 (55.22 g, 33 mmol), methoxybenzene (1.44 mL, 13.3 mmol), and 1,4-dioxane (880 mL). The mixture was treated with 4 M hydrogen chloride in dioxane (883 mL, 3.53 mol) to give a clear solution that became hazy and deposited a thick red oil that was difficult to stir. A spatula was used to loosen the red oil. After 4 hrs, additional 4 M HCl/dioxane (90 mL, 0.36 mol) was added and the reaction stirred for an additional 7 h until complete by LC/MS. The solvent was removed in vacuo at 45° C. to afford a solid that was triturated with ethyl ether (1 L), collected by filtration, and washed with ethyl ether (≈0.5-1 L). The isolated light pink solid was dried in vacuum oven (55-60° C.) for 6 h to give (3S,3'S)-4-piperidin-4-yl-3-(1,2,3,4-tetrahydroquinolin-3-yl)-butyric acid methyl ester dihydrochloride salt Compound C6 (50.87 g, 98%).

$^1$H NMR (300 MHz, DMSO-D$_6$) δ 7.2-6.8 (m, 4H), 3.58 (s, 3H), 3.33-3.21 (m, 3H), 3.0-2.4 (m, 6H), 2.33-2.26 (m, 1H), 2.04 (m, 2H), 1.82-1.76 (m, 2H), 1.59 (m, 1H), 1.4-1.1 (m,

4H); HPLC (Thermo Betabasic®-C-18, 4.6×150 mm, ambient, $H_2O:CH_3CN$ 95:5 to 5:95 in 12 min, $H_2O$ and acetonitrile buffered with 0.1% TFA, flow rate: 1.5 mL min$^{-1}$, UV detection: 210 nm, 254 nm) >99% area, retention time: 4.85 min; LC/MS (ES+) m/z 317.3 (M+1); Anal. Calcd for $C_{19}H_{28}N_2O_2$-2HCl-0.35$H_2O$-0.60$C_4H_{10}O$: C, 57.30; H, 7.98; N, 6.24; Cl, 15.81. Found: C, 56.94; H, 8.13; N, 6.70; Cl, 15.77. Karl Fisher Titration Calcd: 1.41%. Found: 1.39% (w/w).

Synthetic Example 56

Preparation of Compound C7

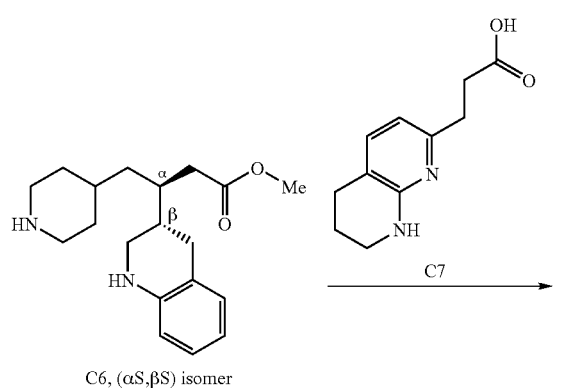

A 200 mL single neck round bottom flask equipped with magnetic stirrer and argon inlet, was charged with a slurry/solution of (3S,3'S)-4-piperidin-4-yl-3-(1,2,3,4-tetrahydroquinolin-3-yl)-butyric acid methyl ester dihydrochloride salt Compound C6 (29.5 g, 75.8 mmol), acid Compound C7 (20.23 g, 83.3 mmol), 1-hydroxybenzotriazole hydrate (5.89 g, 37.9 mmol) and dimethylformamide (295 mL). The reaction mixture was purged with an argon stream (15-20 min) and chilled in an ice bath and 1-(3-dimethylaminopropyl)-3-ethylcarbodiimide hydrochloride (EDCl, 15.98 g, 83.3 mmol) was added in one portion. Diisopropylethylamine (39.64 mL, 227 mmol) was added in a dropwise fashion. The reaction mixture was stirred for 60 min, removed from ice/water bath, and stirred at rt for 17 hrs until the reaction was complete. The reaction mixture was poured into saturated sodium bicarbonate (3 L) and extracted with ethyl acetate (4×750 mL). The combined organic phases were washed with saturated ammonium chloride (2×500 mL) and brine (3×500 mL), dried (MgSO$_4$ and Na$_2$SO$_4$) and concentrated to give crude amide product (35.4 g). The crude product was dissolved in dichloromethane and loaded onto an Analogix® column (2 runs —SiO$_2$-220 g) and eluted (linear gradient, dichloromethane to 1:6:3:90 NH$_4$OH/IPA/EtOH/dichloromethane) to give a crude Compound C8 (4.1 g), followed by pure Compound C8 (31.7 g). The mixed fractions were dissolved in dichloromethane and loaded onto an Isco® column (SiO$_2$-120 g) and eluted (linear gradient, dichloromethane to 1.5:6:3:89.5 NH$_4$OH/IPA/EtOH/dichloromethane) to give additional product (2.7 g). The product from each purification was combined and concentrated from chloroform to provide the title Compound C8 (34.4 g, 83% yield).

$^1$H NMR (300 MHz, DMSO-D$_6$) δ 7.00 (m, 1H), 6.84-6.80 (m, 2H), 6.42-6.38 (m, 2H), 6.28-6.23 (m, 2H), 5.60 (br s, 1H), 4.35 (br d, J=13 Hz, 1H), 3.82 (br d, J=13 Hz, 1H), 3.59 (s, 3H), 3.3-3.1 (m, 3H), 3.0-2.8 (m, 2H), 2.7-2.4 (m, 10H), 2.29-2.27 (m, 1H), 1.98 (m, 1H), 1.8-1.4 (m, 6H), 1.30 (m, 1H), 1.14 (m, 1H), 0.88 (m, 2H); HPLC: (Agilent Eclipse® XDB-C 18, 3.0×150 mm, 45° C., A:B 85:15 to 15:85 in 27 min, (A) 10 mM ammonium acetate/H$_2$O (B) 10 mM ammonium acetate/(H$_2$O:acetonitrile, 1:9, flow rate: 0.6 mL min$^{-1}$, UV detection: 220-400 nm), >99% area, retention time: 21.3 min: LC/MS (ES+) m/z 505.4 (M+1); Anal. Calcd for $C_{30}H_{40}N_4O_3$-0.4 CHCl$_3$-0.25$H_2O$: C, 65.56; H, 7.40; N, 10.06; Cl, 7.64. Found: C, 65.70; H, 7.42; N, 10.09; Cl, 7.89; residue after ignition: <0.10%; Karl Fisher Titration Calcd: 0.81%. Found: 0.87% (w/w).

Synthetic Example 57

(3S,3'S)-4-[1-(3-5,6,7,8-tetrahydro-[1,8]naphthyridin-2-yl-propionyl)-piperidin-4-yl]-3-(1,2,3,4-tetrahydroquinolin-3-yl)-butyric acid Formula (Ia)

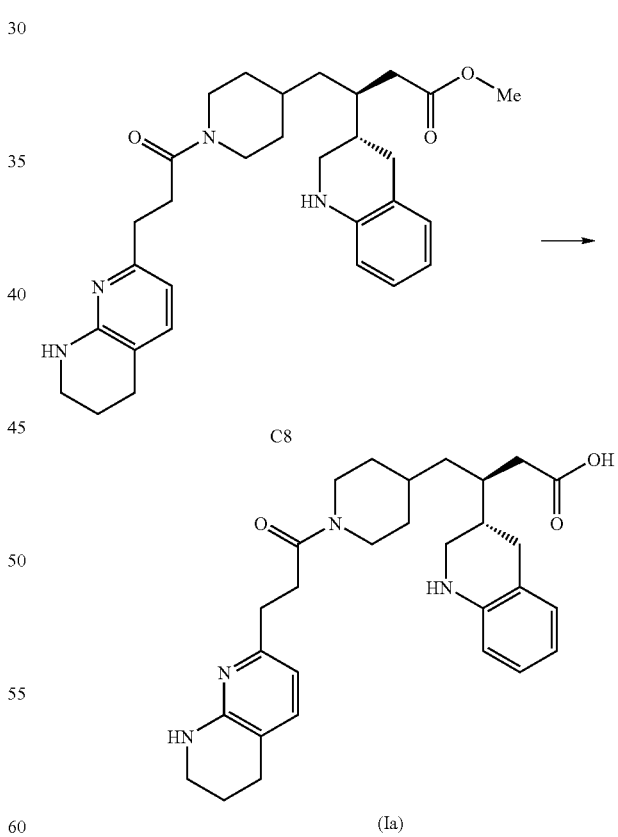

A 1-L one-neck round bottom flask, equipped with magnetic stirrer and argon inlet, was charged with Compound C8 (34.44 g, 62.8 mmol), methanol (138 mL, 3.40 mol), and 3 M sodium hydroxide solution (62.8 mL, 188 mmol). Argon was bubbled through the mixture to remove oxygen (30 min) and the reaction mixture was stirred at rt (18 hrs) and then concentrated to remove methanol. The oily aqueous residue was diluted with water (700 mL) and the pH was adjusted to 6.5 with 2 M hydrochloric acid (~2 N, ~100 mL) and sodium hydroxide (1 N) to give a white slurry. The slurry was extracted with dichloromethane (3×300 mL). The resulting turbid solution of combined organics was diluted with THF, dried ($Na_2SO_4$) and concentrated to give the title compound of Formula (Ia) (34.7 g, 97%) mixed with THF (~0.75 eq).

$^1$H NMR (300 MHz, DMSO-$D_6$) δ 7.05 (d, J=7 Hz, 1H), 6.84-6.80 (m, 2H), 6.43-6.37 (m, 2H), 6.29 (d, J=7 Hz, 1H), 5.63 (br s, 1H), 4.35 (br d, J=13 Hz, 1H), 3.82 (br d, J=13 Hz, 1H), 3.2-3.1 (m, 3H), 3.0-2.8 (m, 2H), 2.7-2.4 (m, 9H), 2.34-2.13 (m, 2H), 1.97 (m, 1H), 1.8-1.4 (m, 6H), 1.19 (m, 1H), 1.14 (m, 1H), 0.87 (m, 2H); HPLC (Agilent Eclipse® XDB-C18, 3.0×150 mm, 45° C., A:B 85:15 to 15:85 in 27 min, (A) 10 mM ammonium acetate/$H_2O$ (B) 10 mM ammonium acetate/($H_2O$:acetonitrile, 1:9, flow rate: 0.6 mL min$^{-1}$, UV detection: 220-400 nm), >98% area, retention time: 11.9 min; LC/MS (ES+) m/z 491.2 (M+1); Anal. Calcd for $C_{29}H_{38}N_4O_3$-0.75 DCM-0.05 THF-0.45$H_2O$: C, 69.10; H, 8.14; N, 10.06; Cl, 0.64. Found: C, 68.73; H, 7.68; N, 9.85; Cl, 0.65. Residue after Ignition: <0.10%. Karl Fisher Titration Calcd: 1.46%. Found: 1.28% (w/w).

Synthetic Example 58

(3S,3'S)-4-[1-(3-5,6,7,8-tetrahydro-[1,8]naphthyridin-2-yl-propionyl)-piperidin-4-yl]-3-(1,2,3,4-tetrahydroquinolin-3-yl)-butyric acid hydrochloride salt Formula (Ia)

The compound of Formula (Ia) (41.15 g, 74.85 mmol) was dissolved in water (617 mL), 1 M aqueous hydrogen chloride (150 mL, 150 mmol), and acetonitrile (93 mL). The resulting solution was syringe filtered (0.45 µm, Nylon) into six-600 mL lyophilization bottles and frozen. These bottles were lyophilized for 5 days to give the desired compound of Formula (Ia) as an HCl salt (40.5 g, 92%)

mp 146-148° C. (decomposition); HPLC (Agilent Eclipse® XDB-C18, 3.0×150 mm, 45° C., A:B 95:5 to 25:75 in 27 min, (A) 10 mM ammonium acetate/$H_2O$ (B) 10 mM ammonium acetate/($H_2O$:acetonitrile, 1:9), flow rate: 0.6 mL min$^{-1}$, UV detection: 220-400 nm), >98% area, retention time: 15.9 min: LC/MS (ES+) m/z 491.2 (M+1); Anal. Calcd for $C_{29}H_{38}N_4O_3$-2.2 HCl-1$H_2O$: C, 59.15; H, 7.22; N, 9.51; Cl, 13.25. Found: C, 59.55; H, 7.47; N, 9.55; Cl, 13.75. Residue after Ignition: <0.10%. Karl Fisher Titration Calcd: 3.06%. Found: 3.36% (w/w).

Additional Data for Chiral HPLC Analysis for Compound C3

Chiral HPLC Method B: Chiralpak AD-H: (4.6×250 mm), isocratic hexane:IPA 80:20, 23° C., flow rate: 1.0 mL min$^{-1}$, UV detection: 254 nm, retention time: 16.5 min for Compound C3, 26.6 min for R-isomer Compound C2, 9 min for Compound C1.

Additional NMR and Optical Rotation Data for Compound C3

$^1$H NMR (300 MHz, CDCl$_3$) δ 8.80 (s, 1H), 8.10 (m, 1H), 7.90 (m, 1H), 7.80 (m, 1H), 7.70 (m, 1H), 7.50 (m, 1H), 4.00 (m, 2H), 3.55 (s, 3H), 3.45 (m, 2H), 2.70 (m, 1H), 2.50 (m, 2H), 1.80 (m, 2H), 1.60 (m, 1H), 1.40 (s, 9H), 1.3-1.0 (m, 4H); LC/MS (ES+) m/z: 413.25 (M+1); Anal. Calcd for $C_{24}H_{32}N_2O_4$-0.2$H_2O$: C, 69.27; H, 7.85, N, 6.73. Found: C, 69.08; H, 7.72; N, 6.35; $[α]_D^{23}$=-23.18°, c 0.48, MeOH.

Synthetic Example 59

(R)-Me-BoPhoz/[Rh(ethylene)$_2$Cl]$_2$ Hydrogenation of Compound C1

A (R)-Me-BoPhoz ligand (6.7 mg, 0.011 mmol) and a [Rh(ethylene)$_2$Cl]$_2$ metal adduct (1.9 mg, 0.005 mmol) were loaded in a glass liner, which was placed in the hydrogenation reactor. The reactor was sealed and purged with nitrogen. Dichloroethane (DCE, 1 mL, anhydrous, degassed) was injected via the injection port and the mixture stirred under nitrogen for 30 min at rt to form in situ the (R)-Me-BoPhoz/[Rh(ethylene)$_2$Cl]$_2$ complex (0.01 mmol, S/C 100/1). After 30 min, Compound C1 (410 mg, 1 mmol) in DCE (4 mL) was injected via the injection port. The substrate stock solution was prepared under nitrogen, using anhydrous, degassed DCE. The resulting mixture was purged five times with hydrogen without stirring and five times with hydrogen while stirring. The reaction mixture was stirred at 60° C., 30 bar $H_2$ for 16 hrs. The crude reaction mixture was analyzed for conversion and ee by chiral HPLC Method B and showed 97% conversion and 93% e.e. in Compound C3. Chiral HPLC Method B: Chiralpak AD-H (4.6×250 mm), isocratic hexane: IPA 80:20, 35° C., flow rate: 1.0 mL min$^{-1}$, UV detection: 210 and 254 nm, retention times: 13.2 min for Compound C3, 25.9 min for the R-isomer Compound C2, 9.6 min for Compound C1. Flash chromatograph (2 cm diameter, 30-35% ethyl acetate in heptane) afforded pure Compound C3 (276 mg, 67%) by NMR and LC/MS.

Synthetic Example 60

Re-aromatization of Compound C4 to Compound C3

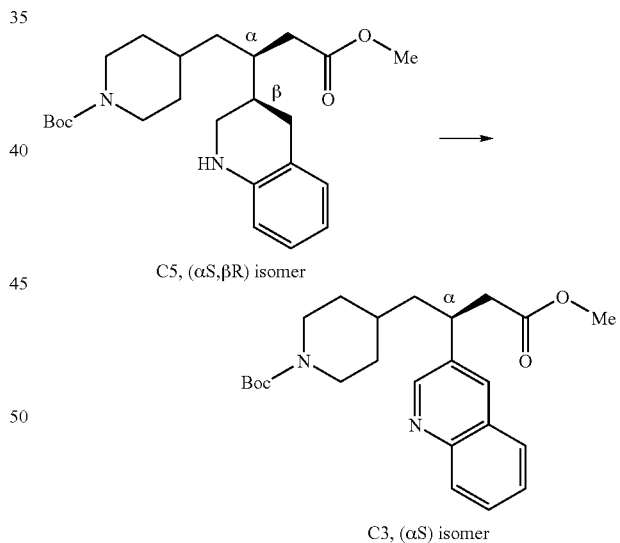

C5, (αS,βR) isomer

C3, (αS) isomer

A solution of Compound C5 (21.6 g, 51.9 mmol) was dissolved in dry toluene (420 mL) and 10% Pd/C (11.3 g) was carefully added. The reaction was brought to a gentle reflux under air. The reaction was refluxed for 6 h and left overnight at room temperature. After another 5 h of reflux, additional 10% Pd/C (2.0 g) was added as a slurry in toluene (20 mL). The reaction mixture was refluxed for an additional 1 h, left at rt overnight, filtered through Celite®, washed several times with toluene, and evaporated. The resulting yellow oil was solidified upon evaporation over the weekend to give an off-white solid (19.4 g) (85-90% pure by NMR and LC). The solid was recrystallized once from heptane (100 mL) to give Compound C3 (15.8 g, 74%, mp 90-102° C.) as an off-white solid. Chiral HPLC (Chiralpak AD-H (4.6×150 mm), isocratic hexane:IPA 80:20, 35° C., flow rate: 1.0 mL min$^{-1}$, UV detection: 210 and 254 nm, retention times: 7 min for Compound C3, 10 min for R-isomer Compound C2, 5.5 min for Compound C1): 99% Compound C3, 0.56% R-isomer Compound C5; Anal. Calcd for $C_{24}H_{32}N_2O_4$: C, 69.88; H, 7.82, N, 6.79. Found: C, 69.87; H, 7.98; N, 6.79. Palladium 169 ppm by ICP.

Synthetic Example 61

Achiral Hydrogenation of Compound C3

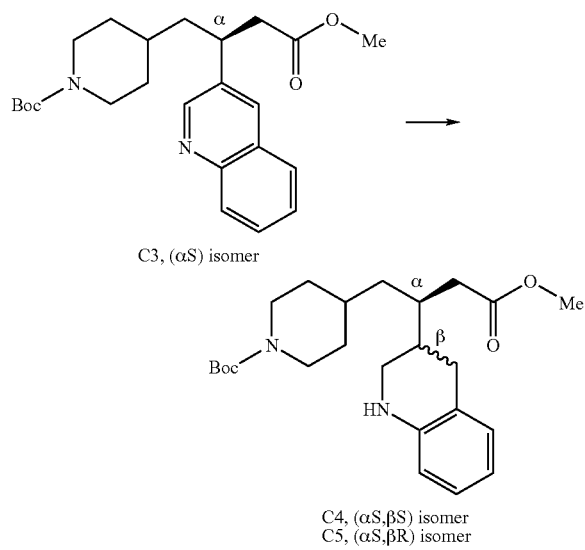

C3, (αS) isomer

C4, (αS,βS) isomer
C5, (αS,βR) isomer

A sample of Compound C3 (48 mg, 0.12 mmol), water (90 mg), and 10% palladium on carbon (50 mg) in methanol was hydrogenated in a Parr apparatus at 53 psig for 28 hrs. After filtration through Celite® and evaporation, the residue was purified on silica gel (elution with 30% ethyl acetate and (0.1% triethylamine in heptane) yielding Compound C4 and Compound C5 (35 mg, 70%), as a mixture of isomers. HPLC Analysis was performed using Chiral HPLC Method A showing 45% of Compound C5 and 45% of Compound C4.

Synthetic Example 62

Preparation of Compound G1 Camphanic Amide from Compound C5 for X-ray Determination of Absolute Configuration of Structure

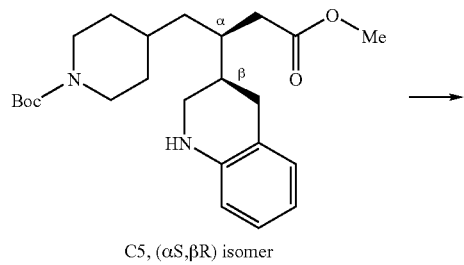

C5, (αS,βR) isomer

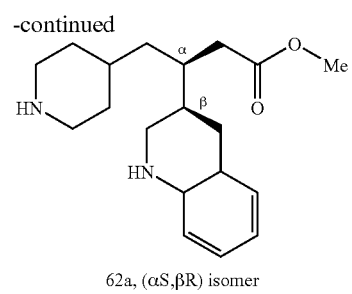

62a, (αS,βR) isomer 62a, (αS,βR) isomer → (1S)-(-)-camphanoyl chloride

G1

A bis-(-)-(S)-camphanic acid amide Compound G1 of (2S, 3'R)-4-Piperidin-4-yl-3-(1',2',3',4'-tetrahydroquinolin-3'-yl)-butyric acid ethyl ster (C5) was prepared by the following procedure:

(2S,3'R)-4-Piperidin-4-yl-3-(1',2',3',4'-tetrahydroquinolin-3'-yl)-butyric acid methyl ester Compound C5 (4.50 g, 10.8 mmol) was dissolved in dioxane (45 mL), and treated with anisole (few drops) and 4 N hydrogen chloride in dioxane (45 mL). After 2 hrs, the reaction mixture was evaporated to give a crude solid (4.5 g). A portion of the solid (2.9 g) was partitioned between saturated sodium carbonate solution (25 mL) and ethyl acetate (25 mL). The organic layer was dried ($Na_2SO_4$) and evaporated to yield (S)-methyl 4-(piperidin-4-yl)-3-((R)-1,2,3,4-tetrahydroquinolin-3-yl)butanoate Compound 62a (2.06 g, 93%, LC/MS: consistent).

Compound 62a (162 mg, 0.51 mmol) was dissolved in dichloromethane (10 mL) under nitrogen and treated with triethylamine (0.21 mL, 1.5 mmol) and (-)-(S)-camphanic acid chloride (277 mg, 1.28 mmol) at 0° C. and stirred for 1.5 hrs. The reaction mixture was poured into saturated sodium bicarbonate solution (25 mL), extracted with dichloromethane (3×25 mL), washed with brine (25 mL), dried ($MgSO_4$) and evaporated. The residue was dissolved in dichloromethane and applied to a flash column (2 cm diameter, gradient elution with 30-35% ethyl acetate in heptane)

affording the bisamide Compound G1 as a colorless oil, which later turned to a solid (234 mg, 68%).

LC/MS (ES+) m/z 677.0 (M+1); $^1$H NMR (300 MHz, CDCl$_3$) δ 7.2-7.1 (m, 4H), 4.6-4.2 (m, 3H), 3.67 (s, 3H), 3.2-2.8 (m, 3H), 2.6-1.6 (m, 14H), 1.22 (s, 3H), 1.18 (s, 3H), 1.10 (s, 6H), 1.00 (s, 6H), 1.5-0.8 (m, 5H), 0.88 (t, J=7 Hz, 2H); Anal. Calcd for C$_{39}$H$_{52}$N$_2$O$_8$: C, 69.21; H, 7.74, N, 4.14. Found: C, 69.44; H, 7.94; N, 4.02.

A small sample of Compound G1 (23 mg) was dissolved in methanol (3 mL) and water was added dropwise until just cloudy. A small amount of methanol was added to clarify and the sample was left to slowly evaporate with a slightly vented aluminum foil cap. When the first solid came out after 1 day, methanol was added to dissolve again and the evaporation was repeated. Crystals formed after 5 days (mp 122-132° C.), and were examined by single-crystal X-ray diffraction.

Synthetic Example 63

Preparation of Compound D1 from Compound C1

Compound C1 (16.67 g, 40.6 mmol, >99% Z-isomer by NMR) was dissolved in THF (48 mL) and methanol (64 mL). To this solution was added LiOH (8.2 g, 200 mmol) dissolved in water (64 mL). The mixture was stirred at room temperature for 1.5 hrs. The progress of the reaction was monitored by HPLC. The reaction was quenched with 1 M HCl (95% of theory, 190 mL) to pH 7 on litmus paper, and concentrated on a rotary evaporator at 27° C. A final amount of 1 M HCl was added (10 mL) with stirring and the solid was collected by filtration, washed with water (2×50 mL) to afford the acid, which was air-dried, then vacuum dried (60° C.) overnight. The brown solid (15 g) was an E/Z mixture of ~10:90 by HPLC. This material was recrystallized from isopropanol (200 mL) by heating to reflux to dissolve the material, allowing the material to cool to ambient temperature and aging for 1-2 h. The white solid was isolated by filtration and washed with ice cold IPA to afford Compound D1 (10.96 g, 68%, m.p. 215.9-216.9° C.). The compound was 98.3% pure Z-isomer by HPLC (R$_t$ 6.868 min). The (E)-isomer was present (1.62% at R$_t$ 6.654 min) (HPLC conditions: Agilent Eclipse, 5 um, C-8, 4.6 mm×150 mm, CH$_3$CN:H$_2$O, 0.1% TFA gradient elution from 10:90 to 90:10 in 12 min, hold 90:10 for 2 min., flow 1.3 mL/min, UV at 254 nm.

LC/MS (ES+) m/z 397 (M+1); $^1$H NMR (300 MHz, CDCl$_3$) δ 8.76 (d, J=2.1 Hz, 1H), 8.02 (m, 1H), 7.82 (d, J=8.1 Hz, 1H), 7.67 (t, J=7.2 Hz, 1H), 7.55 (t, J=7.5 Hz, 1H), 6.35 (br s, 1H), 6.09 (s, 1H), 4.00 (br m, 2H), 2.51 (m, 4H), 1.61 (d, J=12.6 Hz, 2H), 1.43 (m, 10H), 1.13 (m, 2H); $^{13}$C NMR (300 MHz, CDCl$_3$) ppm 168.1, 154.7, 152.1, 149.7, 146.0, 134.4, 132.7, 128.0, 127.9, 127.5, 127.1, 121.5, 79.4, 47.1, 43.5, 33.9, 31.8, 28.4; Anal. Calcd for C$_{23}$H$_{28}$N$_2$O$_4$: C, 69.67; H, 7.12, N, 7.07. Found: C, 69.63; H, 7.19; N, 7.06. Palladium: 74 ppm by ICP, ash <0.1%.

While the foregoing specification teaches the principles of the present invention, with examples provided for the purpose of illustration, it will be understood that the practice of the invention encompasses all of the usual variations, adaptations and modifications as come within the scope of the following claims and their equivalents.

Throughout this application, various publications are cited. These publications are hereby incorporated by reference in their entirety into this application to describe more fully the state of the art to which this invention pertains.

What is claimed is:
1. A process for preparing a compound of Formula (Ia) and intermediates thereof:

Formula (Ia)

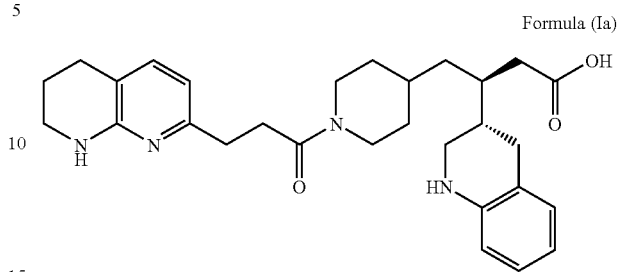

comprising the steps of:
Step 1. reacting a Compound C1 with:
a first hydrogen source selected from gaseous hydrogen or an excess of formic acid,
a first ligand-metal complex consisting essentially of a first ligand selected from the group consisting of (R)-PhanePhos, (S)-PhanePhos, (R)-An-PhanePhos, (S)-An-PhanePhos, (R)-Xyl-PhanePhos, (S)-Xyl-Phane-Phos, (R)-MeOXyl-PhanePhos, (S)-MeOXyl-PhanePhos, (R)-iPr-PhanePhos, (S)-iPr-PhanePhos, (R)-Me-BoPhoz, (S)-Me-BoPhoz, CF$_3$Ph-(R)-Me-BoPhoz, CF$_3$Ph-(S)-Me-BoPhoz, (R)-Phenethyl-(R)-Me-BoPhoz, (R)-Phenethyl-(S)-Me-BoPhoz, 3,4-diCl-Ph-(R)-Me-BoPhoz, 3,4-diCl-Ph-(S)-Me-BoPhoz, Xyl-(R)-Me-BoPhoz, Xyl-(S)-Me-BoPhoz, (R)-Binol-(R)-Me-BoPhoz, (R)-Binol-(S)-Me-BoPhoz, (S)-Binol-(S)-Me-BoPhoz, (S)-Binol-(R)-Me-BoPhoz, PCy-(R)-Me-BoPhoz, PCy-(S)-Me-BoPhoz, (R)-iPr-BoPhoz, (S)-iPr-BoPhoz, (R)-Phenethyl-(S)-BoPhoz, (R)-Phenethyl-(R)-BoPhoz, (S)-Phenethyl-(R)-BoPhoz, (S)-Phenethyl-(S)-BoPhoz, (R)-Ph-BoPhoz, (S)-Ph-BoPhoz, (R)-Bn-BoPhoz and (S)-Bn-BoPhoz,
conjugated with a first metal adduct selected from the group consisting of [Rh(COD)$_2$]BF$_4$, [Rh(COD)$_2$]OTf, [Rh(ethylene)$_2$Cl]$_2$, [Rh(ethylene)$_2$(acac)], [Rh(CO)$_2$(acac)], [Rh(COD)(acac)], [Ru(COD)(CF$_3$COO)$_2$]$_2$, [Ru(COD)(methylallyl)$_2$], [Ru(benzene)Cl$_2$]$_2$, [Ru(p-cymene)Cl$_2$]$_2$, [Ir(COD)Cl]$_2$, [Ir(COD)$_2$]BF$_4$ and [Ir(COD)$_2$]BAr$_F$,
in a first solvent selected from the group consisting of MeOH, EtOH, IPA, DCE, THF, toluene, EtOAc, DMF and mixtures thereof,
in the presence of an optional first additive selected from the group consisting of AcOH, Et$_3$N, HBF$_4$, HBF$_4$ etherate, HCl, HCl etherate, CF$_3$COOH, CH$_3$COOH and TsOH, and, when present, is in an amount up to about 1.2 Eq., at an elevated first temperature having a range of from about 25° C. to about 70° C., and
an elevated first pressure having a range of from about 3 bar to about 30 bar, to provide a substantially pure Compound C3:

-continued

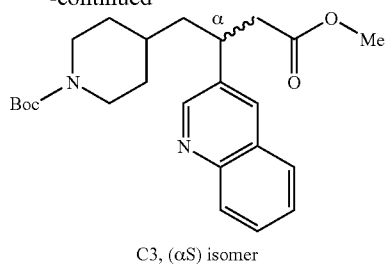

C3, (αS) isomer

Step 2. reacting Compound C3 with:
- a second hydrogen source that is gaseous hydrogen,
- and a hydrogenation agent selected from either 10% Pd/C or a second ligand-metal complex,
  - wherein the second ligand-metal complex consists essentially of a second ligand and an [Ir(COD)Cl]₂ metal adduct combined with iodine in an amount up to about 0.1 Eq.,
  - wherein 10% Pd/C is present in a range of weight % of from about 5% (w/w) to about 20% (w/w), and
  - wherein the second ligand is selected from the group consisting of (R)—P-Phos, (S)—P-Phos, (R)-Xyl-P-Phos, (S)-Xyl-P-Phos, (S)-Tol-P-Phos, (R)-Me-BoPhoz, (S)-Me-BoPhoz, (R)-Xyl-Binap and (S)-Xyl-Binap,
- in a second solvent selected from the group consisting of MeOH, DCE, EtOH, IPA, THF, toluene, EtOAc and MTBE and mixtures thereof,
- in the presence of an optional second additive selected from the group consisting of Et₃N, iPr₂—NH, Cy₂NH, (R)-Ph-ethyl-NH₂, (S)-Ph-ethyl-NH₂, KI, KOH, K₂CO₃, (R/S)-camphorsulfonic acid and CH₃COOH, and, when present, is in an amount up to about 1.2 Eq.,
- at an elevated second temperature that is in a range of from about 40° C. to about 60° C., and
- an elevated second pressure that is in a range of from about 3 bar to about 25 bar, or is in a range of from about 10 bar to about 25 bar, or is in a range of from about 3 bar to about 10 bar,
- to provide an isomeric mixture of a Compound C4 and Compound C5:

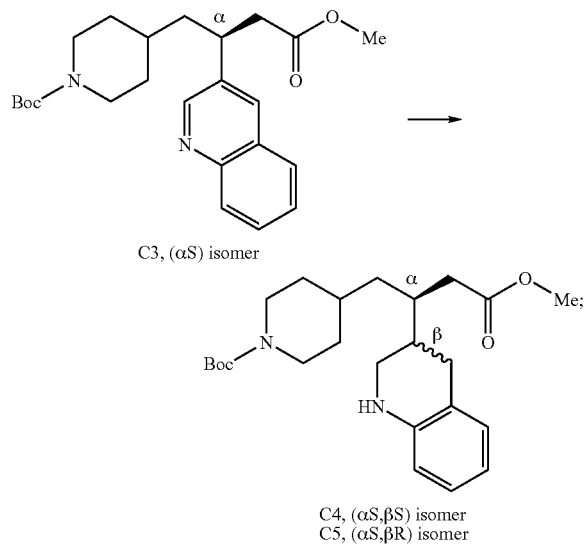

C4, (αS,βS) isomer
C5, (αS,βR) isomer

Step 3. separating each of Compound C4 and Compound C5 from the isomeric mixture;

Step 4. optionally dehydrogenating Compound C5 to Compound C3, and then repeating Step 2 using said dehydrogenated Compound C3 as the starting material;

Step 5. deprotecting the Compound C4 to provide a Compound C6:

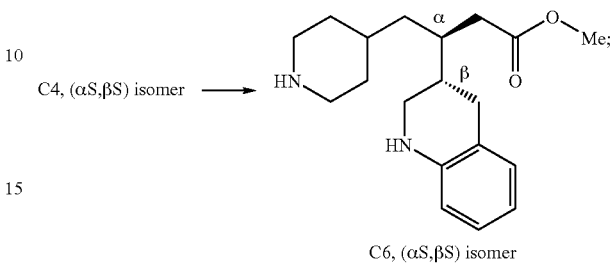

C4, (αS,βS) isomer → C6, (αS,βS) isomer

Step 6. reacting Compound C6 with a Compound C7 to provide a Compound C8:

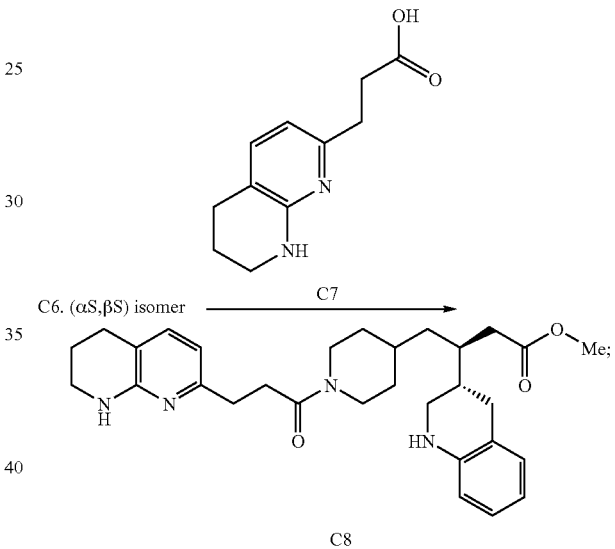

C6, (αS,βS) isomer →^(C7) C8

Step 7. converting Compound C8 to the compound of Formula (Ia).

2. The process of claim 1 for making a substantially pure Compound C2 comprising the step of:
  reacting a Compound C1 with a first hydrogen source, a first ligand-metal complex consisting essentially of a first ligand conjugated with a first metal adduct, in a first solvent in the presence of an optional first additive at an elevated first temperature and an elevated first pressure to provide a substantially pure Compound C2

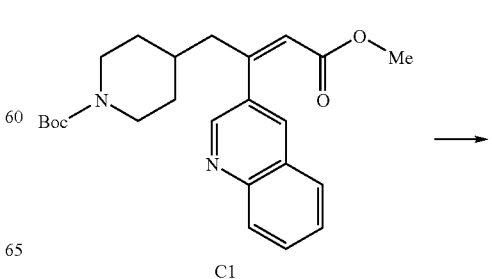

C1

-continued

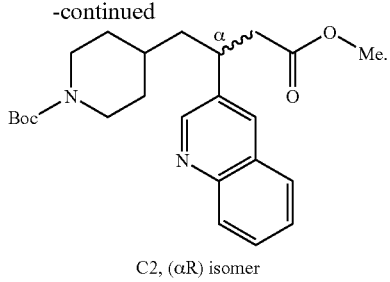

C2, (αR) isomer

3. The process of claim 1, wherein
the first hydrogen source is gaseous hydrogen;
the first ligand-metal complex is (R)-Me-BoPhoz&[Ir(COD)Cl]$_2$;
the first solvent is DCE;
the first temperature is about 70° C.; and
the first pressure is about 25 bar;
wherein, when the hydrogenation agent is a second ligand-metal complex that is (R)-Me-BoPhoz&[Ir(COD)Cl]$_2$ combined with iodine in an amount of about 0.1 Eq., then the second solvent is EtOAc; the second temperature is about 50° C.; and the second pressure is about 25 bar; and,
wherein, when the hydrogenation agent is 10% Pd/C in an amount of about 10% (w/w); then the second solvent is IPA; the optional second additive is Et$_3$N in an amount of about 0.75 Eq.; the second temperature is about 40° C.; and, the second pressure is about 10 bar.

4. The process of claim 1, further comprising the steps:
Step 1. reacting a Compound D1 with a first hydrogen source, a first ligand-metal complex consisting essentially of a first ligand conjugated with a first metal adduct, in a first solvent in the presence of an optional first additive at an elevated first temperature and an elevated first pressure to provide a substantially pure Compound D3:

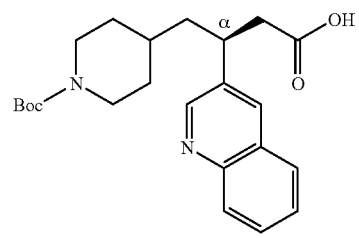

D1

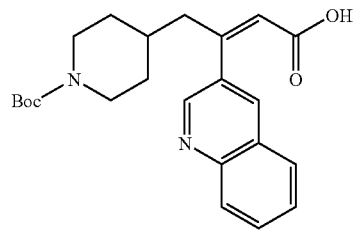

D3, (αS) isomer

Step 2. optionally converting the Compound D3 hydroxy group to provide Compound C3 having a —O—C$_{1-8}$alkyl group, and carrying forward Compound C3 according to Step 2 of claim 1;
Step 3. reacting Compound D3 with a second hydrogen source and a hydrogenation agent in a second solvent in the presence of an optional second additive at an elevated second temperature and an elevated second pressure to provide an isomeric mixture of a Compound D4 and Compound D5:

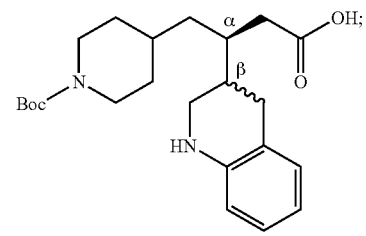

D3, (αS) isomer

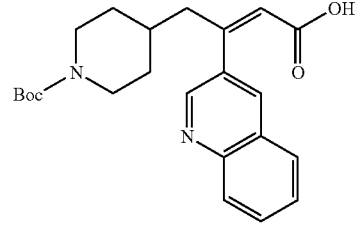

D4, (αSβS) isomer
D5, (αS,βR) isomer and
Step 4. converting the hydroxy group in the isomeric mixture of Compound D4 and Compound D5 to an —O—C$_{1-8}$alkyl group to provide an isomeric mixture of Compound C4 and Compound C5; and carrying forward the isomeric mixture of Compound C4 and Compound C5 according to Step 3 of claim 1.

5. The process of claim 1 for making a substantially pure Compound D2 comprising the step of:
reacting a Compound D1 with a first hydrogen source, a first ligand-metal complex consisting essentially of a first ligand conjugated with a first metal adduct, in a first solvent in the presence of an optional first additive at an elevated first temperature and an elevated first pressure to provide a substantially pure Compound D2:

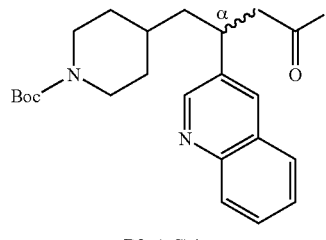

D1

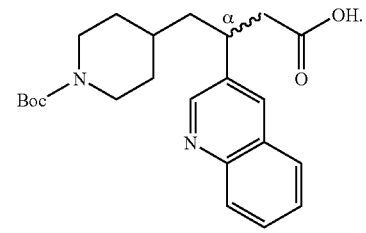

D2, (αR) isomer

6. The process of claim 4, wherein
the first ligand is selected from the group consisting of (R)-Xyl-PhanePhos, (S)-Xyl-PhanePhos, (R)-Phane- Phos, (S)-PhanePhos, (R)-An-PhanePhos, (S)-An-PhanePhos, (R)-MeOXyl-PhanePhos, (S)-MeOXyl-PhanePhos, PCy-(R)-Me-BoPhoz and PCy-(S)-Me-BoPhoz, and the first metal adduct is selected from the group consisting of [Rh(COD)$_2$]BF$_4$, [Rh(COD)$_2$]OTf, [Ru(COD)(CF$_3$COO)$_2$]$_2$, [Ru(COD)(methylallyl)$_2$], [Ru(benzene)Cl$_2$]$_2$ and [Ir(COD)Cl]$_2$.

7. The process of claim 6, wherein
the first hydrogen source is gaseous hydrogen;
the first ligand-metal complex is (R)-Xyl-PhanePhos&[Ru(COD)(CF$_3$COO)$_2$]$_2$;
the first solvent is MeOH;
the first temperature is about 40° C.;
the first pressure is about 10 bar;
the second hydrogen source is gaseous hydrogen; and
the hydrogenation agent is selected from either 10% Pd/C or a second ligand-metal complex,
wherein, when the hydrogenation agent is a second ligand-metal complex that is (R)-Me-BoPhoz&[Ir(COD)Cl]$_2$ combined with iodine in an amount of about 0.1 Eq., then the second solvent is EtOAc; the second temperature is about 50° C.; and the second pressure is about 25 bar; and,
wherein, when the hydrogenation agent is 10% Pd/C in an amount of about 10% (w/w); then the second solvent is MeOH; the optional second additive is Et$_3$N in an amount of about 0.75 Eq.; the second temperature is about 40° C.; and,
the second pressure is about 10 bar.

8. The process of claim 1, wherein the process provides an enantiomer or diastereomer of a compound of Formula (Ia) selected from the group consisting of:
4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid,
(3R,3'R)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid,
(3R,3'R)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid methyl ester,
(3R,3'S)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid,
(3R,3'S)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid methyl ester,
(3S,3'R)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid,
(3S,3'R)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid methyl ester,
(3S,3'S)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid,
(3S,3'S)-4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid methyl ester, and
4-[1-(3-5,6,7,8-tetrahydro-[1,8]naphthyridin-2-yl-propionyl)-piperidin-4-yl]-3-(1,2,3,4-tetrahydro-quinolin-3-yl)-butyric acid methyl ester.

9. The process of claim 1, wherein the starting material in Step 1 is selected from the group consisting of:
(Z)-4-(3-methoxycarbonyl-2-quinolin-3-yl-allyl)-piperidine-1-carboxylic acid tert-butyl ester, and
(Z)-4-(3-carboxy-2-quinolin-3-yl-allyl)-piperidine-1-carboxylic acid tert-butyl ester.

* * * * *